US006063782A

United States Patent [19]

Kimura et al.

[11] Patent Number: 6,063,782

[45] Date of Patent: May 16, 2000

[54] PYRROLOPYRIDAZINE DERIVATIVES

[75] Inventors: Tomio Kimura; Nobuhiko Shibakawa; Hiroshi Fujiwara; Etsuro Itoh; Keiji Matsunobu, all of Ube; Keiichi Tabata, Tanashi; Hiroshi Yasuda, Yokohama; Yoshimi Fujihara, *deceased, late of* Ube, *all of* Japan, *by* Fumie Fujihara, *legal representative*

[73] Assignees: Sankyo Company, Limited, Tokyo; Ube Industries, Ltd., Ube, both of Japan

[21] Appl. No.: 08/676,375

[22] Filed: Jul. 17, 1996

Related U.S. Application Data

[63] Continuation of application No. PCT/JP95/00038, Jan. 18, 1995, abandoned.

[30] Foreign Application Priority Data

Jan. 19, 1994 [JP] Japan .................................... 6-003988

[51] Int. Cl.[7] ..................... A61K 31/5025; C07D 487/04

[52] U.S. Cl. ............................................ 514/248; 544/236

[58] Field of Search ............................. 544/236; 514/248

[56] References Cited

U.S. PATENT DOCUMENTS

| | | | |
|---|---|---|---|
| 4,988,695 | 1/1991 | Brown | 544/235 |
| 5,534,515 | 7/1996 | Grundler | 544/236 |

FOREIGN PATENT DOCUMENTS

| | | | |
|---|---|---|---|
| WO 91/17164 | 11/1991 | WIPO . | |
| 92-06979 | 4/1992 | WIPO | 544/236 |
| WO 92/06974 | 4/1992 | WIPO . | |
| WO 93/08190 | 4/1993 | WIPO | 544/236 |

*Primary Examiner*—Emily Bernhardt

*Attorney, Agent, or Firm*—Frishauf, Holtz, Goodman, Langer & Chick, P.C.

[57] ABSTRACT

Pyrrolopyridazine derivatives having the general formula.

(I)

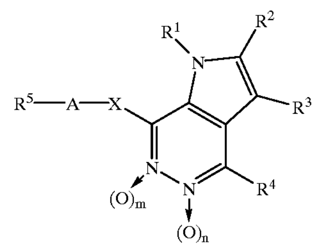

In the above formula, $R^1$ represents a $C_2$–$C_6$alkenyl-group, a halogeno-$C_2$–$C_6$-alkenyl group, a $C_6$–$C_{10}$ aryl-$C_2$–$C_6$-alkenyl group, a $C_2$–$C_6$ alkynyl group, a $C_3$–$C_7$ cycloalkyl group, a $C_3$–$C_7$ cycloalkyl-$C_1$–$C_6$-alkyl group, a $C_5$–$C_7$ cycloalkenyl-$C_1$–$C_6$-alkyl group or a halogeno-$C_1$–$C_6$-alkyl group; $R^2$ and $R^3$ are the same or different and each represents a hydrogen atom, a $C_1$–$C_6$ alkyl group or a $C_6$–$C_{10}$ aryl group; $R^4$ represents a hydrogen atom or a $C_1$–$C_6$ alkyl group; $R^5$ represents a $C_6$–$C_{10}$ aryl group or a 5–10 membered heteroaryl group comtaining heteroatom(s) selected from nitrogen, oxygen and sulfur;

46 Claims, No Drawings

PYRROLOPYRIDAZINE DERIVATIVES

This application is a continuation application of International Application PCT/JP95/00038 filed Jan. 18, 1995 (Chapter II) now abandoned.

TECHNOLOGICAL FIELD

The present invention concerns pyrrolopyridazine derivatives or pharmaceutically acceptable salts thereof which have an excellent gastric juice secretion inhibiting activity, gastric mucosa protective activity and an excellent antibacterial activity against *Helicobacter pylori;* and an anti-ulcer agent comprising these derivatives or salts thereof as the active ingredient.

BACKGROUND TECHNOLOGY

It is said that peptic ulcer occurs when the balance between the attacking factors to gastric mucosa and defensive factors for gastric mucosa is lost. Inhibition of gastric juice secretion which is one of the attacking factors is useful for prevention and therapy of gastric ulcer. Hitherto, as drugs effective for inhibition of gastric juice secretion, anticholinergic agents and histamine $H_2$ receptor antagonistic agents such as cimetidine etc., have been widely employed in clinic. However, when a histamine $H_2$ receptor antagonistic agent has been used for therapy for a long period, recurrence of ulcer during interrupted administration of the drug is a serious problem. Though the recurrence of ulcers is considered to be due to decreased defensive factors at the site of gastric mucosa, its relationship with *Helicobacter pylori* has been recently indicated. Accordingly, an excellent anti-ulcer agent is desired, which strongly inhibits gastric juice secretion, i.e., an attacking factor, protects gastric mucosa and has an excellent antibacterial activity against *Helicobacter pylori.*

As pyrrolopyridazine derivatives having a gastric juice secretion inhibiting activity and gastric mucosa protective activity, a compound shown below, for example, has been known (WO 91/17164, WO 92/06979, WO 93/08190 etc.). However, its effects are not sufficient, and it has been desired to develop a compound having more potent activity.

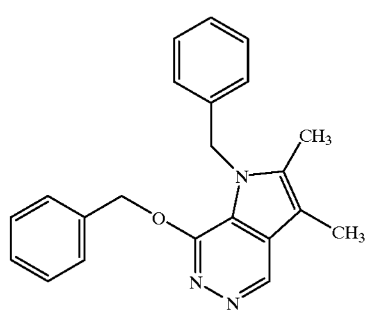

DISCLOSURE OF INVENTION

In order to solve the problem mentioned above, the present inventors studied eagerly the synthesis of pyrrolopyridazine derivatives and their pharmacological activities for many years, aiming at the development of an excellent anti-ulcer agent which strongly inhibits gastric juice secretion, i.e., an attacking factor, protects gastric mucosa and has an excellent antibacterial activity against *Helicobacter pylori.* Our study resulted in finding that pyrrolopyridazine derivatives having specific substituents have an excellent antibacterial activity against *Helicobacter pylori* as well as a strong gastric juice secretion inhibiting activity and gastric mucosa protective activity; and in completion of the present invention.

(Constitution of Invention)

Pyrrolopyridazine derivatives of the present invention have the general formula.

(I)

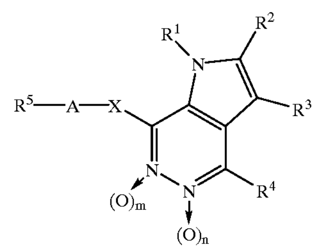

In the formula above:

$R^1$ represents a $C_2$–$C_6$ alkenyl group, a halogeno-$C_2$–$C_6$-alkenyl group, a $C_6$–$C_{10}$ aryl-$C_2$–$C_6$-alkenyl group, a $C_2$–$C_6$alkynyl group, a $C_3$–$C_7$ cycloalkyl group, a ($C_3$–$C_7$ cycloalkyl)-$C_1$–$C_6$-alkyl group, a ($C_5$–$C_7$ cycloalkenyl)-$C_1$–$C_6$-alkyl group, or a halogeno-$C_1$–$C_6$-alkyl group;

$R^2$ and $R^3$ are the same or different, and each represents a hydrogen atom, a $C_1$–$C_6$ alkyl group, or a $C_6$–$C_{10}$ aryl group;

$R^4$ represents a hydrogen atom, or a $C_1$–$C_6$ alkyl group;

$R^5$ represents a $C_6$–$C_{10}$ aryl group, or a from 5- to 10-membered heteroaryl group in which the hetero atom(s) are selected from the group consisting of nitrogen, oxygen and sulfur atoms;

A represents a $C_1$–$C_3$ alkylene group;

X represents an imino (NH) group, an oxygen atom, a sulfur atom; or a methylene group;

m represents 0 or 1; and n represents 0 or 1.

The $C_2$–$C_6$ alkenyl group or the $C_2$–$C_6$ alkenyl moiety of the halogeno-$C_2$–$C_6$-alkenyl group, and the $C_6$–$C_{10}$ aryl-$C_2$–$C_6$-alkenyl group included in the definitions of $R^1$ may be, for example: vinyl, 1-propenyl, 2-propenyl, isopropenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-2-butenyl, 3-methyl-2-butenyl, 1-hexenyl, 2-hexenyl, propan-1,2-dienyl, butan-1,2-dienyl, pentan-1,2-dienyl or hexan-1,2-dienyl; preferably a $C_2$–$C_5$ alkenyl group (particularly, vinyl, 1-propenyl, 2-propenyl, isopropenyl, 1-butenyl, 2-butenyl, 3-butenyl, 2-methyl-2-propenyl, 2-pentenyl, 3-pentenyl, 3-methyl-2-butenyl or propan-1,2-dienyl group); and more preferably a $C_3$–$C_4$ alkenyl group (particularly, 1-propenyl, 2-propenyl, 1-butenyl, 2-butenyl or 2-methyl-2-propenyl group).

The halogeno-$C_2$–$C_6$-alkenyl group included in the definitions of $R^1$ may be, for example: 2,2-difluorovinyl, 3-fluoro-2-propenyl, 2-chloro-2-propenyl, 3-chloro-2-propenyl, 3-bromo-2-propenyl, 3-iodo-2-propenyl, 3,3-difluoro-2-propenyl, 2,3-dichloro-2-propenyl, 3,3-dichloro-2-propenyl, 2,3-dibromo-2-propenyl, 3,3-dibromo-2-propenyl, 4,4,4-trifluoro-2-butenyl, 5-fluoro-2-pentenyl or 6-fluoro-2-hexenyl group; and preferably 3-chloro-2-propenyl, 3,3-dichloro-2-propenyl or 4,4,4-trifluoro-2-butenyl group.

The $C_6$–$C_{10}$ aryl moiety of the ($C_6$–$C_{10}$ aryl)-$C_2$–$C_6$-alkenyl group included in the definitions of $R^1$ and the $C_6$–$C_{10}$ aryl group included in the definitions of $R^2$, $R^3$ and $R^5$ may be, for example: a phenyl group or a naphthyl group; and preferably a phenyl group. The group may have substituent(s) optionally on the ring, and the substituents may be, for example: a $C_1$–$C_6$ alkyl group mentioned later; a $C_1$–$C_6$ alkoxy group such as methoxy, ethoxy, propoxy, isopropoxy, butoxy, isobutoxy, pentoxy or hexyloxy; a halogen atom such as fluoro, chloro, bromo or iodo; a halogeno-$C_1$–$C_6$-alkyl group such as fluoromethyl, chloromethyl, difluoromethyl, trifluoromethyl, 2-fluoroethyl, 2-chloroethyl, 2-bromoethyl, 2-iodoethyl, 2,2,2-trifluoroethyl, 3-fluoropropyl, 4-fluorobutyl, 5-fluoropentyl or 6-fluorohexyl; or a halogeno-$C_1$–$C_6$-alkoxy group such as fluoromethoxy, difluoromethoxy, trifluoromethoxy, 2-fluoroethoxy, 2-chloroethoxy, 2-bromoethoxy, 2-iodoethoxy, 2,2,2-trifluoroethoxy, 3-fluoropropoxy, 4-fluorobutoxy, 5-fluoropentoxy or 6-fluorohexyloxy; preferably a $C_1$–$C_4$ alkyl group, a $C_1$–$C_4$ alkoxy group, a halogen atom group or a halogeno-$C_1$–$C_4$-alkyl group; and more preferably methyl, methoxy, fluoro or chloro for the group included in the definitions of $R^1$, $R^2$ and $R^3$ and methyl, methoxy, fluoro, chloro trifluoromethyl or difluoromethoxy (particularly fluoro or chloro) for the group included in the difinition of $R^5$.

The ($C_6$–$C_{10}$ aryl)-$C_2$–$C_6$ alkenyl group included in the definitions of $R^1$ may be, for example: 2-phenylethenyl, 3-phenyl-2-propenyl, 4-phenyl-3-butenyl, 5-phenyl-4-pentenyl, 6-phenyl-5-hexenyl, 3-methylphenyl-2-propenyl, 3-methoxyphenyl-2-propenyl, 3-fluorophenyl-2-propenyl, 3-chlorophenyl-2-propenyl or 3-naphthyl-2-propenyl; preferably 3-phenyl-2-propenyl, 4-phenyl-3-butenyl, 5-phenyl-4-pentenyl, 3-methylphenyl-2-propenyl, 3-methoxyphenyl-2-propenyl, 3-fluorophenyl-2-propenyl, 3-chlorophenyl-2-propenyl or 3-naphthyl-2-propenyl; and more preferably 3-phenyl-2-propenyl.

The $C_2$–$C_6$ alkynyl group included in the definitions of $R^1$ may be, for example; ethynyl, 2-propynyl, 2-butynyl, 2-pentynyl or 2-hexynyl; preferably a $C_2$–$C_4$ alkynyl group; and more preferably 2-propynyl.

The $C_3$–$C_7$ cycloalkyl group or the $C_3$–$C_7$ cycloalkyl moiety of the ($C_3$–$C_7$ cycloalkyl)-$C_1$–$C_6$-alkyl group included in the definitions of $R^1$ may be, for example: cyclopropyl, cyclobutyl, cyclopentyl, cyclohexyl or cycloheptyl; preferably cyclopropyl or cyclohexyl; and particularly preferably cyclopropyl. The group may have optionally substituent(s) on the ring; and the substituent may be, for example: a $C_1$–$C_6$ alkyl group mentioned later; preferably a $C_1$–$C_4$ alkyl group; more preferably methyl or ethyl; and particularly preferably methyl.

The ($C_3$–$C_7$ cycloalkyl)-$C_1$–$C_6$-alkyl group included in the definitions of $R^1$ may be, for example: cyclopropylmethyl, methylcyclopropylmethyl, cyclobutylmethyl, cyclopentylmethyl, cyclohexylmethyl, methylcyclohexylmethyl, cycloheptylmethyl, 2-cyclopropylethyl, 3-cyclopropylpropyl, 4-cyclopropylbutyl, 5-cyclopropylpentyl or 6-cyclopropylheptyl; preferably cyclopropylmethyl, 2-methylcyclopropylmethyl or cyclohexylmethyl; and particularly preferably cyclopropylmethyl or 2-methylcyclopropylmethyl.

The ($C_5$–$C_7$ cycloalkenyl)-$C_1$–$C_6$-alkyl group included in the definitions of $R^1$ may be, for example: cyclopentenylmethyl, cyclohexenylmethyl, cycloheptenylmethyl, 2-cyclopentenylethyl, 3-cyclopentenylpropyl, 4-cyclopentenylbutyl, 5-cyclopentenylpentyl, 6-cyclopentenylhexyl, 2-cyclohexenylethyl, 3-cyclohexenylpropyl, 4-cyclohexenylbutyl, 5-cyclohexenylpentyl or 6-cyclohexenylhexyl; preferably cyclopenten-1-ylmethyl or cyclohexen-1-ylmethyl; and more preferably cyclopenten-1-ylmethyl.

The halogeno-$C_1$–$C_6$-alkyl group included in the definitions of $R^1$ may be, for example; fluoromethyl, chloromethyl, difluoromethyl, trifluoromethyl, 2-fluoroethyl, 2-chloroethyl, 2-bromoethyl, 2-iodoethyl, 2,2-difluoroethyl, 2,2,2-trifluoroethyl; 3-fluoropropyl, 4-fluorobutyl, 5-fluoropentyl or 6-fluorohexyl; preferably a halogeno-$C_1$–$C_4$-alkyl group; more preferably difluoromethyl, 2-fluoroethyl, 2-chloroethyl, 2-bromoethyl, 2-iodoethyl, 2,2-difluoroethyl, 2,2,2-trifluoroethyl, 3-fluoropropyl or 4-fluorobutyl; and particularly preferably 2,2,2-trifluoroethyl or 3-fluoropropyl.

The $C_1$–$C_6$ alkyl group included in the definitions of $R^2$, $R^3$ and $R^4$ may be, for example: methyl, ethyl, propyl, isopropyl, butyl, isobutyl, pentyl or hexyl; preferably a $C_1$–$C_4$ alkyl group; more preferably methyl or ethyl; and particularly preferably methyl.

The from 5- to 10-membered heteroaryl group having the hetero atom(s) selected from the group consisting of nitrogen, oxygen and sulfur atoms included in the definitions of $R^5$ may be, for example: pyrrolyl, indolyl, furyl, benzofuryl, thienyl, benzothienyl, oxazolyl, benzoxazolyl, isoxazolyl, benzisoxazolyl, thiazolyl, benzothiazolyl, isothiazolyl, benzisothiazolyl, imidazolyl, benzimidazolyl, pyrazolyl, benzopyrazolyl, 1,3,4-oxadiazolyl, 1,3,4-thiadiazolyl, pyridyl, quinolyl, isoquinolyl, pyrimidinyl, pyrazinyl or pyridazinyl; preferably furyl, thienyl, oxazolyl, benzoxazolyl, thiazolyl, benzothiazolyl, imidazolyl, benzimidazolyl, 1,3,4-oxadiazolyl, 1,3,4-thiadiazolyl, pyridyl, pyrazinyl or pyridazinyl; and more preferably furyl, thienyl or pyridyl. The heteroaryl group may have substituent(s) on the ring and the substituent on the from 5- to 6-membered hetero ring may be, for example: a $C_1$–$C_6$ alkyl group or halogen atom mentioned above; particularly preferably methyl, fluoro or chloro and the substituent on the phenyl ring may be the same group as mentioned above for the aryl group.

The $C_1$–$C_3$ alkylene group in the definition of A may be, for example: methylene, ethylene, propylene or trimethylene; and preferably methylene.

X may be preferably an oxygen atom, a sulfur atom or a methylene group; more preferably an oxygen atom or a methylene group; and particularly preferably an oxygen atom.

m may be preferably 0; and when m is 1, X may be preperably a methylene group.

n may be preferably 0.

The compound having the general formula (I) mentioned above can be converted, if necessary, to its pharmaceutically acceptable salts. The salt may be, preferably an acid addition salt, for example: a hydrohalide such as hydrofluoride, hydrochloride, hydrobromide or hydroiodide; a nitrate; a perchlorate; a sulfate; a phosphate; a carbonate; a $C_1$–$C_4$ alkylsulfonate such as methanesulfonate, trifluoromethanesulfonate or ethanesulfonate; a $C_6$–$C_{10}$ arylsulfonate such as benzenesulfonate or p-toluenesulfonate; a carboxylate such as acetate, propionate, butyrate, benzoate, fumarate, succinate, citrate, tartarate, oxalate, malonate or maleate; or an amino acid salt such as glutamate or asparate. In addition, the scope of the present invention includes any hydrate of Compound (I).

In Compound (I), there are optical isomers due to the asymmetric carbon atom(s) in the molecule, and/or geometric-isomers due to the double bond(s) in the molecule in some cases. The scope of the present invention covers all these stereoisomers and any mixtures thereof.

In the general formula (I), there may be mentioned as a preferable compound:

(1) A compound in which $R^1$ is a $C_2$–$C_5$ alkenyl group; a substituted $C_3$ $C_4$ alkenyl group with fluoro, chloro or bromo; a $C_6$ aryl-$C_3$–$C_5$-alkenyl group; a $C_3$–$C_4$ alkynyl group; a cyclopropyl group; a $C_3$–$C_6$ cycloalkylmethyl group; or a halogeno-$C_1$–$C_4$-alkyl group;

(2) A compound in which $R^1$ is a $C_2$–$C_5$ alkenyl group; a $C_3$–$C_4$ alkenyl group substituted with fluoro or chloro; a 3-($C_6$ aryl)-2-propenyl group; 2-propynyl group; a cyclopropylmethyl group; 2-methylcyclopropylmethyl group; a cyclopeneten-1-ylmethyl group; or a fluoro-$C_2$–$C_3$ alkyl group;

(3) A compound in which $R^1$ is 1-propenyl, 2-propenyl, 1-butenyl, 2-butenyl, 2-methyl-2-propenyl, propan-1,2-dienyl, 3-phenyl-2-propenyl, 2-propynyl, cyclopropylmethyl, 2-methylcyclopropylmethyl, cyclopenten-1-ylmethyl, 2,2,2-trifluoroethyl or 3-fluoropropyl;

(4) A compound in which $R^1$ is 1-propenyl, 2-propenyl, 1-butenyl, 2-butenyl, 2methyl-2-propenyl, 3-phenyl-2-propenyl, cyclopropylmethyl or 2-methylcyclopropylmethyl;

(5) A compound in which $R^2$ and $R^3$ are the same or different, and each is a hydrogen atom, a $C_1$–$C_4$ alkyl group or a $C_6$ aryl group;

(6) A compound in which $R^2$ and $R^3$ are the same or different, and each is a hydrogen atom, a $C_1$–$C_3$ alkyl group or a phenyl group;

(7) A compound in which $R^2$ and $R^3$ are the same or different, and each is a hydrogen atom or a $C_1$–$C_2$ alkyl group;

(8) A compound in which $R^2$ and $R^3$ are the same, and each is a methyl group;

(9) A compound in which $R^4$ is a hydrogen atom or a $C_1$–$C_4$ alkyl group;

(10) A compound in which $R^4$ is a hydrogen atom or a $C_1$–$C_2$ alkyl group;

(11) A compound in which $R^4$ is a hydrogen atom;

(12) A compound in which $R^5$ is a phenyl group optionally substituted with $C_1$–$C_4$ alkyl, $C_1$–$C_4$ alkoxy, halogen, halogen-$C_1$–$C_4$-alkyl or halogen-$C_1$–$C_4$-alkoxy, a naphthyl group, a furyl group, a thienyl group, an oxazolyl group, a benzoxazolyl group, a thiazolyl group, a benzothiazolyl group, an imidazolyl group, a benzimidazolyl group, a 1,3,4-oxadiazolyl group, a 1,3,4-thiadiazolyl group, a pyridyl group, a pyrazinyl group or a pyridazinyl group;

(13) A compound in which $R^5$ is a phenyl group optionally substituted with methyl, methoxy, fluoro, chloro, fluoromethyl, trifluoromethyl, fluoromethoxy or difluoromethoxy, a furyl group, a thienyl group, an oxazolyl group, a benzoxazolyl group, a thiazolyl group, a benzothiazolyl group, an imidazolyl group, a benzimidazolyl group or a pyridyl group;

(14) A compound in which $R^5$ is a phenyl group optionally substituted with methyl, methoxy, fluoro, chloro, fluoromethyl, trifluoromethyl, fluoromethoxy or difluoromethoxy, a furyl group, a thienyl group or a pyridyl group;

(15) A compound in which $R^5$ is a phenyl group optionally substituted with fluoro, chloro, trifluoromethyl or difluoromethoxy;

(16) A compound in which $R^5$ is a phenyl group optionally substituted with fluoro or chloro;

(17) A compound in which A is a methylene group;

(18) A compound in which X is an oxygen atom, sulfur atom or methylene group;

(19) A compound in which X is an oxygen atom or methylene group;

(20) A compound in which X is an oxygen atom;

(21) A compound in which m is 0; and

(22) A compound in which n is 0.

In addition, any optional combination of, from (1) to (4), from (5) to (8), from (9) to (11), from (12) to (16), (17), from (18) to (20), (21) and (22), may provide a more preferable compound as mentioned below:

(23) A compound in which:

$R^1$ is an $C_2$–$C_5$ alkenyl group; a $C_3$–$C_4$ alkenyl group substituted with fluoro, chloro or bromo; a $C_6$ aryl-$C_3$–$C_5$-alkenyl group; a $C_3$–$C_4$ alkynyl group; a cyclopropyl group; a $C_3$–$C_6$ cycloalkylmethyl group; or a halogeno-$C_1$-$C_4$-alkyl group;

$R^2$ and $R^3$ are the same or different, and each is a hydrogen atom, a $C_1$–$C_4$ alkyl group, or a $C_6$ aryl group;

$R^4$ is a hydrogen atom or a $C_1$–$C_4$ alkyl group;

$R^5$ is a phenyl group optionally substituted with $C_1$–$C_4$ alkyl, a $C_1$–$C_4$ alkoxy, halogen, halogeno-$C_1$–$C_4$-alkyl or halogeno-$C_1$–$C_4$-alkoxy, a naphthyl group, a furyl group, a thienyl group, an oxazolyl group, a benzoxazolyl group, a thiazolyl group, a benzothiazolyl group, an imidazolyl group, a benzimidazolyl group, a 1,3,4-oxadiazolyl group, a 1,3,4-thiadiazolyl group, a pyridyl group, a pyrazinyl group or a pyridazinyl group;

A is a methylene group;

X is an oxygen atom, sulfur atom or a methylene group; and

When n is 1, m is 0;

(24) A compound in which:

$R^1$ is an $C_2$–$C_5$ alkenyl group; a $C_3$–$C_4$ alkenyl group substituted with fluoro or chloro; a 3-($C_6$ aryl)-2-propenyl group; a 2-propynyl group; a cyclopropyl group; a cyclopropylmethyl group; 2-methylcyclopropylmethyl group; a cyclopenten-1-ylmethyl group; or a fluoro-$C_2$–$C_3$-alkyl group;

$R^2$ and $R^3$ are the same or different, and each is a hydrogen atom, an $C_1$–$C_3$ alkyl group, or a phenyl group;

$R^4$ is a hydrogen atom or a $C_1$–$C_2$ alkyl group;

$R^5$ is a phenyl group optionally substituted with methyl, methoxy, fluoro, chloro, fluoromethyl, trifluoromethyl, fluoromethoxy or difluoromethoxy, a furyl group, a thienyl group, an oxazolyl group, a benzoxazolyl group, a thiazolyl group, a benzothiazolyl group, an imidazolyl group, a benzimidazolyl group or a pyridyl group;

A is a methylene group;

X is an oxygen atom, sulfur atom or a methylene group; and m is 0;

(25) A compound in which:

$R^1$ is a 1-propenyl, 2-propenyl, 1-butenyl, 2-butenyl, 2-methyl-2-propenyl, propan-1,2-dienyl, 3-phenyl-2-propenyl, 2-propynyl, cyclopropylmethyl, 2-methylcyclopropylmethyl, cyclopenten-1-ylmethyl, 2,2,2-trifluoroethyl or 3-fluoropropyl group;

$R^2$ and $R^3$ are the same or different, and each is a hydrogen atom or a $C_1$–$C_2$ alkyl group;

$R^4$ is a hydrogen atom or a $C_1$–$C_2$ alkyl group;

$R^5$ is a phenyl group optionally substituted with fluoro, chloro, trifluoromethyl or difluoromethoxy;

A is a methylene group;

X is an oxygen atom or a methylene group;

m is 0; and n is 0;

(26) A compound in which:

$R^1$ is a 1-propenyl, 2-propenyl, 1-butenyl, 2-butenyl, 2-methyl-2-propenyl, 3-phenyl-2-propenyl, cyclopropylmethyl or 2-methylcyclopropylmethyl group;

$R^2$ and $R^3$ are the same, and each is methyl group;

$R^4$ is a hydrogen atom;

$R^5$ is a phenyl group optionally substituted with fluoro or chloro;

A is a methylene group;

X is an oxygen atom;

m is 0; and n is 0.

In Tables 1, 2 and 3 below, typical compounds of the present invention are shown for example but these compounds do not limit the scope of the present invention. The compounds listed in Tables 1, 2 and 3 have the structures of Compound (I-1), Compound (I-2) and Compound (I-3), respectively.

(I-1)

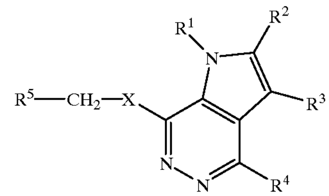

(I-2)

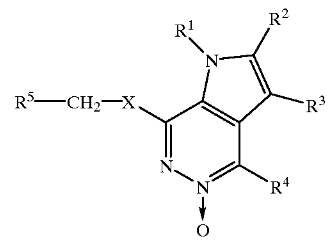

(I-3)

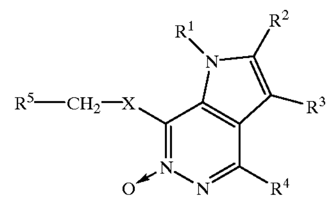

TABLE 1

| Example Compd. No. | $R^1$ | $R^2$ | $R^3$ | $R^4$ | $R^5$ | X |
|---|---|---|---|---|---|---|
| 1-1 | $CH{=}CH_2$ | Me | Me | H | Ph | 0 |
| 1-2 | $CH{=}CHCH_3$ | Me | Me | H | Ph | 0 |
| 1-3 | $CH_2CH{=}CH_2$ | Me | Me | H | Ph | 0 |
| 1-4 | $C(CH_3){=}CH_2$ | Me | Me | H | Ph | 0 |
| 1-5 | $CH{=}CHCH_2CH_3$ | Me | Me | H | Ph | 0 |
| 1-6 | $CH_2CH{=}CHCH_3$ | Me | Me | H | Ph | 0 |
| 1-7 | $CH_2CH_2CH{=}CH_2$ | Me | Me | H | Ph | 0 |
| 1-8 | $C(CH_3){=}CHCH_3$ | Me | Me | H | Ph | 0 |
| 1-9 | $CH(CH_3)CH{=}CH_2$ | Me | Me | H | Ph | 0 |
| 1-10 | $CH{=}C(CH_3)CH_3$ | Me | Me | H | Ph | 0 |
| 1-11 | $CH_2C(CH_3){=}CH_2$ | Me | Me | H | Ph | 0 |
| 1-12 | $CH{=}CHCH_2CH_2CH_3$ | Me | Me | H | Ph | 0 |
| 1-13 | $CH_2CH{=}CHCH_2CH_3$ | Me | Me | H | Ph | 0 |
| 1-14 | $CH_2CH_2CH{=}CHCH_3$ | Me | Me | H | Ph | 0 |
| 1-15 | $CH_2CH_2CH_2CH{=}CH_2$ | Me | Me | H | Ph | 0 |
| 1-16 | $C(CH_3){=}CHCH_2CH_3$ | Me | Me | H | Ph | 0 |
| 1-17 | $CH_2C(CH_3){=}CHCH_3$ | Me | Me | H | Ph | 0 |
| 1-18 | $CH_2CH{=}C(CH_3)CH_3$ | Me | Me | H | Ph | 0 |
| 1-19 | $CH_2CH{=}CHPh$ | Me | Me | H | Ph | 0 |
| 1-20 | $CH_2CH_2CH{=}CHPh$ | Me | Me | H | Ph | 0 |
| 1-21 | $CH_2CH_2CH_2CH{=}CHPh$ | Me | Me | H | Ph | 0 |
| 1-22 | $CH_2CH{=}CH$(2-FPh) | Me | Me | H | Ph | 0 |
| 1-23 | $CH_2CH{=}CH$(3-FPh) | Me | Me | H | Ph | 0 |
| 1-24 | $CH_2CH{=}CH$(4-FPh) | Me | Me | H | Ph | 0 |
| 1-25 | $CH_2CH{=}CH$(2-ClPh) | Me | Me | H | Ph | 0 |
| 1-26 | $CH_2CH{=}CH$(3-ClPh) | Me | Me | H | Ph | 0 |
| 1-27 | $CH_2CH{=}CH$(4-ClPh) | Me | Me | H | Ph | 0 |
| 1-28 | $CH_2CH{=}CH$(2-MePh) | Me | Me | H | Ph | 0 |
| 1-29 | $CH_2CH{=}CH$(3-MePh) | Me | Me | H | Ph | 0 |
| 1-30 | $CH_2CH{=}CH$(4-MePh) | Me | Me | H | Ph | 0 |
| 1-31 | $CH_2CH{=}CH$(2-OMePh) | Me | Me | H | Ph | 0 |
| 1-32 | $CH_2CH{=}CH$(3-OMePh) | Me | Me | H | Ph | 0 |
| 1-33 | $CH_2CH{=}CH$(4-OMePh) | Me | Me | H | Ph | 0 |

TABLE 1-continued

| Example Compd. No. | $R^1$ | $R^2$ | $R^3$ | $R^4$ | $R^5$ | X |
|---|---|---|---|---|---|---|
| 1-34 | $CH_2CH{=}CH$(1-Naph) | Me | Me | H | Ph | 0 |
| 1-35 | $CH_2CH{=}CH$(2-Naph) | Me | Me | H | Ph | 0 |
| 1-36 | $CH_2CH{=}CF_2$ | Me | Me | H | Ph | 0 |
| 1-37 | $CH_2CH{=}CHCl$ | Me | Me | H | Ph | 0 |
| 1-38 | $CH_2C(Cl){=}CH_2$ | Me | Me | H | Ph | 0 |
| 1-39 | $CH_2C(Cl){=}CHCl$ | Me | Me | H | Ph | 0 |
| 1-40 | $CH_2CH{=}CCl_2$ | Me | Me | H | Ph | 0 |
| 1-41 | $CH_2C(Br){=}CHBr$ | Me | Me | H | Ph | 0 |
| 1-42 | $CH_2CH{=}CHCF_3$ | Me | Me | H | Ph | 0 |
| 1-43 | $CH_2CH{=}CBr_2$ | Me | Me | H | Ph | 0 |
| 1-44 | C—CH | Me | Me | H | Ph | 0 |
| 1-45 | $CH_2C{\equiv}CH$ | Me | Me | H | Ph | 0 |
| 1-46 | $CH_2C{\equiv}CCH_3$ | Me | Me | H | Ph | 0 |
| 1-47 | $CH_2C{\equiv}CCH_2CH_3$ | Me | Me | H | Ph | 0 |
| 1-48 | $CH{=}C{=}CH_2$ | Me | Me | H | Ph | 0 |
| 1-49 | $CH{=}C{=}CHCH_3$ | Me | Me | H | Ph | 0 |
| 1-50 | $CH{=}C{=}CHCH_2CH_3$ | Me | Me | H | Ph | 0 |
| 1-51 | $CH_2Pr^c$ | Me | Me | H | Ph | 0 |
| 1-52 | $CH_2Bu^c$ | Me | Me | H | Ph | 0 |
| 1-53 | $CH_2Pn^c$ | Me | Me | H | Ph | 0 |
| 1-54 | $CH_2Hx^c$ | Me | Me | H | Ph | 0 |
| 1-55 | $CH_2Hp^c$ | Me | Me | H | Ph | 0 |
| 1-56 | $CH_2CH_2Pr^c$ | Me | Me | H | Ph | 0 |
| 1-57 | $(CH_2)_3Pr^c$ | Me | Me | H | Ph | 0 |
| 1-58 | $(CH_2)_4Pr^c$ | Me | Me | H | Ph | 0 |
| 1-59 | $Pr^c$ | Me | Me | H | Ph | 0 |
| 1-60 | $Bu^c$ | Me | Me | H | Ph | 0 |
| 1-61 | $Pn^c$ | Me | Me | H | Ph | 0 |
| 1-62 | $Hx^c$ | Me | Me | H | Ph | 0 |
| 1-63 | $Hp^c$ | Me | Me | H | Ph | 0 |
| 1-64 | $CH_2$(1-Pnte$^c$) | Me | Me | H | Ph | 0 |
| 1-65 | $CH_2$(1-Hxe$^c$) | Me | Me | H | Ph | 0 |
| 1-66 | $CH_2$(1-Hpte$^c$) | Me | Me | H | Ph | 0 |
| 1-67 | $CHF_2$ | Me | Me | H | Ph | 0 |
| 1-68 | $CH_2CH_2F$ | Me | Me | H | Ph | 0 |
| 1-69 | $CH_2CHF_2$ | Me | Me | H | Ph | 0 |
| 1-70 | $CH_2CF_3$ | Me | Me | H | Ph | 0 |
| 1-71 | $(CH_2)_3F$ | Me | Me | H | Ph | 0 |
| 1-72 | $(CH_2)_4F$ | Me | Me | H | Ph | 0 |
| 1-73 | $CH_2CH_2Cl$ | Me | Me | H | Ph | 0 |
| 1-74 | $CH_2CH_2Br$ | Me | Me | H | Ph | 0 |
| 1-75 | $CH_2CH_2I$ | Me | Me | H | Ph | 0 |
| 1-76 | $CH{=}CH_2$ | Me | Me | H | 4-FPh | 0 |
| 1-77 | $CH{=}CHCH_3$ | Me | Me | H | 4-FPh | 0 |
| 1-78 | $CH_2CH{=}CH_2$ | Me | Me | H | 4-FPh | 0 |
| 1-79 | $C(CH_3){=}CH_2$ | Me | Me | H | 4-FPh | 0 |
| 1-80 | $CH{=}CHCH_2CH_3$ | Me | Me | H | 4-FPh | 0 |
| 1-81 | $CH_2CH{=}CHCH_3$ | Me | Me | H | 4-FPh | 0 |
| 1-82 | $CH_2CH_2CH{=}CH_2$ | Me | Me | H | 4-FPh | 0 |
| 1-83 | $C(CH_3){=}CHCH_3$ | Me | Me | H | 4-FPh | 0 |
| 1-84 | $CH(CH_3)CH{=}CH_2$ | Me | Me | H | 4-FPh | 0 |
| 1-85 | $CH{=}C(CH_3)CH_3$ | Me | Me | H | 4-FPh | 0 |
| 1-86 | $CH_2C(CH_3){=}CH_2$ | Me | Me | H | 4-FPh | 0 |
| 1-87 | $CH{=}CHCH_2CH_2CH_3$ | Me | Me | H | 4-FPh | 0 |
| 1-88 | $CH_2CH{=}CHCH_2CH_3$ | Me | Me | H | 4-FPh | 0 |
| 1-89 | $CH_2CH_2CH{=}CHCH_3$ | Me | Me | H | 4-FPh | 0 |
| 1-90 | $CH_2CH_2CH_2CH{=}CH_2$ | Me | Me | H | 4-FPh | 0 |
| 1-91 | $C(CH_3){=}CHCH_2CH_3$ | Me | Me | H | 4-FPh | 0 |
| 1-92 | $CH_2C(CH_3){=}CHCH_3$ | Me | Me | H | 4-FPh | 0 |
| 1-93 | $CH_2CH{=}C(CH_3)CH_3$ | Me | Me | H | 4-FPh | 0 |
| 1-94 | $CH_2CH{=}CHPh$ | Me | Me | H | 4-FPh | 0 |
| 1-95 | $CH_2CH_2CH{=}CHPh$ | Me | Me | H | 4-FPh | 0 |
| 1-96 | $CH_2CH_2CH_2CH{=}CHPh$ | Me | Me | H | 4-FPh | 0 |
| 1-97 | $CH_2CH{=}CH$(2-FPh) | Me | Me | H | 4-FPh | 0 |
| 1-98 | $CH_2CH{=}CH$(3-FPh) | Me | Me | H | 4-FPh | 0 |
| 1-99 | $CH_2CH{=}CH$(4-FPh) | Me | Me | H | 4-FPh | 0 |
| 1-100 | $CH_2CH{=}CH$(2-ClPh) | Me | Me | H | 4-FPh | 0 |
| 1-101 | $CH_2CH{=}CH$(3-ClPh) | Me | Me | H | 4-FPh | 0 |
| 1-102 | $CH_2CH{=}CH$(4-ClPh) | Me | Me | H | 4-FPh | 0 |
| 1-103 | $CH_2CH{=}CH$(2-MePh) | Me | Me | H | 4-FPh | 0 |
| 1-104 | $CH_2CH{=}CH$(3-MePh) | Me | Me | H | 4-FPh | 0 |
| 1-105 | $CH_2CH{=}CH$(4-MePh) | Me | Me | H | 4-FPh | 0 |
| 1-106 | $CH_2CH{=}CH$(2-OMePh) | Me | Me | H | 4-FPh | 0 |
| 1-107 | $CH_2CH{=}CH$(3-OMePh) | Me | Me | H | 4-FPh | 0 |
| 1-108 | $CH_2CH{=}CH$(4-OMePh) | Me | Me | H | 4-FPh | 0 |
| 1-109 | $CH_2CH{=}CH$(1-Naph) | Me | Me | H | 4-FPh | 0 |

TABLE 1-continued

| Example Compd. No. | $R^1$ | $R^2$ | $R^3$ | $R^4$ | $R^5$ | X |
|---|---|---|---|---|---|---|
| 1-110 | $CH_2CH{=}CH$(2-Naph) | Me | Me | H | 4-FPh | 0 |
| 1-111 | $CH_2CH{=}CF_2$ | Me | Me | H | 4-FPh | 0 |
| 1-112 | $CH_2CH{=}CHCl$ | Me | Me | H | 4-FPh | 0 |
| 1-113 | $CH_2C(Cl){=}CH_2$ | Me | Me | H | 4-FPh | 0 |
| 1-114 | $CH_2C(Cl){=}CHCl$ | Me | Me | H | 4-FPh | 0 |
| 1-115 | $CH_2CH{=}CCl_2$ | Me | Me | H | 4-FPh | 0 |
| 1-116 | $CH_2C(Br){=}CHBr$ | Me | Me | H | 4-FPh | 0 |
| 1-117 | $CH_2CH{=}CHCF_3$ | Me | Me | H | 4-FPh | 0 |
| 1-118 | $CH_2CH{=}CBr_2$ | Me | Me | H | 4-FPh | 0 |
| 1-119 | $C{\equiv}CH$ | Me | Me | H | 4-FPh | 0 |
| 1-120 | $CH_2C{\equiv}CH$ | Me | Me | H | 4-FPh | 0 |
| 1-121 | $CH_2C{\equiv}CCH_3$ | Me | Me | H | 4-FPh | 0 |
| 1-122 | $CH_2C{=}CCH_2CH_3$ | Me | Me | H | 4-FPh | 0 |
| 1-123 | $CH{=}C{=}CH_2$ | Me | Me | H | 4-FPh | 0 |
| 1-124 | $CH{=}C{=}CHCH_3$ | Me | Me | H | 4-FPh | 0 |
| 1-125 | $CH{=}C{=}CHCH_2CH_3$ | Me | Me | H | 4-FPh | 0 |
| 1-126 | $CH_2Pr^c$ | Me | Me | H | 4-FPh | 0 |
| 1-127 | $CH_2Bu^c$ | Me | Me | H | 4-FPh | 0 |
| 1-128 | $CH_2Pn^c$ | Me | Me | H | 4-FPh | 0 |
| 1-129 | $CH_2Hx^c$ | Me | Me | H | 4-FPh | 0 |
| 1-130 | $CH_2Hp^c$ | Me | Me | H | 4-FPh | 0 |
| 1-131 | $CH_2CH_2Pr^c$ | Me | Me | H | 4-FPh | 0 |
| 1-132 | $(CH_2)_3Pr^c$ | Me | Me | H | 4-FPh | 0 |
| 1-133 | $(CH_2)_4Pr^c$ | Me | Me | H | 4-FPh | 0 |
| 1-134 | $Pr^c$ | Me | Me | H | 4-FPh | 0 |
| 1-135 | $Bu^c$ | Me | Me | H | 4-FPh | 0 |
| 1-136 | $Pn^c$ | Me | Me | H | 4-FPh | 0 |
| 1-137 | $Hx^c$ | Me | Me | H | 4-FPh | 0 |
| 1-138 | $Hp^c$ | Me | Me | H | 4-FPh | 0 |
| 1-139 | $CH_2$(1-$Pnte^c$) | Me | Me | H | 4-FPh | 0 |
| 1-140 | $CH_2$(1-$Hxe^c$) | Me | Me | H | 4-FPh | 0 |
| 1-14i | $CH_2$(1-$Hpte^c$) | Me | Me | H | 4-FPh | 0 |
| 1-142 | $CHF_2$ | Me | Me | H | 4-FPh | 0 |
| 1-143 | $CH_2CH_2F$ | Me | Me | H | 4-FPh | 0 |
| 1-144 | $CH_2CHF_2$ | Me | Me | H | 4-FPh | 0 |
| 1-145 | $CH_2CF_3$ | Me | Me | H | 4-FPh | 0 |
| 1-146 | $(CH_2)_3F$ | Me | Me | H | 4-FPh | 0 |
| 1-147 | $(CH_2)_4F$ | Me | Me | H | 4-FPh | 0 |
| 1-148 | $CH_2CH_2Cl$ | Me | Me | H | 4-FPh | 0 |
| 1-149 | $CH_2CH_2Br$ | Me | Me | H | 4-FPh | 0 |
| 1-150 | $CH_2CH_2I$ | Me | Me | H | 4-FPh | 0 |
| 1-151 | $CH{=}CH_2$ | Me | Me | H | 2,4-diFPh | 0 |
| 1-152 | $CH{=}CHCH_3$ | Me | Me | H | 2,4-diFPh | 0 |
| 1-153 | $CH_2CH{=}CH_2$ | Me | Me | H | 2,4-diFPh | 0 |
| 1-154 | $C(CH_3){=}CH_2$ | Me | Me | H | 2,4-diFPh | 0 |
| 1-155 | $CH{=}CHCH_2CH_3$ | Me | Me | H | 2,4-diFPh | 0 |
| 1-156 | $CH_2CH{=}CHCH_3$ | Me | Me | H | 2,4-diFPh | 0 |
| 1-157 | $CH_2CH_2CH{=}CH_2$ | Me | Me | H | 2,4-diFPh | 0 |
| 1-158 | $C(CH_3){=}CHCH_3$ | Me | Me | H | 2,4-diFPh | 0 |
| 1-159 | $CH(CH_3)CH{=}CH_2$ | Me | Me | H | 2,4-diFPh | 0 |
| 1-160 | $CH{=}C(CH_3)CH_3$ | Me | Me | H | 2,4-diFPh | 0 |
| 1-161 | $CH_2C(CH_3){=}CH_2$ | Me | Me | H | 2,4-diFPh | 0 |
| 1-162 | $CH{=}CHCH_2CH_2CH_3$ | Me | Me | H | 2,4-diFPh | 0 |
| 1-163 | $CH_2CH{=}CHCH_2CH_3$ | Me | Me | H | 2,4-diFPh | 0 |
| 1-164 | $CH_2CH_2CH{=}CHCH_3$ | Me | Me | H | 2,4-diFPh | 0 |
| 1-165 | $CH_2CH_2CH_2CH{=}CH_2$ | Me | Me | H | 2,4-diFPh | H |
| 1-166 | $C(CH_3){=}CHCH_2CH_3$ | Me | Me | H | 2,4-diFPh | 0 |
| 1-167 | $CH_2C(CH_3){=}CHCH_3$ | Me | Me | H | 2,4-diFPh | 0 |
| 1-168 | $CH_2CH{=}C(CH_3)CH_3$ | Me | Me | H | 2,4-diFPh | 0 |
| 1-169 | $CH_2CH{=}CHPh$ | Me | Me | H | 2,4-diFPh | 0 |
| 1-170 | $CH_2CH_2CH{=}CHPh$ | Me | Me | H | 2,4-diFPh | 0 |
| 1-171 | $CH_2CH_2CH_2CH{=}CHPh$ | Me | Me | H | 2,4-diFPh | 0 |
| 1-172 | $CH_2CH{=}CH$(2-FPh) | Me | Me | H | 2,4-diFPh | 0 |
| 1-173 | $CH_2CH{=}CH$(3-FPh) | Me | Me | H | 2,4-diFPh | 0 |
| 1-174 | $CH_2CH{=}CH$(4-FPh) | Me | Me | H | 2,4-diFPh | 0 |
| 1-175 | $CH_2CH{=}CH$(2-ClPh) | Me | Me | H | 2,4-diFPh | 0 |
| 1-176 | $CH_2CH{=}CH$(3-ClPh) | Me | Me | H | 2,4-diFPh | 0 |
| 1-177 | $CH_2CH{=}CH$(4-ClPh) | Me | Me | H | 2,4-diFPh | 0 |
| 1-178 | $CH_2CH{=}CH$(2-MePh) | Me | Me | H | 2,4-diFPh | 0 |
| 1-179 | $CH_2CH{=}CH$(3-MePh) | Me | Me | H | 2,4-diFPh | 0 |
| 1-180 | $CH_2CH{=}CH$(4-MePh) | Me | Me | H | 2,4-diFPh | 0 |
| 1-181 | $CH_2CH{=}CH$(2-OMePh) | Me | Me | H | 2,4-diFPh | 0 |
| 1-182 | $CH_2CH{=}CH$(3-OMePh) | Me | Me | H | 2,4-diFPh | 0 |
| 1-183 | $CH_2CH{=}CH$(4-OMePh) | Me | Me | H | 2,4-diFPh | 0 |
| 1-184 | $CH_2CH{=}CH$(1-Naph) | Me | Me | H | 2,4-diFPh | 0 |
| 1-185 | $CH_2CH{=}CH$(2-Naph) | Me | Me | H | 2,4-diFPh | 0 |

TABLE 1-continued

| Example Compd. No. | $R^1$ | $R^2$ | $R^3$ | $R^4$ | $R^5$ | X |
|---|---|---|---|---|---|---|
| 1-186 | $CH_2CH{=}CF_2$ | Me | Me | H | 2,4-diFPh | 0 |
| 1-187 | $CH_2CH{=}CHCl$ | Me | Me | H | 2,4-diFPh | 0 |
| 1-188 | $CH_2C(Cl){=}CH_2$ | Me | Me | H | 2,4-diFPh | 0 |
| 1-189 | $CH_2C(Cl){=}CHCl$ | Me | Me | H | 2,4-diFPh | 0 |
| 1-190 | $CH_2CH{=}CCl_2$ | Me | Me | H | 214-diFPh | 0 |
| 1-191 | $CH_2C(Br){=}CHBr$ | Me | Me | H | 2,4-diFPh | 0 |
| 1-192 | $CH_2CH{=}CHCF_3$ | Me | Me | H | 2,4-diFPh | 0 |
| 1-193 | $CH_2CH{=}CBr_2$ | Me | Me | H | 2,4-diFPh | 0 |
| 1-194 | $C{\equiv}CH$ | Me | Me | H | 2,4-diFPh | 0 |
| 1-195 | $CH_2C{\equiv}CH$ | Me | Me | H | 2,4-diFPh | 0 |
| 1-196 | $CH_2C{\equiv}CCH_3$ | Me | Me | H | 2,4-diFPh | 0 |
| 1-197 | $CH_2C{\equiv}CCH_2CH_3$ | Me | Me | H | 2,4-diFPh | 0 |
| 1-198 | $CH{=}C{=}CH_2$ | Me | Me | H | 2,4-diFPh | 0 |
| 1-199 | $CH{=}C{=}CHCH_3$ | Me | Me | H | 2,4-diFPh | 0 |
| 1-200 | $CH{=}C{=}CHCH_2CH_3$ | Me | Me | H | 2,4-diFPh | 0 |
| 1-201 | $CH_2Pr^c$ | Me | Me | H | 2,4-diFPh | 0 |
| 1-202 | $CH_2Bu^c$ | Me | Me | H | 2,4-diFPh | 0 |
| 1-203 | $CH_2Pn^c$ | Me | Me | H | 2,4-diFPh | 0 |
| 1-204 | $CH_2Hx^c$ | Me | Me | H | 2,4-diFPh | 0 |
| 1-205 | $CH_2Hp^c$ | Me | Me | H | 2,4-diFPh | 0 |
| 1-206 | $CH_2CH_2Pr^c$ | Me | Me | H | 2,4-diFPh | 0 |
| 1-207 | $(CH_2)_3Pr^c$ | Me | Me | H | 2,4-diFPh | 0 |
| 1-208 | $(CH_2)_4Pr^c$ | Me | Me | H | 2,4-diFPh | 0 |
| 1-209 | $Pr^c$ | Me | Me | H | 2,4-diFPh | 0 |
| 1-210 | $Bu^c$ | Me | Me | H | 2,4-diFPh | 0 |
| 1-211 | $Pn^c$ | Me | Me | H | 2,4-diFPh | 0 |
| 1-212 | $Hx^c$ | Me | Me | H | 2,4-diFPh | 0 |
| 1-213 | $Hp^c$ | Me | Me | H | 2,4-diFPh | 0 |
| 1-214 | $CH_2(1\text{-}Pnte^c)$ | Me | Me | H | 2,4-diFPh | 0 |
| 1-215 | $CH_2(1\text{-}Hxe^c)$ | Me | Me | H | 2,4-diFPh | 0 |
| 1-216 | $CH_2(1\text{-}Hpte^c)$ | Me | Me | H | 2,4-diFPh | 0 |
| 1-217 | CHF2 | Me | Me | H | 2,4-diFPh | 0 |
| 1-218 | $CH_2CH_2F$ | Me | Me | H | 2,4-diFPh | 0 |
| 1-219 | $CH_2CHF_2$ | Me | Me | H | 2,4-diFPh | 0 |
| 1-220 | $CH_2CF_3$ | Me | Me | H | 2,4-diFPh | 0 |
| 1-221 | $(CH_2)_3F$ | Me | Me | H | 2,4-diFPh | 0 |
| 1-222 | $(CH_2)_4F$ | Me | Me | H | 2,4-diFPh | 0 |
| 1-223 | $CH_2CH_2Cl$ | Me | Me | H | 2,4-diFPh | 0 |
| 1-224 | $CH_2CH_2Br$ | Me | Me | H | 2,4-diFPh | 0 |
| 1-225 | $CH_2CH_2I$ | Me | Me | H | 2,4-diFPh | 0 |
| 1-226 | $CH_2CH{=}CH_2$ | Me | Me | H | 4-ClPh | 0 |
| 1-227 | $CH_2CH{=}CHCH_3$ | Me | Me | H | 4-ClPh | 0 |
| 1-228 | $CH_2C{\equiv}CH$ | Me | Me | H | 4-ClPh | 0 |
| 1-229 | $CH_2Pr^c$ | Me | Me | H | 4-ClPh | 0 |
| 1-230 | $CH_2CH{=}CHPh$ | Me | Me | H | 4-ClPh | 0 |
| 1-231 | $CH_2CH{=}CH_2$ | Me | Me | H | 2,4-diClPh | 0 |
| 1-232 | $CH_2CH{=}CHCH_3$ | Me | Me | H | 214-diClPh | 0 |
| 1-233 | $CH_2C{\equiv}CH$ | Me | Me | H | 2,4-diClPh | 0 |
| 1-234 | $CH_2Pr^c$ | Me | Me | H | 2,4-diClPh | 0 |
| 1-235 | $CH_2CH{=}CHPh$ | Me | Me | H | 2,4-diClPh | 0 |
| 1-236 | $CH_2CH{=}CH_2$ | Me | Ne | H | 2-FPh | 0 |
| 1-237 | $CH_2CH{=}CHCH_3$ | Me | Me | H | 2-FPh | 0 |
| 1-238 | $CH_2C{\equiv}CH$ | Me | Me | H | 2-FPh | 0 |
| 1-239 | $CH_2Pr^c$ | Me | Me | H | 2-FPh | 0 |
| 1-240 | $CH_2CH{=}CHPh$ | Me | Me | H | 2-FPh | 0 |
| 1-241 | $CH_2CH{=}CH_2$ | Me | Me | H | 3-FPh | 0 |
| 1-242 | $CH_2CH{=}CHCH_3$ | Me | Me | H | 3-FPh | 0 |
| 1-243 | $CH_2C{\equiv}CH$ | Me | Me | H | 3-FPh | 0 |
| 1-244 | $CH_2Pr^c$ | Me | Me | H | 3-FPh | 0 |
| 1-245 | $CH_2CH{=}CHPh$ | Me | Me | H | 3-FPh | 0 |
| 1-246 | $CH_2CH{=}CH_2$ | Me | Me | H | 2-ClPh | 0 |
| 1-247 | $CH_2CH{=}CHCH_3$ | Me | Me | H | 2-ClPh | 0 |
| 1-248 | $CH_2C{\equiv}CH$ | Me | Me | H | 2-ClPh | 0 |
| 1-249 | $CH_2Pr^c$ | Me | Me | H | 2-ClPh | 0 |
| 1-250 | $CH_2CH{=}CHPh$ | Me | Me | H | 2-ClPh | 0 |
| 1-251 | $CH_2CH{=}CH_2$ | Me | Me | H | 3-ClPh | 0 |
| 1-252 | $CH_2CH{=}CHCH_3$ | Me | Me | H | 3-ClPh | 0 |
| 1-253 | $CH_2CH{=}CH_2$ | Me | Me | H | 4-MePh | 0 |
| 1-254 | $CH_2CH{=}CHCH_3$ | Me | Me | H | 2-MePh | 0 |
| 1-255 | $CH_2C{\equiv}CH$ | Me | Me | H | 3-MePh | 0 |
| 1-256 | $CH_2CH{=}CH_2$ | Me | Me | H | 2-OMePh | 0 |
| 1-257 | $CH_2CH{=}CHCH_3$ | Me | Me | H | 3-OMePh | 0 |
| 1-258 | $CH_2C{\equiv}CH$ | Me | Me | H | 4-OMePh | 0 |
| 1-259 | $CH_2CH{=}CH_2$ | Me | Me | H | $4\text{-}CF_3Ph$ | 0 |
| 1-260 | $CH_2CH{=}CHCH_3$ | Me | Me | H | $4\text{-}CF_3Ph$ | 0 |
| 1-261 | $CH_2CH{=}CH_2$ | Me | Me | H | $4\text{-}OCHF_2Ph$ | 0 |

TABLE 1-continued

| Example Compd. No. | $R^1$ | $R^2$ | $R^3$ | $R^4$ | $R^5$ | X |
|---|---|---|---|---|---|---|
| 1-262 | $CH_2CH{=}CHCH_3$ | Me | Me | H | 4-$OCHF_2$Ph | 0 |
| 1-263 | $CH_2CH{=}CH_2$ | Me | Et | H | Ph | 0 |
| 1-264 | $CH_2CH{=}CH_2$ | Me | Pr | H | Ph | 0 |
| 1-265 | $CH_2CH{=}CH_2$ | Me | $Pr^i$ | H | Ph | 0 |
| 1-266 | $CH_2CH{=}CH_2$ | Me | Bu | H | Ph | 0 |
| 1-267 | $CH_2CH{=}CH_2$ | Me | $Bu^i$ | H | Ph | 0 |
| 1-268 | $CH_2CH{=}CH_2$ | Me | $Bu^s$ | H | Ph | 0 |
| 1-269 | $CH_2CH{=}CH_2$ | Me | $Bu^t$ | H | Ph | 0 |
| 1-270 | $CH_2CH{=}CH_2$ | Me | Ph | H | Ph | 0 |
| 1-271 | $CH_2CH{=}CH_2$ | Me | 2-FPh | H | Ph | 0 |
| 1-272 | $CH_2CH{=}CH_2$ | Me | 3-FPh | H | Ph | 0 |
| 1-273 | $CH_2CH{=}CH_2$ | Me | 4-FPh | H | Ph | 0 |
| 1-274 | $CH_2CH{=}CH_2$ | Me | 2,4-diFPh | H | Ph | 0 |
| 1-275 | $CH_2CH{=}CH_2$ | Me | 4-ClPh | H | Ph | 0 |
| 1-276 | $CH_2CH{=}CH_2$ | Me | 4-MePh | H | Ph | 0 |
| 1-277 | $CH_2CH{=}CH_2$ | Me | 4-OMePh | H | Ph | 0 |
| 1-278 | $CH_2CH{=}CH_2$ | Me | Et | H | 4-FPh | 0 |
| 1-279 | $CH_2CH{=}CH_2$ | Me | Pr | H | 4-FPh | 0 |
| 1-280 | $CH_2CH{=}CH_2$ | Me | $Pr^i$ | H | 4-FPh | 0 |
| 1-281 | $CH_2CH{=}CH_2$ | Me | Bu | H | 4-FPh | 0 |
| 1-282 | $CH_2CH{=}CH_2$ | Me | $Bu^i$ | H | 4-FPh | 0 |
| 1-283 | $CH_2CH{=}CH_2$ | Me | $Bu^s$ | H | 4-FPh | 0 |
| 1-284 | $CH_2CH{=}CH_2$ | Me | $Bu^t$ | H | 4-FPh | 0 |
| 1-285 | $CH_2CH{=}CH_2$ | Me | Ph | H | 4-FPh | 0 |
| 1-286 | $CH_2CH{=}CH_2$ | Me | 2-FPh | H | 4-FPh | 0 |
| 1-287 | $CH_2CH{=}CH_2$ | Me | 3-FPh | H | 4-FPh | 0 |
| 1-288 | $CH_2CH{=}CH_2$ | Me | 4-FPh | H | 4-FPh | 0 |
| 1-289 | $CH_2CH{=}CH_2$ | Me | 2,4-diFPh | H | 4-FPh | 0 |
| 1-290 | $CH_2CH{=}CH_2$ | Me | 4-ClPh | H | 4-FPh | 0 |
| 1-291 | $CH_2CH{=}CH_2$ | Me | 4-MePh | H | 4-FPh | 0 |
| 1-292 | $CH_2CH{=}CH_2$ | Me | 4-OMePh | H | 4-FPh | 0 |
| 1-293 | $CH_2CH{=}CH_2$ | Me | Et | H | 2,4-diFPh | 0 |
| 1-294 | $CH_2CH{=}CH_2$ | Me | Pr | H | 2,4-diFPh | 0 |
| 1-295 | $CH_2CH{=}CH_2$ | Me | $Pr^i$ | H | 2,4-diFPh | 0 |
| 1-296 | $CH_2CH{=}CH_2$ | Me | Bu | H | 2,4-diFPh | 0 |
| 1-297 | $CH_2CH{=}CH_2$ | Me | $Bu^i$ | H | 2,4-diFPh | 0 |
| 1-298 | $CH_2CH{=}CH_2$ | Me | $Bu^s$ | H | 2,4-diFPh | 0 |
| 1-299 | $CH_2CH{=}CH_2$ | Me | $Bu^t$ | H | 2,4-diFPh | 0 |
| 1-300 | $CH_2CH{=}CH_2$ | Me | Ph | H | 2,4-diFPh | 0 |
| 1-301 | $CH_2CH{=}CH_2$ | Me | 2-FPh | H | 2,4-diFPh | 0 |
| 1-302 | $CH_2CH{=}CH_2$ | Me | 3-FPh | H | 2,4-diFPh | 0 |
| 1-303 | $CH_2CH{=}CH_2$ | Me | 4-FPh | H | 2,4-diFPh | 0 |
| 1-304 | $CH_2CH{=}CH_2$ | Me | 2,4-diFPh | H | 2,4-diFPh | 0 |
| 1-305 | $CH_2CH{=}CH_2$ | Me | 4-ClPh | H | 2,4-diFPh | 0 |
| 1-306 | $CH_2CH{=}CH_2$ | Me | 4-MePh | H | 2,4-diFPh | 0 |
| 1-307 | $CH_2CH{=}CH_2$ | Me | 4-OMePh | H | 2,4-diFPh | 0 |
| 1-308 | $CH_2CH{=}CHCH_3$ | Me | Et | H | Ph | 0 |
| 1-309 | $CH_2CH{=}CHCH_3$ | Me | Pr | H | Ph | 0 |
| 1-310 | $CH_2$ CH=CHCH3 | Me | $Pr^i$ | H | Ph | 0 |
| 1-311 | $CH_2CH{=}CHCH_3$ | Me | Bu | H | Ph | 0 |
| 1-312 | $CH_2CH{=}CHCH_3$ | Me | $Bu^i$ | H | Ph | 0 |
| 1-313 | $CH_2CH{=}CHCH_3$ | Me | $Bu^s$ | H | Ph | 0 |
| 1-314 | $CH_2CH{=}CHCH_3$ | Me | $Bu^t$ | H | Ph | 0 |
| 1-315 | $CH_2CH{=}CHCH_3$ | Me | Ph | H | Ph | 0 |
| 1-316 | $CH_2CH{=}CHCH_3$ | Me | 2-FPh | H | Ph | 0 |
| 1-317 | $CH_2CH{=}CHCH_3$ | Me | 3-FPh | H | Ph | 0 |
| 1-318 | $CH_2CH{=}CHCH_3$ | Me | 4-FPh | H | Ph | 0 |
| 1-319 | $CH_2CH{=}CHCH_3$ | Me | 2,4-diFPh | H | Ph | 0 |
| 1-320 | $CH_2CH{=}CHCH_3$ | Me | 4-ClPh | H | Ph | 0 |
| 1-321 | $CH_2CH{=}CHCH_3$ | Me | 4-MePh | H | Ph | 0 |
| 1-322 | $CH_2CH{=}CHCH_3$ | Me | 4-OMePh | H | Ph | 0 |
| 1-323 | $CH_2CH{=}CHCH_3$ | Me | Et | H | 4-FPh | 0 |
| 1-324 | $CH_2CH{=}CHCH_3$ | Me | Pr | H | 4-FPh | 0 |
| 1-325 | $CH_2CH{=}CHCH_3$ | Me | $Pr^i$ | H | 4-FPh | 0 |
| 1-326 | $CH_2CH{=}CHCH_3$ | Me | Bu | H | 4-FPh | 0 |
| 1-327 | $CH_2CH{=}CHCH_3$ | Me | $Bu^i$ | H | 4-FPh | 0 |
| 1-328 | $CH_2CH{=}CHCH_3$ | Me | $Bu^s$ | H | 4-FPh | 0 |
| 1-329 | $CH_2CH{=}CHCH_3$ | Me | $Bu^t$ | H | 4-FPh | 0 |
| 1-330 | $CH_2CH{=}CHCH_3$ | Me | Ph | H | 4-FPh | 0 |
| 1-331 | $CH_2CH{=}CHCH_3$ | Me | 2-FPh | H | 4-FPh | 0 |
| 1-332 | $CH_2CH{=}CHCH_3$ | Me | 3-FPh | H | 4-FPh | 0 |
| 1-333 | $CH_2CH{=}CHCH_3$ | Me | 4-FPh | H | 4-FPh | 0 |
| 1-334 | $CH_2CH{=}CHCH_3$ | Me | 2,4-diFPh | H | 4-FPh | 0 |
| 1-335 | $CH_2CH{=}CHCH_3$ | Me | 4-ClPh | H | 4-FPh | 0 |
| 1-336 | $CH_2CH{=}CHCH_3$ | Me | 4-MePh | H | 4-FPh | 0 |
| 1-337 | $CH_2CH{=}CHCH_3$ | Me | 4-OMePh | H | 4-FPh | 0 |

TABLE 1-continued

| Example Compd. No. | $R^1$ | $R^2$ | $R^3$ | $R^4$ | $R^5$ | X |
|---|---|---|---|---|---|---|
| 1-338 | $CH_2CH{=}CHCH_3$ | Me | Et | H | 2,4-diFPh | 0 |
| 1-339 | $CH_2CH{=}CHCH_3$ | Me | Pr | H | 2,4-diFPh | 0 |
| 1-340 | $CH_2CH{=}CHCH_3$ | Me | $Pr^i$ | H | 2,4-diFPh | 0 |
| 1-341 | $CH_2CH{=}CHCH_3$ | Me | Bu | H | 2,4-diFPh | 0 |
| 1-342 | $CH_2CH{=}CHCH_3$ | Me | $Bu^i$ | H | 2,4-diFPh | 0 |
| 1-343 | $CH_2CH{=}CHCH_3$ | Me | $Bu^s$ | H | 2,4-diFPh | 0 |
| 1-344 | $CH_2CH{=}CHCH_3$ | Me | $Bu^t$ | H | 2,4-diFPh | 0 |
| 1-345 | $CH_2CH{=}CHCH_3$ | Me | Ph | H | 2,4-diFPh | 0 |
| 1-346 | $CH_2CH{=}CHCH_3$ | Me | 2-FPh | H | 2,4-diFPh | 0 |
| 1-347 | $CH_2CH{=}CHCH_3$ | Me | 3-FPh | H | 2,4-diFPh | 0 |
| 1-348 | $CH_2CH{=}CHCH_3$ | Me | 4-FPh | H | 2,4-diFPh | 0 |
| 1-349 | $CH_2CH{=}CHCH_3$ | Me | 2,4-diFPh | H | 2,4-diFPh | 0 |
| 1-350 | $CH_2CH{=}CHCH_3$ | Me | 4-ClPh | H | 2,4-diFPh | 0 |
| 1-351 | $CH_2CH{=}CHCH_3$ | Me | 4-MePh | H | 2,4-diFPh | 0 |
| 1-352 | $CH_2CH{=}CHCH_3$ | Me | 4-OMePh | H | 2,4-diFPh | 0 |
| 1-353 | $CH_2CH{=}CH_2$ | Et | Me | H | Ph | 0 |
| 1-354 | $CH_2CH{=}CH_2$ | Pr | Me | H | Ph | 0 |
| 1-355 | $CH_2CH{=}CH_2$ | $Pr^i$ | Me | H | Ph | 0 |
| 1-356 | $CH_2CH{=}CH_2$ | Bu | Me | H | Ph | 0 |
| 1-357 | $CH_2CH{=}CH_2$ | $Bu^i$ | Me | H | Ph | 0 |
| 1-358 | $CH_2CH{=}CH_2$ | $Bu^s$ | Me | H | Ph | 0 |
| 1-359 | $CH_2CH{=}CH_2$ | $Bu^t$ | Me | H | Ph | 0 |
| 1-360 | $CH_2CH{=}CH_2$ | Ph | Me | H | Ph | 0 |
| 1-361 | $CH_2CH{=}CH_2$ | 2-FPh | Me | H | Ph | 0 |
| 1-362 | $CH_2CH{=}CH_2$ | 3-FPh | Me | H | Ph | 0 |
| 1-363 | $CH_2CH{=}CH_2$ | 4-FPh | Me | H | Ph | 0 |
| 1-364 | $CH_2CH{=}CH_2$ | 2,4-diFPh | Me | H | Ph | 0 |
| 1-365 | $CH_2CH{=}CH_2$ | 4-ClPh | Me | H | Ph | 0 |
| 1-366 | $CH_2CH{=}CH_2$ | 4-MePh | Me | H | Ph | 0 |
| 1-367 | $CH_2CH{=}CH_2$ | 4-OMePh | Me | H | Ph | 0 |
| 1-368 | $CH_2CH{=}CH_2$ | Et | Me | H | 4-FPh | 0 |
| 1-369 | $CH_2CH{=}CH_2$ | Pr | Me | H | 4-FPh | 0 |
| 1-370 | $CH_2CH{=}CH_2$ | $Pr^i$ | Me | H | 4-FPh | 0 |
| 1-371 | $CH_2CH{=}CH_2$ | Bu | Me | H | 4-FPh | 0 |
| 1-372 | $CH_2CH{=}CH_2$ | $Bu^i$ | Me | H | 4-FPh | 0 |
| 1-373 | $CH_2CH{=}CH_2$ | $Bu^s$ | Me | H | 4-FPh | 0 |
| 1-374 | $CH_2CH{=}CH_2$ | $Bu^t$ | Me | H | 4-FPh | 0 |
| 1-375 | $CH_2CH{=}CH_2$ | Ph | Me | H | 4-FPh | 0 |
| 1-376 | $CH_2CH{=}CH_2$ | 2-FPh | Me | H | 4-FPh | 0 |
| 1-377 | $CH_2CH{=}CH_2$ | 3-FPh | Me | H | 4-FPh | 0 |
| 1-378 | $CH_2CH{=}CH_2$ | 4-FPh | Me | H | 4-FPh | 0 |
| 1-379 | $CH_2CH{=}CH_2$ | 2,4-diFPh | Me | H | 4-FPh | 0 |
| 1-380 | $CH_2CH{=}CH_2$ | 4-ClPh | Me | H | 4-FPh | 0 |
| 1-381 | $CH_2CH{=}CH_2$ | 4-MePh | Me | H | 4-FPh | 0 |
| 1-382 | $CH_2CH{=}CH_2$ | 4-OMePh | Me | H | 4-FPh | 0 |
| 1-383 | $CH_2CH{=}CH_2$ | Et | Me | H | 2,4-diFPh | 0 |
| 1-384 | $CH_2CH{=}CH_2$ | Pr | Me | H | 2,4-diFPh | 0 |
| 1-385 | $CH_2CH{=}CH_2$ | $Pr^i$ | Me | H | 2,4-diFPh | 0 |
| 1-386 | $CH_2CH{=}CH_2$ | Bu | Me | H | 2,4-diFPh | 0 |
| 1-387 | $CH_2CH{=}CH_2$ | $Bu^i$ | Me | H | 2,4-diFPh | 0 |
| 1-388 | $CH_2CH{=}CH_2$ | $Bu^s$ | Me | H | 2,4-diFPh | 0 |
| 1-389 | $CH_2CH{=}CH_2$ | $Bu^t$ | Me | H | 2,4-diFPh | 0 |
| 1-390 | $CH_2CH{=}CH_2$ | Ph | Me | H | 2,4-diFPh | 0 |
| 1-391 | $CH_2CH{=}CH_2$ | 2-FPh | Me | H | 2,4-diFPh | 0 |
| 1-392 | $CH_2CH{=}CH_2$ | 3-FPh | Me | H | 2,4-diFPh | 0 |
| 1-393 | $CH_2CH{=}CH_2$ | 4-FPh | Me | H | 2,4-diFPh | 0 |
| 1-394 | $CH_2CH{=}CH_2$ | 2,4-diFPh | Me | H | 2,4-diFPh | 0 |
| 1-395 | $CH_2CH{=}CH_2$ | 4-ClPh | Me | H | 2,4-diFPh | 0 |
| 1-396 | $CH_2CH{=}CH_2$ | 4-MePh | Me | H | 2,4-diFPh | 0 |
| 1-397 | $CH_2CH{=}CH_2$ | 4-OMePh | Me | H | 2,4-diFPh | 0 |
| 1-398 | $CH_2CH{=}CHCH_3$ | Et | Me | H | Ph | 0 |
| 1-399 | $CH_2CH{=}CHCH_3$ | Pr | Me | H | Ph | 0 |
| 1-400 | $CH_2CH{=}CHCH_3$ | $Pr^i$ | Me | H | Ph | 0 |
| 1-401 | $CH_2CH{=}CHCH_3$ | Bu | Me | H | Ph | 0 |
| 1-402 | $CH_2CH{=}CHCH_3$ | $Bu^i$ | Me | H | Ph | 0 |
| 1-403 | $CH_2CH{=}CHCH_3$ | $Bu^s$ | Me | H | Ph | 0 |
| 1-404 | $CH_2CH{=}CHCH_3$ | $Bu^t$ | Me | H | Ph | 0 |
| 1-405 | $CH_2CH{=}CHCH_3$ | Ph | Me | H | Ph | 0 |
| 1-406 | $CH_2CH{=}CHCH_3$ | 2-FPh | Me | H | Ph | 0 |
| 1-407 | $CH_2CH{=}CHCH_3$ | 3-FPh | Me | H | Ph | 0 |
| 1-408 | $CH_2CH{=}CHCH_3$ | 4-FPh | Me | H | Ph | 0 |
| 1-409 | $CH_2CH{=}CHCH_3$ | 2,4-diFPh | Me | H | Ph | 0 |
| 1-410 | $CH_2CH{=}CHCH_3$ | 4-ClPh | Me | H | Ph | 0 |
| 1-411 | $CH_2CH{=}CHCH_3$ | 4-MePh | Me | H | Ph | 0 |
| 1-412 | $CH_2CH{=}CHCH_3$ | 4-OMePh | Me | H | Ph | 0 |
| 1-413 | $CH_2CH{=}CHCH_3$ | Et | Me | H | 4-FPh | 0 |

TABLE 1-continued

| Example Compd. No. | $R^1$ | $R^2$ | $R^3$ | $R^4$ | $R^5$ | X |
|---|---|---|---|---|---|---|
| 1-414 | $CH_2CH=CHCH_3$ | Pr | Me | H | 4-FPh | 0 |
| 1-415 | $CH_2CH=CHCH_3$ | $Pr^i$ | Me | H | 4-FPh | 0 |
| 1-416 | $CH_2CH=CHCH_3$ | Bu | Me | H | 4-FPh | 0 |
| 1-417 | $CH_2CH=CHCH_3$ | $Bu^i$ | Me | H | 4-FPh | 0 |
| 1-418 | $CH_2CH=CHCH_3$ | $Bu^s$ | Me | H | 4-FPh | 0 |
| 1-419 | $CH_2CH=CHCH_3$ | $Bu^t$ | Me | H | 4-FPh | 0 |
| 1-420 | $CH_2CH=CHCH_3$ | Ph | Me | H | 4-FPh | 0 |
| 1-421 | $CH_2CH=CHCH_3$ | 2-FPh | Me | H | 4-FPh | 0 |
| 1-422 | $CH_2CH=CHCH_3$ | 3-FPh | Me | H | 4-FPh | 0 |
| 1-423 | $CH_2CH=CHCH_3$ | 4-FPh | Me | H | 4-FPh | 0 |
| 1-424 | $CH_2CH=CHCH_3$ | 2,4-diFPh | Me | H | 4-FPh | 0 |
| 1-425 | $CH_2CH=CHCH_3$ | 4-ClPh | Me | H | 4-FPh | 0 |
| 1-426 | $CH_2CH=CHCH_3$ | 4-MePh | Me | H | 4-FPh | 0 |
| 1-427 | $CH_2CH=CHCH_3$ | 4-OMePh | Me | H | 4-FPh | 0 |
| 1-428 | $CH_2CH=CHCH_3$ | Et | Me | H | 2,4-diFPh | 0 |
| 1-429 | $CH_2CH=CHCH_3$ | Pr | Me | H | 2,4-diFPh | 0 |
| 1-430 | $CH_2CH=CHCH_3$ | $Pr^i$ | Me | H | 2,4-diFPh | 0 |
| 1-431 | $CH_2CH=CHCH_3$ | Bu | Me | H | 2,4-diFPh | 0 |
| 1-432 | $CH_2CH=CHCH_3$ | $Bu^i$ | Me | H | 2,4-diFPh | 0 |
| 1-433 | $CH_2CH=CHCH_3$ | $Bu^s$ | Me | H | 2,4-diFPh | 0 |
| 1-434 | $CH_2CH=CHCH_3$ | $Bu^t$ | Me | H | 2,4-diFPh | 0 |
| 1-435 | $CH_2CH=CHCH_3$ | Ph | Me | H | 2,4-diFPh | 0 |
| 1-436 | $CH_2CH=CHCH_3$ | 2-FPh | Me | H | 2,4-diFPh | 0 |
| 1-437 | $CH_2CH=CHCH_3$ | 3-FPh | Me | H | 2,4-diFPh | 0 |
| 1-438 | $CH_2CH=CHCH_3$ | 4-FPh | Me | H | 2,4-diFPh | 0 |
| 1-439 | $CH_2CH=CHCH_3$ | 2,4-diFPh | Me | H | 2,4-diFPh | 0 |
| 1-440 | $CH_2CH=CHCH_3$ | 4-ClPh | Me | H | 2,4-diFPh | 0 |
| 1-441 | $CH_2CH=CHCH_3$ | 4-MePh | Me | H | 2,4-diFPh | 0 |
| 1-442 | $CH_2CH=CHCH_3$ | 4-OMePh | Me | H | 2,4-diFPh | 0 |
| 1-443 | $CH_2CH=CH_2$ | Me | Me | H | Ph | NH |
| 1-444 | $CH_2Pr^c$ | Me | Me | H | Ph | NH |
| 1-445 | $CH_2CH=CH_2$ | Me | Me | H | 4-FPh | S |
| 1-446 | $CH_2CH=CH_2$ | Me | Me | H | 4-FPh | NH |
| 1-447 | $CH_2CH=CH_2$ | Me | Me | H | 2,4-diFPh | S |
| 1-448 | $CH_2CH=CH_2$ | Me | Me | H | 2,4-diFPh | NH |
| 1-449 | $CH_2CH=CH_2$ | Me | Me | H | 4-ClPh | S |
| 1-450 | $CH_2CH=CH_2$ | Me | Me | H | 4-ClPh | NH |
| 1-451 | $CH_2CH=CH_2$ | Me | Me | H | 2,4-diClPh | S |
| 1-452 | $CH_2CH=CH_2$ | Me | Me | H | 2,4-diClPh | NH |
| 1-453 | $CH_2CH=CH_2$ | Me | Me | Me | Ph | 0 |
| 1-454 | $CH_2CH=CH_2$ | Me | Me | Me | 4-FPh | 0 |
| 1-455 | $CH_2CH=CH_2$ | Me | Me | Me | 2,4-diFPh | 0 |
| 1-456 | $CH_2CH=CH_2$ | Me | Me | Me | 4-ClPh | 0 |
| 1-457 | $CH_2CH=CH_2$ | Me | Me | Me | 2,4-diClPh | 0 |
| 1-458 | $CH_2CH=CHCH_3$ | Me | Me | H | Ph | S |
| 1-459 | $CH_2CH=CHCH_3$ | Me | Me | H | Ph | NH |
| 1-460 | $CH_2CH=CHCH_3$ | Me | Me | H | 4-FPh | S |
| 1-461 | $CH_2CH=CHCH_3$ | Me | Me | H | 4-FPh | NH |
| 1-462 | $CH_2CH=CHCH_3$ | Me | Me | H | 2,4-diFPh | S |
| 1-463 | $CH_2CH=CHCH_3$ | Me | Me | H | 2,4-diFPh | NH |
| 1-464 | $CH_2CH=CHCH_3$ | Me | Me | H | 4-ClPh | S |
| 1-465 | $CH_2CH=CHCH_3$ | Me | Me | H | 4-ClPh | NH |
| 1-466 | $CH_2CH=CHCH_3$ | Me | Me | H | 2,4-diClPh | S |
| 1-467 | $CH_2CH=CHCH_3$ | Me | Me | H | 2,4-diClPh | NH |
| 1-468 | $CH_2CH=CHCH_3$ | Me | Me | Me | Ph | 0 |
| 1-469 | $CH_2CH=CHCH_3$ | Me | Me | Me | 4-FPh | 0 |
| 1-470 | $CH_2CH=CHCH_3$ | Me | Me | Me | 2,4-diFPh | 0 |
| 1-471 | $CH_2CH=CHCH_3$ | Me | Me | Me | 4-ClPh | 0 |
| 1-472 | $CH_2CH=CHCH_3$ | Me | Me | Me | 2,4-diClPh | 0 |
| 1-473 | $CH_2CH=CH_2$ | Me | Me | H | 2-Thi | 0 |
| 1-474 | $CH_2CH=CH_2$ | Me | Me | H | 3-Thi | 0 |
| 1-475 | $CH_2CH=CH_2$ | Me | Me | H | 2-Fur | 0 |
| 1-476 | $CH_2CH=CH_2$ | Me | Me | H | 2-Thiaz | 0 |
| 1-477 | $CH_2CH=CH_2$ | Me | Me | H | 2-Pyr | 0 |
| 1-478 | $CH_2CH=CH_2$ | Me | Me | H | 3-Pyr | 0 |
| 1-479 | $CH_2CH=CH_2$ | Me | Me | H | 4-Pyr | 0 |
| 1-480 | $CH_2CH=CH_2$ | Me | Me | H | 2-Oxaz | 0 |
| 1-481 | $CH_2CH=CH_2$ | Me | Me | H | 2-Imidz | 0 |
| 1-482 | $CH_2CH=CH_2$ | Me | Me | H | 2-Bezoxaz | 0 |
| 1-483 | $CH_2CH=CH_2$ | Me | Me | H | 2-Bezthiaz | 0 |
| 1-484 | $CH_2CH=CH_2$ | Me | Me | H | 2-Bezimidz | 0 |
| 1-485 | $CH_2CH=CH_2$ | Me | Me | H | 3-Pyridz | 0 |
| 1-486 | $CH_2CH=CH_2$ | Me | Me | H | 2-Pyraz | 0 |
| 1-487 | $CH_2CH=CH_2$ | Me | Me | H | 2-(1,3,4-TDA) | 0 |
| 1-488 | $CH_2CH=CHCH_3$ | Me | Me | H | 2-Thi | 0 |
| 1-489 | $CH_2CH=CHCH_3$ | Me | Me | H | 3-Thi | 0 |

TABLE 1-continued

| Example Compd. No. | $R^1$ | $R^2$ | $R^3$ | $R^4$ | $R^5$ | X |
|---|---|---|---|---|---|---|
| 1-490 | $CH_2CH{=}CHCH_3$ | Me | Me | H | 2-Fur | 0 |
| 1-491 | $CH_2CH{=}CHCH_3$ | Me | Me | H | 2-Thiaz | 0 |
| 1-492 | $CH_2$ CH=CHCH3 | Me | Me | H | 2-Pyr | 0 |
| 1-493 | $CH_2CH{=}CHCH_3$ | Me | Me | H | 3-Pyr | 0 |
| 1-494 | $CH_2CH{=}CHCH_3$ | Me | Me | H | 4-Pyr | 0 |
| 1-495 | $CH_2CH{=}CHCH_3$ | Me | Me | H | 2-Oxaz | 0 |
| 1-496 | $CH_2CH{=}CHCH_3$ | Me | Me | H | 2-Imidz | 0 |
| 1-497 | $CH_2CH{=}CHCH_3$ | Me | Me | H | 2-Bezoxaz | 0 |
| 1-498 | $CH_2CH{=}CHCH_3$ | Me | Me | H | 2-Bezthiaz | 0 |
| 1-499 | $CH_2CH{=}CHCH_3$ | Me | Me | H | 2-Bezimidz | 0 |
| 1-500 | $CH_2CH{=}CHCH_3$ | Me | Me | H | 3-Pyridz | 0 |
| 1-501 | $CH_2CH{=}CHCH_3$ | Me | Me | H | 2-Pyraz | 0 |
| 1-502 | $CH_2CH{=}CHCH_3$ | Me | Me | H | 2-(1,3,4-TDA) | 0 |
| 1-503 | $CH_2CH{=}CHCH_3$ | Me | Me | H | 2,6-diFPh | 0 |
| 1-504 | $CH_2CH{=}CHCH_3$ | Me | Me | H | 3,5-diFPh | 0 |
| 1-505 | $CH_2CH{=}CHCH_3$ | Me | Me | H | 2-Cl-6-FPh | 0 |
| 1-506 | $CH{=}CHCH_3$ | Me | Me | H | Ph | NH |
| 1-507 | $CH_2CH{=}CH_2$ | Me | Me | H | Ph | S |
| 1-508 | $CH_2CH{=}CHCH_2CH_2CH_3$ | Me | Me | H | Ph | 0 |
| 1-509 | $CH_2CH{=}CHCH_2CH_2CH_3$ | Me | Me | H | 4-FPh | 0 |
| 1-510 | $CH_2CH{=}CHCH_2CH_2CH_3$ | Me | Me | H | 2,4-diFPh | 0 |
| 1-511 | $CH_2CH{=}CH_2$ | H | Me | H | Ph | 0 |
| 1-512 | $CH_2CH{=}CHCH_3$ | H | Me | H | Ph | 0 |
| 1-513 | $CH_2CH{=}CH_2$ | H | Me | H | 4-FPh | 0 |
| 1-514 | $CH_2CH{=}CHCH_3$ | H | Me | H | 4-FPh | 0 |
| 1-515 | $CH_2CH{=}CH_2$ | H | Me | H | 2,4-diFPh | 0 |
| 1-516 | $CH_2CH{=}CHCH_3$ | H | Me | H | 2,4-diFPh | 0 |
| 1-517 | $CH_2CH{=}CH_2$ | Me | H | H | Ph | 0 |
| 1-518 | $CH_2CH{=}CHCH_3$ | Me | H | H | Ph | 0 |
| 1-519 | $CH_2CH{=}CH_2$ | Me | H | H | 4-FPh | 0 |
| 1-520 | $CH_2CH{=}CHCH_3$ | Me | H | H | 4-FPh | 0 |
| 1-521 | $CH_2CH{=}CH_2$ | Me | H | H | 2,4-diFPh | 0 |
| 1-522 | $CH_2CH{=}CHCH_3$ | Me | H | H | 2,4-diFPh | 0 |
| 1-523 | $CH_2CH{=}CH_2$ | Me | Me | H | 4-Cl-2-FPh | 0 |
| 1-524 | $CH_2CH{=}CHCH_3$ | Me | Me | H | 4-Cl-2-FPh | 0 |
| 1-525 | $CH_2CH{=}CH_2$ | Me | Me | H | 2,6-diClPh | 0 |
| 1-526 | $CH_2CH{=}CHCH_3$ | Me | Me | H | 2,6-diClPh | 0 |
| 1-527 | $CH_2CH{=}CH_2$ | Me | Me | H | 2,5-diClPh | 0 |
| 1-528 | $CH_2CH{=}CHCH_3$ | Me | Me | H | 2,5-diClPh | 0 |
| 1-529 | $CH_2CH{=}CH_2$ | Me | Me | H | 2,4,6-triFPh | 0 |
| 1-530 | $CH_2CH{=}CHCH_3$ | Me | Me | H | 2,4,6-triFPh | 0 |
| 1-531 | $CH_2CH{=}CH_2$ | Me | Me | H | 2,4,6-triClPh | 0 |
| 1-532 | $CH_2CH{=}CHCH_3$ | Me | Me | H | 2,4,6-triClPh | 0 |
| 1-533 | $CH_2CH{=}CH_2$ | Me | Me | H | 2,6-diFPh | 0 |
| 1-534 | $CH_2CH{=}CH_2$ | Me | Me | H | 3,5-diFPh | 0 |
| 1-535 | $CH_2CH{=}CH_2$ | Me | Me | H | 2-Cl-6-FPh | 0 |
| 1-536 | $CH_2CH{=}CH_2$ | Me | Me | H | 2,5-diFPh | 0 |
| 1-537 | $CH_2CH{=}CHCH_3$ | Me | Me | H | 2,5-diFPh | 0 |
| 1-538 | $CH_2(2\text{-}MePr^c)$ | Me | Me | H | Ph | 0 |
| 1-539 | $CH_2(2\text{-}MePr^c)$ | Me | Me | H | 4-FPh | 0 |
| 1-540 | $CH_2(2\text{-}MePr^c)$ | Me | Me | H | 2,4-diFPh | 0 |
| 1-541 | $CH{=}CH_2$ | Me | Me | H | Ph | S |
| 1-542 | $CH{=}CHCH_3$ | Me | Me | H | Ph | S |
| 1-543 | $CH_2C(CH_3){=}CH_2$ | Me | Me | H | Ph | S |
| 1-544 | $CH_2CH{=}CHCH_2CH_3$ | Me | Me | H | Ph | S |
| 1-545 | $CH_2CH{=}C(CH_3)CH_3$ | Me | Me | H | Ph | S |
| 1-546 | $CH_2CH{=}CHPh$ | Me | Me | H | Ph | S |
| 1-547 | $CH_2CH{=}CH(4\text{-}FPh)$ | Me | Me | H | Ph | S |
| 1-548 | $CH_2CH{=}CF_2$ | Me | Me | H | Ph | S |
| 1-549 | $CH_2CH{=}CHCl$ | Me | Me | H | Ph | S |
| 1-550 | $CH_2C(Cl){=}CH_2$ | Me | Me | H | Ph | S |
| 1-551 | $CH_2CH{=}CCl_2$ | Me | Me | H | Ph | S |
| 1-552 | $CH_2C{\equiv}CH$ | Me | Me | H | Ph | S |
| 1-553 | $CH{=}C{=}CH_2$ | Me | Me | H | Ph | S |
| 1-554 | $CH_2Pr^c$ | Me | Me | H | Ph | S |
| 1-555 | $Pr^c$ | Me | Me | H | Ph | S |
| 1-556 | $Hx^c$ | Me | Me | H | Ph | S |
| 1-557 | $CH_2CH_2F$ | Me | Me | H | Ph | S |
| 1-558 | $CH_2CHF_2$ | Me | Me | H | Ph | S |
| 1-559 | $CH_2CF_3$ | Me | Me | H | Ph | S |
| 1-560 | $(CH_2)_3F$ | Me | Me | H | Ph | S |
| 1-561 | $CH{=}CH_2$ | Me | Me | H | 4-FPh | S |
| 1-562 | $CH{=}CHCH_3$ | Me | Me | H | 4-FPh | S |
| 1-563 | $C(CH_3){=}CH_2$ | Me | Me | H | 4-FPh | S |
| 1-564 | $CH{=}CHCH_2CH_3$ | Me | Me | H | 4-FPh | S |
| 1-565 | $CH_2C(CH_3){=}CH_2$ | Me | Me | H | 4-FPh | S |

TABLE 1-continued

| Example Compd. No. | $R^1$ | $R^2$ | $R^3$ | $R^4$ | $R^5$ | X |
|---|---|---|---|---|---|---|
| 1-566 | $CH_2CH{=}CHPh$ | Me | Me | H | 4-FPh | S |
| 1-567 | $CH_2CH{=}CH(4\text{-}FPh)$ | Me | Me | H | 4-FPh | S |
| 1-568 | $CH_2CH{=}CF_2$ | Me | Me | H | 4-FPh | S |
| 1-569 | $CH_2CH{=}CHCl$ | Me | Me | H | 4-FPh | S |
| 1-570 | $CH_2CH{=}CCl_2$ | Me | Me | H | 4-FPh | S |
| 1-571 | $CH_2C{\equiv}CH$ | Me | Me | H | 4-FPh | S |
| 1-572 | $CH_2Pr^c$ | Me | Me | H | 4-FPh | S |
| 1-573 | $CH_2Hx^c$ | Me | Me | H | 4-FPh | S |
| 1-574 | $Pr^c$ | Me | Me | H | 4-FPh | S |
| 1-575 | $Hx^c$ | Me | Me | H | 4-FPh | S |
| 1-576 | $(CH_2)_3F$ | Me | Me | H | 4-FPh | S |
| 1-577 | $C(CH_3){=}CH_2$ | Me | Me | H | 2,4-diFPh | S |
| 1-578 | $CH{=}CHCH_2CH_3$ | Me | Me | H | 2,4-diFPh | S |
| 1-579 | $CH_2CH{=}CHPh$ | Me | Me | H | 2,4-diFPh | S |
| 1-580 | $CH_2CH{=}CF_2$ | Me | Me | H | 2,4-diFPh | S |
| 1-581 | $CH_2CH{=}CHCl$ | Me | Me | H | 2,4-diFPh | S |
| 1-582 | $CH_2C{\equiv}CH$ | Me | Me | H | 2,4-diFPh | S |
| 1-583 | $CH{=}C{=}CH_2$ | Me | Me | H | 2,4-diFPh | S |
| 1-584 | $CH_2Pr^c$ | Me | Me | H | 2,4-diFPh | S |
| 1-585 | $CH_2Hx^c$ | Me | Me | H | 2,4-diFPh | S |
| 1-586 | $Pr^c$ | Me | Me | H | 2,4-diFPh | S |
| 1-587 | $CH_2Pr^c$ | Me | Me | H | 4-ClPh | S |
| 1-588 | $CH_2Pr^c$ | Me | Me | H | 2,4-diClPh | S |
| 1-589 | $CH_2CH{=}CH_2$ | Me | Me | H | 2-FPh | S |
| 1-599 | $CH_2CH{=}CHCH_3$ | Me | Me | H | 2-FPh | S |
| 1-591 | $CH_2Pr^c$ | Me | Me | H | 2-FPh | S |
| 1-592 | $CH_2CH{=}CH_2$ | Me | Me | H | 3-FPh | S |
| 1-593 | $CH_2CH{=}CHCH_3$ | Me | Me | H | 3-FPh | S |
| 1-594 | $CH_2Pr^c$ | Me | Me | H | 3-FPh | S |
| 1-595 | $CH_2CH{=}CH_2$ | Me | Me | H | 2-ClPh | S |
| 1-596 | $CH_2CH{=}CHCH_3$ | Me | Me | H | 2-ClPh | S |
| 1-597 | $CH_2Pr^c$ | Me | Me | H | 2-ClPh | S |
| 1-598 | $CH_2CH{=}CH_2$ | Me | Me | H | 3-ClPh | S |
| 1-599 | $CH_2CH{=}CHCH_3$ | Me | Me | H | 3-ClPh | S |
| 1-600 | $CH_2CH{=}CH_2$ | Me | Me | H | $4\text{-}CF_3Ph$ | S |
| 1-601 | $CH_2CH{=}CHCH_3$ | Me | Me | H | $4\text{-}CF_3Ph$ | S |
| 1-602 | $CH_2CH{=}CH_2$ | Me | Et | H | Ph | S |
| 1-603 | $CH_2CH{=}CH_2$ | Me | Et | H | 4-FPh | S |
| 1-604 | $CH_2CH{=}CH_2$ | Me | Et | H | 2,4-diFPh | S |
| 1-605 | $CH_2CH{=}CHCH_3$ | Me | Et | H | Ph | S |
| 1-606 | $CH_2CH{=}CHCH_3$ | Me | Et | H | 4-FPh | S |
| 1-607 | $CH_2CH{=}CHCH_3$ | Me | Et | H | 2,4-diFPh | S |
| 1-608 | $CH_2CH{=}CH_2$ | Et | Me | H | Ph | S |
| 1-609 | $CH_2CH{=}CH_2$ | Et | Me | H | 4-FPh | S |
| 1-610 | $CH_2CH{=}CH_2$ | Et | Me | H | 2,4-diFPh | S |
| 1-611 | $CH_2CH{=}CHCH_3$ | Et | Me | H | Ph | S |
| 1-612 | $CH_2CH{=}CHCH_3$ | Et | Me | H | 4-FPh | S |
| 1-613 | $CH_2CH{=}CHCH_3$ | Et | Me | H | 2,4-diFPh | S |
| 1-614 | $CH_2CH{=}CH_2$ | Me | Me | H | 2-Thi | S |
| 1-615 | $CH_2CH{=}CH_2$ | Me | Me | H | 2-Fur | S |
| 1-616 | $CH_2CH{=}CH_2$ | Me | Me | H | 3-Pyr | S |
| 1-617 | $CH_2CH{=}CHCH_3$ | Me | Me | H | 2-Thi | S |
| 1-618 | $CH_2CH{=}CHCH_3$ | Me | Me | H | 2-Fur | S |
| 1-619 | $CH_2CH{=}CHCH_3$ | Me | Me | H | 2-Pyr | S |
| 1-620 | $CH_2CH{=}CHCH_3$ | Me | Me | H | 3-Pyr | S |
| 1-621 | $CH_2CH{=}CHCH_3$ | Me | Me | H | 2,6-diFPh | S |
| 1-622 | $CH_2CH{=}CHCH_3$ | Me | Me | H | 3,5-diFPh | S |
| 1-623 | $CH_2CH{=}CHCH_3$ | Me | Me | H | 2-Cl-6-FPh | S |
| 1-624 | $CH_2CH{=}CH_2$ | Me | Me | H | 4-Cl-2-FPh | S |
| 1-625 | $CH_2CH{=}CHCH_3$ | Me | Me | H | 4-Cl-2-FPh | S |
| 1-626 | $CH_2CH{=}CHCH_3$ | Me | Me | H | 2,6-diClPh | S |
| 1-627 | $CH_2(2\text{-}MePr^c)$ | Me | Me | H | 4-FPh | S |
| 1-628 | $CH_2(2\text{-}MePr^c)$ | Me | Me | H | 2,4-diFPh | S |
| 1-629 | $CH{=}CH_2$ | Me | Me | H | Ph | $CH_2$ |
| 1-630 | $CH{=}CHCH_3$ | Me | Me | H | Ph | $CH_2$ |
| 1-631 | $CH_2CH{=}CH_2$ | Me | Me | H | Ph | $CH_2$ |
| 1-632 | $CH_2CH{=}CHCH_3$ | Me | Me | H | Ph | $CH_2$ |
| 1-633 | $CH_2C(CH_3){=}CH_2$ | Me | Me | H | Ph | $CH_2$ |
| 1-634 | $CH_2CH{=}CHCH_2CH_3$ | Me | Me | H | Ph | $CH_2$ |
| 1-635 | $CH_2CH{=}C(CH_3)CH_3$ | Me | Me | H | Ph | $CH_2$ |
| 1-636 | $CH_2CH{=}CHPh$ | Me | Me | H | Ph | $CH_2$ |
| 1-637 | $CH_2CH{=}CH(4\text{-}FPh)$ | Me | Me | H | Ph | $CH_2$ |
| 1-638 | $CH_2CH{=}CF_2$ | Me | Me | H | Ph | $CH_2$ |
| 1-639 | $CH_2CH{=}CHCl$ | Me | Me | H | Ph | $CH_2$ |
| 1-640 | $CH_2C(Cl){=}CH_2$ | Me | Me | H | Ph | $CH_2$ |
| 1-641 | $CH_2CH{=}CCl_2$ | Me | Me | H | Ph | $CH_2$ |

TABLE 1-continued

| Example Compd. No. | $R^1$ | $R^2$ | $R^3$ | $R^4$ | $R^5$ | X |
|---|---|---|---|---|---|---|
| 1-642 | $CH_2C\equiv CH$ | Me | Me | H | Ph | $CH_2$ |
| 1-643 | $CH=C=CH_2$ | Me | Me | H | Ph | $CH_2$ |
| 1-644 | $CH_2Pr^c$ | Me | Me | H | Ph | $CH_2$ |
| 1-645 | $Pr^c$ | Me | Me | H | Ph | $CH_2$ |
| 1-646 | $Hx^c$ | Me | Me | H | Ph | $CH_2$ |
| 1-647 | $CH_2CH_2F$ | Me | Me | H | Ph | $CH_2$ |
| 1-648 | $CH_2CHF_2$ | Me | Me | H | Ph | $CH_2$ |
| 1-649 | $CH_2CF_3$ | Me | Me | H | Ph | $CH_2$ |
| 1-656 | $(CH_2)_3F$ | Me | Me | H | Ph | $CH_2$ |
| 1-651 | $CH=CH_2$ | Me | Me | H | 4-FPh | $CH_2$ |
| 1-652 | $CH=CHCH_3$ | Me | Me | H | 4-FPh | $CH_2$ |
| 1-653 | $CH_2CH=CH_2$ | Me | Me | H | 4-FPh | $CH_2$ |
| 1-654 | $C(CH_3)=CH_2$ | Me | Me | H | 4-FPh | $CH_2$ |
| 1-655 | $CH=CHCH_2CH_3$ | Me | Me | H | 4-FPh | $CH_2$ |
| 1-656 | $CH_2CH=CHCH_3$ | Me | Me | H | 4-FPh | $CH_2$ |
| 1-657 | $CH_2C(CH_3)=CH_2$ | Me | Me | H | 4-FPh | $CH_2$ |
| 1-658 | $CH_2CH=CHPh$ | Me | Me | H | 4-FPh | $CH_2$ |
| 1-659 | $CH_2CH=CH$(4-FPh) | Me | Me | H | 4-FPh | $CH_2$ |
| 1-660 | $CH_2CH=CF_2$ | Me | Me | H | 4-FPh | $CH_2$ |
| 1-661 | $CH_2CH=CHCl$ | Me | Me | H | 4-FPh | $CH_2$ |
| 1-662 | $CH_2CH=CCl_2$ | Me | Me | H | 4-FPh | $CH_2$ |
| 1-663 | $CH_2C\equiv CH$ | Me | Me | H | 4-FPh | $CH_2$ |
| 1-664 | $CH_2Pr^c$ | Me | Me | H | 4-FPh | $CH_2$ |
| 1-665 | $CH_2Hx^c$ | Me | Me | H | 4-FPh | $CH_2$ |
| 1-666 | $Pr^c$ | Me | Me | H | 4-FPh | $CH_2$ |
| 1-667 | $Hx^c$ | Me | Me | H | 4-FPh | $CH_2$ |
| 1-668 | $(CH_2)_3F$ | Me | Me | H | 4-FPh | $CH_2$ |
| 1-669 | $CH_2CH=CH_2$ | Me | Me | H | 2,4-diFPh | $CH_2$ |
| 1-670 | $C(CH_3)=CH_2$ | Me | Me | H | 2,4-diFPh | $CH_2$ |
| 1-671 | $CH=CHCH_2CH_3$ | Me | Me | H | 2,4-diFPh | $CH_2$ |
| 1-672 | $CH_2CH=CHCH_3$ | Me | Me | H | 2,4-diFPh | $CH_2$ |
| 1-673 | $CH_2CH=CHPh$ | Me | Me | H | 2,4-diFPh | $CH_2$ |
| 1-674 | $CH_2CH=CF_2$ | Me | Me | H | 2,4-diFPh | $CH_2$ |
| 1-675 | $CH_2CH=CHCl$ | Me | Me | H | 2,4-diFPh | $CH_2$ |
| 1-676 | $CH_2C\equiv CH$ | Me | Me | H | 2,4-diFPh | $CH_2$ |
| 1-677 | $CH=C=CH_2$ | Me | Me | H | 2,4-diFPh | $CH_2$ |
| 1-678 | $CH_2Pr^c$ | Me | Me | H | 2,4-diFPh | $CH_2$ |
| 1-679 | $CH_2Hx^c$ | Me | Me | H | 2,4-diFPh | $CH_2$ |
| 1-680 | $Pr^c$ | Me | Me | H | 2,4-diFPh | $CH_2$ |
| 1-681 | $CH_2CH=CH_2$ | Me | Me | H | 4-ClPh | $CH_2$ |
| 1-682 | $CH_2CH=CHCH_3$ | Me | Me | H | 4-ClPh | $CH_2$ |
| 1-683 | $CH_2Pr^c$ | Me | Me | H | 4-ClPh | $CH_2$ |
| 1-684 | $CH_2CH=CH_2$ | Me | Me | H | 2,4-diClPh | $CH_2$ |
| 1-685 | $CH_2CH=CHCH_3$ | Me | Me | H | 2,4-diClPh | $CH_2$ |
| 1-686 | $CH_2Pr^c$ | Me | Me | H | 2,4-diClPh | $CH_2$ |
| 1-687 | $CH_2CH=CH_2$ | Me | Me | H | 2-FPh | $CH_2$ |
| 1-688 | $CH_2CH=CHCH_3$ | Me | Me | H | 2-FPh | $CH_2$ |
| 1-689 | $CH_2Pr^c$ | Me | Me | H | 2-FPh | $CH_2$ |
| 1-690 | $CH_2CH=CH_2$ | Me | Me | H | 3-FPh | $CH_2$ |
| 1-691 | $CH_2CH=CHCH_3$ | Me | Me | H | 3-FPh | $CH_2$ |
| 1-692 | $CH_2Pr^c$ | Me | Me | H | 3-FPh | $CH_2$ |
| 1-693 | $CH_2CH=CH_2$ | Me | Me | H | 2-ClPh | $CH_2$ |
| 1-694 | $CH_2CH=CHCH_3$ | Me | Me | H | 2-ClPh | $CH_2$ |
| 1-695 | $CH_2Pr^c$ | Me | Me | H | 2-ClPh | $CH_2$ |
| 1-696 | $CH_2CH=CH_2$ | Me | Me | H | 3-ClPh | $CH_2$ |
| 1-697 | $CH_2CH=CHCH_3$ | Me | Me | H | 3-ClPh | $CH_2$ |
| 1-698 | $CH_2CH=CH_2$ | Me | Me | H | 4-$CF_3$Ph | $CH_2$ |
| 1-699 | $CH_2CH=CHCH_3$ | Me | Me | H | 4-$CF_3$Ph | $CH_2$ |
| 1-700 | $CH_2CH=CH_2$ | Me | Et | H | Ph | $CH_2$ |
| 1-701 | $CH_2CH=CH_2$ | Me | Et | H | 4-FPh | $CH_2$ |
| 1-702 | $CH_2CH=CH_2$ | Me | Et | H | 2,4-diFPh | $CH_2$ |
| 1-703 | $CH_2CH=CHCH_3$ | Me | Et | H | Ph | $CH_2$ |
| 1-704 | $CH_2CH=CHCH_3$ | Me | Et | H | 4-FPh | $CH_2$ |
| 1-705 | $CH_2CH=CHCH_3$ | Me | Et | H | 2,4-diFPh | $CH_2$ |
| 1-706 | $CH_2CH=CH_2$ | Et | Me | H | Ph | $CH_2$ |
| 1-707 | $CH_2CH=CH_2$ | Et | Me | H | 4-FPh | $CH_2$ |
| 1-708 | $CH_2CH=CH_2$ | Et | Me | H | 2,4-diFPh | $CH_2$ |
| 1-709 | $CH_2CH=CHCH_3$ | Et | Me | H | Ph | $CH_2$ |
| 1-710 | $CH_2CH=CHCH_3$ | Et | Me | H | 4-FPh | $CH_2$ |
| 1-711 | $CH_2CH=CHCH_3$ | Et | Me | H | 2,4-diFPh | $CH_2$ |
| 1-712 | $CH_2CH=CH_2$ | Me | Me | H | 2-Thi | $CH_2$ |
| 1-713 | $CH_2CH=CH_2$ | Me | Me | H | 2-Fur | $CH_2$ |
| 1-714 | $CH_2CH=CH_2$ | Me | Me | H | 3-Pyr | $CH_2$ |
| 1-715 | $CH_2CH=CHCH_3$ | Me | Me | H | 2-Thi | $CH_2$ |
| 1-716 | $CH_2CH=CHCH_3$ | Me | Me | H | 2-Fur | $CH_2$ |
| 1-717 | $CH_2CH=CHCH_3$ | Me | Me | H | 2-Pyr | $CH_2$ |

TABLE 1-continued

| Example Compd. No. | $R^1$ | $R^2$ | $R^3$ | $R^4$ | $R^5$ | X |
|---|---|---|---|---|---|---|
| 1-718 | $CH_2CH{=}CHCH_3$ | Me | Me | H | 3-Pyr | $CH_2$ |
| 1-719 | $CH_2CH{=}CHCH_3$ | Me | Me | H | 2,6-diFPh | $CH_2$ |
| 1-720 | $CH_2CH{=}CHCH_3$ | Me | Me | H | 3,5-diFPh | $CH_2$ |
| 1-721 | $CH_2CH{=}CHCH_3$ | Me | Me | H | 2-Cl-6-FPh | $CH_2$ |
| 1-722 | $CH_2CH{=}CH_2$ | Me | Me | H | 4-Cl-2-FPh | $CH_2$ |
| 1-723 | $CH_2CH{=}CHCH_3$ | Me | Me | H | 4-Cl-2-FPh | $CH_2$ |
| 1-724 | $CH_2CH{=}CHCH_3$ | Me | Me | H | 2,6-diClPh | $CH_2$ |
| 1-725 | $CH_2(2\text{-}MePr^c)$ | Me | Me | H | 4-FPh | $CH_2$ |
| 1-726 | $CH_2(2\text{-}MePr^c)$ | Me | Me | H | 2,4-diFPh | $CH_2$ |
| 1-727 | $CH_2(2\text{-}MePr^c)$ | Me | Me | H | Ph | S |
| 1-728 | $CH_2(2\text{-}MePr^c)$ | Me | Me | H | Ph | $CH_2$ |
| 1-729 | $CH_2CH{=}CHCH_3$ | Me | Pn | H | Ph | 0 |
| 1-730 | $CH_2CH{=}CHCH_3$ | Me | Pn | H | 4-FPh | 0 |
| 1-731 | $CH_2CH{=}CHCH_3$ | Me | Pn | H | 2,4-diFPh | 0 |
| 1-732 | $CH_2CH{=}CHCH_3$ | Me | Pn | H | 4-FPh | $CH_2$ |
| 1-733 | $CH_2CH{=}CHCH_3$ | Me | Pn | H | 2,4-diFPh | $CH_2$ |
| 1-734 | $CH{=}CHCH_3$ | H | Me | H | 4-FPh | 0 |
| 1-735 | $CH_2Pr^c$ | H | Me | H | 4-FPh | 0 |
| 1-736 | $CH_2Pr^c$ | H | Me | H | 2,4-diFPh | 0 |
| 1-737 | $CH_2(2\text{-}MePr^c)$ | H | Me | H | 4-FPh | 0 |
| 1-738 | $CH_2(2\text{-}MePr^c)$ | H | Me | H | 2,4-diFPh | 0 |

TABLE 2

| Example Compd. No. | $R^1$ | $R^2$ | $R^3$ | $R^4$ | $R^5$ | X |
|---|---|---|---|---|---|---|
| 2-1 | $CH{=}CH_2$ | Me | Me | H | Ph | 0 |
| 2-2 | $CH{=}CHCH_3$ | Me | Me | H | Ph | 0 |
| 2-3 | $CH_2CH{=}CH_2$ | Me | Me | H | Ph | 0 |
| 2-4 | $CH_2CH{=}CHCH_3$ | Me | Me | H | Ph | 0 |
| 2-5 | $CH_2C(CH_3){=}CH_2$ | Me | Me | H | Ph | 0 |
| 2-6 | $CH_2CH{=}CHCH_2CH_3$ | Me | Me | H | Ph | 0 |
| 2-7 | $CH_2CH{=}C(CH_3)CH_3$ | Me | Me | H | Ph | 0 |
| 2-8 | $CH_2CH{=}CHPh$ | Me | Me | H | Ph | 0 |
| 2-9 | $CH_2CH{=}CH(4\text{-}FPh)$ | Me | Me | H | Ph | 0 |
| 2-10 | $CH_2CH{=}CF_2$ | Me | Me | H | Ph | 0 |
| 2-11 | $CH_2CH{=}CHCl$ | Me | Me | H | Ph | 0 |
| 2-12 | $CH_2C(Cl){=}CH_2$ | Me | Me | H | Ph | 0 |
| 2-13 | $CH_2CH{=}CCl_2$ | Me | Me | H | Ph | 0 |
| 2-14 | $CH_2C{\equiv}CH$ | Me | Me | H | Ph | 0 |
| 2-15 | $CH{=}C{=}CH_2$ | Me | Me | H | Ph | 0 |
| 2-16 | $CH_2Pr^c$ | Me | Me | H | Ph | 0 |
| 2-17 | $Pr^c$ | Me | Me | H | Ph | 0 |
| 2-18 | $Hx^c$ | Me | Me | H | Ph | 0 |
| 2-19 | $CH_2CH_2F$ | Me | Me | H | Ph | 0 |
| 2-20 | $CH_2CHF_2$ | Me | Me | H | Ph | 0 |
| 2-21 | $CH_2CF_3$ | Me | Me | H | Ph | 0 |
| 2-22 | $(CH_2)_3F$ | Me | Me | H | Ph | 0 |
| 2-23 | $CH{=}CH_2$ | Me | Me | H | 4-FPh | 0 |
| 2-24 | $CH{=}CHCH_3$ | Me | Me | H | 4-FPh | 0 |
| 2-25 | $CH_2CH{=}CH_2$ | Me | Me | H | 4-FPh | 0 |
| 2-26 | $C(CH_3){=}CH_2$ | Me | Me | H | 4-FPh | 0 |
| 2-27 | $CH{=}CHCH_2CH_3$ | Me | Me | H | 4-FPh | 0 |
| 2-28 | $CH_2CH{=}CHCH_3$ | Me | Me | H | 4-FPh | 0 |
| 2-29 | $CH_2C(CH_3){=}CH_2$ | Me | Me | H | 4-FPh | 0 |
| 2-30 | $CH_2CH{=}CHPh$ | Me | Me | H | 4-FPh | 0 |
| 2-31 | $CH_2CH{=}CH(4\text{-}FPh)$ | Me | Me | H | 4-FPh | 0 |
| 2-32 | $CH_2CH{=}CF_2$ | Me | Me | H | 4-FPh | 0 |
| 2-33 | $CH_2CH{=}CHCl$ | Me | Me | H | 4-FPh | 0 |
| 2-34 | $CH_2CH{=}CCl_2$ | Me | Me | H | 4-FPh | 0 |
| 2-35 | $CH_2C{\equiv}CH$ | Me | Me | H | 4-FPh | 0 |
| 2-36 | $CH_2Pr^c$ | Me | Me | H | 4-FPh | 0 |
| 2-37 | $CH_2Hx^c$ | Me | Me | H | 4-FPh | 0 |
| 2-38 | $Pr^c$ | Me | Me | H | 4-FPh | 0 |
| 2-39 | $Hx^c$ | Me | Me | H | 4-FPh | 0 |
| 2-40 | $(CH_2)_3F$ | Me | Me | H | 4-FPh | 0 |
| 2-41 | $CH_2CH{=}CH_2$ | Me | Me | H | 2,4-diFPh | 0 |
| 2-42 | $C(CH_3){=}CH_2$ | Me | Me | H | 2,4-diFPh | 0 |
| 2-43 | $CH{=}CHCH_2CH_3$ | Me | Me | H | 2,4-diFPh | 0 |
| 2-44 | $CH_2CH{=}CHCH_3$ | Me | Me | H | 2,4-diFPh | 0 |

TABLE 2-continued

| Example Compd. No. | $R^1$ | $R^2$ | $R^3$ | $R^4$ | $R^5$ | X |
|---|---|---|---|---|---|---|
| 2-45 | $CH_2CH{=}CHPh$ | Me | Me | H | 2,4-diFPh | 0 |
| 2-46 | $CH_2CH{=}CF_2$ | Me | Me | H | 2,4-diFPh | 0 |
| 2-47 | $CH_2CH{=}CHCl$ | Me | Me | H | 2,4-diFPh | 0 |
| 2-48 | $CH_2C{\equiv}CH$ | Me | Me | H | 2,4-diFPh | 0 |
| 2-49 | $CH{=}C{=}CH_2$ | Me | Me | H | 2,4-diFPh | 0 |
| 2-50 | $CH_2Pr^c$ | Me | Me | H | 2,4-diFPh | 0 |
| 2-51 | $CH_2Hx^c$ | Me | Me | H | 2,4-diFPh | 0 |
| 2-52 | $Pr^c$ | Me | Me | H | 2,4-diFPh | 0 |
| 2-53 | $CH_2CH{=}CH_2$ | Me | Me | H | 4-ClPh | 0 |
| 2-54 | $CH_2CH{=}CHCH_3$ | Me | Me | H | 4-ClPh | 0 |
| 2-55 | $CH_2Pr^c$ | Me | Me | H | 4-ClPh | 0 |
| 2-56 | $CH_2CH{=}CH_2$ | Me | Me | H | 2,4-diClPh | 0 |
| 2-57 | $CH_2CH{=}CHCH_3$ | Me | Me | H | 2,4-diClPh | 0 |
| 2-58 | $CH_2Pr^c$ | Me | Me | H | 2,4-diClPh | 0 |
| 2-59 | $CH_2CH{=}CH_2$ | Me | Me | H | 2-FPh | 0 |
| 2-60 | $CH_2CH{=}CHCH_3$ | Me | Me | H | 2-FPh | 0 |
| 2-61 | $CH_2Pr^c$ | Me | Me | H | 2-FPh | 0 |
| 2-62 | $CH_2CH{=}CH_2$ | Me | Me | H | 3-FPh | 0 |
| 2-63 | $CH_2CH{=}CHCH_3$ | Me | Me | H | 3-FPh | 0 |
| 2-64 | $CH_2Pr^c$ | Me | Me | H | 3-FPh | 0 |
| 2-65 | $CH_2CH{=}CH_2$ | Me | Me | H | 2-ClPh | 0 |
| 2-66 | $CH_2CH{=}CHCH_3$ | Me | Me | H | 2-ClPh | 0 |
| 2-67 | $CH_2Pr^c$ | Me | Me | H | 2-ClPh | 0 |
| 2-68 | $CH_2CH{=}CH_2$ | Me | Me | H | 3-ClPh | 0 |
| 2-69 | $CH_2CH{=}CHCH_3$ | Me | Me | H | 3-ClPh | 0 |
| 2-70 | $CH_2CH{=}CH_2$ | Me | Me | H | $4\text{-}CF_3Ph$ | 0 |
| 2-71 | $CH_2CH{=}CHCH_3$ | Me | Me | H | $4\text{-}CF_3Ph$ | 0 |
| 2-72 | $CH_2CH{=}CH_2$ | Me | Et | H | Ph | 0 |
| 2-73 | $CH_2CH{=}CH_2$ | Me | Et | H | 4-FPh | 0 |
| 2-74 | $CH_2CH{=}CH_2$ | Me | Et | H | 2,4-diFPh | 0 |
| 2-75 | $CH_2CH{=}CHCH_3$ | Me | Et | H | Ph | 0 |
| 2-76 | $CH_2CH{=}CHCH_3$ | Me | Et | H | 4-FPh | 0 |
| 2-77 | $CH_2CH{=}CHCH_3$ | Me | Et | H | 2,4-diFPh | 0 |
| 2-78 | $CH_2CH{=}CH_2$ | Et | Me | H | Ph | 0 |
| 2-79 | $CH_2CH{=}CH_2$ | Et | Me | H | 4-FPh | 0 |
| 2-80 | $CH_2CH{=}CH_2$ | Et | Me | H | 2,4-diFPh | 0 |
| 2-81 | $CH_2CH{=}CHCH_3$ | Et | Me | H | Ph | 0 |
| 2-82 | $CH_2CH{=}CHCH_3$ | Et | Me | H | 4-FPh | 0 |
| 2-83 | $CH_2CH{=}CHCH_3$ | Et | Me | H | 2,4-diFPh | 0 |
| 2-84 | $CH_2CH{=}CH_2$ | Me | Me | H | 2-Thi | 0 |
| 2-85 | $CH_2CH{=}CH_2$ | Me | Me | H | 2-Fur | 0 |
| 2-86 | $CH_2CH{=}CH_2$ | Me | Me | H | 3-Pyr | 0 |
| 2-87 | $CH_2CH{=}CHCH_3$ | Me | Me | H | 2-Thi | 0 |
| 2-88 | $CH_2CH{=}CHCH_3$ | Me | Me | H | 2-Fur | 0 |

TABLE 2-continued

| Example Compd. No. | $R^1$ | $R^2$ | $R^3$ | $R^4$ | $R^5$ | X |
|---|---|---|---|---|---|---|
| 2-89 | $CH_2CH=CHCH_3$ | Me | Me | H | 2-Pyr | 0 |
| 2-90 | $CH_2CH=CHCH_3$ | Me | Me | H | 3-Pyr | 0 |
| 2-91 | $CH_2CH=CHCH_3$ | Me | Me | H | 2,6-diFPh | 0 |
| 2-92 | $CH_2CH=CHCH_3$ | Me | Me | H | 3,5-diFPh | 0 |
| 2-93 | $CH_2CH=CHCH_3$ | Me | Me | H | 2-Cl-6-FPh | 0 |
| 2-94 | $CH_2CH=CH_2$ | Me | Me | H | 4-Cl-2-FPh | 0 |
| 2-95 | $CH_2CH=CHCH_3$ | Me | Me | H | 4-Cl-2-FPh | 0 |
| 2-96 | $CH_2CH=CHCH_3$ | Me | Me | H | 2,6-diClPh | 0 |
| 2-97 | $CH_2(2\text{-}MePr^c)$ | Me | Me | H | 4-FPh | 0 |
| 2-98 | $CH_2(2\text{-}MePr^c)$ | Me | Me | H | 2,4-diFPh | 0 |
| 2-99 | $CH_2(2\text{-}MePr^c)$ | Me | Me | H | Ph | 0 |
| 2-100 | $CH=CH_2$ | Me | Me | H | Ph | S |
| 2-101 | $CH=CHCH_3$ | Me | Me | H | Ph | S |
| 2-102 | $CH_2CH=CH_2$ | Me | Me | H | Ph | S |
| 2-103 | $CH_2CH=CHCH_3$ | Me | Me | H | Ph | S |
| 2-104 | $CH_2C(CH_3)=CH_2$ | Me | Me | H | Ph | S |
| 2-105 | $CH_2CH=CHCH_2CH_3$ | Me | Me | H | Ph | S |
| 2-106 | $CH_2CH=C(CH_3)CH_3$ | Me | Me | H | Ph | S |
| 2-107 | $CH_2CH=CHPh$ | Me | Me | H | Ph | S |
| 2-108 | $CH_2CH=CCl_2$ | Me | Me | H | Ph | S |
| 2-109 | $CH_2C\equiv CH$ | Me | Me | H | Ph | S |
| 2-110 | $CH=C=CH_2$ | Me | Me | H | Ph | S |
| 2-111 | $CH_2Pr^c$ | Me | Me | H | Ph | S |
| 2-112 | $Pr^c$ | Me | Me | H | Ph | S |
| 2-113 | $Hx^c$ | Me | Me | H | Ph | S |
| 2-114 | $CH_2CH_2F$ | Me | Me | H | Ph | S |
| 2-115 | $CH_2CHF_2$ | Me | Me | H | Ph | S |
| 2-116 | $CH_2CF_3$ | Me | Me | H | Ph | S |
| 2-117 | $(CH_2)_3F$ | Me | Me | H | Ph | S |
| 2-118 | $CH=CHCH_3$ | Me | Me | H | 4-FPh | S |
| 2-119 | $CH_2CH=CH_2$ | Me | Me | H | 4-FPh | S |
| 2-120 | $CH_2CH=CHCH_3$ | Me | Me | H | 4-FPh | S |
| 2-121 | $CH_2C(CH_3)=CH_2$ | Me | Me | H | 4-FPh | S |
| 2-122 | $CH_2CH=CHPh$ | Me | Me | H | 4-FPh | S |
| 2-123 | $CH_2Pr^c$ | Me | Me | H | 4-FPh | S |
| 2-124 | $CH_2Hx^c$ | Me | Me | H | 4-FPh | S |
| 2-125 | $CH_2CH=CH_2$ | Me | Me | H | 2,4-diFPh | S |
| 2-126 | $CH_2CH=CHCH_3$ | Me | Me | H | 2,4-diFPh | S |
| 2-127 | $CH_2CH=CH_2$ | Me | Me | H | 4-ClPh | S |
| 2-128 | $CH_2CH=CHCH_3$ | Me | Me | H | 4-ClPh | S |
| 2-129 | $CH_2CH=CH_2$ | Me | Me | H | 2,4-diClPh | S |
| 2-130 | $CH_2CH=CHCH_3$ | Me | Me | H | 2,4-diClPh | S |
| 2-131 | $CH_2CH=CH_2$ | Me | Me | H | 2-FPh | S |
| 2-132 | $CH_2CH=CH_2$ | Me | Me | H | 3-FPh | S |
| 2-133 | $CH_2CH=CH_2$ | Me | Me | H | $4\text{-}CF_3Ph$ | S |
| 2-134 | $CH_2CH=CH_2$ | Me | Et | H | Ph | S |
| 2-135 | $CH_2CH=CHCH_3$ | Et | Me | H | Ph | S |
| 2-136 | $CH_2CH=CHCH_3$ | Et | Me | H | 4-FPh | S |
| 2-137 | $CH_2CH=CHCH_3$ | Me | Me | H | 2-Pyr | S |
| 2-138 | $CH_2CH=CHCH_3$ | Me | Me | H | 2-Cl-6-FPh | S |
| 2-139 | $CH_2CH=CH_2$ | Me | Me | H | 4-Cl-2-FPh | S |
| 2-140 | $CH_2CH=CHCH_3$ | Me | Me | H | 4-Cl-2-FPh | S |
| 2-141 | $CH_2CH=CHCH_3$ | Me | Me | H | 2,6-diClPh | S |
| 2-142 | $CH_2(2\text{-}MePr^c)$ | Me | Me | H | 4-FPh | S |
| 2-143 | $CH_2(2\text{-}MePr^c)$ | Me | Me | H | 2,4-diFPh | S |
| 2-144 | $CH_2(2\text{-}MePr^c)$ | Me | Me | H | Ph | S |
| 2-145 | $CH=CH_2$ | Me | Me | H | Ph | $CH_2$ |
| 2-146 | $CH=CHCH_3$ | Me | Me | H | Ph | $CH_2$ |
| 2-147 | $CH_2CH=CH_2$ | Me | Me | H | Ph | $CH_2$ |
| 2-148 | $CH_2CH=CHCH_3$ | Me | Me | H | Ph | $CH_2$ |
| 2-149 | $CH_2C(CH_3)=CH_2$ | Me | Me | H | Ph | $CH_2$ |
| 2-150 | $CH_2CH=CHCH_2CH_3$ | Me | Me | H | Ph | $CH_2$ |
| 2-151 | $CH_2CH=C(CH_3)CH_3$ | Me | Me | H | Ph | $CH_2$ |
| 2-152 | $CH_2CH=CHPh$ | Me | Me | H | Ph | $CH_2$ |
| 2-153 | $CH_2CH=CCl_2$ | Me | Me | H | Ph | $CH_2$ |
| 2-154 | $CH_2C\equiv CH$ | Me | Me | H | Ph | $CH_2$ |
| 2-155 | $CH=C=CH_2$ | Me | Me | H | Ph | $CH_2$ |
| 2-156 | $CH_2Pr^c$ | Me | Me | H | Ph | $CH_2$ |
| 2-157 | $Pr^c$ | Me | Me | H | Ph | $CH_2$ |
| 2-158 | $Hx^c$ | Me | Me | H | Ph | $CH_2$ |
| 2-159 | $CH_2CH_2F$ | Me | Me | H | Ph | $CH_2$ |
| 2-160 | $CH_2CHF_2$ | Me | Me | H | Ph | $CH_2$ |
| 2-161 | $CH_2CF_3$ | Me | Me | H | Ph | $CH_2$ |
| 2-162 | $(CH_2)_3F$ | Me | Me | H | Ph | $CH_2$ |
| 2-163 | $CH=CHCH_3$ | Me | Me | H | 4-FPh | $CH_2$ |
| 2-164 | $CH_2CH=CH_2$ | Me | Me | H | 4-FPh | $CH_2$ |
| 2-165 | $CH_2CH=CHCH_3$ | Me | Me | H | 4-FPh | $CH_2$ |
| 2-166 | $CH_2C(CH_3)=CH_2$ | Me | Me | H | 4-FPh | $CH_2$ |
| 2-167 | $CH_2CH=CHPh$ | Me | Me | H | 4-FPh | $CH_2$ |
| 2-168 | $CH_2Pr^c$ | Me | Me | H | 4-FPh | $CH_2$ |
| 2-169 | $CH_2Hx^c$ | Me | Me | H | 4-FPh | $CH_2$ |
| 2-170 | $CH_2CH=CH_2$ | Me | Me | H | 2,4-diFPh | $CH_2$ |
| 2-171 | $CH_2CH=CHCH_3$ | Me | Me | H | 2,4-diFPh | $CH_2$ |
| 2-172 | $CH_2CH=CH_2$ | Me | Me | H | 4-ClPh | $CH_2$ |
| 2-173 | $CH_2CH=CHCH_3$ | Me | Me | H | 4-ClPh | $CH_2$ |
| 2-174 | $CH_2CH=CH_2$ | Me | Me | H | 2,4-diClPh | $CH_2$ |
| 2-175 | $CH_2CH=CHCH_3$ | Me | Me | H | 2,4-diClPh | $CH_2$ |
| 2-176 | $CH_2CH=CH_2$ | Me | Me | H | 2-FPh | $CH_2$ |
| 2-177 | $CH_2CH=CH_2$ | Me | Me | H | 3-FPh | $CH_2$ |
| 2-178 | $CH_2CH=CH_2$ | Me | Me | H | $4\text{-}CF_3Ph$ | $CH_2$ |
| 2-179 | $CH_2CH=CH_2$ | Me | Et | H | Ph | $CH_2$ |
| 2-180 | $CH_2CH=CHCH_3$ | Et | Me | H | Ph | $CH_2$ |
| 2-181 | $CH_2CH_2=CHCH_3$ | Et | Me | H | 4-FPh | $CH_2$ |
| 2-182 | $CH_2CH=CHCH_3$ | Me | Me | H | 2-Pyr | $CH_2$ |
| 2-183 | $CH_2CH=CHCH_3$ | Me | Me | H | 2-Cl-6-FPh | $CH_3$ |
| 2-184 | $CH_2CH=CH_2$ | Me | Me | H | 4-Cl-2-FPh | $CH_3$ |
| 2-185 | $CH_2CH=CHCH_3$ | Me | Me | H | 4-Cl-2-FPh | $CH_2$ |
| 2-186 | $CH_2CH=CHCH_3$ | Me | Me | H | 2,6-diClPh | $CH_2$ |
| 2-187 | $CH_2(2\text{-}MePr^c)$ | Me | Me | H | 4-FPh | $CH_2$ |
| 2-188 | $CH_2(2\text{-}MePr^c)$ | Me | Me | H | 2,4-diFPh | $CH_2$ |
| 2-189 | $CH_2(2\text{-}MePr^c)$ | Me | Me | H | Ph | $CH_2$ |
| 2-190 | $CH_2CH=CHCH_3$ | Me | Pn | H | 4-FPh | 0 |
| 1-191 | $CH_2CH=CHCH_3$ | Me | Pn | H | 2,4-diFPh | 0 |
| 2-192 | $CH_2CH=CHCH_3$ | Me | Pn | H | Ph | $CH_2$ |
| 2-193 | $CH_2CH=CHCH_3$ | Me | Pn | H | 4-FPh | $CH_2$ |
| 2-194 | $CH_2CH=CHCH_3$ | Me | Pn | H | 2,4-diFPh | $CH_2$ |

TABLE 3

| Example Compd. No. | $R^1$ | $R^2$ | $R^3$ | $R^4$ | $R^5$ | X |
|---|---|---|---|---|---|---|
| 3-1 | $CH_2CH=CH_2$ | Me | Me | H | Ph | 0 |
| 3-2 | $CH_2CH=CHCH_3$ | Me | Me | H | Ph | 0 |
| 3-3 | $CH_2C(CH_3)=CH_2$ | Me | Me | H | Ph | 0 |
| 3-4 | $CH_2C\equiv CH$ | Me | Me | H | Ph | 0 |
| 3-5 | $CH_2Pr^c$ | Me | Me | H | Ph | 0 |
| 3-6 | $CH=CH_2$ | Me | Me | H | 4-FPh | 0 |
| 3-7 | $CH=CHCH_3$ | Me | Me | H | 4-FPh | 0 |
| 3-8 | $CH_2CH=CH_2$ | Me | Me | H | 4-FPh | 0 |
| 3-9 | $CH_2CH=CHCH_3$ | Me | Me | H | 4-FPh | 0 |
| 3-10 | $CH_2C{-}CH$ | Me | Me | H | 4-FPh | 0 |
| 3-11 | $CH_2Pr^c$ | Me | Me | H | 4-FPh | 0 |
| 3-12 | $CH_2Hx^c$ | Me | Me | H | 4-FPh | 0 |
| 3-13 | $CH_2CH=CH_2$ | Me | Me | H | 2,4-diFPh | 0 |
| 3-14 | $CH_2CH=CHCH_3$ | Me | Me | H | 2,4-diFPh | 0 |
| 3-15 | $CH_2C\equiv CH$ | Me | Me | H | 2,4-diFPh | 0 |
| 3-16 | $CH_2Pr^c$ | Me | Me | H | 2,4-diFPh | 0 |
| 3-17 | $CH_2CH=CH_2$ | Me | Me | H | 4-ClPh | 0 |
| 3-18 | $CH_2CH=CHCH_3$ | Me | Me | H | 4-ClPh | 0 |
| 3-19 | $CH_2Pr^c$ | Me | Me | H | 4-ClPh | 0 |
| 3-20 | $CH_2CH=CH_2$ | Me | Me | H | 2,4-diClPh | 0 |
| 3-21 | $CH_2CH=CHCH_3$ | Me | Me | H | 2,4-diClPh | 0 |
| 3-22 | $CHPr^c$ | Me | Me | H | 2,4-diClPh | 0 |
| 3-23 | $CH_2CH=CHCH_3$ | Me | Me | H | 2,6-diFPh | 0 |
| 3-24 | $CH_2CH=CHCH_3$ | Me | Me | H | 3,5-diFPh | 0 |
| 3-25 | $CH_2CH=CHCH_3$ | Me | Me | H | 2-Cl-6-FPh | 0 |
| 3-26 | $CH_2(2\text{-}MePr^c)$ | Me | Me | H | 4-FPh | 0 |
| 3-27 | $CH_2(2\text{-}MePr^c)$ | Me | Me | H | 2,4-diFPh | 0 |
| 3-28 | $CH_2(2\text{-}MePr^c)$ | Me | Me | H | Ph | 0 |
| 3-29 | $CH_2CH=CH_2$ | Me | Me | H | Ph | S |
| 3-30 | $CH_2CH=CHCH_3$ | Me | Me | H | Ph | S |
| 3-31 | $CH_2C(CH_3)=CH_2$ | Me | Me | H | Ph | S |
| 3-32 | $CH_2C\equiv CH$ | Me | Me | H | Ph | S |
| 3-33 | $CH_2Pr^c$ | Me | Me | H | Ph | S |
| 3-34 | $CH=CH_2$ | Me | Me | H | 4-FPh | S |

TABLE 3-continued

| Example Compd. No. | $R^1$ | $R^2$ | $R^3$ | $R^4$ | $R^5$ | X |
|---|---|---|---|---|---|---|
| 3-35 | $CH{=}CHCH_3$ | Me | Me | H | 4-FPh | S |
| 3-36 | $CH_2CH{=}CH_2$ | Me | Me | H | 4-FPh | S |
| 3-37 | $CH_2CH{=}CHCH_3$ | Me | Me | H | 4-FPh | S |
| 3-38 | $CH_2C{\equiv}CH$ | Me | Me | H | 4-FPh | S |
| 3-39 | $CH_2Pr^c$ | Me | Me | H | 4-FPh | S |
| 3-40 | $CH_2Hx^c$ | Me | Me | H | 4-FPh | S |
| 3-41 | $CH_2CH{=}CH_2$ | Me | Me | H | 2,4-diFPh | S |
| 3-42 | $CH_2CH{=}CHCH_3$ | Me | Me | H | 2,4-diFPh | S |
| 3-43 | $CH_2C{\equiv}CH$ | Me | Me | H | 2,4-diFPh | S |
| 3-44 | $CH_2Pr^c$ | Me | Me | H | 2,4-diFPh | S |
| 3-45 | $CH_2CH{=}CH_2$ | Me | Me | H | 4-ClPh | S |
| 3-46 | $CH_2CH{=}CHCH_3$ | Me | Me | H | 4-ClPh | S |
| 3-47 | $CH_2Pr^c$ | Me | Me | H | 4-ClPh | S |
| 3-48 | $CH_2CH{=}CH_2$ | Me | Me | H | 2,4-diClPh | S |
| 3-49 | $CH_2CH{=}CHCH_3$ | Me | Me | H | 2,4-diClPh | S |
| 3-50 | $CH_2Pr^c$ | Me | Me | H | 2,4-diClPh | S |
| 3-51 | $CH_2CH{=}CHCH_3$ | Me | Me | H | 2,6-diFPh | S |
| 3-52 | $CH_2CH{=}CHCH_3$ | Me | Me | H | 3,5-diFPh | S |
| 3-53 | $CH_2CH{=}CHCH_3$ | Me | Me | H | 2-Cl-6-FPh | S |
| 3-54 | $CH_2(2\text{-}MePr^c)$ | Me | Me | H | 4-FPh | S |
| 3-55 | $CH_2(2\text{-}MePr^c)$ | Me | Me | H | 2,4-diFPh | S |
| 3-56 | $CH_2(2\text{-}MePr^c)$ | Me | Me | H | Ph | S |
| 3-57 | $CH{=}CH_2$ | Me | Me | H | Ph | $CH_2$ |
| 3-58 | $CH{=}CHCH_3$ | Me | Me | H | Ph | $CH_2$ |
| 3-59 | $CH_2CH{=}CH_2$ | Me | Me | H | Ph | $CH_2$ |
| 3-60 | $CH_2(CH{=}CHCH_3$ | Me | Me | H | Ph | $CH_2$ |
| 3-61 | $CH_2C(CH_3){=}CH_2$ | Me | Me | H | Ph | $CH_2$ |
| 3-62 | $CH_2CH{=}CHCH_2CH_3$ | Me | Me | H | Ph | $CH_2$ |
| 3-63 | $CH_2CH{=}C(CH_3)CH_3$ | Me | Me | H | Ph | $CH_2$ |
| 3-64 | $CH_2CH{=}CHPh$ | Me | Me | H | Ph | $CH_2$ |
| 3-65 | $CH_2CH{=}CCl_2$ | Me | Me | H | Ph | $CH_2$ |
| 3-66 | $CH_2C{\equiv}CH$ | Me | Me | H | Ph | $CH_2$ |
| 3-67 | $CH{=}C{=}CH_2$ | Me | Me | H | Ph | $CH_2$ |
| 3-68 | $CH_2Pr^c$ | Me | Me | H | Ph | $CH_2$ |
| 3-69 | $Pr^c$ | Me | Me | H | Ph | $CH_2$ |
| 3-70 | $Hx^c$ | Me | Me | H | Ph | $CH_2$ |
| 3-71 | $CH_2CH_2F$ | Me | Me | H | Ph | $CH_2$ |
| 3-72 | $CH_2CHF_2$ | Me | Me | H | Ph | $CH_2$ |
| 3-73 | $CH_2CF_3$ | Me | Me | H | Ph | $CH_2$ |
| 3-74 | $(CH_2)_3F$ | Me | Me | H | Ph | $CH_2$ |
| 3-75 | $CH{=}CHCH_3$ | Me | Me | H | 4-FPh | $CH_2$ |
| 3-76 | $CH_2CH{=}CH_2$ | Me | Me | H | 4-FPh | $CH_2$ |
| 3-77 | $CH_2CH{=}CHCH_3$ | Me | Me | H | 4-FPh | $CH_2$ |
| 3-78 | $CH_2C(CH_3){=}CH_2$ | Me | Me | H | 4-FPh | $CH_2$ |
| 3-79 | $CH_2CH{=}CHPh$ | Me | Me | H | 4-FPh | $CH_2$ |
| 3-80 | $CH_2Pr^c$ | Me | Me | H | 4-FPh | $CH_2$ |
| 3-81 | $CH_2Hx^c$ | Me | Me | H | 4-FPh | $CH_2$ |
| 3-82 | $CH_2CH{=}CH_2$ | Me | Me | H | 2,4-diFPh | $CH_2$ |
| 3-83 | $CH_2CH{=}CHCH_2$ | Me | Me | H | 2,4-diFPh | $CH_2$ |
| 3-84 | $CH_2CH{=}CH_2$ | Me | Me | H | 4-ClPh | $CH_2$ |
| 3-85 | $CH_2CH{=}CHCH_3$ | Me | Me | H | 4-ClPh | $CH_2$ |
| 3-86 | $CH_2CH{=}CH_2$ | Me | Me | H | 2,4-diClPh | $CH_2$ |
| 3-87 | $CH_2CH{=}CHCH_3$ | Me | Me | H | 2,4-diClPh | $CH_2$ |
| 3-88 | $CH_2CH{=}CH_2$ | Me | Me | H | 2-FPh | $CH_2$ |
| 3-89 | $CH_2CH{=}CH_2$ | Me | Me | H | 3-FPh | $CH_2$ |
| 3-90 | $CH_2CH{=}CH_2$ | Me | Me | H | $4\text{-}CF_3Ph$ | $CH_2$ |
| 3-91 | $CH_2CH{=}CH_2$ | Me | Et | H | Ph | $CH_2$ |
| 3-92 | $CH_2CH{=}CHCH_3$ | Et | Me | H | Ph | $CH_2$ |
| 3-93 | $CH_2CH{=}CHCH_3$ | Et | Me | H | 4-FPh | $CH_2$ |
| 3-94 | $CH_2CH{=}CHCH_3$ | Me | Me | H | 2-Pyr | $CH_2$ |
| 3-95 | $CH_2CH{=}CHCH_3$ | Me | Me | H | 2-Cl-6-FPh | $CH_2$ |
| 3-96 | $CH_2CH{=}CH_2$ | Me | Me | H | 4-Cl-2-FPh | $CH_2$ |
| 3-97 | $CH_2CH{=}CHCH_3$ | Me | Me | H | 4-Cl-2-FPh | $CH_2$ |
| 3-98 | $CH_2CH{=}CHCH_3$ | Me | Me | H | 2,6-diClPh | $CH_2$ |
| 3-99 | $CH_2(2\text{-}MePr^c)$ | Me | Me | H | 4-FPh | $CH_2$ |
| 3-100 | $CH_2(2\text{-}MePr^c)$ | Me | Me | H | 2,4-diFPh | $CH_2$ |
| 3-101 | $CH_2(2\text{-}MePr^c)$ | Me | Me | H | Ph | $CH_2$ |

In these Tables above, the group names are abbreviated as follows.

Benzimidz: Benzimidazolyl group
Benzoxaz: Benzoxazolyl group
Benzothiaz: Benzothiazolyl group
Bu: Butyl group
$Bu^c$: Cyclobutyl group
$Bu^i$: Isobutyl group
$Bu^s$: s-Butyl group
$Bu^t$: t-Butyl group
Et: Ethyl group
Fur: Furyl group
$Hx^c$: Cyclohexyl group
$Hxe^c$: Cyclohexenyl group
$Hpte^c$: Cycloheptenyl group
$Hp^c$: Cycloheptyl group
Imidz: Imidazolyl group
Me: Methyl group
Naph: Naphthyl group
Oxaz: Oxazolyl group
$Pnte^c$: Cyclopentenyl group
Ph: Phenyl group
Pn: Pentyl group
$Pn^c$: Cyclopentyl group
Pr: Propyl group
$Pr^c$: Cyclopentyl group
$Pr^i$:Isopropyl group
Pyr: Pyridyl group
Pyraz: Pyrazinyl group
Pyridz: Pyridazinyl group
TDA: Thiadiazolyl group
Thi: Thienyl group
Thiaz: Thiazolyl group Among the compounds listed above:

preferable compounds are as follows: Compounds Nos. 1-1, 1-2, 1-3, 1-6, 1-11, 1-13, 1-18, 1-19, 1-24, 1-36, 1-37, 1-38, 1-39, 1-40, 1-42, 1-45, 1-48, 1-51, 1-59, 1-62, 1-68, 1-69, 1-70, 1-71, 1-76, 1-77, 1-78, 1-79, 1-80, 1-81, 1-86, 1-94, 1-99, 1-111, 1-112, 1-115, 1-120, 1-126, 1-129, 1-134, 1-137, 1-146, 1-153, 1-154, 1-155, 1-156, 1-169, 1-186, 1-187, 1-195, 1-198, 1-201, 1-204, 1-209, 1-226, 1-227, 1-229, 1-231, 1-232, 1-234, 1-236, 1-237, 1-239, 1-241, 1-242, 1-244, 1-246, 1-247, 1-249, 1-251, 1-252, 1-259, 1-260, 1-263, 1-278, 1-293, 1-308, 1-323, 1-338, 1-353, 1-368, 1-383, 1-398, 1-413, 1-428, 1-445, 1-447, 1-449, 1-451, 1-458, 1-460, 1-461, 1-462, 1-464, 1-466, 1-473, 1-475, 1-478, 1-488, 1-490, 1-492, 1-493, 1-503, 1-504, 1-505, 1-506, 1-507, 1-523, 1-524, 1-526, 1-539, 1-540, 1-619, 1-623, 1-631, 1-632, 1-644, 1-653, 1-656, 1-664, 1-669, 1-672, 1-678, 1-725, 1-726, 1-728, 1-729, 1-734, 2-3, 2-4, 2-5, 2-6, 2-8, 2-13, 2-14, 2-16, 2-17, 2-21, 2-24, 2-25, 2-28, 2-36, 2-38, 2-41, 2-44, 2-50, 2-52, 2-53, 2-54, 2-55, 2-56, 2-57, 2-58, 2-59, 2-60, 2-61, 2-65, 2-66, 2-67, 2-76, 2-93, 2-94, 2-95, 2-96, 2-97, 2-98, 2-119, 2-120, 2-123, 2-126, 2-127, 2-128, 2-130, 2-138, 2-139, 2-140, 2-142, 2-143, 2-147, 2-148, 2-156, 2-164, 2-165, 2-168, 2-170, 2-171, 2-173, 2-175, 2-183, 2-184, 2-185, 2-186, 2-187, 2-188, 2-189, 3-59, 3-60, 3-68, 3-76, 3-77, 3-80, 3-82, 3-83, 3-99, 3-100 and 3-101;

more preferable compounds are as follows: Compounds Nos. 1-1, 1-3, 1-6, 1-11, 1-13, 1-18, 1-19, 1-39, 1-40, 1-42, 1-45, 1-48, 1-51, 1-59, 1-62, 1-68, 1-69, 1-70, 1-71, 1-77, 1-78, 1-81, 1-86, 1-94, 1-126, 1-129, 1-153, 1-156, 1-226, 1-231, 1-232, 1-236, 1-241, 1-259, 1-263, 1-323, 1-413, 1-445, 1-447, 1-449, 1-451, 1-458, 1-460, 1-462, 1-464, 1-466, 1-492, 1-505, 1-507, 1-523, 1-524, 1-526, 1-539, 1-540, 1-619, 1-623, 1-631, 1-632, 1-644, 1-653, 1-656, 1-664, 1-669, 1-672, 1-678, 1-725, 1-726, 1-728, 1-729, 2-3, 2-4, 2-5, 2-6, 2-8, 2-13, 2-14, 2-16, 2-17, 2-21, 2-24, 2-25, 2-28, 2-36, 2-41, 2-44, 2-50, 2-53, 2-54, 2-56, 2-57, 2-59, 2-76, 2-93, 2-94, 2-95, 2-96, 2-97, 2-98, 2-119, 2-120, 2-126, 2-127, 2-128, 2-130, 2-138, 2-139, 2-140, 2-142, 2-143, 2-148, 2-164, 2-165, 2-168, 2-171, 2-187, 3-60, 3-76, 3-77, 3-83, 3-99, 3-100 and 3-101;

much more preferable compounds are as follows: Compounds Nos. 1-3, 1-6, 1-11, 1-13, 1-19, 1-39, 1-40, 1-42, 1-45, 1-51, 1-59, 1-70, 1-77, 1-78, 1-81, 1-126, 1-153, 1-156, 1-226, 1-231, 1-232, 1-236, 1-323, 1-445, 1-447, 1-449, 1-451, 1-460, 1-462, 1-464, 1-466, 1-505, 1-523, 1-524, 1-526, 1-539, 1-540, 1-619, 1-623, 1-631, 1-632, 1-644, 1-653, 1-656, 1-664, 1-669, 1-672, 1-678, 1-725, 1-726, 1-728, 2-4, 2-5, 2-16, 2-24, 2-25, 2-28, 2-36, 2-41, 2-44, 2-50, 2-53, 2-56, 2-76, 2-93, 2-95, 2-97, 2-98, 2-119, 2-120, 2-148, 2-164, 2-165, 2-168, 2-171, 2-187, 3-60, 3-77 and 3-83; and particularly preferable componds are as follows;

Compound No. 1-6: 1-(2-Butenyl)-7-benzyloxy-2,3-dimethylpyrrolo[2,3-d]pyridazine;

Compound No. 1-11: 7-Benzyloxy-2,3-dimethyl-1-(2-methyl-2-propenyl)pyrrolo[2,3-d]pyridazine;

Compound No. 1-45: 7-Benzyloxy-2,3-dimethyl-1-(2-propynyl)pyrrolo[2,3-d]pyridazine;

Compound No. 1-51: 7-Benzyloxy-1-cyclopropylmethyl-2,3-dimethylpyrrolo[2,3-d]pyridazine;

Compound No. 1-77: 7-(4-Fluorobenzyloxy)-2,3-dimethyl-1-(1-propenyl)pyrrolo[2,3-d]pyridazine;

Compound No. 1-78: 7-(4-Fluorobenzyloxy)-2,3-dimethyl-1-(2-propenyl)pyrrolo[2,3-d]pyridazine;

Compound No. 1-81: 1-(2-Butenyl)-7-(4-fluorobenzyloxy)-2,3-dimethylpyrrolo[2,3-d]pyridazine;

Compound No. 1-126: 1-Cyclopropylmethyl-7-(4-fluorobenzyloxy)-2,3-dimethylpyrrolo[2,3-d]pyridazine;

Compound No. 1-153: 7-(2,4-Difluorobenzyloxy)-2,3-dimethyl-1-(2-propenyl)pyrrolo[2,3-d]pyridazine;

Compound No. 1-156: 1-(2-Butenyl)-7-(2,4-difluorobenzyloxy)-2,3-dimethylpyrrolo[2,3-d]pyridazine;

Compound No. 1-226: 7-(4-Chlorobenzyloxy)-2,3-dimethyl-1-(2-propenyl)pyrrolo[2,3-d]pyridazine;

Compound No. 1-231: 7-(2,4-Dichlorobenzyloxy)-2,3-dimethyl-1-(2-propenyl)pyrrolo[2,3-d]pyridazine;

Compound No. 1-232: 1-(2-Butenyl)-7-(2,4-dichlorobenzyloxy)-2,3-dimethylpyrrolo[2,3-d]pyridazine;

Compound No. 1-236: 7-(2-Fluorobenzyloxy)-2,3-dimethyl-1-(2-propenyl)pyrrolo[2,3-d]pyridazine;

Compound No. 1-323: 1-(2-Butenyl)-3-ethyl-7-(4-fluorobenzyloxy)-2-methylpyrrolo[2,3-d]pyridazine;

Compound No. 1-445: 7-(4-Fluorobenzylthio)-2,3-dimethyl-1-(2-propenyl)pyrrolo[2,3-d]pyridazine;

Compound No. 1-460: 1-(2-Butenyl)-7-(4-fluorobenzylthio)-2,3-dimethylpyrrolo[2,3-d]pyridazine;

Compound No. 1-462: 1-(2-Butenyl)-7-(2,4-difluorobenzylthio)-2,3-dimethylpyrrolo[2,3-d]pyridazine;

Compound No. 1-505: 1-(2-Butenyl)-7-(2-chloro-6-fluorobenzyloxy)-2,3-dimethylpyrrolo[2,3-d]pyridazine;

Compound No. 1-524: 1-(2-Butenyl)-7-(4-chloro-2-fluorobenzyloxy)-2,3-dimethylpyrrolo[2,3-d]pyridazine;

Compound No. 1-539: 7-(4-Fluorobenzyloxy)-2,3-dimethyl-1-(2-methylcyclopropylmethyl)pyrrolo[2,3-d]pyridazine;

Compound No. 1-540: 7-(2,4-Difluorobenzyloxy)-2,3-dimethyl-1-(2-methylcyclopropylmethyl)pyrrolo[2,3-d]pyridazine;

Compound No. 1-631: 2,3-Dimethyl-7-phenethyl-1-(2-propenyl)pyrrolo[2,3-d]pyridazine;

Compound No. 1-632: 1-(2-Butenyl)-2,3-dimethyl-7-phenethylpyrrolo[2,3-d]pyridazine;

Compound No. 1-653: 7-(4-Fluorophenethyl)-2,3-dimethyl-1-(2-propenyl)pyrrolo[2,3-d]pyridazine;

Compound No. 1-656: 1-(2-Butenyl)-7-(4-fluorophenethyl)-2,3-dimethylpyrrolo[2,3-d]pyridazine;

Compound No. 1-664: 1-Cyclopropylmethyl-7-(4-fluorophenethyl)-2,3-dimethylpyrrolo[2,3-d]pyridazine;

Compound No. 1-669: 7-(2,4-Difluorophenethyl)-2,3-dimethyl-1-(2-propenyl)pyrrolo[2,3-d]pyridazine;

Compound No. 1-672: 1-(2-Butenyl)-7-(2,4-difluorophenethyl)-2,3-dimethylpyrrolo[2,3-d]pyridazine;

Compound No. 1-678: 1-Cyclopropylmethyl-7-(2,4-difluorophenethyl)-2,3-dimethylpyrrolo[2,3-d]pyridazine;

Compound No. 1-725: 7-(4-Fluorophenethyl)-2,3-dimethyl-1-(2-methylcyclopropylmethyl)pyrrolo[2,3-d]pyridazine;

Compound No. 1-726: 7-(2,4-Difluorophenethyl)-2,3-dimethyl-1-(2-methylcyclopropylmethyl)pyrrolo[2,3-d]pyridazine;

Compound No. 1-728: 2,3-Dimethyl-1-(2-methylcyclopropylmethyl)-7-phenethylpyrrolo[2,3-d]-pyridazine;

Compound No. 2-28: 1-(2-Butenyl)-7-(4-fluorobenzyloxy)-2,3-dimethylpyrrolo[2,3-d]pyridazine-5-oxide;

Compound No. 2-44: 1-(2-Butenyl)-7-(2,4-difluorobenzyloxy)-2,3-dimethylpyrrolo[2,3-d]pyridazine-5-oxide;

Compound No. 2-171: 1-(2-Butenyl)-7-(2,4-difluorophenethyl)-2,3-dimethylpyrrolo[2,3-d]pyridazine-5-oxide; and Compound No. 3-83: 1-(2-Butenyl)-7-(2,4-difluorophenethyl)-2,3-dimethylpyrrolo[2,3-d]pyridazine-6-oxide.

The pyrrolopyridazine derivatives in the present invention can easily be prepared by the methods summarized in the following reaction scheme:

Method A

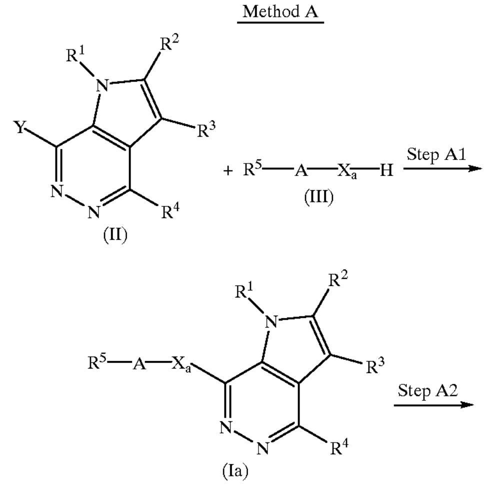

(II)
(III)
(Ia)

-continued

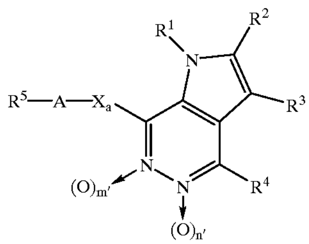

(Ib)

Method B

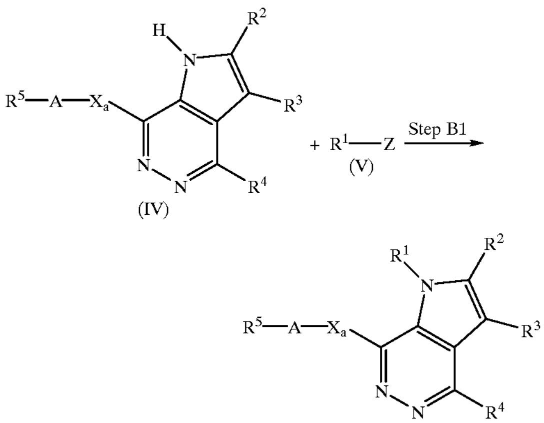

(IV) (V) (Ia)

Method C

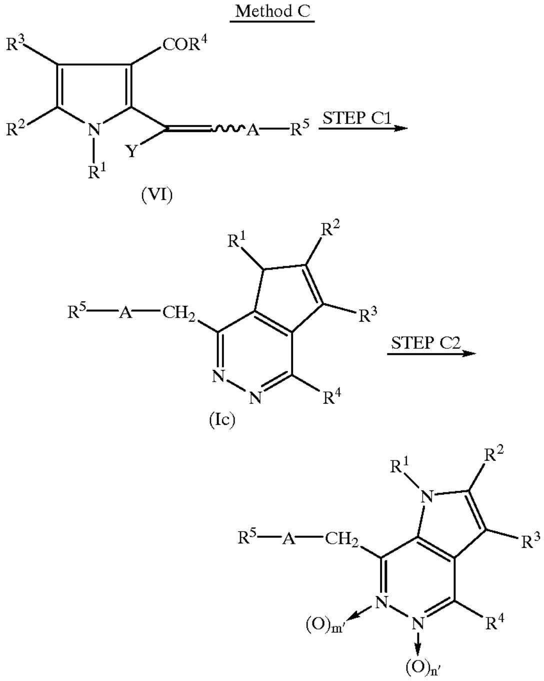

(VI) (Ic) (Id)

In the above formulae, $R^1$, $R^2$, $R^3$, $R^4$, $R^5$ and A are as defined above;

Xa represents an imino group, an oxygen or sulfur atom;

Y represents a halogen atom (preferably chlorine, bromine or iodine);

Z represents a halogen atom (preferably chlorine, bromine or iodine); a $C_1$–$C_4$alkanesulfonyloxy group optionally substituted with halogen atom(s) (such as methanesulfonyloxy, ethanesulfonyloxy, propanesulfonyloxy, butanesulfonyloxy, trifluoromethanesulfonyloxy or trichloromethanesulfonyloxy); a $C_6$–$C_{10}$arylsulfonyloxy group (such as benzenesulfonyloxy or p-toluenesulfonyloxy); or a halogeno-acetoxy group (such as trifluoroacetoxy or trichloroacetoxy);

m' is 0 or 1; and n' is 0 or 1, provided that both of m' and n' are not concurrently 0.

Method A involves the preparation of the compounds of formulae (Ia) and (Ib), that is, a formula (I) wherein X represents an imino group, an oxygen or a sulfur atom.

Step A1 is a step to prepare a compound of formula (Ia), that is, a formula (I) wherein X represents an imino group, an oxygen or a sulfur atom and n is 0, by reacting a compound of general formula (II) with a compound of general formula (III) in a solvent or without solvent in the presence or absence of a base.

The base used in this step may be, for example, an alkali metal hydride such as lithium hydride, sodium hydride or potassium hydride; alkali metal amides such as lithium amide, sodium amide or potassium amide; alkali metal carbonates such as sodium carbonate, potassium carbonate or lithium carbonate; alkali metal alkoxides such as sodium methoxide, sodium ethoxide, potassium tert-butoxide or lithium ethoxide; or organic amines such as triethylamine, tributylamine, diisopropylethylamine, N-methylmorpholine, pyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU); preferably an alkali metal hydride (particularly sodium hydride) or alkali metal alkoxide (particularly potassium tert-butoxide). The reaction in this reaction proceeds in the absence of a base. In order to carry out efficiently the reaction, it may be conducted in the presence of quaternary ammonium salts such as benzyltriethylammonium chloride or tetrabutylammonium chloride, crown ethers such as 18-crown-6 or dibenzo-18-crown-6 etc.

There is no particular limitation upon the nature of the solvent used in this step, provided that it has no adverse effect upon the reaction. Examples of suitable solvents include: for example, aliphatic hydrocarbons such as hexane, heptane, ligroin or petroleum ether; aromatic hydrocarbons such as benzene, toluene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitriles such as acetonitrile or isobutyronitrile; amides such as formamide, dimethylformamide, dimethylacetamide, N-methyl-2-pyrrolidone or hexamethylphosphoric triamide; sulfoxides such as dimethylsulfoxide or sulfolane; and mixtures of two or more of these organic solvents; and preferably ethers (particularly tetrahydrofuran or dioxane).

The compound of formula (Ia) may also be prepared by reacting a compound of formula (III) wherein Xa is an oxygen or sulfur atom, with an alkali metal (preferably sodium) in the presence of a solvent (preferably ethers) to give the corresponding alkolate or thiolate and subsequently by reacting the product with a compound of formula (II).

The reaction temperature is usually from 0° to 250° C. (preferably from room temperature to 200° C.). The time required for the reaction varies depending upon the reaction temperature and other factors, but it is from one minute to 50 hours (preferably from 5 minutes to 30 hours).

Where a compound of formula (II) wherein $R^1$ is an alkenyl or alkynyl group, is used as a reactant, a compound of formula (Ia) produced may be converted to an isomer by isomerization.

After completion of the reaction, the desired compound of formula (Ia) in this reaction may be recovered from the reaction mixture by conventional means. An example of one such technique comprises: filtering conveniently off insoluble material, if any; and distilling off the solvent under reduced pressure; or after distilling off the solvent under reduced pressure, adding water to the residue; extracting with a water-immiscible organic solvent such as ethyl acetate; drying the extract over anhydrous magnesium sulfate or the like; and finally distilling off the solvent. The product, if necessary, may be purified by conventional means such as recrystallization, column chromatography and the like. Step A2 is a step to prepare a compound of formula (Ib), that is, a compound of formula (I) wherein X represents an imino group, an oxygen or sulfur atom; m is m'; and n is n' (m' and n' are as defined above), by reacting a compound of formula (Ia) with an oxidizing agent in the presence of an inert solvent.

Examples of oxidizing agents used include: for example, peroxy acids such as peracetic acid, perbenzoic acid or m-chloroperoxybenzoic acid; hydrogen peroxide; or alkali metal salts of peroxyhalogenous acid such as sodium meta-perchlorate, sodium meta-periodate or potassium meta-periodate; preferably peroxy acids or hydrogen peroxide; and particularly preferably m-chloroperoxybenzoic acid.

There is no particular limitation upon the nature of the solvents used in this step, provided that it has no adverse effect upon the reaction and may dissolve the starting material to some extent. Examples of suitable solvents include: for example, hydrocarbons such as hexane, benzene, toluene or xylene; halogenated hydrocarbons such as dichloromethane, chloroform, carbon tetrachloride, dichloroethane, chlorobenzene or dichlorobenzene; alcohols such as methanol, ethanol, propanol or butanol; esters such as ethyl acetate, propyl acetate, butyl acetate or ethyl propionate; carboxylic acids such as acetic acid or propionic acid; water; and mixtures of two or more of these solvents; and preferably halogenated hydrocarbons (particularly dichloromethane or chloroform) or carboxylic acids (particularly acetic acid).

The reaction temperature is usually from −20° to 150° C. (preferably from 0° C. to 100° C.). The time required for the reaction varies depending upon the reaction temperature and other factors but it is from 10 minutes to 5 hours (preferably from 20 minutes to 2 hours).

After completion of the reaction, the desired compound of formula (Ib) in this reaction may be recovered from the reaction mixture by conventional means. An example of one such technique comprises: filtering conveniently off insoluble material, if any; and distilling off the solvent under reduced pressure; or after distilling off the solvent under reduced pressure, adding water to the residue; extracting with a water-immiscible organic solvent such as ethyl acetate; drying the extract over anhydrous magnesium sulfate or the like; and finally distilling off the solvent. The product, if necessary, may be purified by conventional means such as recrystallization, column chromatography and the like.

Method B is an alternative method to prepare a compound of formula (Ia).

Step B1 is a step to prepare a compound of formula (Ia) by reacting a compound of general formula (IV) with a compound of general formula (V) in an inert solvent or without solvent in the presence or absence of a base. The reaction may be carried out in a similar manner to that of Step A1 in Method A.

Method C is a method to prepare the compounds of formulae (Ic) and (Id) that is, a compound of formula (I) wherein X represents a methylene group.

Step C1 is a step to prepare a compound of formula (Ic) by reacting a compound of formula (VI) with hydrazine or its hydrate in an inert solvent.

There is no particular limitation upon the nature of the inert solvent used in this step, provided that it has no adverse effect upon the reaction and may dissolve the starting material-to some extent. Examples of suitable solvents include: for example, ethers such as diethyl ether, diisopropyl ether, tetrahydrofuran, dioxane, dimethoxyethane or diethylene glycol dimethyl ether; alcohols such as methanol, ethanol, propanol or butanol; carboxylic acids such as acetic acid or propionic acid; amides such as formamide, dimethylformamide, dimethylacetamide, N-methyl-2-pyrrolidone or hexamethylphosphoric triamide; amines such as triethylamine or pyridine; and water; and preferably alcohols (particularly ethanol) or carboxylic acids (particularly acetic acid).

The reaction temperature is usually from −50° to 150° C. (preferably from −10° to 100° C.). The time required for the reaction varies depending upon the reaction temperature and other factors, but it is from 10 minutes to 12 hours (preferably from 30 minutes to 5 hours).

After completion of the reaction, the desired compound of formula (Ic) in this reaction may be recovered from the reaction mixture by conventional means. An example of one such technique comprises: filtering conveniently off insoluble material, if any; and distilling off the solvent under reduced pressure; or after distilling off the solvent under reduced pressure, adding water to the residue; extracting with a water-immiscible organic solvent such as ethyl acetate; drying the extract over anhydrous magnesium sulfate or the like; and finally distilling off the solvent. The product, if necessary, may be purified by conventional means such as recrystallization, column chromatography and the like.

Step C2 is a step to prepare a compound of formula (Id), that is, a compound of formula (I) wherein X represents a methylene group; m is m'; and n is n' (m' and n' are as defined above), by reacting a compound of formula (Ic) with an oxidizing agent in an inert solvent and the step may be carried out in a similar manner to that of step A2.

The starting materials of formulae (II), (IV) and (VI), may easily be prepared by methods summarized in the following reaction scheme:

Method D

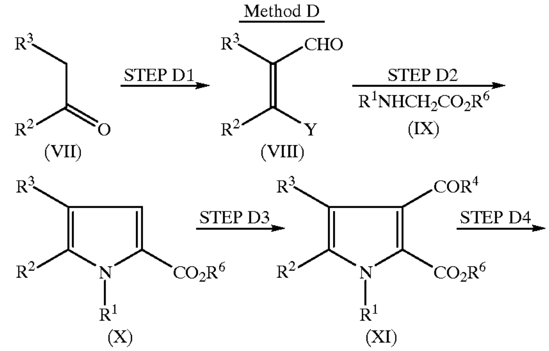

-continued

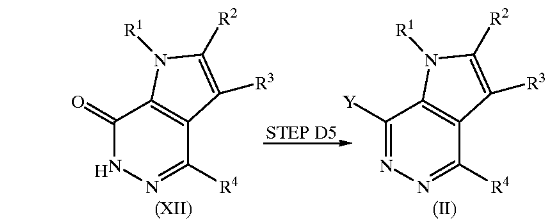

Method E

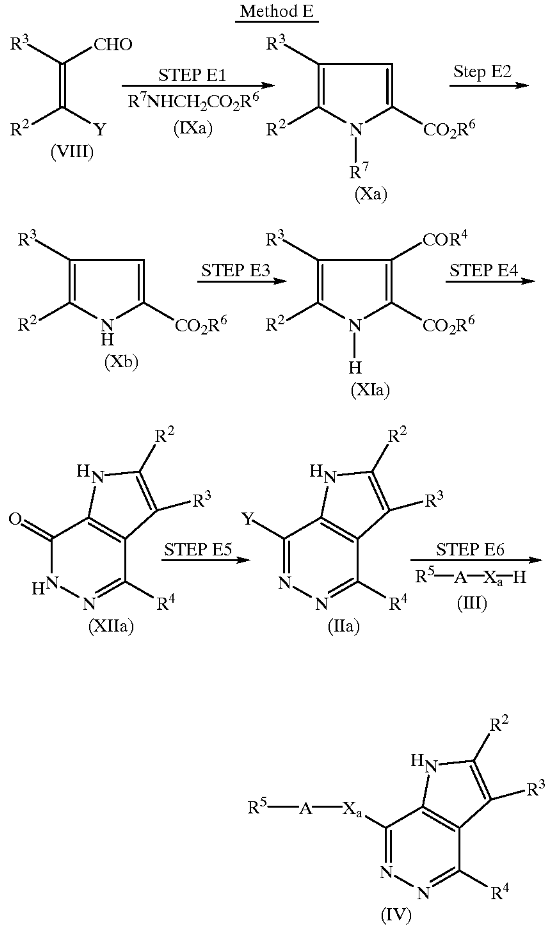

Method F

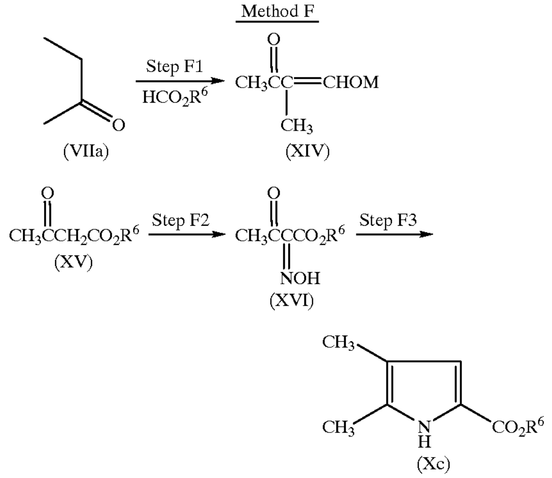

-continued

Method G

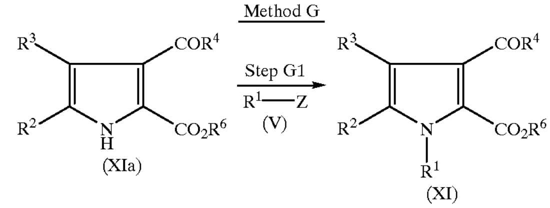

Method H

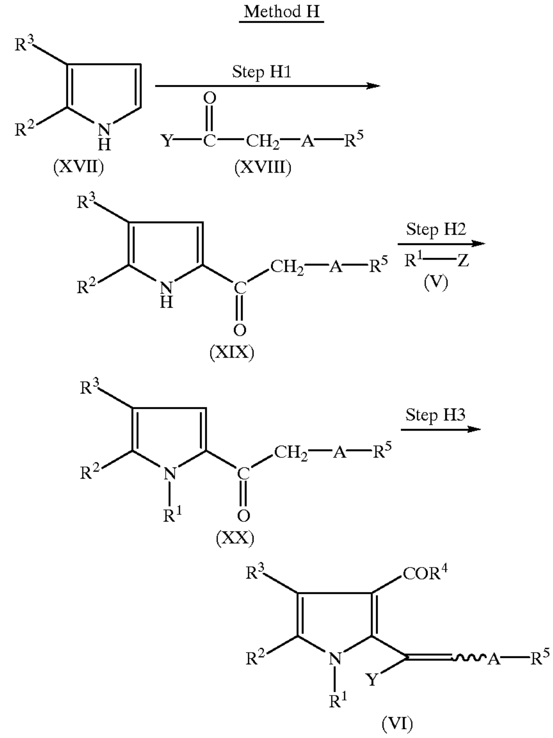

Method I $$\underset{(XXI)}{R^1NH_2} + \underset{(XXII)}{YCH_2CO_2R^6} \xrightarrow{\text{Step I1}} \underset{(IX)}{R^1NHCH_2CO_2R^6}$$

Method J $$\underset{(XXIII)}{R^7\text{—}Y} + \underset{(XXIV)}{H_2NCH_2CO_2R^6} \xrightarrow{\text{Step J1}} \underset{(IXa)}{R^7NHCH_2CO_2R^6}$$

In the above formulae, $R^1$, $R^2$, $R^3$, $R^4$ $R^5$, A, Xa, Y and Z are as defined above;

$R^6$ represents a $C_1$–$C_6$ alkyl group;

$R^7$ represents an amino-protecting group, and preferably a tert-butoxycarbonyl group, a $C_6$-arylmethyl group such as a benzyl, p-methoxybenzyl or p-bromobenzyl or a $C_6$-arylmethoxycarbonyl group such as benzyloxycarbonyl, p-methoxybenzyloxycarbonyl or a p-bromobenzyloxycarbonyl; and M represents an alkali metal such as lithium, sodium or potassium (preferably sodium).

Method D is a method to prepare a compound of formula (II).

Step D1 is a step to prepare a compound of general formula (VIII) by reacting a compound of general formula (VII) with a Vilsmeier reagent such as phosphorus oxychloride-dimethylformamide, phosphorus oxybromide-dimethylformamide or oxalyl chloride-dimethylformamide in an inert solvent (for example, halogenated hydrocarbons such as dichloromethane, chloroform, carbon tetrachloride or 1,2-dichloroethane; or amides such as a dimethylformamide) at from −10° to 150° C. (preferably from 0° C. to 100° C.) for from 15 minutes to 12 hours (preferably from 30 minutes to 5 hours).

Step D2 is a step to prepare a compound of general formula (X) by reacting a compound of formula (VIII) with a compound of general formula (IX) in an inert solvent (for example, aromatic hydrocarbons such as benzene or toluene; halogenated hydrocarbons such as dichloromethane or chloroform; ethers such as diethyl ether, diisopropyl ether, tetrahydrofuran or dioxane; alcohols such as methanol, ethanol or propanol; amides such as dimethylformamide or dimethylacetamide; or amines such as triethylamine or pyridine) in the presence of a base (for example, organic amines such as triethylamine or pyridine) at a temperature of from −10° to 150° C. (preferably from 0° to 50° C.) for from 30 minutes to 24 hours (preferably 1 to 10 hours).

Step D3 is a step to prepare a compound of general formula (XI). A Compound of formula (XI) wherein $R^4$ is a hydrogen atom, may be prepared by reacting a compound of formula (X) with a Vilsmeier reagent in a similar manner to Step D1. A compound of formula (XI) wherein $R^4$ represents a $C_1$–$C_6$ alkyl group may be prepared by reacting a compound of formula (X) with an acid anhydride or acid halide having a formula:

$$(R^4aCO)_2O \text{ or } R^4aCOY$$

(wherein Y is as defined above, and $R^4a$ represents a $C_1$–$C_6$ alkyl group) in an inert solvent (for example, aromatic hydrocarbons such as benzene, toluene or nitrobenzene; halogenated hydrocarbons such as dichloromethane, chloroform, carbon tetrachloride or 1,2-dichloroethane; or carbon disulfide) in the presence of a Lewis acid (for example, aluminium chloride, stannic chloride or zinc chloride) at from −10° to 150° C. (preferably from 0° to 100° C.) for from 10 minutes to 12 hours (preferably 30 minutes to 5 hours).

Step D4 is a step to prepare a compound of general formula (XII) by reacting a compound of formula (XI) with hydrazine or its hydrate in an inert solvent in a similar manner to Step C1 in Method C described above.

Step D5 is a step to prepare a compound of formula (II) by reacting a compound of formula (XII) with a halogenating agent (for example, phosphorus oxychloride, phosphorus oxybromide, oxalyl chloride, thionyl chloride, phosphorus pentachloride or phosphorus pentabromide) in an inert solvent (for example, halogenated hydrocarbons such as dichloromethane or chloroform; ethers such as diethyl ether, tetrahydrofuran or dioxane; amides such as dimethylformamide or dimethylacetamide; or sulfoxides such as dimethylsulfoxide) or without solvent at from 10° to 150° C. (preferably from 50° to 120° C.) for from 30 minutes to 12 hours (preferably from 1 to 5 hours).

Method E is a method to prepare a compound of formula (IV).

Step E1 is a step to prepare a compound of general formula (Xa) by reacting a compound of general formula (VIII) with a compound of general formula (IXa) in a similar manner to Step D2 in Method D described before.

Step E2 is a step to prepare a compound of general formula (Xb) by removing the amino-protecting group of a compound of formula (Xa).

When the amino-protecting group is a tert-butoxycarbonyl group, it may be removed by treating with an acid (for example, inorganic acids such as hydrogen chloride, hydrochloric acid, sulfuric acid or nitric acid; or organic acids such as acetic acid, trifluoroacetic acid, methanesulfonic acid or p-toluenesulfonic acid) in an inert solvent (for example, halogenated hydrocarbons such as dichloromethane, chloroform or carbon tetrachloride; or ethers such as ether, tetrahydrofuran or dioxane) at a temperature of from −10° to 100° C. (preferably from −5° to 50° C.) for from 5 minutes to 48 hours (preferably from 30 minutes to 10 hours).

When the amino-protecting group is a $C_6$ arylmethyl or $C_6$ arylmethoxycarbonyl group, it may be removed by reacting with hydrogen of from 1 to 10 atmospheric pressures in the presence of a catalyst (for example, palladium on charcoal, palladium black, platinum oxide, platinum black or the like, preferably palladium on charcoal) in an inert solvent (for example, alcohols such as methanol, ethanol or isopropanol; ethers such as ether, tetrahydrofuran or dioxane; or mixtures of two or more of these solvents) from 0° to 100° C. (preferably from 200 to 70° C.) for from 5 minutes to 48 hours (preferably from 1 to 24 hours).

Step E3 is a step to prepare a compound of general formula (XIa) by acylating a compound of formula (Xb) in a similar manner to Step D3 in Method D described before.

Step E4 is a step to prepare a compound of general formula (XIIa) by reacting a compound of formula (XIa) with hydrazine or its hydrate in a similar manner to Step C1 in Method C described before.

Step E5 is a step to prepare a compound of general formula (IIa) by reacting a compound of formula (XIIa) with a halogenating agent in a similar manner to Step D5 in Method D described before.

Step E6 is a step to prepare a compound of general formula (IV) by reacting a compound of formula (IIa) with a compound of formula (III) in a similar manner to Step A1 in Method A described before.

Method F is a method to prepare a compound of formula (Xc) which is an intermediate in Method E, that is, a compound of formula (Xb) wherein each of $R^2$ and $R^3$ is a methyl group.

Step F1 is a step to prepare a compound of general formula (XIV) by reacting a compound of general formula (VIIa) with a compound of general formula (XIII) in an inert solvent (for example, hydrocarbons such as hexane, benzene or toluene; ethers such as diethyl ether, diisopropyl ether, tetrahydrofuran, dioxane, dimethoxyethane or diethylene glycol dimethyl ether; or amides such as dimethylformamide or dimethylacetamide) in the presence of a base (for example, alkali metals such as lithium, sodium or potassium; alkali metal hydrides such as lithium hydride, sodium hydride or potassium hydride; alkali metal amides such as lithium amide, sodium amide or potassium amide; or alkali metal alkoxides such as lithium ethoxide, sodium methoxide, sodium ethoxide or potassium tert-butoxide) at from −10° to 100° C. (preferably from 0° to 50° C.) for from 30 minutes to 48 hours (preferably from 2 to 20 hours).

Step F2 is a step to prepare a compound of general formula (XVI) by reacting a compound of general formula (XV) with an alkali metal nitrite (for example, lithium nitrite, sodium nitrite, potassium nitrite or the like) in an inert solvent (for example,-ethers such as diethyl ether, tetrahydrofuran, dioxane or dimethoxyethane; carboxylic acids such as acetic acid or propionic acid; amides such as dimethylformamide or dimethylacetamide; water; or mixtures of two or more of these solvents) at from −20° to 50° C. (preferably from 0° to 20° C.) for from 15 minutes to 48 hours (preferably from 30 minutes to 20 hours).

Step F3 is a step to prepare a compound of formula (Xc) by reacting a compound of formula (XVI) with a compound of formula (XIV) in an inert solvent (for example, ethers such as diethyl ether, tetrahydrofuran, dioxane or dimethoxyethane; carboxylic acids such as acetic acid or propionic acid; amides such as dimethylformamide or dimethylacetamide; water; or mixtures of two or more of these solvents) in the presence of a reducing agent (for example, zinc, tin, iron or the like) at from 20° to 150° C. (preferably from 50° to 100° C.) for from 30 minutes to 10 hours (preferably from 1 to 5 hours).

Method G is an alternative method to prepare a compound of formula (XI) which is an intermediate in Method D.

Step G1 is a step to prepare a compound of formula (XI) by reacting a compound of general formula (XIa) with a compound of formula (V) in a similar manner to Step B1 in Method B described before.

Method H is a method to prepare a compound of formula (VI).

Step H1 is a step to prepare a compound of general formula (XIX) by reacting a compound of general formula (XVII) with a Grignard reagent having a general formula:

$R^6$—Mg—Y (wherein $R^6$ to Y are as defined above) in an inert solvent (for example, ethers such as diethyl ether, diisopropyl ether, tetrahydrofuran, dioxane or dimethoxyethane) at from −10° to 100° C. (preferably from 0° to 70° C.) for from 10 minutes to 6 hours (preferably from 20 minutes to 2 hours) to give a magnesium compound and subsequently by reacting the magnesium compound with a compound of general formula (XVIII) at from −100° to 50° C. (preferably from −78° to 0° C.) for from 10 minutes to 6 hours (preferably from 30 minutes to 3 hours).

Step H2 is a step to prepare a compound of general formula (XX) by reacting a compound of formula (XIX) with a compound of formula (V) in a similar manner to Step B1 in Method B described before.

Step H3 is a step to prepare a compound of general formula (VI). A compound of formula (VI) wherein $R^4$ represents a hydrogen atom may be prepared by reacting a compound of formula (XX) with a Vilsmeier reagent in a similar manner to Step D1 in Method described before. A compound of formula (VI) wherein $R^4$ represents a $C_1$–$C_6$ alkyl group may be prepared by reacting a compound of formula (XX) with a compound having formula: 4 4

$(R^4aCO)_2O$ or $R^4aCOY$ (wherein $R^4$a and Y are as defined above) in a similar manner to Step D3 in Method D described before and subsequently by reacting the product with a Vilsmeier reagent in a similar manner as Step D1 of Method D described before.

Method I is a method to prepare a compound of formula (IX) which is a starting compound in Method D.

Step I1 is a step to prepare a compound of formula (IX) by reacting a compound of general formula (XXI) with a compound of general formula (XXII) in an inert solvent (for example, hydrocarbons such as hexane, benzene or toluene; halogenated hydrocarbons such as dichloromethane or chloroform; ethers such as diethyl ether, diisopropyl ether, tetrahydrofuran, dioxane or dimethoxyethane; ketones such as acetone or methyl ethyl ketone; amides such as dimethylformamide or dimethylacetamide; or sulfoxides such as dimethylsulfoxide) in the presence or absence of a base (for example, alkali metal carbonates such as lithium carbonate, sodium carbonate or potassium carbonate; or organic amines such as triethylamine, tributylamine, diisopropylethylamine, N-methylmorpholine, pyridine, picoline or 4-(N,N-dimethylamino)pyridine) at from −10° to 150° C. (preferably from 0° C. to 100° C.) for from 30 minutes to 48 hours (preferably from 1 to 20 hours). Method J is a method to prepare a compound of general formula (IXa) which is a starting compound in Method E.

Step J1 is a step to prepare a compound of formula (IXa) by reacting a compound of general formula (XXIII) with a compound of general formula (XXIV) in a similar manner to Step I1 in Method I described before.

A compound of formula (Ia), (Ib), (Ic), (Id), (II), (VI), (X), (XI) or (XII), wherein $R^1$ represents a halogeno-alkyl group, if desired, may be dehydrohalogenated by treating with a base (for example, organic amines such as DBN, DBU, DABCO or the like) in an inert solvent (for example, ethers such as diethyl ether, tetrahydrofuran or dioxane) at from 0° to 150° C. (preferably from 50° to 100° C.) for from 30 minutes to 20 hours (preferably from 1 to 10 hours) to give an alkenyl derivative.

After completion of the reaction, each of the desired compounds in the above reactions may be recovered from the reaction mixture by conventional means. For example, one such technique comprises: filtering conveniently off insoluble material, if any; and distilling off the solvent under reduced pressure; or after distilling off the solvent under reduced pressure, adding water to the residue; extracting with a water-immiscible organic solvent such as ethyl acetate; drying the extract over anhydrous magnesium sulfate etc.; and finally distilling off the solvent. The product, if necessary, may be purified by conventional means, such as recrystallization, column chromatography or the like.

(Effect of Invention)

The pyrrolopyridazine derivatives of the present invention have an excellent gastric secretion inhibiting acitivty, gastric mucosa protective activity and antibacterial activity against *Helicobacter pylori.* Therefore, the derivatives are useful as a preventive and therapeutic agent for ulcerous diseases such as peptic ulcer, acute or chronic gastric ulcer, duodenal ulcer, gastritis, reflux esophagitis, gastroesophageal parareflexia, dyspepsia, gastric hyperacidity, Zollinger-Ellison syndrome etc., as a preventive agent for postoperative ulcerous diseases or as an antibacterial agent against *Helicobacter pylori.*

[Possible usefulness in industry]

As mentioned above, the pyrrolopyridazine derivatives (I) of the present invention have an excellent gastric secretion inhibiting activity and so on, and the derivatives are useful as a preventive or therapeutic agent for ulcerous diseases. The mode of administration of the pyrrolopyridazine derivatives (I) to use as a preventive or therapeutic agent for ulcerous diseases, may be oral administration by use of, for example, tablets, capsules, granules, powders, syrups etc.; or parenteral administration by use of, for example, injections. These drug preparations can be prepared according to conventional means by use of additives including: vehicles such as lactose, mannite, corn starch, crystalline cellulose etc.; binders such as cellulose derivatives, gum arabic, gelatin etc.; disintegrators such as calcium carboxymethylcellulose etc.; lubricants such as talc, magnesium stearate etc.; stabilizers; corrigents; solvents for injection such as water, ethanol, glycerin etc. The dosage may be variable depending on the symptom, age of patients etc., but a dosage from 1 mg to 1000 mg (preferably from 10 mg to 500 mg) for an adult may be administered once or divided into several doses a day.

[The best embodiment in order to perform the invention]

The following Examples, Referential Examples and Test Examples illustrate the invention in more detail. However such examples are not to be construed as being limitative of the scope of the invention.

EXAMPLE 1

1-(2-Butenyl)-7-(4-fluorobenzyloxy)-2,3-dimethylpyrrolo [2, 3-d]pyridazine 0.85 g (0.0076 mole) of potassium tert-butoxide was added to a solution of 0.48 g-(0.0038 mole) of 4-fluorobenzyl alcohol and 0.08 g (0.0003 mole) of 18-crown-6 in 30 ml of tetrahydrofuran and the mixture was stirred at room temperature for 10 minutes. 0.45 g (0.0019 mole) of 1-(2-butenyl)-7-chloro-2,3-dimethylpyrrolo[2,3-d] pyridazine was then added to the mixture and stirred at room temperature for 8 hours. After completion of the reaction, the reaction mixture was poured into ice-water and the aqueous mixture was extracted with dichloromethane. The extract was dried over anhydrous sodium sulfate and the solvent was distilled off under reduced pressure. The residue was purified by column chromatography through silica gel using a 4:1 mixture of toluene and ethyl acetate as an eluent. An oily material thus obtained was crystallized in hexane to give 0.39 g of 1-(2-butenyl)-7 -(4-fluorobenzyloxy)-2,3-dimethylpyrrolo[2,3-d]pyridazine (cis/trans=13/87) as a pale brown powder.

m.p.: 93–103° C.

Mass spectrum (CI, m/z): 326 ($M^+$+1).

NMR spectrum ($CDCl_3$, δppm): 1.50–1.67 (m, 3H), 2.26 (s, 3H), 2.31 (s, 3H), 4.79–4.89 (m, 1.74H), 4.98–5.04 (m, 0.26H), 5.10–5.58 (m, 2H), 5.67 (s, 2H), 7.00–7.12 (m, 2H), 7.41–7.54 (m, 2H), 8.97 (s, 1H).

Elementary analysis (%): Calc'd for $C_{17}H_{20}FN_3O$: C, 70.17; H, 6.07; N, 12.91, Found: C, 70.20; H, 6.18; N, 12.84.

EXAMPLE 2

7-Benzyloxy-2,3-dimethyl-1-(3-methyl-2-butenyl)pyrrolo [2,3-d]pyridazine

The title compound was prepared as a white powder in -6.2% yeild in a similar procedure to that described in Example 1 by using 7-chloro-2,3-dimethyl-1-(3-methyl-2-butenyl)pyrrolo[2,3-d]pyridazine and benzyl alcohol.

m.p.: 104–105° C.

Mass spectrum (CI, m/z): 322 ($M^+$+1).

NMR spectrum ($CDCl_3$, δppm): 1.60 (s, 3H), 1.63 (s, 3H), 2.26 (s, 3H), 2.33 (s, 3H), 4.98 (d;J=6 Hz, 2H), 5.11 (t;J=6 Hz, 1H), 5.73 (s, 2H), 7.30–7.42 (m, 3H), 7.50–7.55 (m, 2H) , 8.99 (s, 1H)

Elementary analysis (%): Calc'd for $C_{20}H_{23}N_3O$: C, 74.74; H, 7.21; N, 13.07, Found: C, 74.74; H, 7.28; N, 12.99.

EXAMPLE 3

7-Benzyloxy-2,3-dimethyl-1-(2-propenyl)pyrrolo[2,3-d] pyridazine

The title compound was prepared as a white powder in 63.2% yield in a similar procedure to that described in Example 1 by using 7-chloro-2,3-dimethyl-1-(2-propenyl) pyrrolo[2,3-d]pyridazine and benzyl alcohol.

m.p.: 115–116° C.

Mass spectrum (CI, m/z): 294 ($M^+$+1).

NMR spectrum ($CDCl_3$, δppm): 2.27 (s, 3H), 2.30 (s, 3H), 4.61 (d;J=16 Hz, 1H), 4.92–5.00 (m, 2H), 5.08 (d;J=10 Hz, 1H), 5.69 (s, 2H), 5.83–5.97 (m, 1H), 7.30–7.53 (m, 5H), 8.99 (s, 1H).

Elementary analysis (%): Calc'd for $C_{18}H_{19}N_3O$: C, 73.70; H, 6.53; N, 14.32, Found: C, 73.69; H, 6.59; N, 14.14.

EXAMPLE 4

7-Benzyloxy-1-cyclopropylmethyl-2,3-dimethylpyrrolo[2, 3-d]pyridazine

The title compound was prepared as a white powder in 69.2% yield in a similar procedure to that described in Example 1 by using 7-chloro-1-cyclopropylmethyl-2,3-dimethylpyrrolo[2,3-d]pyridazine and benzyl alcohol.

m.p.: 123–124° C.

Mass spectrum (CI, m/z): 308 ($M^+$+1).

NMR spectrum ($CDCl_3$, δppm): 0.21–0.45 (m, 4H), 1.06–1.21 (m, 1H), 2.28 (s, 3H), 2.39 (s, 3H), 4.24 (d;J=8 Hz, 2H), 5.70 (s, 2H), 7.29–7.56 (m, 5H), 8.99 (s, 1H).

Elementary analysis (%): Calc'd for $C_{19}H_{21}N_3O$: C, 74.24; H, 6.89.; N, 13.67, Found; C, 74.42; H, 6.90; N, 13.66.

EXAMPLE 5

7-Benzyloxy-1-(2-butenyl)-2,3-dimethylpyrrolo[2,3-d] pyridazine

The title compound (cis/trans=21/79) was prepared as pale brown crystals in 78.6 % yield in a similar procedure to that described in Example 1 by using 1-(2-butenyl)-7-chloro-2,3-dimethylpyrrolo[2,3-d]pyridazine [cis/trans (18/82)] and benzyl alcohol.

m.p.: 81–84° C.

Mass spectrum (CI, m/z): 308 ($M^+$+1).

NMR spectrum ($CDCl_3$, δppm): 1.50–1.66 (m, 3H), 2.25 (s, 3H), 2.31 (s, 3H), 4.79–4.91 (m, 1.58H), 4.97–5.07 (m, 0.42H), 5.10–5.61 (m, 2H), 5.71 (s, 2H), 7.27–7.56 (m, 5H), 8.97 (s, 1H).

Elementary analysis (%): Calc'd for $C_{19}H_{21}N_3O$: C, 74.24; H, 6.89; N, 13.67, Found: C, 74.14; H, 6.97; N, 13.57.

EXAMPLE 6

7-Benzyloxy-2,3-dimethyl-1-(3-phenyl-2-propenyl)pyrrolo [2,3-d]pyridazine

The title compound (trans) was prepared as pale brown crystals in 85.4% yield in a similar procedure to that described in Example 1 by using 7-chloro-2,3-dimethyl-1-(3-phenyl-2-propenyl)pyrrolo[2,3-d]pyridazine (trans) and benzyl alcohol.

m.p.: 132–134° C.

Mass spectrum (CI, m/z): 370 ($M^+$+1).

NMR spectrum ($CDCl_3$, δppm): 2.28 (s, 3H), 2.37 (s, 3H), 5.10 (d;J=5 Hz, 2H), 5.71 (s, 2H), 6.07 (d;J=16 Hz, 1H), 6.22 (dt;J=16 Hz, 5 Hz, 1H), 7.10–7.55 (m, 10H), 9.00 (s, 1H).

Elementary analysis (%): Calc'd for $C_{24}H_{23}N_3O$: C, 78.02; H, 6.27; N, 11.37, Found: C, 78.09; H, 6.28; N, 11.32.

EXAMPLE 7

7-(4-Fluorobenzyloxy)-2,3-dimethyl-1-(2-propenyl)pyrrolo [2,3-d]pyridazine

The title compound was prepared as a white powder in 22.1% yield in a similar procedure to that described in Example 1 by using 7-chloro-2,3-dimethyl-1-(2-propenyl) pyrrolo[2,3-d]pyridazine and 4-fluorobenzyl alcohol.

m.p.: 125–126° C.

Mass spectrum (CI, m/z): 312 ($M^+$+1).

NMR spectrum ($CDCl_3$, δppm): 2.27 (s, 3H), 2.30 (s, 3H), 4.62 (d;J=14 Hz, 1H), 4.90–4.97 (m, 2H), 5.07 (d;J=10 Hz, 1H), 5.65 (s, 2H), 5.81–5.96 (m, 1H), 7.01–7.11 (m, 2H), 7.43–7.42 (m, 2H), 8.99 (s, 1H).

Elementary analysis (%): Calc'd for $C_{18}H_{18}FN_3O$: C, 69.43; H, 5.83; N, 13.50, Found: C, 69.23; H, 5.94; N, 13.45.

EXAMPLE 8

7-(3-Fluorobenzyloxy)-2,3-dimethyl-1-(2-propenyl)pyrrolo[2,3-d]pyridazine

The title compound was prepared as white cottony crystals in 71.4% yield in a similar procedure to that described in Example 1 by using 7-chloro-2,3-dimethyl-1-(2-propenyl)pyrrolo[2,3-d]pyridazine and 3-fluorobenzyl alcohol.

m.p.: 85–86° C.

Mass spectrum (CI, m/z) : 312 ($M^+$+1).

NMR spectrum ($CDCl_3$, δppm): 2.28 (s, 3H), 2.31 (s, 3H), 4.63 (d;J=14 Hz, 1H), 4.94–5.02 (m, 2H), 5.11 (d;J=10 Hz, 1H), 5.70 (s, 2H), 5.86–6.01 (m, 1H), 6.98–7.07 (m, 1H), 7.16–7.40 (m, 3H), 9.00 (s, 1H).

Elementary analysis (%): Calc'd for $C_{18}H_{18}FN_3O$: C, 69.44; H, 5.83; N, 13.50, Found: C, 69.34; H, 5.85; N, 13.40.

EXAMPLE 9

7-(2,4-Difluorobenzyloxy)-2,3-dimethyl-1-(2-propenyl)pyrrolo[2,3-d]pyridazine

The title compound was prepared as a white powder in 26.6% yield in a similar procedure to that described in Example 1 by using 7-chloro-2,3-dimethyl-1-(2-propenyl)pyrrolo[2,3-d]pyridazine and 2,4-difluorobenzyl alcohol.

m.p.: 125–126° C.

Mass spectrum (CI, m/z): 330 ($M^+$+1).

NMR spectrum ($CDCl_3$, δppm): 2.25 (s, 3H), 2.30 (s, 3H), 4.62 (d;J=14 Hz, 1H), 4.90 (d;J=5 Hz, 2H), 5.05 (d;J=10 Hz, 1H), 5.71 (9, 2H), 5.81–5.91 (m, 1H), 6.80–6.90 (m, 2H), 7.51–7.57 (m, 1H), 8.98 (s, 1H).

Elementary analysis (%): Calc'd for $C_{18}H_{17}F_2N_3O$: C, 65.64; H, 5.20; N, 12.76, Found: C, 65.64; H, 5.21; N, 12.74.

EXAMPLE 10

7-(2-Fluorobenzyloxy)-2,3-dimethyl-1-(2-propenyl)nvrrolo[2,3-d]pyridazine

The title compound was prepared as a white powder in 74.8% yield in a similar procedure to that described in Example 1 by using 7-chloro-2,3-dimethyl-1-(2-propenyl)pyrrolo[2,3-d]pyridazine and 2-fluorobenzyl alcohol.

m.p.: 83–84° C.

Mass spectrum (CI, m/z): 312 ($M^+$+1).

NMR spectrum ($CDCl_3$, δppm): 2.25 (s, 3H), 2.30 (s, 3H), 4.63 (d;J=14 Hz, 1H), 4.89–4.95 (m, 2H), 5.04 (d;J=10 Hz, 1H), 5.77 (s, 2H), 5.81–5.95 (m, 1H), 7.04–7.19 (m, 2H), 7.27–7.38 (m, 1H), 7.51–7.59 (m, 1H), 8.99 (s, 1H).

Elementary analysis (%): Calc'd for $C_{18}H_{18}FN_3O$: C, 69.44; H, 5.83; N, 13.50, Found: C, 69.42; H, 5.87; N, 13.45.

EXAMPLE 11

7-Benzyloxy-2,3-dimethyl-1-(2-pentenyl)pyrrolo[2,3-d]pyridazine

The title compound (trans) was prepared as a white powder in 75.9% yield in a similar procedure to that described in Example 1 by using 7-chloro-2,3-dimethyl-1-(2-pentenyl)pyrrolo[2,3-d]pyridazine (trans) and benzyl alcohol.

m.p.: 92–93° C.

Mass spectrum (CI, m/z): 322 ($M^+$+1).

NMR spectrum ($CDCl_3$, δppm): 0.95 (t;J=12 Hz, 3H), 1.98–2.12 (m, 2H), 2.26 (s, 3H), 2.31 (s, 3H), 4.92–5.08 (m, 2H), 5.23–5.34 (m, 1H), 5.39–5.52 (m, 1H), 5.71 (s, 2H), 7.28–7.55 (m, 5H), 8.96 (s, 1H).

Elementary analysis (%): Calc'd for $C_{20}H_{23}N_3O$: C, 74.74; H, 7.21; N, 13.07, Found: C, 74.86; H, 7.31; N, 13.02.

EXAMPLE 12

7-(4-Chlorobenzyloxy)-2,3-dimethyl-1-(2-propenyl)povrrolo[2,3-d]pyridazine

The title compound was prepared as white crystals in 50.7% yield in a similar procedure to that described in Example 1 by using 7-chloro-2,3-dimethyl-1-(2-propenyl)pyrrolo[2,3-d]pyridazine and 4-chlorobenzyl alcohol.

m.p.: 98–99° C.

Mass spectrum (CI, m/z): 328 ($M^+$+1), 330 ($M^+$+3).

NMR spectrum ($CDCl_3$, δppm): 2.26 (s, 3H), 2.31 (s, 3H), 4.62 (d;J=14 Hz, 1H), 4.89–4.97 (m, 2H), 5.09 (d;J=10 Hz, 1H), 5.66 (s, 2H), 5.82–5.97 (m, 1H), 7.35 (d;J=8 Hz, 2H), 7.43 (d;J=8 Hz, 2H)., 8.99 (s, 1H).

Elementary analysis (%): Calc'd for $C_{18}H_{18}ClN_3O$: C, 65.95; H, 5.53; N, 12.82, Found: C, 65.95; H, 5.56; N, 12.78.

EXAMPLE 13

7-Benzyloxy-2,3-dimethyl-1-vinylpyrrolo[2,3-d]pyridazine

The title compound was prepared as a white powder in 59.7% yield in a similar procedure to that described in Example 1 by using 7-chloro-2,3-dimethyl-1-vinylpyrrolo[2,3-d]pyridazine and benzyl alcohol.

m.p.: 85–86° C.

Mass spectrum (CI, m/z): 280 ($M^+$+1).

NMR spectrum ($CDCl_3$, δppm): 2.28 (s, 3H), 2.43 (s, 3H), 5.18 (d;J=8 Hz, 1H), 5.22 (d;J=17 Hz, 1H), 5.72 (s, 2H), 7.29–7.57 (m, 6H) , 9.00 (s, 1H)

Elementary analysis (%): Calc'd for $C_{17}H_{17}N_3O$: C, 73.10; H, 6.13; N, 15.04, Found: C, 73.04; H, 6.30; N, 14.71.

EXAMPLE 14

7-Benzyloxy-2,3-dimethyl-1-(2-methyl-2-propenyl)-ovrrolo[2,3-d]pyridazine

The title compound was prepared as white crystals in 89.3% yield in a similar procedure to that described in Example 1 by using 7-chloro-2,3-dimethyl-1-(2-methyl-2-propenyl)pyrrolo[2,3-d]pyridazine and benzyl alcohol.

m.p.: 106–107° C.

Mass spectrum (CI, m/z): 308 ($M^+$+1).

NMR spectrum ($CDCl_3$, δppm): 1.60 (s, 3H), 2.26 (s, 6H), 4.01 (s, 1H), 4.76 (s, 1H), 4.81 (s, 2H), 5.66 (s, 2H), 7.30–7.51 (m, 5H), 9.00 (s, 1H).

Elementary analysis(%): Calc'd for $C_{19}H_{21}N_3O$: C, 74.24; H, 6.89; N, 13.67, Found: C, 74.18; H, 6.92; N, 13.67.

EXAMPLE 15

7-Benzyloxy-2,3-dimethyl-1-(2,2,2-trifluoroethyl)pyrrolo[2,3-d]pyridazine

The title compound was prepared as a white powder in 65.20% yield in a similar procedure to that described in Example 1 by using 7-chloro-2,3-dimethyl-1-(2,2,2-trifluoroethyl)pyrrolo[2,3-d]pyridazine and benzyl alcohol.

m.p.: 83–84° C.

Mass spectrum (CI, m/z): 336 ($M^+$+1).

NMR spectrum ($CDCl_3$, δppm): 2.27 (s, 3H), 2.37 (s, 3H), 4.93 (q, J=9 Hz, 2H), 5.70 (s, 2H), 7.30–7.58 (m, 5H), 9.01 (s, 1H).

Elementary analysis (%): Calc'd for $C_{17}H_{16}F_3N_3O$: C, 60.89; H, 4.81; N, 12.53, Found: C, 60.96; H, 4.77; N, 12.45.

EXAMPLE 16

7-Benzyloxy-1-cyclopropyl-2,3-dimethylpyrrolo[2,3-d]pyridazine

The title compound was prepared as a white powder in 78.6% yield in a similar procedure to that described in Example 1 by using 7-chloro-1-cyclopropyl-2,3-dimethylpyrrolo[2,3-d]pyridazine and benzyl alcohol.

m.p.: 121–122° C.

Mass spectrum (CI, m/z): 294 ($M^+$+1).

NMR spectrum ($CDCl_3$, δppm): 0.87–1.10 (m, 4H), 2.22 (s, 3H), 2.43 (s, 3H), 3.18–3.28 (m, 1H), 5.69 (s, 2H), 7.30–7.59 (m, 5H) , 8.95 (s, 1H)

Elementary analysis (%): Calc'd for $C_{18}H_{19}N_3O$: C, 73.69; H, 6.53; N, 14.33, Found: C, 73.78; H, 6.56; N, 14.37.

EXAMPLE 17

7-(2,4-Dichlorobenzyloxy)-2,3-dimethyl-1-(2-propenyl)pyrrolo[2,3-d]pyridazine

The title compound was prepared as white crystals in 76.5% yield in a similar procedure to that described in Example 1 by using 7-chloro-2,3-dimethyl-1-(2-propenyl)pyrrolo[2,3-d]pyridazine and 2,4-dichlorobenzyl alcohol.

m.p.: 98–99° C.

Mass spectrum (CI, m/z): 361 ($M^+$), 363 ($M^+$+2).

NMR spectrum ($CDCl_3$, δppm): 2.26 (s, 3H), 2.30 (s, 3H), 4.63 (d, J=16 Hz, 1H), 4.91–4.98 (m, 2H), 5.05–5.09 (d;J=11 Hz, 1H), 5.77 (s, 2H), 5.83–5.98 (m, 1H), 7.20–7.29 (m, 1H), 7.42–7.56 (m, 2H), 9.00 (s, 1H).

Elementary analysis (%): Calc'd for $C_{18}H_{17}Cl_2N_3O$: C, 59.68; H, 4.73; N, 11.60, Found: C, 59.71; H, 4.79; N, 11.52.

EXAMPLE 18

7-Benzyloxy-1-(2-fluoroethyl)-2,3-dimethylpyrrolo[2,3-d]pyridazine

The title compound was prepared as white crystals in 76.2% yield in a similar procedure to that described in Example 1 by using 7-chloro-1-(2-fluoroethyl)-2,3-dimethylpyrrolo[2,3-d]pyridazine and benzyl alcohol.

m.p.: 106–107° C.

Mass spectrum (CI, m/z): 300 ($M^+$+1).

NMR spectrum ($CDCl_3$, 67 ppm): 2.27 (s, 3H), 2.35 (s, 3H), 4.51 (s, 2H), 4.64 (dt;J=21 Hz, 4 Hz, 2H), 5.69 (s, 2H), 7.29–7.51 (m, 5H), 8.99 (s, 1H).

Elementary analysis (%): Calc'd for $C_{17}H_{18}FN_3O$: C, 68.21; H, 6.06; N, 14.04, Found: C, 68.05; H, 6.09; N, 14.03.

EXAMPLE 19

7-Benzyloxy-1-(3-fluoropropyl)-2,3-dimethylpyrrolo[2,3-d]pyridazine

The title compound was prepared as white crystals in 71.2% yield in a similar procedure to that described in Example 1 by using 7-chloro-1-(3-fluoropropyl)-2,3-dimethylpyrrolo[2,3-d]pyridazine and benzyl alcohol.

m.p.: 100–101° C.

Mass spectrum (CI, m/z): 314 ($M^+$+1).

NMR spectrum ($CDCl_3$, δppm): 1.95–2.15 (m, 2H), 2.25 (s, 3H), 2.35 (s, 3H), 4.23 (dt;J=48 Hz, 6 Hz, 2H), 4.40 (t;J=8 Hz, 2H), 5.69 (s, 2H), 7.31–7.53 (m, 5H), 8.98 (s, 1H).

Elementary analysis (%): Calc'd for $C_{18}H_{20}FN_3O$: C, 68.99; H, 6.43; N, 13.41, Found: C, 69.05; H, 6.52; N, 13.20.

EXAMPLE 20

7-Benzyloxy-1-(2,2-difluoroethyl)-2,3-dimethylpyrrolo[2,3-d]pyridazine

The title compound was prepared as a white powder in 71.6% yield in a similar procedure to that described in Example 1 by using 7-chloro-1-(2,2-difluoroethyl)-2,3-dimethylpyrrolo[2,3-d]pyridazine and benzyl alcohol.

m.p.: 128–131° C.

Mass spectrum (CI, m/z): 318 ($M^+$+1).

NMR spectrum ($CDCl_3$, δppm): 2.26 (s, 3H), 2.35 (s, 3H), 4.62 (tt;J=14 Hz, 5 Hz, 2H), 5.72 (s, 2H), 5.96 (tt;J=56 Hz, 5 Hz, 1H) , 7.31–7.53 (m, 5H) , 9.00 (s, 1H).

Elementary analysis (%): Calc'd for $C_{17}H_{17}F_2N_3O$: C, 64.34; H, 5.40; N, 13.24, Found: C, 64.35; H, 5.33; N, 13.11.

EXAMPLE 21

1-(2-Butenyl)-7-(2,4-dichlorobenzyloxy)-2,3-dimethylpyrrolo[2,3-d]pyridazine

The title compound (cis/trans=25/75) was prepared as white crystals in 72.4% yield in a similar procedure to that described in Example 1 by using 1-(2-butenyl)-7-chloro-2,3-dimethylpyrrolo[2,3-d]pyridazine (cis/trans=21/79) and 2,4-dichlorobenzyl alcohol.

m.p.: 133–134° C.

Mass spectrum (CI, m/z): 376. ($M^+$+1), 378 ($M^+$+3), 380 ($M^+$+5).

NMR spectrum ($CDCl_3$, δppm): 1.56–1.67 (m, 3H), 2.26 (s, 3H), 2.32 (s, 3H), 4.82–4.89 (m, 1.5H), 5.00–5.05 (m, 0.5H), 5.16–5.25 (m, 0.75H), 5.30–5.39 (m, 0.25H), 5.47–5.60 (m, 1H), 5.80 (s, 2H), 7.20–7.27 (m, 1H), 7.43 (s, 1H), 7.50–7.56 (m, 1H), 8.97 (s, 1H).

Elementary analysis (%): Calc'd for $C_{19}H_{19}Cl_2N_3O$: C, 60.65; H, 5.09; N, 11.17, Found: C, 60.76; H, 5.10; N, 11.14.

EXAMPLE 22

1-(2-Butenyl)-7-(2,4-difluorobenzyloxy)-2,3-dimethylpyrrolo[2,3-d]pyridazine

The title compound (cis/trans=18/82) was prepared as a pale yellow powder in 43.1% yield in a similar procedure to that described in Example 1 by using 1-(2-butenyl)-7-chloro-2,3-dimethylpyrrolo[2,3-d]pyridazine (cis/trans=21/79) and 2,4-difluorobenzyl alcohol.

m.p.: 93–95° C.

Mass spectrum (CI, m/z): 344 ($M^+$+1).

NMR spectrum ($CDCl_3$, δppm): 1.54–1.65 (m, 3H), 2.24 (s, 3H), 2.31 (s, 3H), 4.80–4.85 (m, 1.64H), 4.97–5.01 (m, 0.36H), 5.15–5.34 (m, 1H), 5.42–5.57 (m, 1H), 5.72 (s, 2H), 6.81–6.90 (m, 2H), 7.51–7.60 (m, 1H), 8.97 (s, 1H).

Elementary analysis (%): Calc'd for $C_{19}H_{19}F_2N_3O$: C, 66.46; H, 5.58; N, 12.24, Found: C, 66.56; H, 5.56; N, 12.15.

EXAMPLE 23

7-Benzyloxy-1-cyclohexyl-2,3-dimethylpyrrolo[2,3-d]pyridazine

The title compound was prepared as a white powder in 92.8% yield in a similar procedure to that described in Example 1 by using 7-chloro-1-cyclohexyl-2,3-dimethylpyrrolo[2,3-d]pyridazine and benzyl alcohol.

m.p.: 174–177° C.

Mass spectrum (CI, m/z): 336 ($M^+$+1).

NMR spectrum ($CDCl_3$, δppm): 1.10–1.44 (m, 2H), 1.48–2.08 (m, 4H), 1.76 (s, 3H), 2.13–2.59 (m, 4H), 2.27 (s, 3H), 3.91–4.19 (m, 1H), 5.70 (s, 2H), 7.29–7.66 (m, 5H), 8.95 (s, 1H).

Elementary analysis (%): Calc'd for $C_{21}H_{25}N_3O$: C, 75.19; H, 7.51; N, 12.53, Found: C, 75.17; H, 7.63; N, 12.50.

EXAMPLE 24

7-(4-Fluorobenzyloxy)-2,3-dimethyl-1-(3-phenyl-2-propenyl)pyrrolo[2,3-d]pyridazine The title compound (trans) was prepared as pale yellow crystals in 47.7% yield in a similar procedure to that described in Example 1 by using 7-chloro-2,3-dimethyl-1-(3-phenyl-2-propenyl)pyrrolo[2,3-d]pyridazine (trans) and 4-fluorobenzyl alcohol.

m.p.: 124–126° C.

Mass spectrum (CI, m/z): 388 ($M^+$+1).

NMR sepctrum ($CDCl_3$, δppm): 2.29 (s, 3H), 2.38 (s, 3H), 5.09 (d;J=5 Hz, 2H), 5.68 (s, 2H) , 6.03 (d;J=17 Hz, 1H) , 6.20 (dt;J=17 Hz, 5 Hz, 1H), 6.91–7.51 (m, 9H), 9.00 (s, 1H).

Elementary analysis (%): Calc'd for $C_{24}H_{22}FN_3O$: C, 74.40; H, 5.72; N, 10.85, Found: C, 74.65; H, 5.75; N, 10.75.

EXAMPLE 25

2,3-Dimethyl-1-(2-propenyl)-7-(4-trifluoromethylbenzyloxy)pyrrolo[2,3-d]pyridazine The title compound was prepared as pale yellow crystals in 52.5% yield in a similar procedure to that described in Example 1 by using 7-chloro-2,3-dimethyl-1-(2-propenyl) pyrrolo[2,3-d]pyridazine and 4-trifluoromethylbenzyl alcohol.

m.p.: 95–96° C.

Mass spectrum (CI, m/z): 362 ($M^+$+1).

NMR spectrum ($CDCl_3$, δppm): 2.27 (s, 3H), 2.32 (s, 3H), 4.63 (d;J=16 Hz, 1H), 4.96 (d;J=4 Hz, 2H), 5.10 (d;J=10 Hz, 1H), 5.75 (s, 2H), 5.87–6.00 (m, 1H), 7.46–7.78 (m, 4H), 9.00 (s, 1H).

Elementary analysis (%): Calc'd for $C_{19}H_{18}F_3N_3O$: C, 63.15; H, 5.02; N, 11.63, Found: C, 63.23; H, 5.02; N, 11.66.

EXAMPLE 26

7-(4-Fluorobenzyloxy)-2,3-dimethyl-1-(2-methyl-2-propenyl)pyrrolo[2,3-d]pyridazine The title compound was prepared as a grayish white powder in 38.7% yield in a similar procedure to that described in Example 1 by using 7-chloro-2,3-dimethyl-1-(2-methyl-2-propenyl)pyrrolo[2,3-d]pyridazine and 4-fluorobenzyl alcohol.

m.p.: 118–120° C.

Mass spectrum (CI, m/z): 326 ($M^+$+1).

NMR spectrum ($CDCl_3$, δppm): 1.62 (s, 3H)., 2.27 (s, 6H), 4.02 (s, 1H), 4.76 (s, 1H), 4.80 (s, 2H), 5.61 (s, 2H), 7.01–7.11 (m, 2H), 7.41–7.50 (m, 2H), 8.99 (s, 1H).

Elementary analysis (%): Calc'd for $C_{19}H_{20}FN_3O$: C, 70.13; H, 6.20; N, 12.91, Found: C, 70.29; H, 6.28; N, 12.68.

EXAMPLE 27

7-Benzyloxy-3-ethyl-2-methyl-1-(2-propenyl)-6pyrrolo[2,3-d]pyridazine

The title compound was prepared as a white powder in 97.0% yield in a similar procedure to that described in Example 1 by using 7-chloro-3-ethyl-2-methyl-1-(2-propenyl)pyrrolo[2,3-d]pyridazine and benzyl alcohol.

m.p.: 82–83° C.

Mass spectrum (CI, m/z): 308 ($M^+$+1).

NMR spectrum ($CDCl_3$, δppm): 1.22 (t;J=8 Hz, 3H), 2.32 (s, 3H), 2.73 (q;J=8 Hz, 2H), 4.61 (d;J=18 Hz, 1H), 4.91–4.99 (m, 2H), 5.08 (d;J=10 Hz, 1H), 5.70 (s, 2H), 5.83–6.00 (m, 1H), 7.27–7.53 (m, 5H), 9.03 (s, 1H).

Elementary analysis (%): Calc'd for $C_{19}H_{21}N_3O$: C, 74.24; H, 6.89; N, 13.67, Found: C, 74.33; H, 6.99; N, 13.61.

EXAMPLE 28

1-(2-Butenyl)-2,3-dimethyl-7-(2-thienylmethyloxy)pyrrolo[2,3-d]pyridazine

The title compound (cis/trans=20/80) was prepared as a grayish white powder in 20.6% yield in a similar procedure to that described in Example 1 by using 1-(2-butenyl)-7-chloro-2,3-dimethylpyrrolo[2,3-d]pyridazine (cis/trans=20/80) and 2-thiophenemethanol.

m.p.: 72–75° C.

Mass spectrum (CI, m/z): 314 ($M^+$+1).

NMR spectrum ($CDCl_3$, δppm): 1.54–1.70 (m, 3H), 2.25 (s, 3H), 2.31 (s, 3H), 4.82–4.89 (m, 1.6H), 4.99–5.04 (m, 0.4H), 5.17–5.38 (m, 1H), 5.43–5.60 (m, 1H), 5.86 (s, 2H), 6.96–7.04 (m, 1H), 7.15–7.21 (m, 1H), 7.29–7.35 (m, 1H), 8.97 (s, 1H).

Elementary analysis (%): Calc'd for $C_{17}H_{19}N_3OS$: C, 65.15; H, 6.11; N, 13.41, Found: C, 65.13; H, 6.12; N, 13.38.

EXAMPLE 29

1-(2-Butenyl)-7-(4-fluorobenzyloxy)-2,3-dimethylpyrrolo[2,3-d]pyridazine

The title compound (cis/trans=98/2) was prepared as pale brown crystals in 59.3% yield in a similar procedure to that described in. Example 1 by using 1-(2-butenyl)-7-chloro-2,3-dimethylpyrrolo[2,3-d]pyridazine (cis/trans=94/6) and 4-fluorobenzyl alcohol.

m.p.: 108–112° C.

Mass spectrum (CI, m/z): 326 ($M^+$+1).

NMR spectrum ($CDCl_3$, δppm): 1.58–1.68 (m, 3H), 2.26 (s, 3H), 2.31 (s, 3H), 4.83–4.89 (m, 0.04H), 4.97–5.04 (m, 1.96H), 5.29–5.60 (m, 2H), 5.68 (9, 2H), 7.00–7.52 (m, 4H), 8.97 (s, 1H).

Elementary analysis (%): Calc'd for $C_{19}H_{20}FN_3O$: C, 70.14; H, 6.20; N, 12.91, Found: C, 69.95; H, 6.22; N, 12.90.

EXAMPLE 30

7-Benzyloxy-1-(2-chloro-2-propenyl)-2,3-dimethylpyrrolo[2,3-d]pyridazine

The title compound was prepared as a white powder in 10.9% yield in a similar procedure to that described in Example 1 by using 7-chloro-1-(2-chloro-2-propenyl)-2,3-dimethylpyrrolo[2,3-d]pyridazine and benzyl alcohol.

m.p.: 88–90° C.

Mass spectrum (CI, m/z): 328 ($M^+$+1), 330 ($M^+$+3).

NMR spectrum ($CDCl_3$, δppm): 2.27 (s, 3H), 2.32 (s, 3H), 4.48 (s, 1H), 5.05 (s, 2H), 5.23 (s, 1H), 5.69 (s, 2H), 7.30–7.54 (m, 5H), 9.00 (s, 1H)

Elementary analysis (%): Calc'd for $C_{18}H_{18}ClN_3O$: C, 65.95; H, 5.54; 12.82, Found: C, 66.00; H, 5.51; N, 12.74.

EXAMPLE 31

1-(2-Butenyl)-7-(4-difluoromethoxybenzyloxy)-2,3-dimethylpyrrolo[2,3-d]pyridazine The title compound (cis/trans=21/79) was prepared as a white powder in 37.8% yield in a similar procedure to that described in Example 1 by using 1-(2-butenyl)-7-chloro-2,3-dimethylpyrrolo[2,3-d]pyridazine (cis/trans=20/80) and 4-difluoromethoxybenzyl alcohol.

m.p.: 109–110° C.

Mass spectrum (CI, m/z): 374 ($M^+$+1).

NMR spectrum ($CDCl_3$, δppm): 1.56–1.68 (m, 3H), 2.25 (s, 3H), 2.33 (s, 3H), 4.84–4.89 (m, 1.58H), 5.00–5.04 (m, 0.42H), 5.14–5.25 (m, 0.79H), 5.30–5.38 (m, 0.21H), 5.45–5.60 (m, 1H), 5.69 (s, 2H), 6.52 (t;J=51 Hz, 1H), 7.13 (d;J=8 Hz, 2H), 7.51 (d;J=8 Hz, 2H), 8.97 (s, 1H).

Elementary analysis (%): Calc'd for $C_{20}H_{21}F_2N_3O_2$: C, 64.43; H, 5.67; N, 11.25, Found: C, 64.28;.H, 5.57; N. 11.32.

EXAMPLE 32

1-(2-Butenyl)-2,3-dimethyl-7-(3-pyridylmethyloxy)pyrrolo[2,3-d]pyridazine

The title compound (cis/trans=22/78) was prepared as a pale yellow powder in 45.9% yield in a similar procedure to that described in Example 1 by using 1-(2-butenyl)-7-chloro-2,3-dimethylpyrrolo[2,3-d]pyridazine (cis/trans=20/80) and 3-pyridinemethanol.

m.p.: 80–81° C.

Mass spectrum (CI, m/z): 309 ($M^+$+1).

NMR spectrum ($CDCl_3$, δppm): 1.57–1.66 (m, 3H), 2.26 (s, 3H), 2.32 (s, 3H), 4.85–4.90 (m, 1.56H), 5.00–5.04 (m, 0.44H), 5.14–5.23 (m, 0.78H), 5.31–5.39 (m, 0.22H), 5.47–5.60 (m, 1H), 5.74 (s, 2H), 7.29–7.34 (m, 1H), 7.82–7.88 (m, 1H), 8.57–8.62 (m, 1H), 8.78 (9, 1H) , 8.98 (s, 1H)

Elementary analysis (%): Calc'd for $C_{18}H_{20}N_4O$: C, 70.11; H, 6.54; N, 18.17, Found: C, 69.83; H, 6.51; N, 18.08.

EXAMPLE 33

1-(2-Butenyl)-2-ethyl-7-(4-fluorobenzyloxy)-3-methylpyrrolo[2,3-d]pyridazine

The title compound (trans) was prepared as a white powder in 41.7% yield in a similar procedure to that described in Example 1 by using 1-(2-butenyl)-7-chloro-2-ethyl-3-methylpyrrolo[2,3-d]pyridazine (cis/trans=4/96) and 4-fluorobenzyl alcohol.

m.p.: 74–76° C.

Mass spectrum (CI, m/z): 340 ($M^+$+1).

NMR spectrum ($CDCl_3$, δppm): 1.20 (t;J=8 Hz, 3H), 1.59 (d;J=7 Hz, 3H), 2.28 (s, 3H), 2.75 (q;J=8 Hz, 2H), 4.81–4.90 (m, 2H), 5.08–5.26 (m, 1H), 5.42–5.57 (m, 1H), 5.66 (s, 2H), 7.07 (t;J=9 Hz, 2H), 7.49 (dd;J=7, 9 Hz, 2H), 8.98 (s, 1H).

Elementary analysis (%): Calc'd for $C_{20}H_{22}$ $FN_3O$: C, 70.77; H, 6.53; N, 12.38, Found: C, 70.78; H, 6.44; N, 12.34.

EXAMPLE 34

7-(4-Fluorobenzylthio)-2,3-dimethyl-1--(2-propenyl) ipyrrolo[2,3-d]pyridazine

The title compound was prepared as a pale yellow powder in 61.6% yield in a similar procedure to that described in Example 1 by using 7-chloro-2,3-dimethyl-1-(2-propenyl) pyrrolo[2,3-d]pyridazine and 4-fluorophenylmethanethiol.

m.p.: 106–109° C.

Mass spectrum (CI, m/z): 328 ($M^+$+1).

NMR spectrum ($CDCl_3$, δppm): 2.27 (s, 3H), 2.31 (s, 3H), 4.48 (d;J=16 Hz, 1H), 4.72 (s, 2H), 5.00–5.10 (m, 2H), 5.12 (d;J=10 Hz, 1H), 5.88–6.02 (m, 1H), 6.90–7.00 (m, 2H), 7.37–7.47 (m, 2H), 9.07 (s, 1H).

Elementary analysis (%): Calc'd for $C_{18}H_{18}FN_3OS$: C, 66.04; H, 5.54; N, 12.83, Found: C, 66.45; H, 5.54; N, 12.58.

EXAMPLE 35

1-Cyclopropylmethyl-7-(4-fluorobenzyloxy)-2,3-dimethylpyrrolo[2,3-d]pyridazine

The title compound was prepared as a white powder in 74.1% yield in a similar procedure to that described in Example 1 by using 77chloro-1-cyclopropylmethyl-2,3-dimethylpyrrolo[2,3-d]pyridazine and 4-fluorobenzyl alcohol.

m.p.: 137–138° C.

Mass spectrum (CI, m/z): 326 ($M^+$+1).

NMR spectrum ($CDCl_3$, δppm): 0.21–0.27 (m, 2H), 0.38–0.45 (m, 2H), 1.05–1.20. (m, 1H), 2.28 (s, 3H), 2.39 (s, 3H), 4.22 (d, J=8 Hz, 2H), 5.66 (s, 2H), 7.05–7.12 (m, 2H), 7.48–7.53 (m, 2H), 8.99 (s, 1H).

Elemetary analysis (%): Calc'd for $C_{19}H_{20}FN_3O$: C, 70.13; H, 6.20; N, 12.91, Found: C, 70.22; H, 6.24; N, 12.89.

EXAMPLE 36

1-(2-Butenyl)-7-furfuryloxy-2,3-dimethylpyrrolo[2,3-d] pyridazine

The title compound (cis/trans=15/85) was prepared as a flesh-colored powder in 12.2% yield in a similar procedure to that described in Example 1 by using 1-(2-butenyl)-7-chloro-2,3-dimethylpyrrolo[2,3-d]pyridazine (cis/trans=20/80) and furfuryl alcohol.

m.p.: 84–85° C.

Mass spectrum (CI, m/z): 298 ($M^+$+1).

NMR spectrum ($CDCl_3$, δppm): 1.58–1.65 (m, 3H), 2.25 (s, 3H), 2.32 (s, 3H), 4.82–4.84 (m, 1.64H), 4.98–5.00 (m, 0.36H), 5.28–5.35 (m, 1H), 5.44–5.49 (m, 1H), 5.66 (s, 2H), 6.38–6.39 (m, 1H), 6.51 (s, 1H), 7.44 (s, 1H), 8.95 (s, 1H).

Elementary analysis (%): Calc'd for $C_{17}H_{19}N_3O_2$: C, 68.67; H, 6.44; N, 14.13, Found: C, 68.45; H, 6.52; N, 14.14.

EXAMPLE 37

1-Cyclohexylmethyl-7-(4-fluorobenzyloxy)-2,3-dimethylpyrrolo[2,3-d]pyridazine

The title compound was prepared as a white powder in 45.6% yield in a similar procedure to that described in Example 1 by using 7-chloro-1-cyclohexylmethyl-2,3-dimethylpyrrolo[2,3-d]pyridazine and 4-fluorobenzyl alcohol.

m.p.: 108–109° C.

Mass spectrum (CI, m/z): 368 ($M^+$+1).

NMR spectrum ($CDCl_3$, δppm): 0.77–0.90 (m, 2H), 0.93–1.09 (m, 3H), 1.24–1.32 (m, 2H), 1.56–1.67 (m, 4H), 2.25 (s, 3H), 2.32 (s, 3H), 4.01 (d, J=7 Hz, 2H), 5.63 (s, 2H), 7.08 (t, J=6 Hz, 2H), 7.50 (dd, J=6 Hz, 3 Hz, 2H), 8.96 (s, 1H).

Elementary analysis (%): Calc'd for $C_{22}H_{26}FN_3O$: C, 71.90; H, 7.09; N, 11.44, Found: C, 71.71; H, 7.05; N, 11.19.

EXAMPLE 38

1-(2-Butenyl)-7-(2,6-difluorobenzyloxy)-2,3-dimethylpyrrolo[2,3-d]pyridazine

The title compound (cis/trans=22/78) was prepared as a white powder in 58.3% yield in a similar procedure to that described in Example 1 by using 1-(2-butenyl)-7-chloro-2,3-dimethylpyrrolo[2,3-d]pyridazine (cis/trans=24/76) and 2,6-difluorobenzyl alcohol.

m.p.: 85–94° C.

Mass spectrum (CI, m/z): 344 ($M^+$+1).

NMR spectrum ($CDCl_3$, δppm): 1.46–1.60 (m, 3H), 2.26 (s, 3H), 2.31 (s, 3H), 4.65–4.79 (m, 1.56H), 4.86–4.94 (m, 0.44H), 5.09–5.51 (m, 2H), 5.78 (s, 2H), 6.87–7.02 (m, 2H), 7.27–7.42 (m, 1H), 8.98 (s, H).

Elementary analysis. (%): Calc'd for $C_{19}H_{19}F_2N_3O$: C, 66.46; H, 5.58; N, 12.24, Found: C, 66.13; H, 5.45; N, 12.25.

EXAMPLE 39

1-(2-Butenyl)-7-(3,5-difluorobenzyloxy)-2,3-dimethylpyrrolo[2,3-d]pyridazine

The title compound (cis/trans=29/71) was prepared as a white powder in 41.6% yield in a similar procedure to that described in Example 1 by using 1-(2-butenyl)-7-chloro-2,3-dimethylpyrrolo[2,3-d]pyridazine (cis/trans=24/76) and 3,5-difluorobenzyl alcohol.

m.p.: 78–84° C.

Mass spectrum (CI, m/z): 344 ($M^+$+1).

NMR spectrum ($CDCl_3$, δppm): 1.51–1.76 (m, 3H), 2.27 (s, 3H), 2.34 (s, 3H), 4.83–4.96 (m, 1.42H), 5.01–5.10 (m, 0.58H), 5.11–5.75 (m, 2H), 5.70 (s, 2H), 6.67–6.82 (m, 1H), 6.93–7.10 (m, 2H), 8.98 (s, H).

Elementary analysis (%): Calc'd for $C_{19}H_{19}F_2N_3O$: C, 66.46; H, 5.58; N, 12.24, Found: C, 66.28; H, 5.58; N, 12.20.

EXAMPLE 40

1-(2-Butenyl)-7-(2-chloro-6-fluorobenzyloxy)-2,3-dimethylpyrrolo[2,3-d]pyridazine The title compound (cis/trans=21/79) was prepared as a pale brown powder in 57.60% yield in a similar procedure to that described in Example 1 by using 1-(2-butenyl)-7-chloro-2,3-dimethylpyrrolo[2,3-d]pyridazine (cis/trans=24/76) and 2-chloro-6-fluorobenzyl alcohol.

m.p.: 103–112° C.

Mass spectrum (CI, m/z): 360 ($M^++1$), 362 ($M^++3$).

NMR spectrum ($CDCl_3$, δppm): 1.41–1.58 (m, 3H), 2.25 (s, 3H), 2.30 (s, 3H), 4.66–4.77 (m, 1.58H), 4.84–4.92 (m, 0.42H), 5.03–5.51 (m, 2H), 4.83 (s, 2H), 6.99–7.12 (m, 1H), 7.21–7.38 (m, 2H), 8.97 (s, 1H).

Elementary analysis (%): Calc'd for $C_{19}H_{19}ClFN_3O$: C, 63.42; H, 5.32; N, 11.68, Found: C, 63.52; H, 5.34; N, 11.60.

EXAMPLE 41

7-Benzyloxy-1-(3,3-dichloro-2-propenyl)-2,3-dimethylpyrrolo[2,3-d]pyridazine 0.13 g (0.0011 mole) of potassium tert-butoxide was added to a suspension of 0.29 g (0.0011 mole) of 7-benzyloxy-2,3-dimethylpyrrolo[2,3-d]pyridazine and 0.03 g (0.0001 mole) of 18-crown-6 in 8 ml of tetrahydrofuran and the resulting mixture was stirred at room temperature for 40 minutes. 0.22 g (0.0011 mole) of 3,3-dichloro-2-propenyl bromide was then added to the mixture and stirred at room temperature for 5 minutes. The reaction mixture was poured into ice-water and the aqueous mixture was extracted with dichloromethane. The extract was dried over anhydrous sodium sulfate and the solvent was distilled off under reduced pressure. The residue was purified by column chromatography through silica gel using a 20:1 mixture of chloroform and methanol as an eluent to give 0.090 g of 7-benzyloxy-1-(3,3-dichloro-2-propenyl)-2,3-dimethylpyrrolo[2,3-d]pyridazine as a yellow powder.

m.p.: 149–151° C.

Mass spectrum (CI, m/z): 362 ($M^++1$), 364 ($M^++3$), 366 ($M^++5$).

NMR spectrum ($CDCl_3$, δppm): 2.26 (s, 3H), 2.35 (s, 3H), 5.06 (d, J=5 Hz, 2H), 5.72 (s, 2H), 5.90 (t, J=5 Hz, 1H), 7.29–7.58 (m, 5H) , 8.99 (s, 1H)

Elementary analysis (%): Calc'd for $C_{18}H_{17}Cl_2N_3O$: C, 59.68; H, 4.73; N; 11.60, Found: C, 60.06; H. 4.99; N, 11.32.

EXAMPLE 42

7-Benzyloxy-2,3-dimethyl-1-(2-propynyl)pyrrolo[2,3-d]pyridazine

The title compound was prepared as a pale yellow powder in 27.40% yield in a similar procedure to that described in Example 41 by using 7-benzyloxy-2,3-dimethylpyrrolo[2,3-d]pyridazine and 3-bromo-1-propyne.

m.p.: 116–117° C.

Mass spectrum (CI, m/z): 292 ($M^++1$).

NMR spectrum ($CDCl_3$, δppm): 2.26 (s, 3H), 2.30–2.35 (m, 1H), 2.44 (s, 3H), 5.18 (d, J=2 Hz, 2H), 5.74 (s, 2H), 7.30–7.44 (m, 3H), 7.53–7.61 (m, 2H), 9.00 (s, 1H).

Elementary analysis (%): Calc'd for $C_{18}H_{17}N_3O$: C, 74.20; H, 5.88; N, 14.42, Found: C, 73.88; H, 5.85; N, 14.36.

EXAMPLE 43

1-(3-Chloro-2-propenyl)-7-(4-fluorobenzyloxy)-2,3-dimethylpyrrolo[2,3-d]pyridazine The title compound (cis/trans=1/1) was prepared as a pale yellow powder in 31.4% yield in a similar procedure to that described in Example 41 by using 7-(4-fluorobenzyloxy)-2,3-dimethylpyrrolo[2,3-d]pyridazine and 1,3-dichloropropene (a mixture of cis and trans isomers).

m.p.: 110–115° C.

Mass spectrum (CI, m/z): 346 ($M^++1$), 348 ($M^++3$).

NMR spectrum ($CDCl_3$, δppm): 2.25 (s, 1.5H), 2.26 (s, 1.5H), 2.33 (s, 1.5H), 2.34 (s, 1.5H), 4.89–4.91 (m, 1H), 5.15–5.17 (m, 1H), 5.64–6.14 (m, 4H), 7.04–7.12 (m, 2H), 7.47–7.50 (m, 2H), 8.98 (m, 1H).

Elementary analysis (%): Calc'd for $C_{18}H_{17}ClFN_3O.¼H_2O$: C, 61.72; H, 5.04; N, 11.99, Found: C, 61.83; H, 4.86; N, 12.04.

EXAMPLE 44

7-(4-Fluorobenzyloxy)-2,3-dimethyl-1-(1-propenyl)-pyrrolo[2,3-d]pyridazine 1.62 g (0.014 mole) of potassium tert-butoxide was added to a solution of 1.02 g (0.0081 mole) of 4-fluorobenzyl alcohol and 0.12 g (0.00045 mole) of 18-crown-6 in 10 ml of tetrahydrofuran and the resulting mixture was stirred at room temperature for 25 minutes. A solution of 0.60 g (0.0027 mole) of 7-chloro-1-(2-propenyl)-2,3-dimethylpyrrolo[2,3-d]pyridazine in 5 ml of tetrahydrofuran was added dropwise to the mixture and stirred at room temperature for 10 hours. After completion of the reaction, the reaction mixture was poured into ice-water and the aqueous mixture was extracted with dichloromethane. The extract was dried over anhydrous sodium sulfate and the solvent was distilled off under reduced pressure. The residue was purified by column chromatography through silica gel using a 2:3 mixture of ethyl acetate and hexane as an eluent to give 0.33 g of 7-(4-fluorobenzyloxy)-2,3-dimethyl-1-(1-propenyl)pyrrolo[2,3-d]pyridazine (trans) as a pale yellow powder.

m.p.: 114–115° C.

Mass spectrum (CI, m/z): 312 ($M^+$, +1).

NMR spectrum ($CDCl_3$, δppm): 1.43 (d, J=8 Hz, 3H), 2.25 (s, 3H), 2.29 (s, 3H), 5.62 (s, 2H), 5.85–5.95 (m, 1H), 6.65–6.71 (m, 1H), 7.02–7.10 (m, 2H), 7.43–7.50 (m, 2H), 9.00 (s, 1H).

Elementary analysis (%): Calc'd for $C_{18}H_{18}FN_3O$: C, 69.44; H, 5.83; N, 13.50, Found: C, 69.79; H, 5.91; N, 13.51.

EXAMPLE 45

7-Benzyloxy-2,3-dimethyl-1-(propane-1,2-dienyl)pyrrolo[2,3-d]pyridazine

The title compound was prepared as pale brown crystals in 37.6% yield in a similar procedure to that described in Example 44 by using 7-chloro-2,3-dimethyl-1-(2-propynyl)pyrrolo[2,3-d]pyridazine and benzyl alcohol.

m.p.: 77–79° C.

Mass spectrum (CI, m/z): 292 ($M^++1$).

NMR spectrum ($CDCl_3$, δppm): 2.27 (s, 3H), 2.41 (s, 3H), 5.37 (s, 1H), 5.40 (s, 1H), 5.73 (s, 2H), 7.28–7.68 (m, 6H), 8.98 (s, 1H).

Elementary analysis (%): Calc'd for $C_{18}H_{17}N_3O$: C, 74.21; H, 5.89; N, 14.42, Found: C, 74.29; H, 5.86; N, 14.31.

EXAMPLE 46

7-Benzylamino-2,3-dimethyl-1-(1-propenyl)pyrrolo[2,3-d]pyridazine

The title compound (trans) was prepared as a beige powder in 31.5% yield in a similar procedure to that described in Example 44 by using 7-chloro-2,3-dimethyl-1-(2-propenyl)pyrrolo[2,3-d]pyridazine and benzylamine.

m.p.: 130–131° C.

Mass spectrum (CI, m/z): 292 ($M^++1$).

NMR spectrum ($CDCl_3$, δppm): 1.44–1.62 (m, 3H), 2.20 (s, 3H), 2.25 (s, 3H), 4.88 (d;J=5 Hz, 2H), 5.11–5.22 (m, 1H), 6.03–6.14 (m, 1H), 6.71–6.78 (m, 1H), 7.20–7.42 (m, 5H), 8.83 (s, 1H).

Elementary analysis (%): Calc'd for $C_{18}H_{20}N_4$: C, 73.04; H, 6.95; N, 18.93, Found: C, 73.53; H, 6.99; N, 18.83.

EXAMPLE 47

1-(2-Butenyl)-7-(4-fluorobenzylamino)-2,3-dimethylpyrrolo[2,3-d]pyridazine

A solution of 0.35 g (0.0015 mole) of 1-(2-butenyl)-7-choro-2,3-dimethylpyrrolo[2,3-d]pyridazine dissolved in 3.5 ml of 4-fluorobenzylamine was heated at 180° C. for 2.5 hours. After completion of the reaction, the reaction mixture was allowed to cool to room temperature and then poured into ice-water. The aqueous mixture was extracted with dichloromethane. The extract was dried over anhydrous sodium sulfate and the solvent was distilled off under reduced pressure. The residue was purified by column chromatography through silica gel using a 30:1 mixture of chloroform and methanol as an eluent to give 0.22 g of 1-(2-butenyl)-7-(4-fluorobenzylamino)-2,3-dimethylpyrrolo[2,3-d]pyridazine (cis/trans=1/4) as a flesh-colored powder.

m.p.: 135–138° C.

Mass spectrum (CI, m/z): 325 ($M^+$+1).

NMR spectrum ($CDCl_3$, δppm): 1.38–1.41 (m, 0.6H), 1.55–1.59 (m, 2.4H), 2.25 (s, 3H), 2.30 (s, 3H), 4.70–4.89 (m, 5H), 5.13–5.46 (m, 1H), 5.51–5.65 (m, 1H), 7.00–7.08 (m, 2H), 7.33–7.42 (m, 2H), 8.85 (s, 1H).

Elementary analysis (%): Calc'd for $C_{19}H_{21}FN_4$: C, 70.35; H, 6.53; N, 17.27, Found: C, 70.08; H, 6.62; N, 17.08.

EXAMPLE 48

1-(2-Butenyl)-7-(4-chloro-2-fluorobenzyloxy)-2,3-dimethylpyrrolo[2,3-d]pyridazine The title compound (cis/trans=24:76) was prepared as a white powder in 63.8% yield in a similar procedure to that described in Example 1 by using using 1-(2-butenyl)-7-chloro-2,3-dimethylpyrrolo[2,3-d]pyridazine (cis/trans=24/76) and 4-chloro-2-fluorobenzyl alcohol.

m.p.: 106–109° C.

Mass spectrum (CI, m/z): 360 ($M^+$+1), 362 ($M^+$+3).

NMR spectrum ($CDCl_3$, δppm): 1.59 (d;J=6 Hz, 2.28H), 1.65 (d;J=6 Hz, 0.72H), 2.24 (s, 3H), 2.30 (s, 3H), 4.82 (d;J=6 Hz, 1.52H), 4.99 (d;J=6 Hz, 0.48 Hz), 5.12–5.60 (m, 2H), 5.73 (s, 2H), 7.12 (d;J=9 Hz, 2H), 7.51 (t;J=9 Hz, 1H), 8.97 (s, 1H).

Elementary analysis (%): Calc'd for $C_{19}H_{19}ClFN_3O$: C, 63.42; H, 5.32; N, 11.68, Found: C, 63.41; H, 5.17; N, 11.54.

EXAMPLE 49

1-(2-Butenyl)-7-(2,6-dichlorobenzyloxy)-2,3-dimethylpyrrolo[2,3-d]pyridazine

The title compound (cis/trans=21:79) was prepared as a pale yellow powder in 83.5% yield in a similar procedure to that described in Example 1 by using 1-(2-butenyl)-7-chloro-2,3-dimethylpyrrolo[2,3-d]pyridazine (cis/trans=24/76) and 2,6-dichlorobenzyl alcohol.

m.p.: 133–14°° C.

Mass spectrum (CI, m/z): 376 ($M^+$+1), 378 ($M^+$+3), 380 ($M^+$+5).

NMR spectrum ($CDCl_3$, δppm): 1.34–1.60 (m, 3H), 2.24 (s, 3H), 2.30 (s, 3H), 4.71 (d;J=6 Hz, 1.58H), 4.89 (d;J=6 Hz, 0.42 Hz), 5.02–5.50 (m, 2H), 5.94 (s, 2H), 7.19–7.47 (m, 3H) , 8.99 (s, 1H).

Elementary analysis (%): Calc'd for $C_{19}H_{19}Cl_2N_3O$: C, 60.65; H, 5.09; N, 11.17, Found: C, 60.53; H, 5.03; N, 11.17.

EXAMPLE 50

1-(2-Butenyl)-7-(4-fluorobenylthio)-2,3-dimethylpyrrolo[2,3-d]pyridazine

The title compound (cis/trans=20:80) was prepared as a pale yellow powder in 64.9% yield in a similar procedure to that described in Example 1 by using 1-(2-butenyl)-7-chloro-2,3-dimethylpyrrolo[2,3-d]pyridazine (cis/trans=23/77) and 4-fluorophenylmethanethiol.

m.p.: 110–115° C.

Mass spectrum (CI, m/z): 342 ($M^+$+1).

NMR spectrum ($CDCl_3$, δppm): 1.58–1.65 (m, 2.4H), 1.73–1.79 (m, 0.6H), 2.25 (s, 3H), 2.31 (s, 3H), 4.74 (s, 2H), 4.93–5.00 (m, 1.6 Hz), 5.07–5.33 (m, 1.4H), 5.46–5.61 (m, 1H), 6.91–7.02 (m, 2H), 7.39–7.48 (m, 2H), 9.06 (s, 1H).

Elementary analysis (%): Calc'd for $C_{19}H_{20}FN_3S$: C, 66.84; H, 5.90; N, 12.31, Found: C, 66.92; H, 5.90; N, 12.23.

EXAMPLE 51

1-(2-Butenyl)-7-(2,4-difluorobenzylthio)-2,3-dimethylpyrrolo[2,3-d]pyridazine

The title compound (cis/trans=16:84) was prepared as pale brown crystals in 39.0% yield in a similar procedure to that described in Example 1 by using 1-(2-butenyl)-7-chloro-2,3-dimethylpyrrolo[2,3-d]pyridazine (cis/trans=22/78) and 2,4-difluorophenylmethanethiol.

m.p.: 122–127° C.

Mass spectrum (CI, m/z): 360 ($M^+$+1).

NMR spectrum ($CDCl_3$, δppm): 1.48–1.68 (m, 2.52H), 1.71–1.80 (m, 0.48H), 2.24 (s, 3H), 2.31 (s, 3H), 4.77 (s, 2H), 4.–88–5.68 (m, 4H), 6.65–6.84 (m, 2H), 7.47–7.63 (m, 1H), 9.06 (s, 1H).

Elementary analysis (%): Calc'd for $C_{19}H_{19}F_2N_3S$: C, 63.49; H, 5.33; N, 11.69, Found: C, 63.67; H, 5.32; N, 11.66.

EXAMPLE 52

1-(2-Butenyl)-7-(2-chloro-6-fluorobenzylthio)-2,3-dimethylpyrrolo[2,3-d]pyridazine The title compound (cis/trans=18:82) was prepared as pale brown crystals in 70.1% yield in a similar procedure to that described in Example 1 by using 1-(2-butenyl)-7-chloro-2,3-dimethylpyrrolo[2,3-d]pyridazine (cis/trans=(22/78) and 2-chloro-6-fluorophenylmethanethiol.

m.p.: 95–117° C.

Mass spectrum (CI, m/z): 376 ($M^+$+1).

NMR spectrum ($CDCl_3$, δppm):. 1.51–1.66 (m, 2.46 H), 1.67–1.77 (m, 0.54H), 2.27 (s, 3H), 2.32 (s, 3H), 4.81–5.62 (m, 6H), 6.93–7.31 (m, 3H), 9.09 (s, 1H).

Elementary analysis (%): Calc'd for $C_{19}H_{19}ClFN_3S$: C, 60.71; H, 5.09; N, 11.18, Found: C, 60.79; H, 5.13; N, 11.11.

EXAMPLE 53

1-(2-Butenyl)-7-(2,4-dichlorobenzylthio)-2,3-dimethylpyrrolo[2,3-d]pyridazine

The title compound (cis/trans=16:84) was prepared as pale brown crystals in 63.2% yield in a similar procedure to that described in Example 1 by using 1-(2-butenyl)-7-chloro-2,3-dimethylpyrrolo[2,3-d]pyridazine (cis/trans=22/78) and 2,4-dichlorophenylmethanethiol.

m.p.: 81–85° C.

Mass spectrum (CI, m/z): 392 ($M^+$+1).

NMR spectrum ($CDCl_3$, δppm): 1.47–1.81 (m, 3H), 2.25 (s, 3H), 2.31 (s, 3H), 4.85 (s, 2H), 4.91–5.02 (m, 1.68H), 5.03–5.13 (m, 0.32H), 5.13–5.64 (m, 2H), 7.07–7.68 (m, 3H), 9.05 (s, 1H).

Elementary analysis (%): Calc'd for $C_{19}H_{19}Cl_2N_3S$: C, 58.16; H, 4.88; N, 10.71, Found: C, 58.01; H, 4.87; N, 10.69.

EXAMPLE 54

1-(2-Butenyl)-2,3-dimethyl-7-(2-pyridylmethylthio)-pyrrolo[2,3-d]pyridazine

The title compound (cis/trans=20/80) was prepared as a yellow oil in 64.8% yield in a similar procedure to that described in Example 1 by using 1-(2-butenyl)-7-chloro-2,3-dimethylpyrrolo[2,3-d]pyridazine (cis/trans-22/78) and 2-pyridylmethanethiol.

Mass spectrum (CI, m/z): 325 ($M^+$+1).

NMR spectrum ($CDCl_3$, δppm): 1.50 (d;J=8 Hz, 2.4H), 1.77 (d;J=8 Hz, 0.6H), 2.26 (s, 3H), 2.31 (s, 3H), 4.92 (s, 2H), 4.96–5.04 (m, 1.6H), 5.10–5.38 (m, 1.4H), 5.48–5.63 (m, 1H), 7.09–7.17 (m, 1H), 7.56–7.62 (m, 2H), 8.54–8.60 (m, 1H), 9.04 (s, 1H).

Elementary analysis (%): Calc'd for $C_{18}H_{20}N_4S.¾H_2O$: C, 63.97; H, 6.41; N, 16.58, Found: C, 64.16; H, 6.14; N, 16.23.

EXAMPLE 55

7-(4-Chlorobenzylthio)-2,3-dimethyl-1-(2-propenyl)pvrrolo[2,3-d]pyridazine

The title compound was prepared as a yellow solid in 70.6% yield in a similar procedure to that described in Example 1 by using 7-chloro-2,3-dimethyl-1-(2-propenyl)pyrrolo[2,3-d]pyridazine and 4-chlorophenylmethanethiol.

m.p.: 107–108° C.

Mass spectrum (CI, m/z): 344 ($M^+$+1).

NMR spectrum ($CDCl_3$, δppm): 2.26 (s, 3H), 2.30 (s, 3H), 4.58 (d;J=14 Hz, 1H), 4.70 (s, 2H), 5.00–5.13 (m, 3H), 5.87–6.01 (m, 1H), 7.19–7.27 (m, 2H), 7.35–7.42 (m, 2H), 9.07 (s, 1H).

Elementary analysis (%): Calc'd for $C_{18}H_{18}ClN_3S$: C, 62.87; H, 5.28; N, 12.22, Found: 62.90; H, 5.44; N, 12.00.

EXAMPLE 56

1-(2-Butenyl)-3-ethyl-7-(4-fluorobenzyloxy)-2-methylpyrrolo[2,3-d]pyridazine

The title compound (cis/trans=22/78) was prepared as a white powder in 63.1% yield in a similar procedure to that described in Example 1 by using 1-(2-butenyl)-7-chloro-3-ethyl-2-methylpyrrolo[2,3-d]pyridazine (cis/trans=26/74) and 4-fluorobenzyl alcohol.

m.p.: 78–83° C.

Mass spectrum (CI, m/z): 340 ($M^+$+1).

NMR spectrum ($CDCl_3$, δppm): 1.22 (t;J=8. Hz, 3H), 1.56–1.68 (m, 3H), 2.32 (s, 3H), 2.71 (q;J=8 Hz, 2H), 4.81–4.89 (m, 1.56H), 5.02 (d;J=8 Hz, 0.44H), 5.13–5.29 (m, 1H), 5.42–5.58 (m, 1H), 5.69 (9, 2H), 7.01–7.12 (m, 2H), 7.42–7.55 (m, 2H), 9.01 (s, 1H).

Elementary analysis (%): Calc'd for $C_{20}H_{22}FN_3O$: C, 70.77; H, 6.53; N, 12.38, Found: C, 70.75; H, 6.56; N, 12.40.

EXAMPLE 57

7-(4-Fluorobenzyloxy)-2,3-dimethyl-1-(2-methylcyclopropylmethyl)pyrrolo[2,3-d]pyridazine The title compound (trans) was prepared as a white powder in 91.60% yield in a similar procedure to that described in Example 1 by using 7-chloro-2,3-dimethyl-1-(2-methylcyclopropylmethyl)pyrrolo[2,3-d]pyridazine and 4-fluorobenzyl alcohol.

m.p.: 121–122° C.

Mass spectrum (CI, m/z): 340 ($M^+$+1).

NMR spectrum ($CDCl_3$, δppm): 0.15 (dt;J=8 Hz, 4 Hz, 1H), 0.39 (dt;J=8 Hz, 4 Hz, 1H), 0.58–0.67 (m, 1H), 0.76–0.85 (m, 1H), 0.90 (d;J=7 Hz, 3H), 2.27 (s, 3H), 2.37 (s, 3H), 4.14 (dd;J=15 Hz, 7 Hz, 1H), 4.28 (dd;J=15 Hz, 7 Hz, 1H), 5.64 (d;J=16 Hz, 1H), 5.68 (d;J=16 Hz, 1H), 7.06–7.13 (m, 2H), 7.48–7.53 (m, 2H), 8.99 (s, 1H).

Elementary analysis (%): Calc'd for $C_{20}H_{22}FN_3O$: C, 70.77; H, 6.53; N, 12.38, Found: C, 70.77; H, 6.57; N, 12.37.

EXAMPLE 58

7-(2,4-Difluorobenzyloxy)-2,3-dimethyl-1-(2-methylcyclopropylmethyl)pyrrolo[2,3-d]pyridazine The title compound (trans) was prepared as a white powder in 63.8% yield in a similar procedure to that described in Example 1 by using 7-chloro-2,3-dimethyl-1-(2-methylcyclopropylmethyl)pyrrolo[2,3-d]pyridazine and 2,4-difluorobenzyl alcohol.

m.p.: 101–102° C.

Mass spectrum (CI, m/z): 358 ($M^+$+1).

NMR spectrum ($CDCl_3$, δppm): 0.10–0.17 (m, 1H), 0.35–0.41 (m, 1H), 0.59–0.63 (m, 1H), 0.78–0.86 (m, 1H), 0.89 (d;J=7 Hz, 3H), 2.26 (s, 3H), 2.36 (s, 3H), 4.10 (dd;J=15 Hz, 7 Hz, 1H), 4.26 (dd;J=15 Hz, 7 Hz, 1H), 5.67–5.77 (m, 2H), 6.84–6.92 (m, 2H), 7.54–7.62 (m, 1H), 8.97 (s, 1H).

Elementary analysis (%): Calc'd for $C_{20}H_{21}F_3N_3O$: C, 67.20; H, 5.92; N, 11.76, Found: C, 67.28; H, 5.91; N. 11.74.

EXAMPLE 59

1-(2-Butenyl)-7-(4-fluorobenzyloxy)-2-methyl-3-pentylpyrrolo[2,3-d]pyridazine

The title compound (cis/trans=14/86) was prepared as a white powder in 49.8% yield in a similar procedure to that described in Example 1 by using 1-(2-butenyl)-7-chloro-2-methyl-3-pentylpyrrolo[2,3-d]pyridazine (cis/trans=20/80) and 4-fluorobenzyl alcohol.

m.p.: 65–69° C.

Mass spectrum (CI, m/z): 382 ($M^+$+1).

NMR spectrum ($CDCl_3$, δppm): 0.89 (t;J=8 Hz, 3H), 1.21–1.40 (m, 9H), 2.33 (s, 3H), 2.68 (t;J=8 Hz, 2H), 4.82–4.89 (m, 1.72H), 5.02 (d;J=8 Hz, 0.28H), 5.07–5.24 (m, 1H), 5.43–5.58 (m, 1H), 5.66 (S, 2H), 7.02–7.12(m 2H) , 7.45–7.52 (mn, 2H) , 8.99 (s, 1H).

Elementary analysis (%): Calc'd for $C_{23}H_{28}FN_3O$: C, 72.41; H, 7.40; N, 11.02, Found: C, 72.44; H, 7.29; N, 11.03.

EXAMPLE 60

7-Benzyloxy-2,3-dimethyl-1-(4,4,4-trifluoro-2-butenyl)-pyrrolo[2,3 -d]pyridazine The title compound was prepared as pale yellow crystals in 20.7% yield in a similar procedure to that described in Example 41-by using 7-benzyloxy-2,3-dimethylpyrrolo[2,3-d]pyridazine and 4,4,4-trifluoro-2-butenyl methanesulfonate.

m.p.: 138–140° C.

Mass spectrum (CI, m/z): 362 ($M^+$+1).

NMR spectrum ($CDCl_3$, δppm): 2.28 (s, 3H), 2.29 (s, 3H), 4.98–5.11 (m, 3H), 5.66 (s, 2H), 6.37–6.48 (m, 1H), 7.32–7.50 (m, 5H) , 9.01 (s, 1H)

Elementary analysis (%): Calc'd for $C_{19}H_{18}F_3N_3O$: C, 63.15; H, 5.02; N, 11.63, Found: C, 63.21; H, 5.06; N, 11.59.

EXAMPLE 61

7-Benzyloxy-1-(2,3-dichloro-2-propenyl)-2,3-dimethylpyrrolo[2,3-d]pyridazine

The title compound was prepared as ocherous powdery crystals in 8.0% yield in a similar procedure to that described in Example 41 by using 7-benzyloxy-2,3-dimethylpyrrolo[2,3-d]pyridazine and 1,2,3-trichloro-1-propene.

Mass spectrum (CI, m/z): 362 ($M^+$+1).

NMR spectrum ($CDCl_3$, δppm): 2.32 (s, 3H), 2.43 (s, 3H), 5.15 (s, 2H), 5.66 (s, 2H), 5.80 (s, 1H), 7.31–7.52 (m, 5H), 9.18 (s, 1H).

EXAMPLE 62

1-(2-Butenyl)-7-(4-fluorophenethyl)-2,3-dimethylpyrrolo[2,3-d]pyridazine 0.10 g (0.0020 mole) of hydrazine hydrate was added to a solution of 0.39 g (0.00113 mole) of 1-(2-butenyl)-2-[1-chloro-3-(4-fluorophenyl)-1-propenyl]-3-formyl-4,5-dimethylpyrrole in 7 ml of ethanol and the resulting mixture was stirred at 75° C. for an hour. After completion of the reaction, the reaction mixture was concentrated under reduced pressure and the concentrate was diluted with ice-water. The aqueous mixture was extracted twice with 30 ml of ethyl acetate. The combined extracts were washed with a saturated aqueous solution of sodium chloride and dried over anhydrous sodium sulfate. The solvent was distilled off under reduced pressure and the residue was purified by column chromatography through silica gel using a 50:1 mixture of chloroform and methanol as an eluent to give 0.23 g of the title compound (cis/trans=22/78) as white powdery crystals.

m.p.: 108–113° C.

Mass spectrum (CI, m/z): 324 ($M^+$+1).

NMR spectrum ($CDCl_3$, δppm): 1.60–1.68 (m, 3H), 2.30 (s, 3H), 2.35 (s, 3H), 3.18–3.26 (m, 2H), 3.49–3.57 (m, 2H), 4.75–4.80 (m, 1.56H), 4.85–5.05 (m, 1H), 5.20–5.30 (m, 0.44H), 5.50–5.67 (m, 1H), 6.94–7.02 (m, 2H), 7.18–7.24 (m, 2H), 9.20 (s, 1H).

Elementary analysis (%): Calc'd for $C_{20}H_{22}FN_3$:C, 74.28; H, 6.85; N, 12.99, Found: C, 74.41; H, 6.99; N, 12.90.

EXMAPLE 63

7-(4-Fluorophenethyl)-2,3-dimethyl-1-(2-methylcyclopropylmethyl)pyrrolo[2,3-d]pyridazine The title compound was prepared as pale yellow powdery crystals in 72.7% yield in a similar procedure to that described in Example 62 by using 7-[1-chloro-3-(4-fluorophenyl)-1-propenyl]-3-formyl-4,5-dimethyl-1-(2-methylcyclopropylmethyl)pyrrole.

m.p.: 112–114° C.

Mass spectrum (CI, m/z): 338 ($M^+$+1).

NMR spectrum ($CDCl_3$, δppm): 0.27–0.41 (m, 2H), 0.57–0.79 (m, 2H), 0.97 (d;J=6 Hz, 3H), 2.29 (s, 3H), 2.39 (s, 3H), 3.19–3.25 (m, 2H), 3.57–3.63 (m, 2H), 4.20 (d;J=6 Hz, 2H), 6.95–7.02 (m, 2H), 7.20–7.27 (m, 2H), 9.18 (s, 1H).

Elementary analysis (%): Calc'd for $C_{21}H_{24}FN_3$: C, 74.75; H, 7.17; N, 12.45, Found: C, 74.63; H, 7.27; N, 12.42.

EXAMPLE 64

1-Cyclopropylmethyl-7-(4-fluorophenethyl)-2,3-dimethylpyrrolo[2,3-d]pyridazine

The title compound was prepared as pale yellow powdery crystals in 53.4% yield in a similar procedure to that described in Example 62 by using 2-[1-chloro-3-(4-fluorophenyl)-1-propenyl-1-cyclopropylmethyl]-3-formyl-4,5-dimethylpyrrole.

m.p.: 172–173° C.

Mass spectrum (CI, m/z): 324 ($M^+$+1).

NMR spectrum ($CDCl_3$, δppm): 0.20–0.26 (m, 2H), 0.52–0.59 (m, 2H), 1.02–1.10 (m, 1H), 2.29 (s, 3H), 2.39 (s, 3H), 3.19–3.25 (m, 2H), 3.58–3.64 (m, 2H), 4.20 (d;J=6 Hz, 2H), 6.95–7.01 (m, 2H), 7.19–7.25 (m, 2H), 9.18 (s, 1H).

Elementary analysis (%): Calc'd for $C_{20}H_{22}FN_3$: C, 74.28; H, 6.86; N, 12.99, Found: C, 74.19; H, 6.88; N, 12.90.

EXAMPLE 65

7-(4-Fluorophenethyl)-2,3-dimethyl-1-(2-propenyl)-pyrrolo[2,3-d]pyridazine

The title compound was prepared as pale yellow powdery crystals in 55.8% yield in a similar procedure to that described in Example 62 by using 2-[1-chloro-3-(4-fluorophenyl)-1-propenyl]-3-formyl-4,5-dimethyl-1-(2-propenyl)pyrrole.

m.p.: 123–124° C.

Mass spectrum (CI, m/z): 310 ($M^+$+1).

NMR spectrum ($CDCl_3$, δppm): 2.30 (s, 3H), 2.34 (s, 3H), 3.19–3.–25 (m, 2H), 3.45–3.51 (m, 2H), 4.46 (d;J=17 Hz, 1H), 4.81–4.84 (m, 2H), 5.16 (d;J=10 Hz, 1H), 5.91–6.04 (m, 1H), 6.94–7.01 (m, 2H), 7.18–7.23 (m, 2H), 9.20 (s, 1H)

Elementary analysis (%): Calc'd for $C_{19}H_{20}FN_3$: C, 73.76; H, 6.52; N, 13.58, Found: C, 73.72; H, 6.61; N, 13.45.

EXAMPLE 66

1-(2-butenyl)—2,3-dimethyl-7-phenethylpyrrolo[2,3-d]pyridazine

The title compound (cis/trans=14/86) was prepared as an ocherous powder in 53.2% yield in a similar procedure to that described in Example 62 by using 1-(2-butenyl)-2-(1-chloro-3-phenyl-1-propenyl)-3-formyl-4,5-dimethylpyrrole (cis/trans=23/77).

m.p.: 98–106° C.

Mass spectrum (CI, m/z): 306 ($M^+$+1).

NMR spectrum ($CDCl_3$, δppm): 1.58–1.65 (m, 3H), 2.29 (s, 3H), 2.34 (s, 3H), 3.19–3.25 (m, 2H), 3.50–3.57 (m, 2H), 4.76–4.79 (m, 1.72H), 4.84–4.89 (m, 0.28H), 4.94–5.02 (m, 1H), 5.56 (br.d, 1H), 7.20–7.35 (m, 5H), 9.20 (s, 1H).

Elementary analysis (%): Calc'd for $C_{20}H_{23}N_3$: C, 78.65; H, 7.59; N, 13.76, Found: C, 78.78; H, 7.61; N, 13.76.

EXAMPLE 67

2,3-Dimethyl-7-phenethyl-1-(2-propenyl)Tpyrrolo[2,3-d]pyridazine

The title compound was prepared as yellow crystals in 56.3% yield in a similar procedure to that described in Example 62 by using 2-(1-chloro-3-phenyl-1-propenyl)-3-formyl-4,5-dimethyl-1-(2-propenyl)pyrrole.

m.p.: 96–98° C.

Mass spectrum (CI, m/z): 292 ($M^+$+1).

NMR spectrum ($CDCl_3$, δppm): 2.30 (s, 3H), 2.34 (s, 3H), 3.20–3.26 (m, 2H), 3.48–3.54 (m, 2H), 4.45 (d;J=17 Hz, 1H), 4.82–4.85 (m, 2H), 5.16 (dd;J=10 Hz, 2 Hz, 1H), 5.98 (ddt; J=17 Hz, 10 Hz, 4 Hz, 1H), 7.16–7.39 (m, 5H), 9.21 (s, 1H)

Elementary analysis (%): Calc'd for $C_{19}H_{21}N_3$: C, 78.31; H, 7.26; N, 14.42, Found: C, 78.28; H, 7.42; N, 14.20.

EXAMPLE 68

2,3-Dimethyl-1-(2-methylcyclopropylmethyl)-7-phenethylpyrrolo[2,3-d]pyridazine

The title compound was prepared as a creamy powder in 50.0%; yield in a similar procedure to that described in Example 62 by using 2-(1-chloro-3-phenyl-1-propenyl)-3-formyl-4,5-dimethyl-1-(2-methylcyclopropylmethyl)pyrrole.

m.p.: 102–103° C.

Mass spectrum (CI, m/z): 320 ($M^+$+1).

NMR spectrum ($CDCl_3$, δppm): 0.26–0.41 (m, 2H), 0.57–0.67 (m, 1H), 0.73–0.80 (m, 1H), 0.97 (d;J=6 Hz, 3H), 2.28 (s, 3H), 2.38 (s, 3H), 3.20–3.26 (m, 2H), 3.60–3.66 (m, 2H), 4.22 (d;J=6 Hz, 2H), 7.14–7.38 (m, 5H), 9.18 (s, 1H).

EXAMPLE 69

1-Cyclopropylmethyl-2,3-dimethyl-7-phenethylopyrrolo[2,3-d]pyridazine

The title compound was prepared as a creamy powder in 69.9% yield in a similar procedure to that described in Example 62 by using 2- (1-chloro-3-phenyl-1-propenyl)-1-cyclopropylmethyl-3-formyl-4,5-dimethylpyrrole.

m.p.: 133–135° C.

Mass spectrum (CI, m/z): 306 ($M^+$+1).

NMR spectrum ($CDCl_3$, δppm): 0.20–0.26 (m, 2H), 0.51–0.58 (m, 2H), 1.02–1.12 (m, 1H), 2.29 (s, 3H), 2.39 (s, 3H), 3.19–3.25 (m, 2H), 3.60–3.67 (m, 2H), 4.22 (d;J=6 Hz, 2H), 7.16–7.36 (m, 5H), 9.19 (s, 1H).

Elementary analysis (%): Calc'd for $C_{20}H_{23}N_3$: C, 78.65; H, 7.59; N, 13.76, Found: C, 78.42; H, 7.62; N, 13.66.

EXAMPLE 70

1-(2-Butenyl)-7-(2,4-difluorophenethyl)-2,3-dimethylpyrrolo[2,3-d]pyridazine

The title compound (cis/trans=20/80) was prepared as pale ocherous powdery crystals in 59.20% yield in a similar procedure to that described in Example 62 by using 1-(2-butenyl)-2-[1-chloro-3-(2,4-difluorophenyl)-1-propenyl]-3-formyl-4,5-dimethylpyrrole.

m.p.: 114–118° C.

Mass spectrum (CI, m/z): 342 ($M^+$+1).

NMR spectrum ($CDCl_3$, δppm): 1.58–1.71 (m, 3H), 2.30 (s, 3H), 2.35 (s, 3H), 3.17–3.26 (m, 2H), 3.45–3.55 (m, 2H), 4.80–5.03 (m, 2.8H), 5.19–5.28 (m, 0.2H), 5.51–5.66 (m, 1H), 6.77–6.84 (m, 2H), 7.22–7.32 (m, 1H), 9.19 (s, 1H).

Elementary analysis (%): Calc'd for $C_{20}H_{21}F_2N_3$: C, 70.36; H, 6.20; N, 12.31, Found: C, 70.52; H, 6.23; N, 12.27.

EXAMPLE 71

7-(2,4-Difluorophenethyl)-2,3-dimethyl-1-(2-methylcyclopropylmethyl)-ovrrolo[2,3-d]pyridazine The title compound was prepared as pale yellow powdery crystals in 64.0% yield in a similar procedure to that described in Example 62 by using 2-[1-chloro-3-(2,4-difluorophenyl)-1-propenyl]-3-formyl-4,5-dimethyl-1-(2-methylcyclopropylmethyl)pyrrole.

m.p.: 105–106° C.

Mass spectrum (CI, m/z): 356 ($M^+$+1).

NMR spectrum ($CDCl_3$, δppm): 0.26–0.42 (m, 2H), 0.59–0.80 (m, 2H), 0.97 (d;J=6 Hz, 3H), 2.29 (s, 3H), 3.40 (s, 3H), 3.17–3.24 (m, 2H), 3.55–3.61 (m, 2H), 4.28 (d;J=6 Hz, 2H), 6.78–6.85 (m, 2H), 7.23–7.32 (m, 1H), 9.18 (s, 1H).

Elementary analysis (%): Calc'd for $C_{21}H_{23}F_2N_3$: C, 70.97; H, 6.52; N; 11.82, Found: C, 71.11; H, 6.54; N, 11.86.

EXAMPLE 72

1-Cyclopropylmethyl-7-(2,4-difluorophenethyl)-2,3-dimethylpyrrolo[2,3-d]pyridazine The title compound was prepared as pale flesh-colored powdery crystals in 69.0% yield in a similar procedure to that described in Example 62 by using 2-[1-chloro-3-(2,4-difluorophenyl)-1-propenyl]-1-cyclopropylmethyl-3-formyl-4,5-dimethylpyrrole.

m.p.: 159–160° C.

Mass spectrum (CI, m/z): 342 ($M^+$+1).

NMR spectrum ($CDCl_3$, δppm): 0.22–0.28 (m, 2H), 0.52–0.59 (m, 2H), 1.01–1.13 (m, 1H), 2.29 (s, 3H), 2.41 (s, 3H), 3.17–3.23 (m, 2H), 3.56–3.62 (m, 2H), 4.28 (d;J=6 Hz, 2H), 6.78–6.85 (m, 2H), 7.23–7.32 (m, 1H), 9.18 (s, 1H).

Elementary analysis (%): Calc'd for $C_{20}H_{21}F_2N_3$.1/5$H_2O$: C, 69.63; H, 6.25; N, 12.18, Found: C, 69.71; H, 6.22; N, 12.12.

EXAMPLE 73

7-(2,4-Difluorophenethyl)-2,3-dimethyl-1-(2-propenyl)-pyrrolo[2,3-d]pyridazine

The title compound was prepared as pale yellow powdery crystals in 66.2% yield in a similar procedure to that described in Example 62 by using 2-[1-chloro-3-(2,4-difluorophenyl)-1-propenyl]-3-formyl-4,5-dimethyl-1-(2-propenyl)pyrrole.

m.p.: 118–119° C.

Mass spectrum (CI, m/z): 328 ($M^+$+1).

NMR spectrum ($CDCl_3$, δppm): 2.30 (s, 3H), 2.35 (s, 3H), 3.17–3.23 (m, 2H), 3.43–3.49 (m, 2H), 4.43 (d;J=17 Hz, 1H), 4.90–4.93 (m, 2H), 5.14 (d;J=10 Hz, 1H), 5.94–6.05 (m, 1H), 6.76–6.84 (m, 2H), 7.22–7.31 (m, 1H) , 9.20 (s, 1H)

Elementary analysis (%): Calc'd for $C_{19}H_{19}F_2N_3$: C, 69.71; H, 5.85; N, 12.84, Found: C, 69.67; H, 5.90; N, 12.81.

EXAMPLE 74

1-(2-Butenyl)-7-(4-fluorobenzyloxy)-2,3-dimethylpyrrolo[2,3-d]pyridazine hydrochloride A solution of 0.36 g (0.01 mole) of hydrogen chloride in 3.0 ml of ethanol was added dropwise with ice-cooling to a solution of 2.00 g (0.00615 mole) of 1-(2-butenyl)-7-(4-fluorobenzyloxy)-2,3-dimethylpyrrolo[2,3-d]pyridazine (cis/trans=1/99) in 160 ml of dry diethyl ether and the resulting mixture was stirred at the same temperature for 20 minutes. The reaction mixture was concentrated at room temperature and the residue was washed with a mixture of 10 ml of ethanol and 120 ml of dry diethyl ether. The solid mass thus obtained was then collected by filtration to give 1.88 g of the title compound (trans) as a white powder.

m.p.: 203–2200C.

Mass spectrum (CI, m/z): 325 ($M^+$+1).

NMR spectrum ($CDCl_3$, δppm): 1.62 (d, J=9 Hz, 3H), 2.32 (s, 3H), 2.46 (s, 3H), 5.00 (d, J=5 Hz, 2H), 5.18–5.72 (m, 4H), 6.99–7.20 (m, 2H), 7.36–7.60 (m, 2H), 9.29 (s, 1H), 17.18 (s, 1H).

Elementary analysis (%): Calc'd for $C_{19}H_{20}$ $FN_3O$.HCl: C, 63.07; H, 5.85; N, 11.61, Found: C, 63.09; H, 5.91; N, 11.61.

EXAMPLE 75

1-(2-Butenyl)-7-(4-fluorobenzyloxy)-2,3-dimethylpyrrolo[2,3-d]pyridazine-5-oxide A solution of 0.72 g (0.0029 mole) of m-chloroperoxybenzoic acid (purity: 700%) in 20 ml of dichloromethane was added to a solution of 0.72 g (0.0029 mole) of 1-(2-butenyl)-7-(4-fluorobenzyloxy)-2,3-dimethylpyrrolo[2,3-d]pyridazine in 70 ml of dichloromethane at room temperature and the resulting mixture was stirred at the same temperature for 30 minutes. After completion of the reaction, the reaction mixture was washed three times with 40 ml each of a saturated aqueous solution of sodium hydrogencarbonate. The dichloromethane layer was dried over anhydrous sodium sulfate and the solvent was distilled off under reduced pressure. The residue was purified by column chromatography through silica gel using a 100:1 to 100:4 mixture of chloroform and methanol as an eluent to give crystals, which were washed with a mixture of ether and hexane to give 0.63 g of the title compound (cis/trans=27/73) as a pale yellow powder.

m.p.: 138–148° C.

Mass spectrum (CI, m/z): 342 ($M^+$+1).

NMR spectrum ($CDCl_3$, δppm): 1.42–1.68 (3H, m), 2.13 (3H, s), 2.30 (3H, s), 4.69–4.83 (1.46H, m), 4.88–4.97 (0.54H, m), 5.11–5.66 (4H, m), 6.98–7.13 (2H, m), 7.39–7.52 (2H, m) , 8.27 (H, s))

Elementary analysis (%): Calc'd for $C_{19}H_{20}FN_3O_2$: C, 66.85; H, 5.91; N, 12.31, Found: C, 66.78; H, 5.88; N, 12.29.

EXAMPLE 76

1-(2-Butenyl)—7-(2,4-difluorobenzyloxy)-2,3-dimethylpyrrolo[2,3-d]pyridazine-5-oxide The title compound (cis/trans=7/93) was prepared as pale yellow powdery crystals in 87.0% yield in a similar procedure to that described in Example 75 by using 1-(2-butenyl)-7-(2,4-difluorobenzyloxy)-2,3-dimethylpyrrolo[2,3-d]pyridazine.

m.p.: 166–168° C.

Mass spectrum (CI, m/z): 360 ($M^+$+1).

NMR spectrum ($CDCl_3$, δppm): 1.58–1.61 (m, 3H), 2.14 (s, 3H), 2.29 (s, 3H), 4.72–4.75 (m, 1.86H), 4.88–4.91 (m, 0.14H), 5.15–5.31 (m, 1H), 5.38–5.50 (m, 1H), 5.59 (s, 2H), 6.83–6.94 (m, 2H), 7.49–7.58 (m, 1H), 8.23 (s, 1H).

Elementary analysis (%): Calc'd for $C_{19}H_{19}F_2N_3O$: C, 63.50; H, 5.33; N, 11.69, Found: C, 63.49.; H, 5.28; N, 11.69.

EXAMPLE 77

1-(2-Butenyl)-7-(2,4-difluorophenethyl)-2,3-dimethylpyrrolo[2,3-d]pyridazine-5-oxide and 1-(2- butenyl)-7-(2,4-difluorophenethyl)-2,3-dimethyliyrrolo[2, 3-d]pyridazine-6-oxide A solution of 0.35 g (0.00142 mole) of m-chloroperoxybenzoic acid (purity: 700%) in 5 ml of dichloromethane was added dropwise to a solution of 0.47 g (0.00138 mole) of 1-(2-butenyl)-7-(2,4-difluorophenethyl)-2,3-dimethylpyrrolo[2,3-d]pyridazine in 10 ml of dichloromethane at room temperature over a period of 30 minutes and the resulting mixture was stirred at the same temperature for an hour. After completion of the reaction, the reaction mixture-was washed three times with 30 ml each of a saturated aqueous solution of sodium hydrogencarbonate. The dichloromethane layer was washed with a saturated aqueous solution of sodium chloride and dried over anhydrous sodium sulfate, and the solvent was distilled off under reduced pressure. The residue was purified by column chromatography through silica gel using a 50:1 mixture of chloroform and methanol as an eluent. The purified product was triturated with a mixture of ether and hexane to give 0.058 g of the 5-oxide of the title compound (cis/trans=25/75) and 0.290 g of the 6-oxide of the title compound (cis/trans=25/75) as a pale yellow powder, respectively. 5-oxide compound m.p.: 104–112° C.

Mass spectrum (CI, m/z): 358 ($M^+$+1).

NMR spectrum ($CDCl_3$, δppm): 1.62–1.70 (m, 3H), 2.25 (s, 3H), 2.30 (s, 3H), 3.08–3.18 (m, 2H), 3.41–3.51 (m, 2H), 4.63–4.67 (m, 1.5H), 4.74–4.78 (m, 0.5H), 4.97–5.07 (m, 0.75H), 5.07–5.13 (m, 0.25H), 5.50–5.66 (m, 1H), 6.75–6.83 (m, 2H), 7.28–7.37 (m, 1H), 8.52 (s, 1H).

Elementary analysis (%): Calc'd for $C_{20}H_{21}F_2N_3O.⅕H_2O$: C, 66.54; H, 5.97; N, 11.64, Found: C, 66.64; H, 5.88; N, 11.55.

6-oxide compound m.p.: 135–141° C.

Mass spectrum (CI, m/z): 358 ($M^+$+1).

NMR spectrum ($CDCl_3$, δppm): 1.62–1.69 (m, 3H), 2.19 (s, 3H), 2.33 (s, 3H), 3.12–3.32 (m, 4H), 4.76–4.78 (m, 1.5H), 4.86–4.87 (m, 0.5H), 4.96–5.09 (m, 0.75H), 5.19–5.25 (m, 0.25H), 5.50–5.67 (m, 1H), 6.76–6.84 (m, 2H), 7.20–7.29 (m, 1H), 8.40 (s, 1H).

Elementary analysis (%): Calc'd for $C_{20}$ $H_{21}F_2N_3$: C, 67.21; H, 5.92; Ni 11.76, Found: C, 66.98; H, 5.99; N, 11.62.

REFERENTIAL EXAMPLE 1

Ethyl 1-(2-butenyl)-5-ethyl-4-methylpyrrole-2-carboxylate (1) 3-Chloro-2-methyl-2-pentenal (a mixture of cis and trans)

27 ml (0.30 mole) of phosphorus oxychloride were added dropwise to 29.2 g (0.40 mole) of dimethylformamide with ice-cooling over a period of 30 minutes and the resulting mixture was stirred at the same temperature for 30 minutes and then at room temperature for 40 minutes. 21 ml (0.21 mole) of 3-pentanone were added thereto over a period of 20 minutes to keep the reaction temperature below 40° C. by ice-cooling, and the mixture was stirred with ice-cooling for 10 minutes and then at room temperature for 2 hours. The reaction mixture was poured into about 300 ml of ice-water by portions and the diluted mixture was neutralized to pH 7–8 with sodium hydrogencarbonate. The mixture was extracted with diethyl ether (once with 200 ml and three times with 100 ml). The combined extracts were washed with a saturated aqueous solution of sodium chloride and dried over anhydrous sodium sulfate. The solvent was distilled off using a rotary evaporator in a bath kept below 30° C. The residue was purified by distilling at 58–61° C./15 mmHg to give 14.8 g of 3-chloro-2-methyl-2-pentenal as a colorless transparent oil.

Mass spectrum (CI, m/z): 133 ($M^+$+1), 135 ($M^+$+3).

NMR spectrum ($CDCl_3$, δppm): 1.23 (t;J=8 Hz, 3/4H), 1.30 (t;J=8 Hz, 9/4H), 1.84 (s, 3/4H), 1.91 (s, 9/4H), 2.65 (q;J=8 Hz, 2/4H), 2.94 (s, 6/4H), 10.02 (s, 3/4H), 10.21 (s, 1/4H).

(2) Ethyl 1-(2-butenyl)-5-ethyl-4-methylpyrrole-2-carboxylate 3.74 g (0.024 mole) of ethyl N-(2-butenyl)glycinate were added to a solution of 5.0 g (0.038 mole) of 3-chloro-2-methyl-2-pentenal in 10 ml of ethanol with stirring, and subsequently 6 ml (0.043 mole) of triethylamine were added thereto and stirred at room temperature for 7 hours. After the precipitates deposited were filtered off, 5.35 g (0.048 mole) of potassium tert-butoxide were added to the filtrate by portions and the mixture was stirred for 30 minutes. The reaction mixture was poured into about 150 ml of a saturated aqueous solution of ammonium chloride and extracted with ethyl acetate (once with 100 ml and twice with 50 ml). The combined extracts were washed with a saturated aqueous solution of sodium chloride and dried over anhydrous sodium sulfate, and the solvent was distilled off. The residue was purified by column chromatography through silica gel using a 3:97 mixture of ethyl acetate and hexane as an eluent to give 1.53 g of ethyl 1-(2-butenyl)-5-ethyl-4-methylpyrrole-2-carboxylate (cis/trans=76/24) as an orange oil.

Mass spectrum (CI, m/z): 236 ($M^+$+1).

NMR spectrum ($CDCl_3$, δppm): 1.10 (t;J=8 Hz, 3H), 1.32 (t;J=7 Hz, 3H), 1.61–1.65 (m, 2.28H), 1.74–1.78 (m, 0.72H), 2.03 (s, 3H), 2.55 (q;J=8 Hz, 2H), 4.20 (q;J=7 Hz, 2H), 4.84–4.90 (m, 1.52H), 4.97–5.03 (m, 0.48H), 5.30–5.38 (m, 1H), 5.52–5.61 (m, 1H), 6.79 (s, 1H).

REFERENTIAL EXAMPLE 2

Ethyl 1-cyclopropyl-4,5-dimethylpyrrole-2-carboxylate

The title compound was prepared as a yellow oil in 41.6% yeild in a similar procedure to that described in Referential Example 1 by using 2-butanone and ethyl N-cyclopropylglycinate.

Mass spectrum (CI, m/z): 208 ($M^+$+1).

NMR spectrum ($CDCl_3$, δppm): 0.79–0.87 (m, 2H), 1.08–1.16 (m, 2H), 1.35 (t;J=8 Hz, 3H), 1.98 (s, 3H), 2.26 (s, 3H), 3.12–3.24 (m, 1H), 4.24 (q;J=8 Hz, 2H), 6.71 (s, 1H).

REFERENTIAL EXAMPLE 3

Ethyl 1-cyclohexyl-4,5-dimethylpyrrole-2-carboxylate

The title compound was prepared as a yellow oil in 18.9g yeild in a similar procedure to that described in Referential Example 1 by using 2-butanone and ethyl N-cyclohexylglycinate.

Mass spectrum (CI, m/z): 250 ($M^+$+1).

NMR spectrum ($CDCl_3$, δppm): 1.32 (t;J=8 Hz, 3H), 1.63–1.94 (m, 6H), 1.98 (s, 3H), 2.03–2.24 (m, 4H), 2.30 (s, 3H), 3.39–3.70 (m, 1H), 4.21 (q;J=8 Hz, 2H), 6.89 (s, 1H).

REFERENTIAL EXAMPLE 4

Ethyl 4-ethyl-5-methyl-1-(2-propenyl)pyrrole-2-carboxylate The title compound was prepared as a yellow oil in 25.60% yeild in a similar procedure to that described in Referential Example 1 by using 2-pentanone and ethyl N-(2-propenyl)glycinate, there was obtained the desired compound as a yellow oil in 25.6-s. yield.

Mass spectrum (CI, m/z): 222 ($M^+$+1).

NMR spectrum ($CDCl_3$, δppm): 1.17 (t;J=8 Hz, 3H), 1.34 (t;J=8 Hz, 3H), 2.16 (s, 3H), 2.42 (q;J=8 Hz, 2H), 4.23 (q;J=8 Hz, 2H), 4.68–4.81 (m, 1H), 4.91–5.00 (m, 2H), 5.04–5.12 (m, 1H), 5.87–6.02 (m, 1H), 6.84 (s, 1H).

REFERENTIAL EXAMPLE 5

Ethyl 1-(2-butenyl)-5-ethyl-3-formyl-4-methylpyrrole-2-carboxylate 1.5 ml (0.0069 mole) of phosphorus oxychloride was added to a solution of 1.38 g (0.0059 mole) of ethyl 1-(2-butenyl-5-ethyl-4-methylpyrrole-2-carboxylate (trans/cis=76/24) in 3 ml of dimethylformamide and the resulting mixture was stirred in an oil bath kept at 100° C. for 2 hours. The reaction mixture cooled was poured into about 50 ml of ice-water by driblets and neutralized to pH 7–8 with a saturated aqueous solution of sodium hydrogencarbonate. The aqueous mixture was then extracted with 50 ml each of ethyl acetate for four times. The combined extracts were washed with a saturated aqueous solution of sodium chloride and dried over anhydrous sodium sulfate, and the solvent was distilled off. The residue was purified by column chromatography through silica gel using a 1:10 mixture of ethyl acetate and hexane as an eluent to give 1.33 g of ethyl 1-(2-butenyl)-5-ethyl-3-formyl-4-methylpyrrole-2-carboxylate (trans/cis =77/23) as a yellow-orange oil.

Mass spectrum (CI, m/z): 264 ($M^+$+1).

NMR spectrum ($CDCl_3$, δppm): 1.11 (t;J=8 Hz, 3H), 1.39 (t;J=7 Hz, 3H), 1.65–1.69 (m, 2.31H), 1.74–1.79 (m, 0.69H), 2.25 (s, 3H), 2.60 (q;J=8 Hz, 2H), 4.38 (q;J=7 Hz, 2H), 4.84–4.91 (m, 1.54H), 4.98–5.02 (m, 0.46H), 5.32–5.43 (m, 1H), 5.52–5.56 (m, 1H), 10.47 (s, 1H).

REFERENTIAL EXAMPLE 6

Ethyl 1-cyclopropyl-3-formyl-4,5-dimethylpyrrole-2-carboxylate

The title compound was prepared as a yellow oil in 37.7% yeild in a similar procedure to that described in Referential Example 5 by using ethyl 1-cyclopropyl-4,5-dimethylpyrrole-2-carboxylate.

Mass spectrum (CI, m/z): 236 ($M^+$+1).

NMR spectrum ($CDCl_3$, δppm): 0.75–0.83 (m, 2H), 1.11–1.20 (m, 2H), 1.40 (t;J=7 Hz, 3H), 2.24 (s, 3H), 2.29 (s, 3H), 3.22–3.33 (m, 1H), 4.41 (q;J=7 Hz, 2H), 10.32 (s, 1H).

REFERENTIAL EXAMPLE 7

Ethyl 1-cyclohexyl-3-formyl-4,5-dimethyl-pyrrole-2-carboxylate

The title compound was prepared as a yellow oil in 47.1% yeild in a similar procedure to that described in Referential Example 5 by using ethyl 1-cyclohexyl-4,5-dimethylpyrrole-2-carboxylate.

Mass spectrum (CI, m/z): 278 ($M^+$+1).

NMR spectrum ($CDCl_3$, δppm): 1.17–1.51 (m, 4H), 1.40 (t;J=8 Hz, 3H), 1.69–2.15 (m, 6H), 2.22 (s, 3H), 2.31 (s, 3H), 4.38 (q;J=8 Hz, 2H), 4.61–4.82 (m, 1H), 10.29 (s, 1H).

REFERENTIAL EXAMPLE 8

Ethyl 4-ethyl-3-formyl-5-methyl-1-(2-propenyl)pyrrole-2-carboxylate

The title compound was prepared as a yellow-orange oil in 42.8% yeild in a similar procedure to that described in Referential Example 5 by using ethyl 4-ethyl-5-methyl-1-(2-propenyl)pyrrole-2-carboxylate.

Mass spectrum (CI, m/z): 250 ($M^+$+1).

NMR spectrum ($CDCl_3$, δppm): 1.10 (t;J=7 Hz, 3H), 1.37 (t;J=7 Hz, 3H), 2.18 (s, 3H), 2.74 (q;J=7 Hz, 2H), 4.37 (q;J=7 Hz, 2H), 4.79 (d;J=17 Hz, 1H), 4.92–4.98 (m, 2H), 5.15 (d;J=11 Hz, 1H), 5.88–6.04 (m, 1H), 10.50 (s, 1H).

REFERENTIAL EXAMPLE 9

Methyl 1-(2-butenyl)-3-formyl-4,5-dimethylpyrrole-2-carboxylate 2.21 g (0.0199 mole) of potassium tert-butoxide were added to a solution of 3.60 g (0.0199 mole) of methyl 3-formyl-4,5-dimethylpyrrole-2-carboxylate and 0.36 g (0.0014 mole) of 18-crown-6 in 220 ml of tetrahydrofuran and the resulting mixture was stirred at room temperature for 45 minutes. 3.60 g (0.0398 mole) of 1-chloro-2-butene (a mixture of cis and trans isomers) was added to the mixture and heated under reflux for 7 hours. 1.80 g (0.0199 mole) of 1-chloro-2-butene were then added thereto and heated under reflux for 22 hours. The reaction mixture was allowed to cool to room temperature, subsequently ice-water was added thereto and the mixture was extracted with ethyl acetate. The extract was washed with water and dried over anhydrous sodium sulfate, and the solvent was distilled off. The residue was purified by column chromatography through silica gel using a 95:5 mixture of toluene and ethyl acetate as an eluent to give 4.50 g (0.0192 mole) of methyl 1-(2-butenyl)-3-formyl-4,5-dimethylpyrrole-2-carboxylate (cis/trans =24/76) as a yellow oil.

Mass spectrum (CI, m/z): 236 ($M^+$+1).

NMR spectrum ($CDCl_3$, δppm): 1.64–1.70 (m, 2.3H), 1.74–1.80 (m, 0.7H), 2.18 (9, 3H), 2.27 (s, 3H), 3.90 (s, 3H), 4.82–4.91 (m, 1.5H), 4.97–5.03 (m, 0.5H), 5.27–5.70 (m, 2H) , 10.45 (s, 1H)

REFERENTIAL EXAMPLE 10

Methyl 3-formyl-4,5-dimethyl-1-(3-methyl-2-butenyl)pyrrole-2-carboxylate

The title compound was prepared as a pale yellow-orange solid in 85.4% yeild in a similar procedure to that described in Referential Example 9 by using methyl 3-formyl-4,5-dimethylpyrrole-2-carboxylate and 1-bromo-3-methyl-2-butene.

Mass spectrum (CI, m/z): 250 ($M^+$+1).

NMR spectrum ($CDCl_3$, δppm): 1.71 (s, 3H), 1.77 (s, 3H), 2.16 (s, 3H), 2.25 (s, 3H), 3.90 (s, 3H), 4.92 (d;J=6 Hz, 2H), 5.10 (t;J=6 Hz, 1H), 10.44 (s, 1H).

REFERENTIAL EXAMPLE 11

Methyl 3-formyl-4,5-dimethyl-1-(2-propenyl)pyrrole-2-carboxylate

The title compound was prepared as a yellow solid in 95.1% yeild in a similar procedure to that described in Referential Example 9 by using methyl 3-formyl-4,5-dimethylpyrrole-2-carboxylate and 3-bromo-1-propene.

Mass spectrum (CI, m/z): 222 ($M^+$+1).

NMR spectrum ($CDCl_3$, δppm): 2.15 (s, 3H), 2.26 (s, 3H), 3.88 (s, 3H), 4.78 (d;J=16 Hz, 1H), 4.97 (d;J=5 Hz, 2H), 5.15 (d;J=10 Hz, 1H), 5.89–6.02 (m, 1H), 10.47 (s, 1H).

REFERENTIAL EXAMPLE 12

Methyl 1-cyclopropylmethyl-3-formyl-4,5-dimethylpyrrole-2-carboxylate

The title compound was prepared as a pale yellow-white solid in 95.1% yeild in a similar procedure to that described in Referential Example 9 by using methyl 3-formyl-4,5-dimethylpyrrole-2-carboxylate and cyclopropyl bromide.

Mass spectrum (CI, m/z): 236 ($M^+$+1).

NMR spectrum ($CDCl_3$, δppm): 0.32–0.60 (m, 4H), 1.08–1.28 (m, 1H), 2.21 (s, 3H), 2.25 (s, 3H), 3.90 (s, 3H), 4.16 (d;J=8 Hz, 2H), 10.43 (s, 1H)

REFERENTIAL EXAMPLE 13

Methyl 3-formyl-4,5-dimethyl-1-(3-phenyl-2-propenyl) pyrrole-2-carboxylate

The title compound (trans) was prepared as a pale brown oil in 93.9% yeild in a similar procedure to that described in Referential Example 9 by using methyl 3-formyl-4,5-dimethylpyrrole-2-carboxylate and 3-chloro-1-phenyl-1-propene (trans).

Mass spectrum (CI, m/z): 298 ($M^+$+1).

NMR spectrum ($CDCl_3$, δppm): 2.22 (s, 3H), 2.27 (s, 3H), 3.90 (s, 3H), 5.12 (d;J=4 Hz, 2H), 6.12–6.34 (m, 2H), 7.17–7.43 (m, 5H) , 10.48 (s, 1H)

REFERENTIAL EXAMPLE 14

Methyl 3-formyl-4,5-dimethyl-1-(2-pentenyl)pyrrole-2-carboxylate

The title compound (trans) was prepared as a yellow-orange oil in 85.1% yeild in a similar procedure to that described in Referential Example 9 by using methyl 3-formyl-4,5-dimethylpyrrole-2-carboxylate and 1-bromo-2-pentene (trans).

Mass spectrum (CI, m/z): 250 ($M^+$+1).

NMR spectrum ($CDCl_3$, δppm): 1.05 (t;J=8 Hz, 3H), 2.09–2.26 (m, 8H), 3.90 (s, 3H), 5.00 (d;J=5 Hz, 2H), 5.21–5.34 (m, 1H), 5.46–5.60 (m, 1H), 10.43 (s, 1H).

REFERENTIAL EXAMPLE 15

Methyl 1-(2-bromoethyl)-3-formyl-4,5-dimethylpyrrole-2-carboxylate

The title compound was prepared as ocherous crystals in 9.4% yeild in a similar procedure to that described in Referential Example 9 by using methyl 3-formyl-4,5-dimethylpyrrole-2-carboxylate and 1,2-dibromoethane.

Mass spectrum (CI, m/z): 288 ($M^+$+1), 290 ($M^+$+3).

NMR spectrum ($CDCl_3$, δppm): 2.27 (s, 6H), 3.60 (t;J=7 Hz, 2H), 3.92 (s, 3H), 4.64 (t;J=7 Hz, 2H), 10.48 (s, 1H).

REFERENTIAL EXAMPLE 16

Methyl 3-formyl-4,5-dimethyl-1-(2-methyl-2-propenyl) pyrrole-2-carboxylate

The title compound was prepared as a pale yellow oil in 86.2% yeild in a similar procedure to that described in Referential Example 9 by using but using methyl 3-formyl-4,5-dimethylpyrrole-2-carboxylate and 3-chloro-2-methyl-1-propene.

Mass spectrum (CI, m/z): 236 ($M^+$+1).

NMR spectrum ($CDCl_3$, δppm): 1.78 (s, 3H), 2.12 (s, 3H), 2.27 (s, 3H), 3.88 (s, 3H), 4.13 (s, 1H), 4.81 (s, 1H), 4.86 (s, 2H) , 10.48 (s, 1H)

REFERENTIAL EXAMPLE 17

Methyl 3-formyl-4,5-dimethyl-1-(2,2,2-trifluoroethyl) pyrrole-2-carboxylate

The title compound was prepared as pale brown crystals in 5.5% yeild in a similar procedure to that described in Referential Example 9 by using methyl 3-formyl-4,5-dimethylpyrrole-2-carboxylate and 1,1,1-trifluoro-2-iodoethane.

Mass spectrum (CI, m/z): 264 ($M^+$+1).

NMR spectrum ($CDCl_3$, δppm): 2.22 (s, 3H), 2.27 (s, 3H), 3.93 (s, 3H), 4.91–5.30 (m, 2H) , 10.47 (s, 1H)

REFERENTIAL EXAMPLE 18

Methyl 1-(2-fluoroethyl)-3-formyl-4,5-dimethylpyrrole-2-carboxylate

The title compound was prepared as pale brown crystals in 77.4% yeild in a similar procedure to that described in Referential Example 9 by using methyl 3-formyl-4,5-dimethylpyrrole-2-carboxylate and 1-bromo-2-fluoroethane.

Mass spectrum (CI, m/z): 228 ($M^+$+1).

NMR spectrum ($CDCl_3$, δppm): 2.23 (s, 3H), 2.27 (s, 3H), 3.90 (s, 3H), 4.46–4.86 (m, 4H), 10.49 (s, 1H).

REFERENTIAL EXAMPLE 19

Methyl 1-(2,2-difluoroethyl)-3-formyl-4,5-dimethylpyrrole-2-carboxylate

The title compound was prepared as flesh-colored crystals in 90.4% yeild in a similar procedure to that described in Referential Example 9 by using methyl 3-formyl-4,5-dimethylpyrrole-2-carboxylate and 2-bromo-1,1-difluoroethane.

Mass spectrum (CI, m/z): 246 ($M^+$+1).

NMR spectrum ($CDCl_3$, δppm): 2.24 (s, 3H), 2.26 (s, 3H), 3.93 (s, 3H), 4.66 (dt;J=4 Hz, 14 Hz, 2H), 6.11 (tt;J=4 Hz, 54 Hz, 1H), 10.49 (s, 1H).

REFERENTIAL EXAMPLE 20

Methyl 1-(2-butenyl)-3-formyl-4,5-dimethylpyrrole-2-carboxylate

The title compound (cis/trans=93/7) was prepared as a pale brown oil in 33.4% yeild in a similar procedure to that described in Referential Example 9 by using methyl 3-formyl-4,5-dimethylpyrrole-2-carboxylate and 2-butenyl methanesulfonate (cis/trans=96/4).

Mass spectrum (CI, m/z): 196 ($M^+$+1).

NMR spectrum ($CDCl_3$, δppm): 1.64–1.70 (m, 0.2H), 1.71–1.82 (m, 2.8H), 2.17 (s, 3H), 2.25 (s, 3H), 3.90 (s, 3H), 4.85–4.91 (m, 0.1H), 4.96–5.06 (m, 1.9H), 5.27–5.70 (m, 2H), 10.44 (s, 1H).

REFERENTIAL EXAMPLE 21

Methyl 1-(2-chloro-2-propenyl)-3-formyl-4,5-dimethylpyrrole-2-carboxylate

The title compound was prepared as pale yellow crystals in 77.5% yeild in a similar procedure to that described in Referential Example 9 by using methyl 3-formyl-4,5-dimethylpyrrole-2-carboxylate and 2,3-dichloro-1-propene.

Mass spectrum (CI, m/z): 256 ($M^+$+1), 258 ($M^{++}$3).

NMR spectrum ($CDCl_3$, δppm): 2.19 (s, 3H), 2.27 (s, 3H), 3.90 (s, 3H), 4.70 (s, 1H), 5.10 (s, 2H), 5.29 (s, 1H), 10.49 (s, 1H).

REFERENTIAL EXAMPLE 22

Methyl 3-formyl-4,5-dimethyl-1-(4,4,4-trifluoro-2-butenyl) pyrrole-2-carboxylate The title compound (trans) was prepared as a pale yellow oil in 60.0% yeild in a similar procedure to that described in Referential Example 9 by using methyl 3-formyl-4,5-dimethylpyrrole-2-carboxylate and 4,4,4-trifluoro-2-butenyl methanesulfonate (trans).

Mass spectrum (CI, m/z): 290 ($M^+$+1).

NMR spectrum ($CDCl_3$, δppm): 2.15 (s, 3H), 2.27 (s, 3H), 3.90 (s, 3H), 5.09–5.13 (m, 2H), 5.22–5.31 (m, 1H), 6.49–6.57 (m, 1H) , 10.48 (s, 1H)

REFERENTIAL EXAMPLE 23

Methyl 1-(3,3-difluoro-2-propenyl)-3-formyl-4,5-dimethylpyrrole-2-carboxylate

The title compound was prepared as a pale yellow oil in 70.4% yeild in a similar procedure to that described in Referential Example 9 by using methyl 3-formyl-4,5-dimethylpyrrole-2-carboxylate and 3-bromo-3,3-difluoro-1-propene.

Mass spectrum (CI, m/z): 258 ($M^+$+1).

NMR spectrum ($CDCl_3$, δppm): 2.20 (s, 3H), 2.25 (s, 3H), 3.91 (s, 3H), 4.50–4.67 (m, 1H), 4.91 (d;J=7 Hz, 2H), 10.46 (s, 1H).

REFERENTIAL EXAMPLE 24

Methyl 1-(3-fluoropropyl)-3-formyl-4,5-dimethylpyrrole-2-carboxylate

The title compound was prepared as pale yellow crystals in 90.89% yeild in a similar procedure to that described in Referential Example 9 by using methyl 3-formyl-4,5-dimethylpyrrole-2-carboxylate and 1-bromo-3-fluoropropane.

Mass spectrum (CI, m/z): 242 ($M^{+}$+1).

NMR spectrum ($CDCl_3$, δppm): 2.01–2.30 (m, 2H), 2.22 (s, 3H), 2.26 (s, 3H), 3.90 (s, 3H), 4.33–4.60 (m, 4H), 10.46 (s, 1H).

REFERENTIAL EXMAPLE 25

Methyl 3-formyl-4,5-dimethyl-1-(2-propynyl)pyrrole-2-carboxylate

The title compound was prepared as white crystals in 89.3% yeild in a similar procedure to that described in Referential Example 9 by using methyl 3-formyl-4,5-dimethylpyrrole-2-carboxylate and 3-bromo-1-propyne.

Mass spectrum (CI, m/z): 220 ($M^{+}$+1).

NMR spectrum ($CDCl_3$, δppm): 2.27 (s, 3H), 2.29 (s, 3H), 2.31 (s, 1H), 3.93 (s, 3H) , 5.18 (s, 2H) , 10.48 (s, 1H)

REFERENTIAL EXAMPLE 26

Methyl 1-(3,3-dichloro-2-propenyl)-3-formyl-4,5-dimethylpyrrole-2-carboxylate

The title compound was prepared as grayish-white crystals in 87.1% yeild in a similar procedure to that described in Referential Example 9 by using methyl 3-formyl-4,5-dimethylpyrrole-2-carboxylate and 1,1, 3-trichloro-1-propene.

Mass spectrum (CI, m/z): 290 ($M^{+}$+1) , 292 ($M^{+}$+3), 294 ($M^{+}$+5).

NMR spectrum ($CDCl_3$, δppm): 2.20 (s, 3H), 2.25 (s, 3H), 3.91 (s, 3H), 5.05 (d;J=6 Hz, 2H), 5.99 (t;J=6 Hz, 1H), 10.46 (s, 1H).

REFERENTIAL EXAMPLE 27

Methyl 1-cyclohexylmethyl-3-formyl-4,5-dimethylpyrrole-2-carboxylate

The title compound was prepared as an orange oil in 79.60% yeild in a similar procedure to that described in Referential Example 9 by using methyl 3-formyl-4,5-dimethylpyrrole-2-carboxylate and cyclohexylmethyl bromide.

Mass spectrum (CI, m/z): 278 ($M^{+}$+1).

NMR spectrum ($CDCl_3$, δppm): 0.83–1.33 (m, 5H), 1.48–1.80(m, 6H), 2.17 (s, 3H), 2.26 (s, 3H), 3.89 (s, 3H), 4.17 (d;J=7 Hz, 2H), 10.42 (s, 1H).

REFERENTIAL EXAMPLE 28

1-(2-Butenyl)-2,3-dimethyl-6,7-dihydropyrrolo[2,3-d]pyridazine-7-one 1.10 g (0.0220 mole) of hydrazine hydrate was added to a solution of 4.50 g (0.0191 mole) of methyl 1-butenyl-3-formyl-4,5-dimethylpyrrole-2-carboxylate (cis/trans=24/76) in 47 ml of acetic acid and the resulting mixture was stirred at 100° C. for 2 hours. The reaction mixture cooled to room temperature was poured into ice-water. Precipitated crystals were collected by filtration and washed with water. The crystals thus obtained were dissolved in 300 ml of dichloromethane and the solution was dried over anhydrous sodium sulfate. Distilling off the solvent gave 3.53 g (0.0163 mole) of 1-(2-butenyl)-2,3-dimethyl-6,7-dihydropyrrolo[2,3-d]-pyridazine-7-one (cis/trans=21/79) as pale brown crystals.

Mass spectrum (CI, m/z): 218 ($M^{+}$+1).

NMR spectrum ($CDCl_3$, δppm): 1.59–1.69 (m, 2.4H), 1.78–1.85 (m, 0.6H), 2.20 (s, 3H), 2.29 (s, 3H), 5.06–5.16 (m, 1.6H), 5.24–5.31 (m, 0.4H), 5.34–5.68 (m, 2H), 8.07 (s, 1H) , 10.29 (s, I[H)

REFERENTIAL EXAMPLE 29

1-Cyclopropyl-2,3-dimethyl-6,7-dihydropyrrolo[2,3-d]pyridazin-7-one

The title compound was prepared as a pale creamy powder in 86.0% yeild in a similar procedure to that described in Referential Example 28 by using ethyl 1-cyclopropyl-3-formyl-4,5-dimethylpyrrole-2-carboxylate.

Mass spectrum (CI, m/z): 204 ($M^{+}$+1).

NMR spectrum ($CDCl_3$, δppm): 1.05–1.13 (m, 2H), 1.23–1.31 (m, 2H), 2.19 (s, 3H), 2.40 (s, 3H), 3.27–3.37 (m, 1H), 8.00 (s, 1H), 9.88 (brs, 1H).

REFERENTIAL EXAMPLE 30

1-Cyclohexyl-2,3-dimethyl-6,7-dihydropyrrolo[2,3-d]pyridazin-7-one

The title compound was prepared as a pale creamy powder in 95.30% yeild in a similar procedure to that described in Referential Example 28 by using ethyl 1-cyclohexyl-3-formyl-4,5-dimethylpyrrole-2-carboxylate Mass spectrum (CI, m/z): 246 ($M^{+}$+1).

NMR spectrum ($CDCl_3$, δppm): 1.15–1.60 (m, 4H), 1.60–2.00 (m, 6H), 2.17 (s, 3H), 2.38 (s, 3H), 4.00–4.41 (m, 1H), 8.03 (s, 1H) , 10.06 (brs, 1H) .

REFERENTIAL EXAMPLE 31

3-Ethyl-2-methyl-1-(2-propenyl)-6,7 -dihydropyrrolo[2,3-d]pyridazin-7-one

The title compound was prepared as a white powder in 86.3% yield in a similar procedure to that described in Referential Example 28 by using ethyl 4-ethyl-3-formyl-5-methyl-1-(2-propenyl)pyrrole-2-carboxylate Mass spectrum (CI, m/z): 218 ($M^{+}$+1).

NMR spectrum ($CDCl_3$, δppm): 1.20 (t;J=8 Hz, 3H), 2.29 (s, 3H), 2.65 (q;J=8 Hz, 2H), 4.79 (d;J=18 Hz, 1H), 5.15 (d;J=9 Hz, 1H), 5.17–5.22 (m, 2H), 5.93–6.08 (m, 1H), 8.11 (s, 1H), 10.17 (brs, 1H).

REFERENTIAL EXAMPLE 32

1-(2-Butenyl)-2-ethyl-3-methyl-6.7-dihydropyrrolo[2,3-d]pyridazin-7-one

The title compound (cis/trans=15/85) was prepared as a white powder in 72.7% yeild in a similar procedure to that described in Referential Example 28 by using ethyl 1-(2-butenyl)-5-ethyl-4-methylpyrrole-2-carboxylate (cis/trans=23/77).

Mass spectrum (CI, m/z): 232 ($M^{+}$+1).

NMR spectrum ($CDCl_3$, δppm): 1.20 (t;J=8 Hz, 3H), 1.66 (d;J=7 Hz, 2.55H), 1.82 (d;J=7 Hz, 0.45H), 2.21 (s, 3H), 2.73 (q;J=8 Hz, 2H), 5.13 (d;J=7 Hz, 1.7H), 5.28 (d;J=7 Hz, 0.3H), 5.35–5.52 (m, 1H), 5.57–5.70 (m, 1H), 8.07 (s, 1H), 10.35 (brs, 1H).

REFERENTIAL EXAMPLE 33

2,3-Dimethyl-1-(3-methyl-2-butenyl)-6.7-dihydropyrrolo[2,3-d]pyridazin-7-one

The title compound was prepared as beige crystals in 90.3% yeild in a similar procedure to that described in Referential Example 28 by using methyl 3-formyl-4,5-dimethyl-1-(3-methyl-2-butenyl)pyrrole-2-carboxylate.

Mass spectrum (CI, m/z): 232 ($M^{+}$+1).

NMR spectrum ($CDCl_3$, δppm): 1.70 (s, 3H), 1.82 (s, 3H), 2.20 (s, 3H), 2.29 (s, 3H), 5.20 (s, 3H), 8.08 (s, 1H), 10.20 (brs, 1H).

REFERENTIAL EXAMPLE 34

2,3-Dimethyl-1-(2-propenyl)-6,7-dihydroiyrrolo[2,3-d] pyridazin-7-one

The title compound was prepared as a grayish-white solid in 99.5% yeild in a similar procedure to that described in Referential Example 28 by using methyl 3-formyl-4,5-dimethyl-1-(2-propenyl)pyrrole-2-carboxylate Mass spectrum (CI, m/z): 204 ($M^{+}$+1).

NMR spectrum ($CDCl_3$, δppm): 2.20 (s, 3H), 2.28 (s, 3H), 4.81 (d;J=16 Hz, 1H), 5.15 (d;J=10 Hz, 1H), 5.21 (d;J=6 Hz, 2H), 5.91–6.08 (m, 1H), 8.07 (s, 1H), 10.09 (brs, 1H).

REFERENTIAL EXAMPLE 35

1-Cyclopropylmethyl-2,3-dimethyl-6,7-dihydropyrrolo[2,3-d]pyridazin-7-one

The title compound was prepared as a white powder in 98.4% yeild in a similar procedure to that described in Referential Example 28 by using methyl 1-cyclopropylmethyl-3-formyl-4,5-dimethylpyrrole-2-carboxylate.

Mass spectrum (CI, m/z): 218 ($M^{+}$+1).

NMR spectrum ($CDCl_3$, δppm): 0.46–0.55 (m, 4H), 1.14–1.29 (m, 1H), 2.20 (s, 3H), 2.36 (s, 3H), 4.43 (d;J=8 Hz, 2H), 8.08 (s, 1H), 10.05 (brs, 1H).

REFERENTIAL EXAMPLE 36

2,3-Dimethyl-1-(3-phenyl-2-propenyl)-6,7-dihydropyrrolo [2,3-d]pyridazin-7-one

The title compound (trans) was prepared as pale brown crystals in 89.9% yeild in a similar procedure to that described in Referential Example 28 by using methyl 3-formyl-4,5-dimethyl-1-(3-phenyl-2-propenyl)pyrrole-2-carboxylate (trans).

Mass spectrum (CI, m/z): 280 ($M^{+}$+1).

NMR spectrum ($CDCl_3$, δppm): 2.21 (s, 3H), 2.33 (s, 3H), 5.33–5.40 (m, 2H), 6.32 (s, 2H), 7.16–7.35 (m, 5H), 8.07 (s, 1H), 9.73 (s, 1H).

REFERENTIAL EXMAPLE 37

2,3-Dimethyl-1-(2-pentenyl)-6,7-dihydropyrrolo[2,3-d] pyridazin-7-one

The title compound (trans) was prepared as pale brown crystals in 89.3% yield in a similar procedure to that described in Referential Example 28 by using methyl 3-formyl-4,5-dimethyl-1-(2-pentenyl)pyrrole-2-carboxylate (trans).

Mass spectrum (CI, m/z): 232 ($M^{+}$+1).

NMR spectrum ($CDCl_3$, δppm): 1.04 (t;J=8 Hz, 3H), 2.15–2.30 (m, 8H), 5.22–5.60 (m, 4H), 8.06 (s, 1H), 10.23 (s, 1H).

REFERENTIAL EXAMPLE 38

2,3-Dimethyl-1-vinyl-6,7-dihydropyrrolo[2,3-d]pyridazin-7-one

The title compound was prepared as a pale yellow foam in 92.6% yield in a similar procedure to that described in Referential Example 28 by using methyl 3-formyl-4,5-dimethyl-1-vinylpyrrole-2-carboxylate.

Mass spectrum (CI, m/z): 190 ($M^{+}$+1).

NMR spectrum ($CDCl_3$, δppm): 2.22 (s, 3H), 2.43 (s, 3H), 5.23 (d;J=9 Hz, 1H), 5.32 (d;J=18 Hz, 1H), 7.84 (dd;J=18 Hz, 9 Hz, 1H), 8.08 (s, 1H), 9.92 (brs, 1H).

REFERENTIAL EXAMPLE 39

2,3-Dimethyl-1-(2-methyl-2-propenyl)-6,7-dihydropyrrolo [2,3-dl pyridazin-7-one

The title compound was prepared as a flesh-colored powder in 90.2i yield in a similar procedure to that described in Referential Example 28 by using methyl 3-formyl-4,5-dimethyl-1-(2-methyl-2-propenyl)pyrrole-2-carboxylate.

Mass spectrum (CI, m/z): 218 ($M^{+}$+1).

NMR spectrum ($CDCl_3$, δppm): 1.72 (s, 3H), 2.21 (s, 3H), 2.25 (s, 3H), 4.30 (s, 1H), 4.82 (s, 1H), 5.12 (s, 2H), 8.09 (s, 1H), 10.30 (brs, 1H).

REFERENTIAL EXAMPLE 40

2,3-Dimethyl-1-(2,2,2-trifluoroethyl)-6,7-dihydropyrrolo[2,3-d]pyridazin-7-one

The title compound was prepared as pale brown crystals in 70.0% yield in a similar procedure to that described in Referential Example 28 by using methyl 3-formyl-4,5-dimethyl-1-(2,2,2-trifluoroethyl)pyrrole-2-carboxylate.

Mass spectrum (CI, m/z): 246 ($M^{+}$+1).

NMR spectrum ($CDCl_3$+DMSO-$D_6$, δppm): 2.22 (s, 3H), 2.35 (s, 3H), 5.29 (q;J=9 Hz, 2H), 8.08 (s, 1H), 11.27 (s, 1H).

REFERENTIAL EXAMPLE 41

1-(2-Fluoroethyl)-2,3-dimethyl-6,7-dihydropyrrolo[2,3-d] pyridazin-7-one

The title compound was prepared as white crystals in 100% yield in a similar procedure to that described in Referential Example 28 by using methyl 1-(2-fluoroethyl)-3-formyl-4,5-dimethylpyrrole-2-carboxylate Mass spectrum (CI, m/z): 210 ($M^{+}$+1).

NMR spectrum ($CDCl_3$+DMSO-$d_6$, δppm): 2.21 (s, 3H), 2.32 (s, 3H), 4.62–4.89 (m, 4H), 8.04 (s, 1H).

REFERENTIAL EXAMPLE 42

1-(2,2-Difluoroethyl)-2,3-dimethyl-6,7-dihydropyrrolo[2,3-d]pyridazin-7-one

The title compound was prepared as a grayish-white powder in 91.0% yield in a similar procedure to that described in Referential Example 28 by using methyl 1-(2,2-difluoroethyl)-3-formyl-4,5-dimethylpyrrole-2-carboxylate.

Mass spectrum (CI, m/z): 228 ($M^{+}$+1).

NMR spectrum ($CDCl_3$+DMSO-$d_6$, δppm): 2.21 (s, 3H), 2.35 (s, 3H), 4.85 (dt;J=4 Hz, 14 Hz, 2H), 6.20 (tt;J=4 Hz, 54 Hz, 1H), 8.07 (s, 1H), 12.10 (brs, 1H).

REFERENTIAL EXAMPLE 43

1-(2-Butenyl)-2,3-dimethyl-6,7-dihydropyrrolo[2,3-d] pyridazin-7-one

The title compound (cis/trans=97/3) was prepared as pale brown crystals in 74.6% yield in a similar procedure to that described in Referential Example 28 by using methyl 1-(2-butenyl)-3-formyl-4,5-dimethylpyrrole-2-carboxylate (cis/trans=93/7).

NMR spectrum ($CDCl_3$, δppm): 1.62–1.68 (m, 0.09H), 1.75–1.85 (m, 2.91H), 2.20 (s, 3H), 2.29 (s, 3H), 5.08–5.14 (m, 0.06H), 5.21–5.31 (m, 1.94H), 5.34–5.70 (m, 2H), 8.05 (s, 1H) , 9.89 (s, 1H)

REFERENTIAL EXAMPLE 44

1-(2-Chloro-2-propenyl)-2,3-dimethyl-6,7-dihydrolyrrolo [2,3-d]pyridazin-7-one

The title compound was prepared as pale yellow crystals in 100% yield in a similar procedure to that described in Referential Example 28 by using methyl 1-(2-chloro-2-propenyl)-3-formyl-4,5-dimethylpyrrole-2-carboxylate (trans).

Mass spectrum (CI, m/z): 238 ($M^{+}$+1), 240 ($M^{+}$+3).

NMR spectrum ($CDCl_3$, δppm): 2.21 (s, 3H), 2.30 (s, 3H), 4.90 (s, 1H), 5.32 (s, 1H), 5.35 (s, 2H), 8.09 (s, 1H), 10.09 (brs, 1H).

REFERENTIAL EXAMPLE 45

2,3-Dimethyl-1-(4,4,4-trifluoro-2-butenyl)-6,7-dihydropyrrolo[2,3-d]pyridazin-7-one The title compound (trans) was prepared as a pale grayish-white powder in 40.0% yield in a similar procedure to that described in Referential Example 28 by using methyl 3-formyl-4,5-dimethyl-1-(4,4,4-trifluoro-2-butenyl)pyrrole-2-carboxylate (trans).

Mass spectrum (CI, m/z): 272 ($M^+$+1).

NMR spectrum ($CDCl_3$+DMSO-$D_6$, δppm): 2.22 (s, 3H), 2.29 (s, 3H), 5.25–5.40 (m, 3H), 6.55–6.63 (m, 1H), 8.08 (s, 1H), 11.90 (brs, 1H).

REFERENTIAL EXAMPLE 46

1-(3,3-Difluoro-2-propenyl)-2,3-dimethyl-6,7-dihydropyrrolo[2,3-d]pyridazin-7-one The title compound was prepared as a pale yellow powder in 83.0% yield in a similar procedure to that described in Referential Example 28 by using methyl 1-(3,3-difluoro-2-propenyl)-3-formyl-4,5-dimethylpyrrole-2-carboxylate Mass spectrum (CI, m/z): 240 ($M^+$+1).

NMR spectrum ($CDCl_3$, δppm): 2.20 (s, 3H), 2.31 (s, 3H), 4.59–4.72 (m, 1H), 5.17 (d;J=8 Hz, 2H), 8.07 (s, 1H), 10.20 (brs, 1H).

REFERENTIAL EXAMPLE 47

1-(3-Fluoropropyl)-2,3-dimethyl-6,7-dihydropyrrolo[2,3-d]pyridazin-7-one

The title compound was prepared as white crystals in 93.0% yield in a similar procedure to that described in Referential Example 28 by using methyl 1-(3-fluoropropyl)-3-formyl-4,5-dimethylpyrrole-2-carboxylate Mass spectrum (CI, m/z): 224 ($M^+$+1).

NMR spectrum ($CDCl_3$, δppm): 2.05–2.37 (m, 2H), 2.20 (s, 3H), 2.33 (s, 3H), 4.47 (dt;J=48 Hz, 6 Hz, 2H), 4.60 (t;J=8 Hz, 2H), 8.07 (s, 1H), 10.20 (brs, 1H).

REFERENTIAL EXAMPLE 48

2,3-Dimethyl-1-(2-propynyl)-6.7-dihydropyrrolo[2,3-d]pyridazin-7-one

The title compound was prepared as white crystals in 100% yield in a similar procedure to that described in Referential Example 28 by using methyl 3-formyl-4,5-dimethyl-1-(2-propynyl)pyrrole-2-carboxylate.

Mass spectrum (CI, m/z): 202 ($M^+$+1).

NMR spectrum ($CDCl_3$+DMSO-$d_6$, δppm): 2.21 (s, 3H), 2.42 (s, 3H), 2.46 (s, 1H), 5.50 (s, 2H), 8.05 (s, 1H), 11.49 (s, 1H).

REFERENTIAL EXAMPLE 49

1-(3,3-Dichloro-2-propenyl)-4,5-dimethyl-6,7-dihydropyrrolo[2,3-d]pyridazin-7-one The title compound was prepared as a grayish-white powder in 96.5% yield in a similar procedure to that described in Referential Example 28 by using methyl 1-(3,3-dichloro-2-propenyl)-3-formyl-4,5-dimethylpyrrole-2-carboxylate.

Mass spectrum (CI, m/z): 272 ($M^+$+1), 274 ($M^+$+3), 276 ($M^+$+5).

NMR spectrum ($CDCl_3$, δppm): 2.20 (s, 3H), 2.32 (s, 3H), 5.33 (d;J=6 Hz, 2H), 6.09 (t;J=6 Hz, 1H), 8.10 (s, 1H), 10.63 (brs, 1H).

REFERENTIAL EXAMPLE 50

1-Cyclohexylmethyl-2,3-dimethyl-6,7-dihydropyrrolo[2,3-d]pyridazin-7-one

The title compound was prepared as a white powder in 85.2% yield in a similar procedure to that described in Referential Example 28 by using methyl 1-cyclohexylmethyl-3-formyl-4,5-dimethylpyrrole-2-carboxylate.

Mass spectrum (CI, m/z): 260 ($M^+$+1).

NMR spectrum ($CDCl_3$, δppm): 1.00–1.29 (m, 5H), 1.47–1.88 (m, 6H), 2.20 (s, 3H), 2.31 (s, 3H), 4.33 (d;J=7 Hz, 2H), 8.08 (s, 1H) , 9.82 (brs, 1H).

REFERENTIAL EXAMPLE 51

1-(2-Butenyl)-7-chloro-2,3-dimethyl-pyrrolo[2,3-d]pyridazine 39 ml (0.43 mole) of phosphorus oxychloride were added to 3.53 g (0.0163 mole) of 1-(2-butenyl)-2,3-dimethyl-6,7-dihydropyrrolo[2,3-d]pyridazin-7-one (cis/trans=24/76) and the mixture was stirred at 97° C. for 2.5 hours. The reaction mixture was allowed to cool to room temperature and added dropwise to water with ice-cooling. The mixture was neutralized with a 40% aqueous solution of sodium hydroxide and extracted with dichloromethane. The extract was washed with water and dried over anhydrous sodium sulfate, and the solvent was distilled off. The residue was purified by column chromatography through silica gel using a 1:1 mixture of toluene and ethyl acetate as an eluent to give 3.59 g (0.0152 mole) of 1-(2-butenyl)-7-chloro-2,3-dimethylpyrrolo[2,3-d]pyridazine (cis/trans=21/79) as pale brown crystals.

Mass spectrum (CI, m/z): 236 ($M^+$+1).

NMR spectrum ($CDCl_3$, δppm): 1.62–1.69 (2.4H, m), 1.79–1.85 (0.6H, m), 2.29 (3H, s), 2.39 (3H, s), 5.02–5.71 (4H, m), 9.17 (1H, s).

REFERENTIAL EXAMPLE 52

7-Chloro-2,3-dimethyl-1-(3-methyl-2-butenyl)pyrrolo[2,3-d]pyridazine

The title compound was prepared as a pink powder in 67.2% yield in a similar procedure to that described in Referential Example 51 by using 2,3-dimethyl-1-(3-methyl-2-butenyl)-6,7-dihydropyrrolo[2,3-d]pyridazin-7-one.

Mass spectrum (CI, m/z): 250 ($M^+$+1), 252 ($M^+$+3).

NMR spectrum ($CDCl_3$, δppm): 1.72 (s, 3H), 1.82 (s, 3H), 2.30 (s, 3H), 2.40 (s, 3H), 5.05–5.19 (m, 3H), 9.19 (s, 1H).

REFERENTIAL EXAMPLE 53

7-Chloro-2,3-dimethyl-1-(2-propenyl)pyrrolo[2,3-d]pyridazine

The title compound was prepared as a pale yellow powder in 94.0% yield in a similar procedure to that described in Referential Example 51 by using 2,3-dimethyl-1-(2-propenyl)-6,7-dihydropyrrolo[2,3-d]pyridazin-7-one.

Mass spectrum (CI, m/z): 222 ($M^+$+1), 224 ($M^+$+3).

NMR spectrum ($CDCl_3$, δppm): 2.30 (s, 3H), 2.39 (s, 3H), 4.63 (d;J=16 Hz, 1H), 5.06–5.21 (m, 3H), 5.93–6.08 (m, 1H), 9.17 (s, 1H).

REFERENTIAL EXAMPLE 54

7-Chloro-1-cyclopropylmethyl-2,3-dimethylpyrrolo[2,3-d]pyridazine

The title compound was prepared as a pale yellow powder in 79.7% yield in a similar procedure to that described in Referential Example 51 by using 1-cyclopropylmethyl-2,3-dimethyl-6,7-dihydropyrrolo[2,3-d]pyridazin-7-one Mass spectrum (CI, m/z): 236 ($M^+$+1), 238 ($M^+$+3).

NMR spectrum ($CDCl_3$, δppm): 0.38–0.60 (m, 4H), 1.16–1.22 (m, 1H), 2.30 (s, 3H), 2.44 (s, 3H), 4.44 (d;J=8 Hz, 2H), 9.16 (s, 1H).

REFERENTIAL EXAMPLE 55

7-Chloro-2,3-dimethyl-1-(2--pentenyl) pyrrolo[2,3-d]pyridazine

The title compound (trans) was prepared as pale brown crystals in 89.7% yield in a similar procedure to that described in Referential Example 51 by using 2,3-dimethyl-1-(2-pentenyl)-6,7-dihydropyrrolo[2,3-d]pyridazin-7-one (trans).

Mass spectrum (CI, m/z): 250 ($M^+$+1), 252 ($M^+$+3).

NMR spectrum ($CDCl_3$, δppm): 1.09 (t;J=8 Hz, 3H), 2.12–2.31 (m, 5H), 2.40 (s, 3H), 5.19 (d;J=7 Hz, 2H), 5.24–5.62 (m, 2H), 9.16 (s, 1H).

REFERENTIAL EXAMPLE 56

7-Chloro-2,3-dimethyl-1-(3-phenyl-2-propenyl)pyrrolo[2,3-d]pyridazine

The title compound (trans) was prepared as pale brown crystals in 82.2% yield in a similar procedure to that described in Referential Example 51 by using 2,3-dimethyl-1-(3-phenyl-2-propenyl)-6,7-dihydropyrrolo[2,3-d]pyridazin-7-one (trans).

Mass spectrum (CI, m/z): 298 ($M^+$+1), 300 ($M^+$+3).

NMR spectrum ($CDCl_3$, δppm): 2.33 (s, 3H), 2.46 (s, 3H), 5.25–5.34 (m, 2H), 6.13 (d;J=17 Hz, 1H), 6.32 (dd;J=17 Hz, 5 Hz, 1H), 7.18–7.40 (m, 5H), 9.21 (s, 1H).

REFERENTIAL EXAMPLE 57

7-Chloro-2,3-dimethyl-1-vinylpyrrolo[2,3-d]pyridazine

The title compound was prepared as a white powder in 65.1% yield in a similar procedure to that described in Referential Example 51 by using 2,3-dimethyl-1-vinyl-6,7-dihydropyrrolo[2,3-d]pyridazin-7-one.

Mass spectrum (CI, m/z): 208 ($M^+$+1), 210 ($M^+$+3).

NMR spectrum ($CDCl_3$, δppm): 2.31 (s, 3H), 2.42 (s, 3H), 5.37 (d;J=17 Hz, 1H), 5.62 (d;J=9 Hz, 1H), 7.34 (dd;J=17 Hz, 9 Hz, 1H), 9.20 (s, 1H).

REFERENTIAL EXAMPLE 58

7-Chloro-2,3-dimethyl-1-(2-methyl-2-propenyl)-pyrrolo[2,3-d]pyridazine

The title compound was prepared as a white powder in 91.2w yield in a similar procedure to that described in Referential Example 51 by using 2,3-dimethyl-1-(2-methyl-2-propenyl)-6,7-dihydropyrrolo[2,3-d]pyridazin-7-one.

Mass spectrum (CI, m/z): 236 ($M^+$+1), 238 ($M^+$+3).

NMR spectrum ($CDCl_3$, δppm): 1.81 (s, 3H), 2.30 (s, 3H), 2.35 (s, 3H), 3.95 (s, 1H), 4.85 (s, 1H), 4.99 (s, 2H), 9.18 (s, 1H).

REFERENTIAL EXAMPLE 59

7-Chloro-2,3-dimethyl-1-(2,2,2-trifluoroethyl)pyrrolo[2,3-d]pyridazine

The title compound was prepared as a white powder in 89.1% yield in a similar procedure to that described in Referential Example 51 by using 2,3-dimethyl-1-(2,2,2-trifluoroethyl)-6,7-dihydropyrrolo[2,3-d]pyridazin-7-one.

Mass spectrum (CI, m/z): 264 ($M^+$+1).

NMR spectrum ($CDCl_3$, δppm): 2.32 (s, 3H), 2.47 (s, 3H), 5.19 (q;J=9 Hz, 2H), 9.22 (s, 1H).

REFERENTIAL EXAMPLE 60

7-Chloro-1-cyclopropyl-2,3-dimethylpyrrolo[2,3-d]pyridazine

The title compound was prepared as a pale creamy powder in 95.5% yield in a similar procedure to that described in Referential Example 51 by using 1-cyclopropyl-2,3-dimethyl-6,7-dihydropyrrolo[2,3-d]pyridazin-7-one.

Mass spectrum (CI, m/z): 222 ($M^+$+1), 224 ($M^+$+3).

NMR spectrum ($CDCl_3$, δppm): 1.05–1.12 (m, 2H), 1.31–1.39 (m, 2H), 2.23 (s, 3H), 2.52 (s, 3H), 3.36–3.45 (m, 1H), 9.10 (s, 1H).

REFERENTIAL EXAMPLE 61

7-Chloro-1-(2-fluoroethyl)-2,3-dimethylpyrrolo[2,3-d]pyridazine

The title compound was prepared as a pale brown powder in 56.2% yield in a similar procedure to that described in Referential Example 51 by using 1-(2-fluoroethyl)-2,3-dimethyl-6,7-dihydropyrrolo[2,3-d]pyridazin-7-one.

Mass spectrum (CI, m/z): 228 ($M^+$+1), 230 ($M^+$+3).

NMR spectrum ($CDCl_3$, δppm): 2.31 (s, 3H), 2.46 (s, 3H), 4.67–4.82 (m, 2H), 4.88 (s, 2H), 9.19 (s, 1H).

REFERENTIAL EXAMPLE 62

7-Chloro-1-(2,2-difluoroethyl)-2,3-dimethylpyrrolo[2,3-d]pyridazine

The title compound was prepared as pale beige crystals in 75.0% yield in a similar procedure to that described in Referential Example 51 by using 1-(2,2-trifluoroethyl)-2,3-dimethyl-6,7-dihydropyrrolo[2,3-d]pyridazin-7-one.

Mass spectrum (CI, m/z): 246 ($M^+$+1), 248 ($M^+$+3).

NMR spectrum ($CDCl_3$, δppm): 2.30 (s, 3H), 2.45 (s, 3H), 4.87 (dt;J=14 Hz, 4 Hz, 2H), 6.14 (tt;J=54 Hz, 4 Hz, 1H), 9.20 (s, 1H).

REFERENTIAL EXAMPLE 63

7-Chloro-1-cyclohexyl-2,3-dimethylpyrrolo[2,3-d]pyridazine

The title compound was prepared as a creamy powder in 84.8% yield in a similar procedure to that described in Referential Example 51 by using 1-cyclohexyl-2,3-dimethyl-6,7-dihydropyrrolo[2,3-d]pyridazin-7-one.

Mass spectrum (CI, m/z): 264 ($M^+$+1), 266 ($M^+$+3).

NMR spectrum ($CDCl_3$, δppm): 1.17–1.64 (m, 4H), 1.89–2.11 (m, 6H), 2.27 (s, 3H), 2.59 (s, 3H), 5.58–5.76 (m, 1H), 9.11 (s, 1H).

REFERENTIAL EXAMPLE 64

7-Chloro-3-ethyl-2-methyl-1-(2-propenyl)-pyrrolo[2,3-d]pyridazine

The title compound was prepared as a pale brown powder in 68.8% yield in a similar procedure to that described in Referential Example 51 by using 3-ethyl-2-methyl-1-(2-propenyl)-6,7-dihydropyrrolo[2,3-d]pyridazin-7-one.

Mass spectrum (CI, m/z): 236 ($M^+$+1), 238 ($M^+$+3).

NMR spectrum ($CDCl_3$, δppm): 1.24 (t;J=8 Hz, 3H), 2.40 (s, 3H), 2.76 (q;J=8 Hz, 2H), 4.63 (d;J=17 Hz, 1H), 5.07–5.20 (m, 3H), 5.94–6.09 (m, 1H) , 9.21 (s, 1H).

REFERENTIAL EXAMPLE 65

1-(2-Butenyl)-7-chloro-2,3-dimethylpyrrolo[2,3-d]pyridazine

The title compound (cis/trans=98/2) was prepared as a pale yellow oil in 84.9% yield in a similar procedure to that described in Referential Example 51 by using 1-(2-butenyl)-2,3-dimethyl-6,7-dihydropyrrolo[2,3-d]pyridazin-7-one (cis/trans=97/3).

Mass spectrum (CI, m/z): 236 ($M^+$+1), 238 ($M^+$+3).

NMR spectrum ($CDCl_3$, δppm): 1.62–1.69 (m, 0.2H), 1.78–1.87 (m, 2.8H), 2.29 (S, 3H), 2.39 (s, 3H), 5.01–5.08 (m, 0.1H), 5.15–5.23 (m, 1.9H), 5.30–5.73 (m, 2H), 9.14 (s, 1H).

REFERENTIAL EXAMPLE 66

7-Chloro-1-(2-chloro-2-propenyl)-2,3-dimethylpyrrolo[2,3-d]pyridazine

The title compound was prepared as grayish-white crystals in 94.4% yield in a similar procedure to that described in Referential Example 51 by using 1-(2-chloro-2-propenyl)-2,3-dimethyl-6,7-dihydropyrrolo[2,3-d]pyridazin-7-one.

Mass spectrum (CI, m/z): 256 ($M^{+}$+1), 258 ($M^{+}$+3), 260 ($M^{+}$+5).

NMR spectrum ($CDCl_3$, δppm): 2.31 (s, 3H), 2.40 (s, 3H), 4.50–4.55 (m, 1H), 5.18–5.26 (m, 2H), 5.30–5.37 (m, 1H), 9.20 (s, 1H).

REFERENTIAL EXAMPLE 67

1-(2-Butenyl)-7-chloro-2-ethyl-3-methylpyrrolo[2,3-d] pyridazine

The title compound (cis/trans=4/96) was prepared as a pale reddish-white powder in 63.4% yield in a similar procedure to that described in Referential Example 51 by using 1-(2-butenyl)-2-ethyl-3-methyl-6,7-dihydropyrrolo[2,3-d]pyridazin-7-one (cis/trans=15/85).

Mass spectrum (CI, m/z): 250 ($M^{+}$+1), 252 ($M^{+}$+3).

NMR spectrum ($CDCl_3$, δppm): 1.23 (t;J=8 Hz, 3H), 1.58–1.67 (m, 2.88H), 2.77–2.84 (m, 0.12H), 2.30 (s, 3H), 2.82 (q;J=8 Hz, 2H), 5.00–5.09 (m, 2H), 5.16–5.30 (m, 1H), 5.53–5.69 (m, 1H), 9.14 (s, 1H).

REFERENTIAL EXAMPLE 68

7-Chloro-2,3-dimethyl-1-(4,4,4-trifluoro-2-butenyl) pyrrolo [2,3-d]pyridazine

The title compound (trans) was prepared as a pale yellow solid in 78.0% yield in a similar procedure to that described in Referential Example 51 by using 2,3-dimethyl-1-(4,4,4-trifluoro-2-butenyl)-6,7-dihydropyrrolo[2,3-d]pyridazin-7-one (trans).

Mass spectrum (CI, m/z): 290 ($M^{+}$+1).

NMR spectrum ($CDCl_3$, δppm): 2.23 (s, 3H), 2.39 (s, 3H), 5.08–5.17 (m, 1H), 5.24–5.30 (m, 2H), 6.55–6.63 (m, 1H), 9.22 (s, 1H).

REFERENTIAL EXAMPLE 69

7-Chloro-1-(3,3-difluoro-2-propenyl)-2,3-dimethylpyrrolo [2,3-d]pyridazine

The title compound was prepared as a white powder in 79.1% yield in a similar procedure to that described in Referential Example 51 by using 1-(3,3-difluoro-2-propenyl)-2,3-dimethyl-6,7-dihydropyrrolo[2,3-d] pyridazin-7-one Mass spectrum (CI, m/z): 258 ($M^{+}$+1), 260 ($M^{+}$+3).

NMR spectrum ($CDCl_3$, δppm): 2.30 (s, 3H), 2.43 (s, 3H), 4.50–4.61 (m, 1H), 5.11–5.18 (m, 2H), 9.18 (s, 1H).

REFERENTIAL EXAMPLE 70

7-Chloro-1-(3-fluoropropyl)-2,3-dimethylpyrrolo[2,3-d] pyridazine

The title compound was prepared as white crystals in 86.9% yield in a similar procedure to that described in Referential Example 51 by using 1-(3-fluoropropyl)-2,3-dimethyl-6,7-dihydropyrrolo[2,3-d]pyridazin-7-one.

Mass spectrum (CI, m/z): 242 ($M^{+}$+1), 244 ($M^{+}$+3).

NMR spectrum ($CDCl_3$, δppm): 2.08–2.36 (m, 2H), 2.30 (s, 3H), 2.44 (s, 3H), 4.49 (dt;J=54 Hz, 6 Hz, 2H), 4.64 (t;J=8 Hz, 2H), 9.17 (s, 1H).

REFERENTIAL EXAMPLE 71

7-Chloro-2,3-dimethyl-1-(2-propynyl) pyrrolo[2,3-d] pyridazine

The title compound was prepared as a white powder in 67.2% yield in a similar procedure to that described in Referential Example 51 by using 2,3-dimethyl-1-(2-propynyl)-6,7-dihydropyrrolo[2,3-d]pyridazin-7-one.

Mass spectrum (CI, m/z): 220 ($M^{+}$+1), 222 ($M^{+}$+3).

NMR spectrum ($CDCl_3$, δppm): 2.30 (s, 3H), 2.39 (S, 1H), 2.50 (S, 3H), 5.31 (s, 2H) , 9.19 (s, 1H)

REFERENTIAL EXAMPLE 72

7-Chloro-1-(3,3-dichloro-2-propenyl)-2,3-dimethylpyrrolo [2,3-d]pyridazine

The title compound was prepared as an ocherous powder in 89.7% yield in a similar procedure to that described in Referential Example 51 by using 1-(3,3-dichloro-2-propenyl)-2,3-dimethyl-6,7-dihydropyrrolo[2,3-d] pyridazin-7-one.

Mass spectrum (CI, m/z): 290 ($M^{+}$+1), 292 ($M^{+}$+3), 294 ($M^{+}$+5).

NMR spectrum ($CDCl_3$, δppm): 2.30 (s, 3H), 2.42 (s, 3H), 5.27 (d;J=6 Hz, 2H), 5.96 (t;J=6 Hz, 1H), 9.17 (s, 1H).

REFERENTIAL EXAMPLE 73

7-Chloro-1-cyclohexylmethyl-2,3-dimethylpyrrolo[2,3-d] pyridazine

The title compound was prepared as a white powder in 95.5% yield in a similar procedure to that described in Referential Example 51 by using 1-cyclohexylmethyl-2,3-dimethyl-6,7-dihydropyrrolo[2,3-d]pyridazin-7-one.

Mass spectrum (CI, m/z): 278 ($M^{+}$+1), 280 ($M^{+}$+3).

NMR spectrum ($CDCl_3$, δppm): 0.95–1.30 (m, 5H), 1.45–1.90 (m, 6H), 2.28 (s, 3H), 2.40 (s, 3H), 4.29 (d;J=8 Hz, 2H), 9.14 (s, 1H).

REFERENTIAL EXAMPLE 74

Methyl 4,5-dimethylpyrrole-2-carboxylate (1) 2-Methyl-3-oxobutanal sodium salt

A mixed solution of 67.6 g (0.93 mole) of 2-butanone and 71.7 g (0.93 mole) of ethyl formate was added to a mixture of 20.5 g (0.891 mole) of sodium and 720 ml of dry diethyl ether with stirring under ice-cooling over 2 hours and the resulting mixture was stirred at the same temperature for 6.5 hours. Precipitated solids were collected by filtration and washed with diethyl ether to give 104 g of 2-methyl-3-oxobutanal'sodium salt as an ocherous solid.

(2) Methyl 4,5-dimethylpyrrole-2-carboxylate

A solution of 40.7 g (0.59 mole) of sodium nitrite in 68 ml of water was added dropwise to a solution of 61.5 g (0.53 mole) of methyl acetoacetate in 208 ml of acetic acid over a period of 3 hours with ice-cooling, and the resulting mixture was stirred at the same temperature for 3 hours and allowed to stand at room temperature overnight. A solution of 104 g (0.852 mole) of 2-methyl-3-oxobutanal'sodium salt prepared in the above (1) in 200 ml of water was added to the reaction mixture, and subsequently 90 g (1.38 moles) of zinc powder was added thereto at 60–64° C. over a period of 2 hours and the mixture was heated under reflux for 30 minutes. The hot reaction mixture thus obtained was poured into 1 kg of ice-water, and the ocherous solids precipitated were collected by filtration and washed with water. The solids were dissolved in 800 ml of ethyl acetate and the insoluble materials originated from zinc was filtered off. The filtrate was dried over anhydrous sodium sulfate and the solvent was distilled off. The concentrate thus obtained was allowed to stand at room temperature overnight, and the precipitated crystals were collected by filtration and washed twice with 25 ml each of a 2:1 mixture of hexane and diethyl ether to give 15.0 g (0.0981 mole) of methyl 4,5-dimethylpyrrole-2-carboxylate as ocherous powdery crystals.

Mass spectrum (CI, m/z): 154 ($M^{+}$+1).

NMR spectrum ($CDCl_3$, δppm): 2.00 (s, 3H), 2.21 (s, 3H), 3.81 (s, 3H), 6.68 (s, 1H), 9.20 (br.s, 1H).

REFERENTIAL EXAMPLE 75

Methyl 3-formyl-4,5-dimethylpyrrole-2-carboxylate 15.0 g (0.0979 mole) of phosphorus oxychloride were dropwise added to a solution of 13.7 g (0.0898 mole) of methyl 4,5-dimethylpyrrole-2-carboxylate in 13 ml (0.17 mole) of dimethylformamide over a period of 1.3 hours with ice-cooling, and the resulting mixture was stirred at room temperature for 0.5 hour and then at 90–100° C. for 0.5 hour. The hot reaction mixture thus obtained was poured into ice-water and dissolved. The solution was adjusted to pH 5–6 with a 10% aqueous solution of sodium hydroxide. The solids precipitated were collected by filtration and then dissolved in 600 ml of ethyl acetate. The filtrate was extracted twice with 200 ml each of ethyl acetate. The combined extracts were washed with water and dried over anhydrous sodium sulfate, and the solvent was distilled off. The residue was washed with a mixture of hexane and ethyl acetate and collected by filtration to give 10.6 g (0.0583 mole) of methyl 3-formyl-4,5-dimethylpyrrole-2-carboxylate as a brown powder.

Mass spectrum (CI, m/z); 182 ($M^+$+1).

NMR spectrum ($CDCl_3$, δppm): 2.24 (s, 3H), 2.26 (s, 3H), 3.92 (s, 3H), 9.29 (br.s, 1H), 10.54 (s, 1H).

REFERENTIAL EXAMPLE 76

Methyl 3-acetyl-4,5-dimethylpyrrole-2-carboxylate 5.0 ml of acetic anhydride were added to a solution of 1.50 g (0.0098 mole) of methyl 4,5-dimethylpyrrole-2-carboxylate in 15 ml of dichloromethane at room temperature and subsequently a mixture of 1.5 ml (0.013 mole) of tin tetrachloride and 4 ml of dichloromethane was dropwise added thereto over a period of 10 minutes. The mixture was stirred for 30 minutes, poured into ice-water, neutralized to pH 7–8 with an aqueous solution of sodium hydrogencarbonate and extracted with dichloromethane. The extract was dried over anhydrous sodium sulfate and the solvent was distilled off under reduced pressure. The residue was purified by column chromatography through silica gel using a 1:2 mixture of ethyl acetate and hexane as an eluent to give 1.61 g of methyl 3-acetyl-4,5-dimethylpyrrole-2-carboxylate as a grayish-white solid.

Mass spectrum (CI, m/z): 196 ($M^+$+1).

NMR spectrum ($CDCl_3$, δppm): 2.02 (s, 3H), 2.20 (s, 3H), 2.57 (s, 3H), 3.85 (s, 3H), 8.95 (brs, 1H).

REFERENTIAL EXAMPLE 77

2,3-Dimethyl-6,7-dihydropyrrolo[2,3-d]pyridazin-7-one 1.50 g (0.030 mole) of hydrazine monohydrate were dropwised added slowly to a solution of 4.00 g (0.022 mole) of methyl 3-formyl-4,5-dimethylpyrrole-2-carboxylate in 80 ml of acetic acid at room temperature and the resulting mixture was stirred at 110° C. for 2 hours. After completion of the reaction, the reaction mixture was poured into ice-water. The resulting precipitates were collected by filtration and washed well with water. The precipitates were dissolved in dichloromethane and the solution was dried over anhydrous sodium sulfate. The solvent was distilled off under reduced pressure to give 3.40 g of 2,3-dimethyl-6,7-dihydropyrrolo[2,3-d]pyridazin-7-one as a grayish-white powder.

Mass spectrum (CI, m/z): 164 ($M^+$+1).

NMR spectrum ($CDCl_3$+DMSO-$d_6$, δppm): 2.18 (s, 3H), 2.31 (s, 3H), 8.03 (s, 1H), 12.04 (brs, 2H).

REFERENTIAL EXAMPLE 78

7-Chloro-2,3-dimethylpyrrolo[2,3-d]pyridazine 45 ml of phosphorus oxychloride were added to 3.35 g (0.021 mole) of 2,3-dimethyl-6,7-dihydropyrrolo[2,3-d]pyridazin-7-one and the mixture was heated under reflux for 2 hours. After completion of the reaction, the reaction mixture was slowly poured into ice-water and the aqueous mixture was neutralized with an aqueous solution of sodium hydroxide. The precipitated yellow solids were collected by filtration and washed well with water. The solids were dissolved in dichloromethane and dried over anhydrous sodium sulfate, and the solvent was distilled off under reduced pressure. The residue was purified by column chromatography through silica gel using a 15:1 mixture of chloroform and methanol as an eluent to give 2.39 g of 7-chloro-2,3-dimethylpyrrolo[2,3-d]pyridazine as a pale yellow powder.

Mass spectrum (CI, m/z): 182 ($M^+$+1), 184 ($M^+$+3).

NMR spectrum ($CDCl_3$+DMSO-$d_6$, δppm): 2.29 (s, 3H), 2.46 (s, 3H), 9.14 (s, 1H), 11.70 (brs, 1H).

REFERENTIAL EXAMPLE 79

7-Benzyloxy-2,3-dimethylpyrrolo[2,3-d]pyridazine 1.35 g (0.0074 mole) of 7-chloro-2,3-dimethylpyrrolo[2,3-d]pyridazine was added to a solution, obtained by adding 0.26 g (0.011 mole) of sodium to 25 ml of benzyl alcohol at room temperature, and the resulting mixture was heated at 115° C. and, in the course of the heating, 10 ml of benzyl alcohol were additionally added thereto. The heating was continued for 30 hours with stirring. After completion of the reaction, the reaction mixture was poured into ice-water and extracted with dichloromethane. The extract was dried over anhydrous sodium sulfate, the solvent was removed under reduced pressure and benzyl alcohol was distilled off under reduced pressure. The residue was purified by column chromatography through silica gel using a 20:1 mixture of chloroform and methanol as an eluent to give 1.15 g of 7-benzyloxy-2,3-dimethylpyrrolo[2,3-d]pyridazine as a pale yellow powder.

Mass spectrum (CI, m/z): 254 ($M^+$+1).

NMR spectrum ($CDCl_3$+DMSO-$d_6$, δppm): 2.23 (s, 3H), 2.38 (s, 3H), 5.69 (s, 2H), 7.30–7.60 (m, 5H), 8.99 (s, 1H), 10.65 (brs, 1H).

REFERENTIAL EXAMPLE 80

7-(4-Fluorobenzyloxy)-2,3-dimethylpyrrolo[2,3-d]pyridazine

The title compound was prepared as pale yellow crystals in 29.8% yield in a similar procedure to that described in Referential Example 79 by using 7-chloro-2,3-dimethylpyrrolo[2,3-d]pyridazine and 4-fluorobenzyl alcohol.

Mass spectrum (CI, m/z): 272 ($M^+$+1).

NMR spectrum ($CDCl_3$+DMSO-$d_6$, δppm): 2.23 (s, 3H), 2.39 (s, 3H), 5.66 (s, 2H), 7.06–7.12 (m, 2H), 7.52–7.61 (m, 2H), 8.92 (s, 1H), 11.40 (brs, 1H).

REFERENTIAL EXAMPLE 81

Methyl 3-formyl-4,5-dimethyl-1-vinylpyrrole-2-carboxylate

A solution of 0.15 g (0.00052 mole) of methyl 1-(2-bromoethyl)-3-formyl-4,5-dimethylpyrrole-2-carboxylate and 0.08 g (0.00052 mole) of 1,8-diazabicyclo[5.4.0]undec-7-ene dissolved in 2 ml of tetrahydrofuran was heated under reflux for 6 hours. The reaction mixture was allowed to cool at room temperature and purified by column chromatography through silica gel using a 9:1 mixture of toluene and ethyl acetate as an eluent to give 0.080 g (74% yield) of methyl 3-formyl-4,5-dimethyl-1-vinylpyrrole-2-carboxylate as pale yellow crystals.

Mass spectrum (CI, m/z): 208 ($M^+$+1).

NMR spectrum ($CDCl_3$, δppm): 2.20 (s, 3H), 2.27 (s, 3H), 3.90 (s, 3H), 5.20 (d;J=17 Hz, 1H), 5.44 (d;J=9 Hz, 1H), 7.12 dd;J=17 Hz, 9 Hz, 1H), 10.49 (s, 1H).

REFERENTIAL EXAMPLE 82

Ethyl 1-(2-butenyl)-4-ethyl-5-methylpyrrole-2-carboxylate

The title compound (cis/trans=25/75) was prepared as a pale yellow oil in 30.1 yield in a similar procedure to that described in Referential Example 1 by using 2-pentane and ethyl N-(2-butenyl)glycinate.

Mass spectrum (CI, m/z): 236 ($M^+$+1).

NMR spectrum ($CDCl_3$, δppm): 1.13 (t;J=7 Hz, 3H), 1.32 (t;J=7 Hz, 3H), 1.62 (d;J=7 Hz, 2.25H), 1.75 (d;J=7 Hz, 0.75H), 2.16 (s, 3H), 2.40 (q;J=7 Hz, 2H), 4.24 (q;J=7 Hz, 2H), 4.87 (d;J=7 Hz, 1.5H), 5.00 (d;J=7 Hz, 0.5H), 5.25–5.41 (m, 1H), 5.49–5.66 (m, 1H), 6.83 (s, 1H).

REFERENTIAL EXAMPLE 83

Ethyl 1-(2-butenyl)-5-methyl-4-pentylpyrrole-2-carboxylate

The title compound (cis/trans=21/79) was prepared as a red oil in 26.1 yield in a similar procedure to that described in Referential Example 1 by using 2-octanone and ethyl N-(2-butenyl)glycinate.

Mass spectrum (CI, m/z): 278 ($M^+$+1).

NMR spectrum ($CDCl_3$, δppm): 0.90 (t;J=7 Hz, 3H), 1.18–1.44 (m, 7H), 1.44–1.60 (m, 2H), 1.65 (d;J=8 Hz, 2.37H), 1.73 (d;J=8 Hz, 0.63H), 2.15 (s, 3H), 2.37 (t;J=7 Hz, 2H), 4.22 (q;J=7 Hz, 2H), 4.84–4.89 (m, 1.58H), 5.01 (d;J=8 Hz, 0.42H), 5.23–5.42 (m, 1H), 5.48–5.63 (m, 1H), 6.79 (s, 1H).

REFERENTIAL EXAMPLE 84

Ethyl 1-(2-butenyl)-4-methylpyrrole-2-carboxylate

The title compound (cis/trans=30/70) was prepared as a pale yellow oil in 44.1 yield in a similar procedure to that described in Referential Example 1 by using propionaldehyde and ethyl N-(2-butenyl)glycinate.

Mass spectrum (CI, m/z): 208 ($M^+$+1).

NMR specrtrum ($CDCl_3$, δppm): 1.32 (t;J=7 Hz, 3H), 1.68 (d;J=8 Hz, 2.1H), 1.74 (d;J=8 Hz, 0.9H), 2.06 (s, 3H), 4.26 (q;J=7 Hz, 2H), 4.79 (d;J=6 Hz, 1.4H), 4.93 (d;J=6 Hz, 0.6H), 5.49–5.68 (m, 2H), 6.62 (s, 1H), 6.77 (s, 1H).

REFERENTIAL EXAMPLE 85

Ethyl 1-(2-butenyl)-4-ethyl-3-formyl-5-methylpyrrole-2-carboxylate

The title compound (cis/trans=27/73) was prepared as an orange oil in 26.5 yield in a similar procedure to that described in Referential Example 5 by using ethyl 1-(2-butenyl)-4-ethyl-5-methylpyrrole-2-carboxylate (cis/trans=25/75).

Mass spectrum (CI, m/z): 264 ($M^+$+1).

NMR spectrum ($CDCl_3$, δppm): 1.08 (t;J=8 Hz, 3H), 1.38 (t;J=8 Hz, 3H), 1.67 (d;J=6 Hz, 2.19H), 1.75 (d;J=6 Hz, 0.81H), 2.19 (s, 3H), 2.72 (q;J=8 Hz, 2H), 4.37 (q;J=8 Hz, 2H), 4.87 (d;J=6 Hz, 1.46H), 4.99 (d;J=6 Hz, 0.54H), 5.30–5.49 (m, 1H), 5.52–5.68 (m, 1H), 10.48 (s, 1H).

REFERENTIAL EXAMPLE 86

Methyl 3-formyl-4,5-dimethyl-1-(2-methylcyclopropylmethyl) pyrrole-2-carboxylate The title compound was prepared as yellow crystals in 92.0% yield in a similar procedure to that described in Referential Example 9 by using methyl 3-formyl- 4,5-dimethylpyrrole-2-carboxylate and 1-bromoethyl-2-methylcyclopropane.

Mass spectrum (CI, m/z): 250 ($M^+$+1).

NMR spectrum ($CDCl_3$, δppm): 0.22–0.31 (m, 1H), 0.46–0.53 (m, 1H), 0.70–0.92 (m, 2H), 1.00 (d;J=6 Hz, 3H), 2.21 (s, 3H), 2.28 (s, 3H), 3.90 (s, 3H), 4.25 (d;J=6 Hz, 2H), 10.43 (s, 1H).

REFERENTIAL EXAMPLE 87

Ethyl 1-(2-butenyl)-3-formyl-5-methyl-4-pentylpyrrole-2-carboxylate

The title compound (cis/trans=22/78) was prepared as an orange oil in 41.4% yield in a similar procedure to that described in Referential Example 5 by using ethyl 1-(2-butenyl)-5-methyl-4-pentylpyrrole-2-carboxylate (cis/trans=21/79).

Mass spectrum (CI, m/z): 306 ($M^+$+1).

NMR spectrum ($CDCl_3$, δppm): 0.88 (t;J=7 Hz, 3H), 1.21–1.53 (m, 9H), 1.68 (d;J=8 Hz, 2.34H), 1.79 (d;J=8 Hz, 0.66H), 2.20 (s, 3H), 2.70 (t;J=7 Hz, 2H), 4.36 (q;J=7 Hz, 2H)., 4.85 (d;J=6 Hz, 1.56H), 4.99 (d;J=7 Hz, 0.44H), 5.30–5.47 (m, 1H), 5.49–5.66 (m, 1H), 10.47 (s, 1H).

REFERENTIAL EXAMPLE 88

1-(2-Butenyl)-3-ethyl-2-methyl-6,7-dihydropyrrolo[2,3-d]pyridazin-7-one

The title compound (cis/trans=23/77) was prepared as a pale yellow powder in 99.0w yield in a similar procedure to that described in Referential Example 28 by using ethyl 1-(2-butenyl)-4-ethyl-3-formyl-5-methylpyrrole-2-carboxylate (cis/trans=25/75).

Mass spectrum (CI, m/z): 232 ($M^+$+1).

NMR spectrum ($CDCl_3$, δppm): 1.20 (t;J=8 Hz, 3H), 1.67 (d;J=8 Hz, 2.31H), 1.80 (d;J=8 Hz, 0.69H), 2.30 (s, 3H), 2.65 (q;J=8 Hz, 2H), 5.13 (d;J=7 Hz, 1.54H), 5.27 (d;J=7 Hz, 0.46H), 5.36–5.53 (m, 1H), 5.55–5.69 (m, 1H), 8.14 (s, 1H), 10.20 (br.s, 1H).

REFERENTIAL EXAMPLE 89

2,3-Dimethyl-1-(2-methylcyclopropylmethyl)-6,7-dihydropyrrolo[2,3-dl]pyridazin-7-one The title compound was prepared as white flaky crystals in 88.7% yield in a similar procedure to that described in Referential Example 28 by using ethyl 3-formyl-4,5-dimethyl-1-(2-methylcyclopropylmethyl)pyrrole-2-carboxylate.

Mass spectrum (CI, m/z): 232 ($M^+$+1).

NMR spectrum ($CDCl_3$, δppm): 0.19–0.26 (m, 1H), 0.61–0.70 (m, 1H), 0.84–1.02 (m, 5H), 2.23 (s, 3H), 2.38 (s, 3H), 4.44 (d;J=6 Hz, 2H), 8.08 (s, 1H), 10.13 (br.s, 1H).

REFERENTIAL EXAMPLE 90

1-(2-Butenyl)-2-methyl-3-pentyl-6,7-dihydropyrrolo[2,3-d]pyridazin-7-one

The title compound (cis/trans=20/80) was prepared as a brownish-white powder in 80.1% yield in a similar procedure to that described in Referential Example 28 by using ethyl 1-(2-butenyl)-3-formyl-5-methyl-4-pentylpyrrole-2-carboxylate (cis/trans=22/78).

Mass spectrum (CI, m/z): 274 ($M^+$+1).

NMR spectrum ($CDCl_3$, δppm): 0.90 (t;J=7 Hz, 3H), 1.21–1.42 (m, 4H), 1.48–1.63 (m, 2H), 1.69 (d;J=7 Hz, 2.4H), 1.80 (d;J=8 Hz, 0.6H), 2.28 (s, 3H), 2.61 (t;J=7 Hz, 2H), 5.07–5.15 (m, 1.6H), 5.28 (d;J=8 Hz, 0.4H), 5.34–5.52 (m, 1H), 5.54–5.69 (m, 1H), 8.06 (s, 1H) , 9.82 (br.s, 1H)

REFERENTIAL EXAMPLE 91

1-(2-Butenyl)-7-chloro-3-ethyl-2-methylpyrrolo[2,3-d]pyridazine

The title compound (cis/trans=26/74) was prepared as ocherous crystals in 80.8% yield in a similar procedure to that described in Referential Example 51 by using 1-(2-butenyl)-3-ethyl-2-methyl-6,7-dihydropyrrolo[2,3-d]pyridazin-7-one (cis/trans=23/77).

Mass spectrum (CI, m/z): 250 ($M^+$+1), 252 ($M^+$+3).

NMR spectrum ($CDCl_3$, δppm): 1.23 (t;J=8 Hz, 3H), 1.66 (d;J=8 Hz, 2.22H), 1.81 (d;J=8 Hz, 0.78H), 2.40 (s, 3H), 2.76 (q;J=8 Hz, 2H), 5.03–5.10 (m, 1.48H), 5.20 (d;J=8 Hz, 0.52H), 5.24–5.41 (m, 1H), 5.55–5.69 (m, 1H), 9.20 (s, 1H).

REFERENTIAL EXAMPLE 92

7-Chloro-2,3-dimethyl-1-(2-methylcyclopropylmethyl) pyrrolo[2,3-d]pyridazine

The title compound was prepared as white crystals in 98.3% yield in a similar procedure to that described in Referential Example 51 by using 2,3-dimethyl-1-(2-methylcyclopropylmethyl)-6,7-dihydropyrrolo[2,3-d] pyridazin-7-one.

Mass spectrum (CI, m/z): 350 ($M^+$+1), 352 ($M^+$+3).

NMR spectrum ($CDCl_3$, δppm): 0.26–0.34 (m, 1H), 0.50–0.59 (m, 1H), 0.76–1.03 (m, 5H), 2.30 (s, 3H), 2.46 (s, 3H), 4.46 (d;J=7 Hz, 2H) , 9.04 (s, 1H)

REFERENTIAL EXAMPLE 93

1-(2-Butenyl)-7-chloro-2-methyl-3-pentylpyrrolo[2,3-d] pyridazine

The title compound (cis/trans=20/80) was prepared as an orange oil in 88.5% yield in a similar procedure to that described in Referential Example 51 by using 1-(2-butenyl)-2-methyl-3-pentyl-6,7-dihydropyrrolo[2,3-d]pyridazin-7-one (cis/trans (20/80).

Mass spectrum (CI, m/z): 292 ($M^+$+1), 294 ($M^+$+3).

NMR spectrum ($CDCl_3$, δppm): 0.88 (t;J=8 Hz, 3H), 1.23–1.40 (m, 4H), 1.55–1.69 (m, 4.4H), 1.81 (d;J=7 Hz, 0.6H), 2.39 (s, 3H), 2.72 (t;J=8 Hz, 2H), 5.05–5.08 (m, 1.6H), 5.19–5.32 (m, 1.4H), 4.56–5.64 (m, 1H), 9.18 (s, 1H).

REFERENTIAL EXAMPLE 94

5–13-(4-Fluorophenyl)propionyl]-2,3-dimethylpyrrole

A solution of 2.50 g (0.263 mole) of 2,3-dimethylpyrrole in 10 ml of dry tetrahydrofuran was added dropwise to a solution of ethylmagnesium bromide in 17 ml of dry tetrahydrofuran, which was prepared from 0.83 g (0.0341 mole) of magnesium chips and 4.02 g (0.0361 mole) of ethyl bromide, at room temperature over a period of 10 minutes. Thereafter, the refluxing mixture was allowed to cool to room temperature over a period of 30 minutes to give 4,5-dimethyl-2-pyrrolemagnesium bromide. A tetrahydrofuran solution of 4,5-dimethyl-2-pyrrolemagnesium bromide prepared above was dropwise added to a solution of 3-(4-fluorophenyl)propionyl chloride in 25 ml of dry tetrahydrofuran, which was prepared from 9.50 g (0.0565 mole) of 3-(4-fluorophenyl)propionic acid and 6.0 ml of thionyl chloride, at −78° C. over a period of about 35 minutes under a stream of nitrogen, and the reaction mixture was allowed to rise to room temperature over a period of about 2 hours. 15 ml of a saturated aqueous solution of ammonium chloride and 50 ml of water were added to the mixture, and the aqueous layer was separated and extracted with ether. The combined ether extract (250 ml) was washed twice with 100 ml each of an about 10% aqueous solution of sodium hydroxide and subsequently with 50 ml of a saturated aqueous solution of sodium chloride, and dried over anhydrous sodium sulfate. The solvent was distilled off under reduced pressure, and the residue was purified by column chromatography through silica gel using a 1:10 mixture of ethyl acetate and hexane as an eluent to give 3.42 g of the title compound as a pale brown solid.

Mass spectrum (CI, m/z): 264 ($M^+$+1).

NMR spectrum ($CDCl_3$, δppm): 2.01 (s, 3H), 2.22 (s, 3H), 2.98 (br.s, 4H), 6.66 (d;J=2 Hz, 1H), 6.92–6.99 (m, 2H), 7.15–7.20 (m, 2H), 9.31 (br.s, 1H).

REFERENTIAL EXAMPLE 95

5-(3-Phenylpropionyl)-2,3-dimethylpyrrole

The title compound was prepared as a pale violet solid in 51.4i yield in a similar procedure to that described in Referential Example 94 by using 3-phenylpropionic acid.

Mass spectrum (CI, m/z): 228 ($M^+$+1).

NMR spectrum ($CDCl_3$, δppm): 2.00 (s, 3H), 2.22 (s, 3H), 3.00 (br.s, 4H), 6.66 (d;J=2 Hz, 1H), 7.17–7.32 (m, 5H), 9.41 (br.s, 1H).

REFERENTIAL EXAMPLE 96

5-[3-(2,4-Difluorophenyl)propionyyl]-2,3-dimethylpyrrole

The title compound was prepared as a brownish-yellow solid in 48.0 yield in a similar procedure to that described in Referential Example 94 by using 3-(2,4-difluorophenyl) propionic acid.

Mass spectrum (CI, m/z): 264 ($M^+$+1).

NMR spectrum ($CDCl_3$, δppm): 2.00 (s, 3H), 2.22 (s, 3H), 2.94–3.05 (m, 4H), 6.66 (d;J=3 Hz, 1H), 6.67–6.81 (m, 2H), 7.14–7.22 (m, 1H) , 9.44 (br.s, 1H)

REFERENTIAL EXAMPLE 97

1-(2-Butenyl)—5-[3-(4-fluorophenyl)propionyl]-2,3-dimethylpyrrole 0.82 g (0.00731 mole) of potassium tert-butoxide was added to a solution of 1.39 g (0.00567 mole) of 5-[3-(4-fluorophenyl)propionyl]-2,3-dimethylpyrrole and 0.19 g (0.00074 mole) of 18-crown-6 in 40 ml of tetrahydrofuran and the resulting mixture was stirred at room temperature for 20 minutes. 1.80 g (0.0115 mole) of 1-bromo-2-butene (a mixture of cis and trans isomers) were added to the mixture and stirred at room temperature for 4 hours. After completion of the reaction, the reaction mixture was poured into ice-water and the aqueous mixture was extracted twice with 80 ml each of ethyl acetate. The extract was wahed with a saturated aqueous solution of sodium chloride and dried over anhydrous sodium sulfate. The solvent was distilled off under reduced pressure and the residue was purified by column chromatography through silica gel using a 1:10 mixture of ethyl acetate and hexane as an eluent to give 0.90 g of the title compound (cis/trans=22/78) as a pale yellow oil.

Mass spectrum (CI, m/z): 300 ($M^+$+1).

NMR spectrum ($CDCl_3$, δppm): 1.58–1.65 (m, 2.34H), 1.71–1.77 (m, 0.66H), 2.01 (s, 3H), 2.14 (s, 3H), 2.90–3.04 (m, 4H), 4.89–4.94 (m, 1.56H), 5.03–5.08 (m, 0.44H), 5.28–5.41 (m, 1H), 5.49–5.60 (m, 1H), 6.76 (s, 1H), 6.92–7.00 (m, 2H), 7.13–7.21 (m, 2H).

REFERENTIAL EXAMPLE 98

5-[3-(4-Fluorophenyl)propionyl]-2,3-dimethyl-1-(2-methylcyclopropylmethyl)-pyrrole The title compound was prepared as a pale yellow oil in 74.20% yield in a similar procedure to that described in Referential Example 97 by using 5-[3-(4-fluorophenyl) propionyl]-2,3-dimethylpyrrole and 2-methylcyclopropylmethyl bromide.

Mass spectrum (CI, m/z): 314 ($M^+$+1).

NMR spectrum ($CDCl_3$, δppm): 0.14–0.21 (m, 1H), 0.41–0.48 (m, 1H), 0.67–0.90 (m, 2H), 0.97 (d;J=6 Hz, 3H), 2.01 (s, 3H), 2.17 (s, 3H), 2.91–3.07 (m, 4H), 4.25–4.28 (m, 2H), 6.77 (s, 1H), 6.91–6.98 (m, 2H), 7.16–7.22 (m, 2H).

REFERENTIAL EXAMPLE 99

1-Cyclopropylmethyl-5-[3-(4-fluorophenyl)propionyl]-2,3-dimethylpyrrole

The title compound was prepared as a pale yellow oil in 64.8% yield in a similar procedure to that described in Referential Example 97 by using 5-[3-(4-fluorophenyl) propionyl]-2,3-dimethylpyrrole and cyclopropylmethyl bromide.

Mass spectrum (CI, m/z): 300 ($M^{+}$+1).

NMR spectrum ($CDCl_3$, δppm): 0.29–0.36 (m, 2H), 0.39–0.49 (m, 2H), 1.07–1.21 (m, 1H), 2.02 (s, 3H), 2.18 (s, 3H), 2.93–3.06 (m, 4H), 4.27 (d;J=7 Hz, 2H), 6.78 (s, 1H), 6.91–6.99 (m, 2H), 7.14–7.22 (m, 2H).

REFERENTIAL EXAMPLE 100

5-[3-(4-Fluorophenyl)propionyl]-2,3-dimethyl-1-(2-propenyl)pyrrole

The title compound was prepared as a pale yellow oil in 60.3% yield in a similar procedure to that described in Referential Example 97 by using. -5-[3-(4-fluorphenyl) propionyl)-2,3-dimethylpyrrole and 3-bromo-1-propene.

Mass spectrum (CI, m/z): 286 ($M^{+}$+1).

NMR spectrum ($CDCl_3$, δppm): 2.01 (s, 3H), 2.13 (s, 3H), 2.91–3.05 (m, 4H), 4.72 (d;J=17 Hz, 1H), 4.99–5.02 (m, 2H), 5.06 (d;J=11 Hz, 1H), 5.86–5.98 (m, 1H), 6.77 (s, 1H), 6.90–6.99 (m, 2H), 7.13–7.21 (m, 2H).

REFERENTIAL EXAMPLE 101

1-(2-Butenyl)-2,3-dimethyl-5-(3-phenylpropionyl)pyrrole

The title compound (cis/trans=23/77) was prepared as a yellow oil in 75.7% yield in a similar procedure to that described in Referential Example 97 by using 2,3-dimethyl-5-(3-phenylpropionyl)pyrrole and 1-bromo-2-butene.

Mass spectrum (CI, m/z): 282 ($M^{+}$+1).

NMR spectrum ($CDCl_3$, δppm): 1.64 (d;J=8 Hz, 2.31H), 1.77 (d;J=8 Hz, 0.69H), 2.01 (s, 3H), 2.17 (s, 3H), 3.02 (br.s, 4H), 4.89–5.96 (m, 1.54H), 5.08 (d;J=7 Hz, 0.46H), 5.28–5.42 (m, 1H), 5.49–5.61 (m, 1H), 6.77 (s, 1H), 7.15–7.32 (m, 5H).

REFERENTIAL EXAMPLE 102

2,3-Dimethyl-5-(3-phenylpropionyl)-1-(2-propenyl)pyrrole

The title compound was prepared as a yellow oil in 86.6% yield in a similar procedure to that described in Referential Example 97 by using 2,3-dimethyl-5-(3-phenylpropionyl) pyrrole and 3-bromomethyl-1-propene.

Mass spectrum (CI, m/z): 268 ($M^{+}$+1).

NMR spectrum ($CDCl_3$, δppm): 2.02 (s, 3H), 2.13 (s, 3H), 2.94–3.10 (m, 4H), 4.70–4.77 (m, 1H), 4.99–5.09 (m, 3H), 5.94 (ddt;J=17 Hz, 11 Hz, 7 Hz, 1H), 6.79 (s, 1H), 7.12–7.33 (m, 5H).

REFERENTIAL EXAMPLE 103

2,3-Dimethyl-1-(2-methylcyclopropylmethyl)-5-(3-phenylpropionyl)pyrrole

The title compound was prepared as a yellow oil in 99.1% yield in a similar procedure to that described in Referential Example 97 by using 2,3-dimethyl-5-(3-phenylpropionyl) pyrrole and 1-bromomethyl-2-methylcyclopropane.

Mass spectrum (CI, m/z); 296 ($M^{+}$+1).

NMR spectrum ($CDCl_3$, δppm): 0.14–0.21 (m, 1H), 0.42–0.49 (m, 1H), 0.68–0.93 (m, 2H), 0.97 (d;J=6 Hz, 3H), 2.01 (s, 3H), 2.17 (s, 3H), 3.05 (br.s, 4H), 4.25–4.34 (m, 2H), 6.78 (s, 1H), 7.12–7.33 (m, 5H).

REFERENTIAL EXAMPLE 104

1-Cyclopropylmethyl-2,3-dimethyl-5-(3-phenylpropionyl) pyrrole

The title compound was prepared as an orange oil in 93.0% yield in a similar procedure to that described in Referential Example 97 by using 2,3-dimethyl-5-(3-phenylpropionyl)pyrrole and bromomethylcyclopropane.

Mass spectrum (CI, m/z): 282 ($M^{+}$+1).

NMR spectrum ($CDCl_3$, δppm): 0.30–0.49 (m, 4H), 1.10–1.25 (m, 1H), 2.02 (s, 3H), 2.17 (s, 3H), 3.03 (br.s, 4H), 4.28 (d;J=7 Hz, 2H), 6.80 (s, 1H), 7.14–7.31 (m, 5H).

REFERENTIAL EXAMPLE 105

1-(2-Butenyl)-5-[3-(2,4-difluorophenyl)propionyl]-2,3-dimethylpyrrole

The title compound (cis/trans=23/77) was prepared as a yellow oil in 55.4% yield in a similar procedure to that described in Referential Example 97 by using 5-[3-(2,4-difluorophenyl)propionyl]-2,3-dimethylpyrrole and 1-bromo-2-butene.

Mass spectrum (CI, m/z): 318 ($M^{+}$+1).

NMR spectrum ($CDCl_3$, δppm): 1.62–1.64 (m, 2.31H), 1.74–1.77 (m, 0.69H), 2.00 (s, 3H), 2.14 (s, 3H), 2.99 (br.s, 4H), 4.89–4.92 (m, 1.54H), 5.04–5.07 (m, 0.46H), 5.28–5.40 (m, 1H), 5.51–5.60 (m, 1H), 6.73–6.80 (m, 3H), 7.14–7.22 (m, 1H).

REFERENTIAL EXAMPLE 106

5-[3-(2,4-Difluorophenyl)propionyl]-2,3-dimethyl-1-(2-methylcyclopropylmethyl)pyrrole The title compound was prepared as a yellow oil in 80.2% yield in a similar procedure to that described in Referential Example 97 by using 5-[3-(2,4-difluorophenyl)propionyl]-2,3-dimethylpyrrole and 2-methylcyclopropylmethyl bromide.

Mass spectrum (CI, m/z): 332 ($M^{+}$+1).

NMR spectrum ($CDCl_3$, δppm): 0.14–0.20 (m, 1H), 0.41–0.48 (m, 1H), 1.67–1.92 (m, 2H), 0.97 (d;J=6 Hz, 3H), 2.01 (s, 3H), 2.17 (s, 3H), 3.00 (br.s, 4H), 4.20–4.32 (m, 2H), 6.73–6.80 (m, 3H), 7.15–7.23 (m, 1H).

REFERENTIAL EXAMPLE 107

1-Cyclopropylmethyl-5-[3-(2,4-difluorophenyl)propionyl]-2,3-dimethylpyrrole

The title compound was prepared as a yellow solid in 85.16 yield in a similar procedure to that described in Referential Example 97 by using 5-[3-(2,4-difluorophenyl) propionyl]-2,3-dimethylpyrrole and cyclopropylmethyl bromide.

Mass spectrum (CI, m/z): 318 ($M^{+}$+1).

NMR spectrum ($CDCl_3$, δppm): 0.30–0.50 (m, 4H), 1.06–1.12 (m, 1H), 2.02 (s, 3H), 2.18 (s, 3H), 3.00 (br.s, 4H), 4.27 (d;J=7 Hz, 2H), 6.72–6.81 (m, 3H), 7.14–7.22 (m, 1H).

REFERENTIAL EXAMPLE 108

5-[3-(2,4-Difluorophenyl)propionyl]-2,3-dimethyl-1-(2-propenyl)pyrrole

The title compound was prepared as a pale yellow oil in 81.7% yield in a similar procedure to that described in Referential Example 97 by using 5-[3-(2,4-difluorophenyl) propionyl]-2,3-dimethylpyrrole and 3-bromo-1-propene.

Mass spectrum (CI, m/z): 304 ($M^{+}$+1).

NMR spectrum ($CDCl_3$, δppm): 2.01 (s, 3H), 2.13 (s, 3H), 2.99 (br.s, 4H), 4.72 (d;J=17 Hz, 1H), 4.98–5.01 (m, 2H), 5.06 (d;J=10 Hz, 1H), 5.86–6.00 (m, 1H), 6.73–6.80 (m, 3H), 7.13–7.21 (m, 1H).

REFERENTIAL EXAMPLE 109

1-(2-Butenyl)-2-[l-chloro-3-(4-fluorophenyl)-1-propenyl]-3-formyl-4,5-dimethylpyrrole 0.38 ml (0.00408 mole) of phosphorus oxychloride was added to 0.29 g (0.00397 mole) of dry dimethylformamide and the mixture was stirred at room temperature for 30 minutes. A solution of 0.89g (0.00297 mole) of 1-(2-butenyl)-5-[3-(4-fluorophenyl)propionyl]-2,3- dimethylpyrrole in 4 ml of dichloromethane was added dropwise to the mixture and stirred at room temperature for 30 minutes. The reaction mixture was poured into ice-water and neutralized with an aqueous solution of sodium hydroxide. The aqueous mixture was extracted with 50 ml each of dichloromethane for three times. The extract was washed with 30 ml of a saturated aqueous solution of sodium hydrogencarbonate and 30 ml of a saturated aqueous solution of sodium chloride in turn and dried over anhydrous sodium sulfate. The solvent was distilled off under reduced pressure and the residue was purified by column chromatography through silica gel using a 1:12 to 1:9 mixture of ethyl acetate and hexane as an eluent to give 0.41 g of the title compound (cis/trans=22/78) as a yellow oil.

Mass spectrum (CI, m/z): 346 ($M^+$+1).

NMR spectrum ($CDCl_3$, δppm): 1.55–1.74 (m, 3H), 2.10 (s, 3H), 2.23 (s, 3H), 3.72 (d;J=7 Hz, 2H), 4.39–4.43 (m, 1.56H), 4.51–4.55 (m, 0.44H), 5.27–5.66 (m, 2H), 6.08 (t;J=7 Hz, 1H), 6.97–7.04 (m, 2H), 7.16–7.24 (m, 2H), 9.77 (s, 1H).

REFERENTIAL EXAMPLE 110

2-[1-Chloro-3-(4-fluorophenyl)-1-propenyl]-3-formyl-4,5-dimethyl-1-(2-methylcyclopropylmethyl)pyrrole The title compound was prepared as a pale brown oil in 71.2% yield in a similar procedure to that described in Referential Example 109 by using 5-[3-(4-fluorophenyl) propionyl]-2,3-dimethyl-1-(2-methylcyclopropylmethyl) pyrrole.

Mass spectrum (CI, m/z): 360 ($M^+$+1).

NMR spectrum ($CDCl_3$, δppm): 0.22–0.28 (m, 1H), 0.34–0.41 (m, 1H), 0.59–0.78 (m, 2H), 0.94 (d;J=6 Hz, 3H), 2.17 (s, 3H), 2.24 (s, 3H), 3.68–3.78 (m, 4H), 6.12 (t;J=7 Hz, 1H), 6.98–7.04 (m, 2H), 7.19–7.26 (m, 2H), 9.76 (s, 1H).

REFERENTIAL EXAMPLE 111

2-[1-Chloro-3-(4-fluorophenyl)-1-propenyl]-1-cyclopropylmethyl-3-formyl-4,5-dimethylpyrrole The title compound was prepared as a pale yellow oil in 72.3% yield in a similar procedure to that described in Referential Example 109 by using 1-cyclopropylmethyl-5-[3-(4-fluorophenyl)propionyl]-2,3-dimethylpyrrole.

Mass spectrum (CI, m/z.): 346 ($M^+$+1).

NMR spectrum ($CDCl_3$, δppm): 0.19–0.30 (m, 2H), 0.48–0.57 (m, 2H), 0.98–1.11 (m, 1H), 2.18 (s, 3H), 2.24 (s, 3H), 3.68 (d;J=7 Hz, 2H), 3.77 (d;J=7 Hz, 2H), 6.13 (t, J=7 Hz, 1H), 6.97–7.04 (m, 2H), 7.19–7.25 (m, 2H), 9.77 (s, 1H).

REFERENTIAL EXAMPLE 112

2-[1-Chloro-3-(4-fluorophenyl)-1-propenyl]-3-formyl-4,5-dimethyl-1-(2-propenyl)pyrrole The title compound was prepared as a yellow oil in 70.8% yield in a similar procedure to that described in Referential Example 109 by using 5-[3-(4-fluorophenyl)propionyl]-2,3-dimethyl-1-(2-propenyl)pyrrole.

Mass spectrum (CI, m/z): 332 ($M^+$+1).

NMR spectrum ($CDCl_3$, δppm): 2.09 (s, 3H), 2.24 (s, 3H), 3.72 (d;J=7 Hz, 2H), 4.46–4.51 (m, 2H), 4.83 (d;J=17 Hz, 1H), 5.14 (d;J=10 Hz, 1H), 5.78–5.92 (m, 1H), 6.09 (t;J=7 Hz, 1H), 6.96–7.04 (m, 2H), 7.15–7.34 (m, 2H), 9.78 (s, 1H).

REFERENTIAL EXAMPLE 113

1-(2-Butenyl)-2-(1-chloro-3-phenyl-1-propenyl)-3-formyl-4,5-dimethylpyrrole

The title compound (cis/trans=23/77) was prepared as an orangish-yellow oil in 61.6? yield in a similar procedure to that described in Referential Example 109 by using 1-(2-butenyl)-2,3-dimethyl-5-(3-phenylpropionyl)pyrrole (cis/trans=23/77).

Mass spectrum (CI, m/z): 328 ($M^+$+1), 330 ($M^+$+3).

NMR spectrum ($CDCl_3$, δppm): 1.61–1.73 (m, 3H), 2.10 (s, 3H), 2.23 (s, 3H), 3.76 (d;J=7 Hz, 2H), 4.40–4.43 (m, 1.54H), 4.50–4.55 (m, 0.46H), 5.30–5.45 (m, 2H), 5.12 (t;J=7 Hz, 1H), 7.22–7.35 (m, 5H), 9.79 (s, 1H).

REFERENTIAL EXAMPLE 114

2-(1-Chloro-3-phenyl-1-propenyl)-3-formyl-4 5-dimethyl-1-(2-propenyl) pyrrole

The title compound was prepared as a red-brown oil in 73.6% yield in a similar procedure to that described in Referential Example 109 by using 2,3-dimethyl-5-(3-phenylpropionyl)-1-(2-propenyl)pyrrole.

Mass spectrum (CI, m/z): 314 ($M^+$+1), 316 ($M^+$+3).

NMR spectrum ($CDCl_3$, δppm): 2.09 (s, 3H), 2.24 (s, 3H), 3.75 (d;J=7 Hz, 2H), 4.47–4.52 (m, 2H), 4.83 (d;J=17 Hz, 1H), 5.14 (d;J=9 Hz, 1H), 5.85 (ddt;J=17 Hz, 9 Hz, 7 Hz, 1H), 6.16 (t;J=7 Hz, 1H), 7.14–7.41 (m, 5H)., 9.80 (s, 1H).

REFERENTIAL EXAMPLE 115

2-(1-Chloro-3-phenyl-1-propenyl)-3-formyl-4,5-dimethyl-1-(2-methylcyclopropylmethyl)pyrrole The title compound was prepared as a yellow-orange oil in 65.9% yield in a similar procedure to that described in Referential Example 109 by using 2,3-dimethyl-1-(2-methylcyclopropylmethyl)-5-(3-phenylpropionyl)pyrrole.

Mass spectrum (CI, m/z): 342 ($M^+$+1), 344 ($M^+$+3).

NMR spectrum ($CDCl_3$, δppm): 0.21–0.28 (m, 1H), 0.34–0.40 (m, 1H), 0.62–0.73 (m, 2H), 0.93 (d;J=6 Hz, 3H), 2.16 (s, 3H), 2.24 (s, 3H), 3.68–3.84 (m, 4H), 6.15 (t;J=7 Hz, 1H), 7.15–7.40 (m, 5H), 9.78 (s, 1H).

REFERENTIAL EXAMPLE 116

2-(1-chloro-3-phenyl-1-propenyl)-1-cyclopropylmethyl-3-formyl-4 5-dimethylpyrrole The title compound was prepared as a yellow-orange oil in 75.5% yield in a similar procedure to that described in Referential Example 109 by using 1-cyclopropylmethyl-2,3-dimethyl-5-(3-phenylpropionyl)pyrrole.

Mass spectrum (CI, m/z): 328 ($M^+$+1), 330 ($M^+$+3).

NMR spectrum ($CDCl_3$, δppm): 0.21–0.27 (m, 2H), 0.47–0.54 (m, 2H), 0.99–1.08 (m, 1H), 2.18 (s, 3H), 2.24 (s, 3H), 2.70–2.84 (m, 4H), 6.17 (t;J=7 Hz, 1H), 7.16–7.40 (m, 5H), 9.78 (s, 1H).

REFERENTIAL EXAMPLE 117

1-(2-Butenyl)-2-[1-chloro-3-(2,4-difluorophenyl)-1-propenyl)-3-formyl-4,5-dimethylpyrrole The title compound (cis/trans=23/77) was prepared as a pale yellow oil in 85.7% yield in a similar procedure to that described in Referential Example 109 by using 1-(2-butenyl)-5-[3-(2,4-difluorophenyl)propionyl]-2,3-dimethylpyrrole.

Mass spectrum (CI, m/z): 364 ($M^+$+1).

NMR spectrum ($CDCl_3$, δppm): 1.59–1.71 (m, 3H), 2.10 (s, 3H), 2.22 (s, 3H), 3.72 (d;J=7 Hz, 2H), 4.39–4.41 (m, 1.54H), 4.51–4.53 (m, 0.46H), 5.27–5.67 (m, 2H), 6.05 (t;J=7 Hz, 1H), 6.77–6.87 (m, 2H), 7.18–7.27 (m, 1H), 9.75 (s, 1H).

REFERENTIAL EXAMPLE 118

2-[1-Chloro-3-(2,4-difluorophenyl)-1-propenyl]-3-formyl-4,5-dimethyl-1-(2-methylcyclopropylmethyl)pyrrole The title compound was prepared as a pale brown oil in 70.8% yield in a similar procedure to that described in Referential Example 109 by using 5-[3-(2,4-difluorophenyl)propionyl]-2,3-dimethyl-1-(2-methylcyclopropylmethyl)pyrrole.

Mass spectrum (CI, m/z): 378 ($M^+$+1).

NMR spectrum ($CDCl_3$, δppm): 0.21–0.28 (m, 1H), 0.33–0.40 (m, 1H), 1.56–1.80 (m, 2H), 0.93 (d;J=6 Hz, 3H), 2.16 (s, 3H), 2.24 (s, 3H), 3.70–3.77 (m, 4H), 6.09 (t;J=7 Hz, 1H), 6.78–6.88 (m, 2H), 7.20–7.30 (m, 1H), 9.75 (s, 1H).

REFERENTIAL EXAMPLE 119

2-[1-Chloro-3-(2,4-difluorophenyl)-1-propenyl]-1-cyclopropylmethyl-3-formyl-4,5-dimethylpyrrole The title compound was prepared as a pale brown oil in 67.8% yield in a similar procedure to that described in Referential Example 109 by using 1-cyclopropylmethyl-5-[3-(2,4-difluorophenyl)propionyl]-2,3-dimethylpyrrole.

Mass spectrum (CI, m/z): 364 ($M^+$+1).

NMR spectrum ($CDCl_3$, δppm): 0.20–0.26 (m, 2H), 0.47–0.54 (m, 2H), 0.98–1.11 (m, 1H), 2.18 (s, 3H), 2.24 (s, 3H), 3.70–3.79 (m, 4H), 6.10 (t;J=7 Hz, 1H), 6.78–6.88 (m, 2H), 7.21–7.29 (m, 1H), 9.75 (s, 1H).

REFERENTIAL EXAMPLE 120

2-[1-Chloro-3-(2,4-difluorophenyl)-1-propenyl]-3-formyl-4,5-dimethyl-1-(2-propenyl)pyrrole The title compound was prepared as a pale brownish-yellow oil in 80.2% yield in a similar procedure to that described in Referential Example 109 by using 5-(3-(2,4-difluorophenyl)propionyl]-2,3-dimethyl-1-(2-propenyl)pyrrole.

Mass spectrum (CI, m/z): 350 ($M^+$+1).

NMR spectrum ($CDCl_3$, δppm): 2.09 (s, 3H), 2.23 (s, 3H), 3.72 (d;J=7 Hz, 2H), 4.46–4.49 (m, 2H), 4.81 (d;J=17 Hz, 1H), 5.14 (d;J=10 Hz, 1H), 5.77–5.91 (m, 1H), 6.06 (t;J=7 Hz, 1H), 6.77–6.86 (m, 2H), 7.18–7.23 (m, 1H), 9.76 (s, 1H).

TEST EXAMPLE 1

Proton.potassium-adenosine triphosphatase ($H^+.K^+$-ATPase) activation test

According to the method reported by Sachs et al. [J. Biol. Chem., 251, 7690 (1976)], a microsomal fraction obtained from homogenized fresh porcine gastric mucosa by density gradient ultracentrifugation was used as the proton.potassium-adenosine triphosphatase preparation, 10 μl of a solution of a test compound in dimethylsulfoxide were added to 0.75 ml of 70 mM tris-HCl buffer solution (magnesium chloride 5 mM, potassium chloride 20 mM and pH=6.85) containing from 30 to 80 μg/ml (in terms of protein concentration) of the enzyme preparation and the mixture was incubated for 45 minutes at 37° C. with shaking at 200 times per minute. The enzyme reaction was initiated by adding 0.25 ml of 8 mM disodium adenosine triphosphate solution. After 20 minutes of the reaction time, the reaction was stopped by adding 1 ml of a 10k trichloroacetic acid-active carbon (100 mg) solution. The reaction solution was centrifuged (4° C., 3000 rpm, 15 minutes) and the inorganic phosphate in the supernatant prepared from adenosine triphosphate by hydrolysis was measured by colorimetry, according to the method of Yoda and Hokin [Biochem. Biophys. Res. Commun., 40, 880 (1970)]. In a similar manner, the amount of inorganic phosphate was measured in a reaction solution in the absence of potassium chloride. From the difference between the phosphate amounts in the presence and absence of potassium chloride, the proton-potassium-adenosine triphosphatase activity was calculated. Based on the activity value in the control and the values in the test compound at the various concentrations tested, the inhibiting rates (%) and then the 50? inhibiting concentrations ($IC_{50}$) to proton.potassium-adenosine triphosphatase activity were obtained. The compounds of Examples 1, 4, 7, 9, 17, 21, 22, 35, 44, 48, 49, 57, 58, 74, 75 and 76 show an excellent activity.

TEST EXAMPLE 2

Gastric acid secretion activity test using pyloric ligation in rats (Shay rat method)

Pyloric ligation was conducted based on the method of Shay et al. [Gastroenterology, 5, 43 (1945)]. Male rats of SD strain were fasted for 24 hours; their abdomens were sectioned during anesthesia under ether. The duodenal and pyloric regions were exposed and the latter was ligated. A solution of a test compound (10 mg/ml) prepared by use of 1.5w parts of dimethylacetamide, 68.5% parts of polyethyleneglycol (PEG-400) and 30% parts of physiological saline solution, was injected into the duodenal region for the dose to be 20 mg/kg by use of a 1-ml syringe and an injection needle (26G). After injection of the test compound, the abdominal region was sutured. The animals were allowed to a stand for 4 hours without feeding food and water and then sacrified with carbon dioxide gas. The stomach was excised and gastric juice was gathered. The gastric juice sample was centrifuged (4° C., 2500 rpm, 15 minutes). The amount of the supernatant was measured to be as the gastric secretion. The acidity of the gastric juice was determined by the amount (ml) of 0.01 N sodium hydroxide solution required for titration of 0.1 ml of the supernatant to pH 7.0 by use of-an auto-titrating apparatus. The value of gastric acid secretion was calculated from the value of gastric secretion and the acidity of gastric juice. The inhibiting rate was obtained from the values of gastric acid secretion of the control group and of the administered group. The compounds of Examples 1, 3, 5, 7, 9, 11, 12, 14, 16, 17, 22, 26, 32, 33, .35, 37, 40, 41, 42, 44, 48, 57, 58, 62 and 68 show an excellent activity.

TEST EXAMPLE 3

Antibacterial activity against *Helicobacter pylori*

The antibacterial activity of the compounds of the present invention were evaluated by measuring the minimum inhibitory concentration values (MIC) of the present compounds against Helicobacter pylori strains 9470, 9472 and 9474.

These strains of *Helicobacter pylori* were incubated for 4 days on a plate medium. The medium was prepared by dissolving brain heart infusion agar (Product of DIFCO) in a defined amount of distilled water, by sterilization in an autoclave, injecting horse blood (Product of Nihon Seibutsu Zairyo Co.) into each plate for the medium to contain 7% of the blood and by solidifying.

Under slightly aerobic conditions, *Helicobacter pylori* cultivated at 37° C. for 4 days was suspended in a physiological saline solution for its inocular size to be about $10^8$ CFU/ml. The suspension was diluted 100 times, and about 10 μl of the diluted suspension was inoculated on a medium for MIC determination.

The medium for MIC determination used had the same compounds as those for preculture. The medium for MIC determination was prepared by mixing one part of 2-fold diluted solutions of the compound dissolved in dimethylsulfoxide with sterilized distilled water and 99 parts of the medium and by solidifying on a dish.

In a similar way to the preculture, Helicobacter pylori was cultivated at 37° C. for 3 days under slightly aerobic conditions. After completion of the culture, the bacterial growth at every inoculated site was observed with the naked eye. The minimum concentration which gave no bacterial growth was regarded as MIC of the compound of the present invention. The compounds of Examples 1, 2, 3, 4, 5, 6, 7, 8, 9, 10, 11, 12, 13, 14, 15, 16, 17, 18, 19, 20, 21, 22, 23, 24, 25, 27, 29, 34, 44, 45, 48, 49, 50, 51, 52, 56, 57, 58, 75 and 76 show an excellent antibacterial activity.

What is claimed is:

1. Pyrrolopyridazine derivatives having a general formula:

(I)

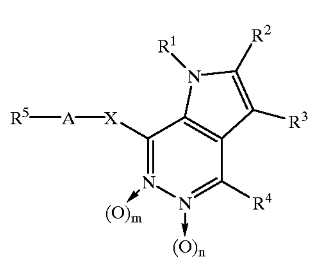

or pharmacologically acceptable salts thereof, wherein $R^1$ represents a $C_2$–$C_5$ alkenyl group, a $C_3$–$C_4$ alkenyl group substituted with fluorine, chorine or bromine, a $C_6$ aryl-$C_3$–$C_5$ alkenyl group, a $C_3$–$C_4$ alkynyl group, a cyclopropyl group, a $C_3$–$C_6$ cycloalkylmethyl group said cycloalkylmethyl group being unsubstituted or substituted by at least one $C_1$–$C_4$ alkyl group or a halogeno-$C_1$–$C_4$ alkyl group, a ($C_5$–$C_7$ cycloalkyl)-$C_1$–$C_6$ alkyl group;

$R^2$ and $R^3$ are the same or different and each represents a hydrogen atom, a $C_1$–$C_4$ alkyl group or a $C_6$ aryl group;

$R^4$ represents a hydrogen atom or a $C_1$–$C_4$ alkyl group;

$R^5$ represents a phenyl group optionally substituted with $C_1$–$C_4$ alkyl, $C_1$–$C_4$ alkoxy, halogen, halogeno-$C_1$–$C_4$ alkyl or halogeno-$C_1$–$C_4$ alkoxy, a naphthyl group, a furyl group, a thienyl group, an oxazolyl group, a benzoxazolyl group, a thiazolyl group, a benzothiazolyl group, an imidazolyl group, a benzoimidazolyl group, a 1,3,4-oxadiazolyl group, a 1,3,4-thiadiazolyl group, a pyridyl group, a pyrazinyl group or a pyridazinyl group;

A represents a methylene group;

X represents an oxygen atom, a sulfur atom or a methylene group; and when n is 1, m is 0.

2. Pyrrolopyridazine derivatives or pharmacologically acceptable salts thereof according to claim 1, wherein $R^1$ represents a $C_2$–$C_5$ alkenyl group, a $C_3$–$C_4$ alkenyl group substituted with fluorine or chlorine, a 3-($C_6$ aryl)-2-propynyl group, a 2-propynyl group, a cyclopropyl group, a cyclopropylmethyl group, a 2-methylcyclopropylmethyl group, a cyclopenten-1-ylmethyl group or a fluoro-$C_2$–$C_3$alkyl group;

$R^2$ and $R^3$ are the same or different and each represents a hydrogen atom, a $C_1$–$C_3$ alkyl group or phenyl group;

$R^4$ represents a hydrogen atom or a $C_1$–$C_2$ alkyl group;

$R^5$ represents a phenyl group optionally substituted with methyl, methoxy, fluorine, chlorine, fluoromethyl, trifluoromethyl, fluoromethoxy or difluoromethoxy, a furyl group, a thienyl group, an oxazolyl group, a benzoxazolyl group, a thiazolyl group, a benzothiazolyl group, an imidazolyl group, a benzoimidazolyl group or a pyridyl group;

A represents a methylene group;

X represents an oxygen atom, a sulfur atom or a methylene group; and m is 0.

3. Pyrrolopyridazine derivatives or pharmacologically acceptable salts thereof according to claim 1, wherein R represents a 1-propenyl, 2-propenyl, 1-butenyl, 2-butenyl, 2-methyl-2-propenyl, propane-1,2-dienyl, 3-phenyl-2-propenyl, 2-propynyl, cyclopropylmethyl, 2-methylcyclopropylmethyl, cyclopenten-1-ylmethyl, 2,2,2-trifluoroethyl or 3-fluoropropyl group;

$R^2$ and $R^3$ are the same or different and each represents a hydrogen atom or a $C_1$–$C_2$ alkyl group;

$R^4$ represents a hydrogen atom or a $C_1$–$C_2$ alkyl group;

$R^5$ represents a phenyl group optionally substituted with fluorine, chlorine, trifluoromethyl or difluoromethoxy;

A represents a methylene group;

X represents an oxygen atom or a methylene group;

m is 0; and n is 0.

4. Pyrrolopyridazine derivatives or pharmacologically acceptable salts thereof according to claim 1, wherein $R^1$ represents a 1-propenyl, 2-propenyl, 1-butenyl, 2-butenyl, 2-methyl-2-propenyl, 3-phenyl-2-propenyl, cyclopropylmethyl or 2-methylcyclopropylmethyl group;

$R^2$ and $R^3$ are the same and each represents a methyl group;

$R^4$ represents a hydrogen atom;

$R^5$ represents a phenyl group optionally substituted with fluorine or chlorine;

A represents a methylene group;

X represents an oxygen atom;

m is 0; and n is 0.

5. A pyrrolopyridazine derivative or pharmacologically acceptable salt thereof selected from the group consisting of 1-(2-butenyl)-7-benzyloxy-2,3-dimethylpyrrolo[2,3-d]pyridazine or pharmacologically acceptable salts thereof, 7-benzyloxy-2,3-dimethyl-1-(2-methyl-2-propenyl)pyrrolo[2,3-d]pyridazine or pharmacologically acceptable salts thereof, 7-benzyloxy-2,3-dimethyl-1-(2-propynyl)pyrrolo[2,3-d]pyridazine or pharmacologically acceptable salts thereof, 7-benzyloxy-1-cyclopropylmethyl-2,3-dimethylpyrrolo[2,3-d]pyridazine or pharmacologically acceptable salts thereof, 7-(4-fluorobenzyloxy)-2,3-dimethyl-1-(1-propenyl)pyrrolo[2,3-d]pyridazine or pharmacologically acceptable salts thereof, 7-(4-fluorobenzyloxy)-2,3-dimethyl-1-(2-propenyl)pyrrolo[2,3-d]pyridazine or pharmacologically acceptable salts thereof, 1-(2-butenyl)-7-(4-fluorobenzyloxy)-2,3-dimethylpyrrolo[2,3-d]pyridazine or pharmacologically acceptable salts thereof, 1-cylcopropylmethyl-7-(4-fluorobenzyloxy)-2,3-dimethylpyrrolo[2,3-d]pyridazine or pharmacologically acceptable salts thereof, 7-(2,4-difluorobenzyloxy)-2,3-dimethyl-1-(2-propenyl)pyrrolo[2,3-d]pyridazine or pharmacologically acceptable salts thereof, 1-(2-butenyl)-7-(2,4-difluorobenzyloxy)-2,3-dimethylpyrrolo[2,3-d]pyridazine or pharmacologically acceptable salts thereof, 7-(4-chlorobenzyloxy)-2,3-dimethyl-1-(2-propenyl) pyrrolo[2,3-d]pyridazine or pharmacologically acceptable salts thereof, 7-(2,4-dichlorobenzyloxy)-2,3-dimethyl-1-(2-propenyl) pyrrolo[2,3-d]pyridazine or pharmacologically acceptable salts thereof, 1-(2-butenyl)-7-(2,4-dichlorobenzyloxy)-2,3-dimethylpyrrolo[2,3-d]pyridazine or pharmacologically acceptable salts thereof, 7-(2-fluorobenzyloxy)-2,3-dimethyl-1-(2-propenyl) pyrrolo[2,3-d]pyridazine or pharmacologically acceptable salts thereof, 1-(2-butenyl)-3-ethyl-7-(4-fluorobenzyloxy)-2-methylpyrrolo[2,3-d]pyridazine or pharmacologically acceptable salts thereof, 7-(4-fluorobenzylthio)-2,3-dimethyl-1-(2-propenyl) pyrrolo[2,3-d]pyridazine or pharmacologically acceptable salts thereof, 1-(2-butenyl)-7-(4-fluorobenzylthio)-2,3-dimethylpyrrolo[2,3-d]pyridazine or pharmacologically acceptable salts thereof, 1-(2-butenyl)-7-(2,4-difluorobenzylthio)-2,3-dimethylpyrrolo[2,3-d]pyridazine or pharmacological acceptable salts thereof, 1-(2-butenyl)-7-(2-chloro-6-fluorobenzyloxy)-2,3-dimethylpyrrolo[2,3-d]pyridazine or pharmacologically acceptable salts thereof, 1-(2-butenyl)-7-(4-chloro-2-fluorobenzyloxy)-2,3-dimethylpyrrolo[2,3-d]pyridazine or pharmacologically acceptable salts thereof, 7-(4-fluorobenzyloxy)-2,3-dimethyl-1-(2-methylcyclopropylmethyl)pyrrolo[2,3-d]pyridazine or pharmacologically acceptable salts thereof, 7-(2,4-difluorobenzyloxy)-2,3-dimethyl-1-(2-methylcyclopropylmethyl)pyrrolo[2,3-d]pyridazine or pharmacologically acceptable salts thereof, 1-(2-butenyl)-7-(4-fluorobenzyloxy)-2,3-dimethylpyrrolo[2,3-d]pyridazine-5-oxide or pharmacologically acceptable salts thereof, 1-(2-butenyl)-7-(2,4-difluorobenzyloxy)-2,3-dimethylpyrrolo[2,3-d]pyridazine-5-oxide or pharmacologically acceptable salts thereof, 7-(2, 4-difluorobenzyloxy)-2,3-dimethyl-1-(2 methylcyclopropylmethyl)pyrrolo[2,3-d]pyridazin or pharmacologically acceptable salts thereof, 2,3-dimethyl-7-phenethyl-1-(2-propenyl)pyrrolo[2,3-d] pyridazine or pharmacologically acceptable salts thereof, 1-(2-butenyl)-2,3-dimethyl-7-phenethylpyrrolo[2,3-d] pyridazine or pharmacologically acceptable salts thereof, 7-(4-fluorophenethyl)-2,3-dimethyl-1-(2 propenyl) pyrrolo[2,3-d]pyridazine or pharmacologically acceptable salts thereof, 1-(2-butenyl)-7-(4-fluorophenethyl)-2,3-dimethylpyrrolo [2,3-d]pyridazine or pharmacologically acceptable salts thereof, 1-cyclopropylmethyl-7-(4-fluorophenethyl)-2,3-dimethylpyrrolo[2,3-d]pyridazine or pharmacologically acceptable salts thereof, 7-(2,4-difluorophenethyl)-2,3-dimethyl-1-(2-propenyl) pyrrolo[2,3-d]pyridazine or pharmacologically acceptable salts thereof, 1-(2-butenyl)-7-(2,4-difluorophenethyl)-2,3-dimethylpyrrolo[2,3-d]pyridazine or pharmacologically acceptable salts thereof, 1-cyclopropylmethyl-7-(2,4-difluorophenethyl)-2,3-dimethylpyrrolo[2,3-d]pyridazine or pharmacologically acceptable salts thereof, 7-(4-fluorophenethyl)-2,3-dimethyl-1-(2-methylcyclopropylmethyl)pyrrolo[2,3-d]pyridazine or pharmacologically acceptable salts thereof, 7-(2,4-difluorophenethyl)-2,3-dimethyl-1-(2-methylcyclopropylmethyl)pyrrolo[2,3-d]pyridazine or pharmacologically acceptable salts thereof, 2,3-dimethyl-1-(2-methylcyclopropylmethyl)-7-phenethylpyrrolo[2,3-d]pyridazine or pharmacologically acceptable salts thereof, 1-(2-butenyl)-7-(4-fluorobenzyloxy)-2,3-dimethylpyrrolo[2,3-d]pyridazine-5-oxide or pharmacologically acceptable salts thereof, 1-(2-butenyl)-7-(2,4-difluorobenzyloxy)-2,3-dimethylpyrrolo[2,3-d]pyridazine-5-oxide or pharmacologically acceptable salts thereof, 1-(2-butenyl)-7-(2,4-difluorophenethyl)-2,3-dimethylpyrrolo[2,3-d]pyridazine-5-oxide or pharmacologically acceptable salts thereof, 1-(2-butenyl)-7-(2,4-difluorophenethyl)-2,3-dimethylpyrrolo[2,3-d]pyridazine-6-oxide or pharmacologically acceptable salts thereof, and 7-(4-fluorobenzyloxy)-2,3-dimethyl-1-(2-methylcyclopropylmethyl)pyrrolo[2,3-d]pyridazine (trans) or pharmacologically acceptable salts thereof.

6. A pyrrolopyridazine derivative according to claim 5 which is 1-(2-Butenyl)-7-benzyloxy-2,3-dimethylpyrrolo[2,3-d]pyridazine or pharmacologically acceptable salts thereof.

7. A pyrrolopyridazine derivative according to claim 5 which is 7-Benzyloxy-2,3-dimethyl-1-(2-methyl-2-propenyl)pyrrolo[2,3-d]pyridazine or pharmacologically acceptable salts thereof.

8. A pyrrolopyridazine derivative according to claim 5 which is 7-Benzyloxy-2,3-dimethyl-1-(2-propynyl)pyrrolo [2,3-d]pyridazine or pharmacologically acceptable salts thereof.

9. A pyrrolopyridazine derivative according to claim 5 which is 7-Benzyloxy-1-cyclopropylmethyl-2,3-dimethylpyrrolo[2,3-d]pyridazine or pharmacologically acceptable salts thereof.

10. A pyrrolopyridazine derivative according to claim 5 which is 7-(4-Fluorobenzyloxy)-2,3-dimethyl-1-(1-propenyl)pyrrolo[2,3-d]pyridazine or pharmacologically acceptable salts thereof.

11. A pyrrolopyridazine derivative according to claim 5 which is 7-(4-Fluorobenzyloxy)-2,3-dimethyl-1-(2-propenyl)pyrrolo[2,3-d]pyridazine or pharmacologically acceptable salts thereof.

12. A pyrrolopyridazine derivative according to claim 5 which is 1-(2-Butenyl)-7-(4-fluorobenzyloxy)-2,3-dimethylpyrrolo[2,3-d]pyridazine or pharmacologically acceptable salts thereof.

13. A pyrrolopyridazine derivative according to claim 5 which is 1-Cyclopropylmethyl-7-(4-fluorobenzyloxy)-2,3 -dimethylpyrrolo[2,3-d]pyridazine or pharmacologically acceptable salts thereof.

14. A pyrrolopyridazine derivative according to claim 5 which is 7-(2 4-Difluorobenzyloxy)-2,3-dimethyl-1-(2-propenyl)pyrrolo[2,3-d]pyridazine or pharmacologically acceptable salts thereof.

15. A pyrrolopyridazine derivative according to claim 5 which is 1-(2-Butenyl)-7-(2,4-difluorobenzyloxy) -2,3-dimethylpyrrolo[2,3-d]pyridazine or pharmacologically acceptable salts thereof.

16. A pyrrolopyridazine derivative according to claim 5 which is 7-(4-Chlorobenzyloxy)-2,3-dimethyl-1-(2-propenyl)pyrrolo[2,3-d]pyridazine or pharmacologically acceptable salts thereof.

17. A pyrrolopyridazine derivative according to claim 5 which is 7-(2,4-Dichlorobenzyloxy)-2,3-dimethyl-1-(2-propenyl)pyrrolo[2,3-d]pyridazine or pharmacologically acceptable salts thereof.

18. A pyrrolopyridazine derivative according to claim 5 which is 1-(2-Butenyl)-7-(2,4-dichlorobenzyloxy)-2,3-dimethylpyrrolo[2,3-d]pyridazine or pharmacologically acceptable salts thereof.

19. A pyrrolopyridazine derivative according to claim 5 which is 7-(2-Fluorobenzyloxy)-2,3-dimethyl-1-(2-propenyl)pyrrolo[2,3-d]pyridazine or pharmacologically acceptable salts thereof.

20. A pyrrolopyridazine derivative according to claim 5 which is 1-(2-Butenyl)-3-ethyl-7-(4-fluorobenzyloxy)-2-methylpyrrolo[2,3-d]pyridazine or pharmacologically acceptable salts thereof.

21. A pyrrolopyridazine derivative according to claim 5 which is 7-(4-Fluorobenzylthio)-2,3-dimethyl-1-(2-propenyl)pyrrolo[2,3-d]pyridazine or pharmacologically acceptable salts thereof.

22. A pyrrolopyridazine derivative according to claim 5 which is 1-(2-Butenyl)-7-(4-fluorobenzylthio)-2,3-dimethylpyrrolo[2,3-d]pyridazine or pharmacologically acceptable salts thereof.

23. A pyrrolopyridazine derivative according to claim 5 which is 1-(2-Butenyl)-7-(2,4-difluorobenzylthio)-2,3-dimethylpyrrolo[2,3-d]pyridazine or pharmacologically acceptable salts thereof.

24. A pyrrolopyridazine derivative according to claim 5 which is 1-(2-Butenyl)-7-(2-chloro-6-fluorobenzyloxy)-2,3-dimethylpyrrolo[2,3-d]pyridazine or pharmacologically acceptable salts thereof.

25. A pyrrolopyridazine derivative according to claim 5 which is 1-(2-Butenyl)-7-(4-chloro-2-fluorobenzyloxy)-2,3-dimethylpyrrolo[2,3-d]pyridazine or pharmacologically acceptable salts thereof.

26. A pyrrolopyridazine derivative according to claim 5 which is 7-(4-Fluorobenzyloxy)-2,3-dimethyl-1-(2 -methylcyclopropylmethyl)pyrrolo[2,3-d]pyridazine or pharmacologically acceptable salts thereof.

27. A pyrrolopyridazine derivative according to claim 5 which is 7-(2,4-Difluorobenzyloxy)-2,3-dimethyl-1-(2-methylcyclopropylmethyl)pyrrolo[2,3 -d]pyridazine or pharmacologically acceptable salts thereof.

28. A pyrrolopyridazine derivative according to claim 5 which is 2,3-Dimethyl-7-phenethyl-1-(2-propenyl)pyrrolo [2,3-d]pyridazine or pharmacologically acceptable salts thereof.

29. A pyrrolopyridazine derivative according to claim 5 which is 1-(2-Butenyl)-2,3-dimethyl-7-phenethylpyrrolo[2,3-d]pyridazine or pharmacologically acceptable salts thereof.

30. A pyrrolopyridazine derivative according to claim 5 which is 7-(4-Fluorophenethyl)-2,3-dimethyl-1-(2-propenyl)pyrrolo[2,3-d]pyridazine or pharmacologically acceptable salts thereof.

31. A pyrrolopyridazine derivative according to claim 5 which is 1-(2-Butenyl)-7-(4-fluorophenethyl)-2,3-dimethylpyrrolo[2,3-d]pyridazine or pharmacologically acceptable salts thereof.

32. A pyrrolopyridazine derivative according to claim 5 which is 1-Cyclopropylmethyl-7-(4-fluorophenethyl)-2,3-dimethylpyrrolo[2,3-d]pyridazine or pharmacologically acceptable salts thereof.

33. A pyrrolopyridazine derivative according to claim 5 which is 7-(2,4-Difluorophenethyl)-2,3-dimethyl-1-(2-propenyl)pyrrolo[2,3-d]pyridazine or pharmacologically acceptable salts thereof.

34. A pyrrolopyridazine derivative according to claim 5 which is 1-(2-Butenyl)-7-(2,4-difluorophenethyl)-2,3-dimethylpyrrolo(2,3-d]pyridazine or pharmacologically acceptable salts thereof.

35. A pyrrolopyridazine derivative according to claim 5 which is 1-Cyclopropylmethyl-7-(2,4-difluorophenethyl)-2,3-dimethylpyrrolo[2,3-d]pyridazine or pharmacologically acceptable salts therefo.

36. A pyrrolopyridazine derivative according to claim 5 which is 7-(4-Fluorophenethyl)-2,3-dimethyl-1-(2-methylcyclopropylmethyl)pyrrolo[2,3-d]pyridazine or pharmacologically acceptable salts thereof.

37. A pyrrolopyridazine derivative according to claim 5 which is 7-(2,4-Difluorophenethyl)-2,3-dimethyl-1-(2-methylcyclopropylmethyl)pyrrolo(2,3-d]pyridazine or pharmacologically acceptable salts thereof.

38. A pyrrolopyridazine derivative according to claim 5 which is 2,3-Dimethyl-1-(2-methylcyclopropylmethyl)-7-phenethylpyrrolo[2,3-d]pyridazine or pharmacologically acceptable salts thereof.

39. A pyrrolopyridazine derivative according to claim 5 which is 1-(2-Butenyl)-7-(4-fluorobenzyloxy)-2,3 -dimethylpyrrolo[2,3-d]pyridazine-5-oxide or pharmacologically acceptable salts thereof.

40. A pyrrolopyridazine derivative according to claim 5 which is 1-(2-Butenyl)-7-(2,4-difluorobenzyloxy)-2,3-dimethylpyrrolo[2,3-d]pyridazine-5-oxide or pharmacologically acceptable salts thereof.

41. A pyrrolopyridazine derivative according to claim 5 which is 1-(2-Butenyl)-7-(2,4-difluorophenethyl)-2,3-dimethylpyrrolo[2,3-d]pyridazine-5-oxide or pharmacologically acceptable salts thereof.

42. A pyrrolopyridazine derivative according to claim 5 which is 1-(2-Butenyl)-7-(2,4-difluorophenethyl)-2,3-dimethylpyrrolo[2,3-d]pyridazine-6-oxide or pharmacologically acceptable salts thereof.

43. A pyrrolopyridazine derivative according to claim 5 which is 7-(4-fluorobenzyloxy)-2,3-dimethyl-1-(2-methylcyclopropylmethyl)pyrrolo[2,3-d]pyridazine (trans) or pharmacologically acceptable salts thereof.

44. An anti-ulcer agent comprising an effective amount of a pyrrolopyridazine derivative or a pharmacologically acceptable salt thereof as claimed in claim 1.

45. An anti-ulcer agent according to claim 44, wherein the active ingredient is selected from:

(2-butenyl)-7-benzyloxy-2,3-dimethylpyrrolo[2,3-d] pyridazine or pharmacologically acceptable salts thereof, 7-benzyloxy-2,3-dimethyl-1-(2-methyl-2-propenyl) pyrrolo[2,3-d]pyridazine or pharmacologically acceptable salts thereof, 7-benzyloxy-2,3-dimethyl-1-(2-propynyl)pyrrolo[2,3-d] pyridazine or pharmacologically acceptable salts thereof, 7-benzyloxy-1-cyclopropylmethyl-2,3-dimethylpyrrolo [2,3-d]pyridazine or pharmacologically acceptable salts thereof, 7-(4-fluorobenzyloxy)-2,3-dimethyl-1-(1-propenyl) pyrrolo[2,3-d]pyridazine or pharmacologically acceptable salts thereof, 7-(4-fluorobenzyloxy)-2,3-dimethyl-1-(2-propenyl) pyrrolo[2,3-d]pyridazine or pharmacologically acceptable salts thereof, 1-(2-butenyl)-7-(4-fluorobenzyloxy)-2,3-dimethylpyrrolo[2,3-d]pyridazine or pharmacologically acceptable salts thereof, 1-cyclopropylmethyl-7-(4-fluorobenzyloxy)-2,3-dimethylpyrrolo[2,3-d]pyridazine or pharmacologically acceptable salts thereof, 7-(2,4-difluorobenzyloxy)-2,3-dimethyl-1-(2-propenyl) pyrrolo[2,3-d]pyridazine or pharmacologically acceptable salts thereof, 1-(2-butenyl)-7-(2,4-difluorobenzyloxy)-2,3-dimethylpyrrolo[2,3-d]pyridazine or pharmacologically acceptable salts thereof, 7-(4-chlorobenzyloxy)-2,3-dimethyl-1-(2-propenyl) pyrrolo[2,3-d]pyridazine or pharmacologically acceptable salts thereof, 7-(2,4-dichlorobenzyloxy)-2,3-dimethyl-1-(2-propenyl) pyrrolo[2,3-d]pyridazine or pharmacologically acceptable salts thereof, 1-(2-butenyl)-7-(2,4-dichlorobenzyloxy)-2,3-dimethylpyrrolo[2,3-d]pyridazine or pharmacologically acceptable salts thereof, 7-(2-fluorobenzyloxy)-2,3-dimethyl-1-(2-propenyl) pyrrolo[2,3-d]pyridazine or pharmacologically acceptable salts thereof, 1-(2-butenyl)-3-ethyl-7-(4-fluorobenzyloxy)-2-methylpyrrolo[2,3-d]pyridazine or pharmacologically acceptable salts thereof, 7-(4-fluorobenzylthio)-2,3-dimethyl-1-(2-propenyl) pyrrolo[2,3-d]pyridazine or pharmacologically acceptable salts thereof, 1-(2-butenyl)-7-(4-fluorobenzylthio)-2,3-dimethylpyrrolo[2,3-d]pyridazine or pharmacologically acceptable salts thereof, 1-(2-butenyl)-7-(2,4-difluorobenzylthio)-2,3-dimethylpyrrolo[2,3-d]pyridazine or pharmacologically acceptable salts thereof, 1-(2-butenyl)-7-(2-chloro-6-fluorobenzyloxy)-2,3-dimethylpyrrolo[2,3-d]pyridazine or pharmacologically acceptable salts thereof, 1-(2-butenyl)-7-(4-chloro-2-fluorobenzyloxy)-2,3-dimethylpyrrolo[2,3-d]pyridazine or pharmacologically acceptable salts thereof, 7-(4-fluorobenzyloxy)-2,3-dimethyl-1-(2-methylcyclopropylmethyl)pyrrolo[2,3-d]pyridazine or pharmacologically acceptable salts thereof, 7-(2,4-difluorobenzyloxy)-2,3-dimethyl-1-(2-methylcyclopropylmethyl)pyrrolo[2,3-d]pyridazine or pharmacologically acceptable salts thereof, 2,3-dimethyl-7-phenethyl-1-(2-propenyl)pyrrolo[2,3-d] pyridazine or pharmacologically acceptable salts thereof, 1-(2-butenyl)-2,3-dimethyl-7-phenethylpyrrolo[2,3-d] pyridazine or pharmacologically acceptable salts thereof, 7-(4-fluorophenethyl)-2,3-dimethyl-1-(2-propenyl) pyrrolo[2,3-d]pyridazine or pharmacologically acceptable salts thereof, 1-(2-butenyl)-7-(4-fluorophenethyl)-2,3-dimethylpyrrolo [2,3-d]pyridazine or pharmacologically acceptable salts thereof, 1-cyclopropylmethyl-7-(4-fluorophenethyl)-2,3-dimethylpyrrolo[2,3-d]pyridazine or pharmacologically acceptable salts thereof, 7-(2,4-difluorophenethyl)-2,3-dimethyl-1-(2-propenyl) pyrrolo[2,3-d]pyridazine or pharmacologically acceptable salts thereof, 1-(2-butenyl)-7-(2,4-difluorophenethyl)-2,3-dimethylpyrrolo[2,3-d]pyridazine or pharmacologically acceptable salts thereof, 1-cyclopropylmethyl-7-(2,4-difluorophenethyl)-2,3-dimethylpyrrolo[2,3-d]pyridazine or pharmacologically acceptable salts thereof, 7-(4-fluorophenethyl)-2,3-dimethyl-1-(2-methylcyclopropylmethyl)pyrrolo[2,3-d]pyridazine or pharmacologically acceptable salts thereof, 7-(2,4-difluorophenethyl)-2,3-dimethyl-1-(2-methylcyclopropylmethyl)pyrrolo[2,3-d]pyridazine or pharmacologically acceptable salts thereof, 2,3-dimethyl-1-(2-methylcyclopropylmethyl)-7-phenethylpyrrolo[2,3-d]pyridazine or pharmacologically acceptable salts thereof, 1-(2-butenyl)-7-(4-fluorobenzyloxy)-2,3-dimethylpyrrolo[2,3-d]pyridazine-5-oxide or pharmacologically acceptable salts thereof, 1-(2-butenyl)-7-(2,4-difluorobenzyloxy)-2,3-dimethylpyrrolo[2,3-d]pyridazine-5-oxide or pharmacologically acceptable salts thereof, A represents a $C_1$–$C_3$ alkylene group; X represents an imino group, an oxygen atom, a sulfur atom or a methylene group; m represents 0 or 1; and n represents 0 or 1 or pharmaceutically acceptable salts thereof. ereof.

46. An anti-ulcer agent comprising an effective amount of a pyrrolopyridazine derivative or a pharmacologically acceptable salt thereof as claimed in claim 43.

* * * * *

UNITED STATES PATENT AND TRADEMARK OFFICE

CERTIFICATE OF CORRECTION

PATENT NO. : 6,063,782
DATED : May 16, 2000
INVENTOR(S) : Kimura et al.

It is certified that error appears in the above-identified patent and that said Letters Patent is hereby corrected as shown below:

Title page,
Item [56], References Cited, FOREIGN PATENT DOCUMENTS,
Before "92-06979" insert -- WO --; delete "WO 92/06974 4/1992 WIPO".

Item [57], ABSTRACT,
Line 12, after "sulfur;" insert :
-- A represents a $C_1$-$C_3$ alkylene group; X represents an imino group, an oxygen atom, a sulfur atom or a methylene group; m represents 0 or 1; and n represents 0 or 1 or pharmaceutically acceptable salts thereof.

The pyrrolopyridazine derivatives of the present invention have an excellent gastric secretion inhibiting activity, gastric mucosa protective activity and antibacterial activity against Helicobacter pylori, and are useful as a preventive or therapeutic agent for ulcerous diseases. --

Column 71,
Line 5, delete "90.89%" and insert -- 90.8% --.
Line 42, delete "79.60%" and insert -- 79.6% --.

Column 72,
Line 22, delete "95.30%" and insert -- 95.3% --.

Column 73,
Line 67, delete "90.2i" and insert -- 90.2% --.

Column 77,
Line 37, delete "91.2w" and insert -- 91.2% --.

Column 86,
Line 4, delete "51.4i" and insert -- 51.4% --.
Line 53, delete "74.20%" and insert -- 74.2% --.

UNITED STATES PATENT AND TRADEMARK OFFICE

CERTIFICATE OF CORRECTION

PATENT NO. : 6,063,782
DATED : May 16, 2000
INVENTOR(S) : Kimura et al.

It is certified that error appears in the above-identified patent and that said Letters Patent is hereby corrected as shown below:

Column 89,
Line 67, delete "61.6?" and insert -- 61.6% --.

Column 94,
Line 7, before "represents" delete "R" and insert -- $R^1$ --.

Column 98,
Line 56, before "(2-butenyl)" insert -- 1- --.

Signed and Sealed this

Tenth Day of September, 2002

Attest:

JAMES E. ROGAN

*Attesting Officer*

*Director of the United States Patent and Trademark Office*

UNITED STATES PATENT AND TRADEMARK OFFICE

CERTIFICATE OF CORRECTION

PATENT NO. : 6,063,782 Page 1 of 1
DATED : May 16, 2000
INVENTOR(S) : Kimura et al.

It is certified that error appears in the above-identified patent and that said Letters Patent is hereby corrected as shown below:

Column 93,
Line 53, after "aryl)-2-", delete "propynyl" and insert -- propenyl --.

Column 94,
Lines 56-58, delete "7-(4-fluorobenzyloxy)-2,3,-dimethyl-1-(2-propenyl)pyrrolo[2,3-d] pyridazine or pharmacologically acceptable salts thereof,".

Column 95,
Lines 49-51, delete "7-(2, 4-difluorobenzyloxy)-2,3-dimethyl-1-(2methylcyclopropylmethyl)pyrrolo[2,3-d]pyridazin or pharmacologically acceptable salts thereof,".

Column 96,
Lines 20-23, delete "1-(2-butenyl)-7-(4-fluorobenzyloxy)-2,3-dimethylpyrrolo[2,3-d] pyridazine-5-oxide or pharmacologically acceptable salts thereof,".
Lines 24-26, delete "1-(2-butenyl)-7-(2,4-difluorobenzyloxy)-2,3-dimethylpyrrolo[2,3-d]pyridazine-5-oxide or pharmacologically acceptable salts thereof,".

Signed and Sealed this

Twenty-seventh Day of September, 2005

JON W. DUDAS
*Director of the United States Patent and Trademark Office*